(12) United States Patent
Chatterjee et al.

(10) Patent No.: US 8,871,754 B2
(45) Date of Patent: Oct. 28, 2014

(54) COMPOUNDS AND COMPOSITIONS FOR THE TREATMENT OF PARASITIC DISEASES

(71) Applicants: Arnab Kumar Chatterjee, San Diego, CA (US); Advait Suresh Nagle, San Diego, CA (US); Prasuna Paraselli, San Diego, CA (US); Ravinder Reddy Kondreddi, Singapore (SG); Seh Yong Leong, Singapore (SG); Pranab Kumar Mishra, San Diego, CA (US); Robert Joseph Moreau, Emeryville, CA (US); Jason Thomas Roland, San Diego, CA (US); Wei Lin Sandra Sim, Singapore (SG); Oliver Simon, Singapore (SG); Liying Jocelyn Tan, Singapore (SG); Bryan K S Yeung, Singapore (SG); Bin Zou, Singapore (SG); Venkatataiah Bollu, San Diego, CA (US)

(72) Inventors: Arnab Kumar Chatterjee, San Diego, CA (US); Advait Suresh Nagle, San Diego, CA (US); Prasuna Paraselli, San Diego, CA (US); Ravinder Reddy Kondreddi, Singapore (SG); Seh Yong Leong, Singapore (SG); Pranab Kumar Mishra, San Diego, CA (US); Robert Joseph Moreau, Emeryville, CA (US); Jason Thomas Roland, San Diego, CA (US); Wei Lin Sandra Sim, Singapore (SG); Oliver Simon, Singapore (SG); Liying Jocelyn Tan, Singapore (SG); Bryan K S Yeung, Singapore (SG); Bin Zou, Singapore (SG); Venkatataiah Bollu, San Diego, CA (US)

(73) Assignees: IRM LLC, Hamilton (BM); Novartis AG, Basel (CH)

( * ) Notice: Subject to any disclaimer, the term of this patent is extended or adjusted under 35 U.S.C. 154(b) by 0 days.

(21) Appl. No.: 14/083,203

(22) Filed: Nov. 18, 2013

(65) Prior Publication Data
US 2014/0155367 A1 Jun. 5, 2014

Related U.S. Application Data

(60) Provisional application No. 61/728,018, filed on Nov. 19, 2012.

(51) Int. Cl.
*C07D 471/04* (2006.01)
*A61K 31/506* (2006.01)
*A61K 31/538* (2006.01)
*A61K 31/437* (2006.01)
*A61K 45/06* (2006.01)

(52) U.S. Cl.
USPC ........ 514/187; 514/300; 514/230.5; 514/275; 514/252.11; 514/297; 514/292; 546/121; 544/105; 544/297

(58) Field of Classification Search
USPC ......... 514/187, 300, 230.5, 275, 252.11, 297, 514/292; 546/121; 544/105, 297
See application file for complete search history.

(56) References Cited

U.S. PATENT DOCUMENTS

| | | | |
|---|---|---|---|
| 6,348,474 B1 | 2/2002 | Kayakiri et al. | |
| 7,105,550 B2 * | 9/2006 | Love et al. | ...... 514/365 |
| 7,662,826 B2 | 2/2010 | Seno et al. | |
| 8,088,385 B2 | 1/2012 | Chesney et al. | |
| 2004/0209878 A1 | 10/2004 | Guzi et al. | |
| 2007/0219218 A1 | 9/2007 | Yu et al. | |
| 2010/0184800 A1 | 7/2010 | Pracitto | |
| 2012/0059162 A1 | 3/2012 | Kusakabe et al. | |

FOREIGN PATENT DOCUMENTS

| | | |
|---|---|---|
| EP | 1217000 | 6/2002 |
| JP | 2001139575 | 5/2001 |
| RU | 2421455 | 6/2011 |

(Continued)

OTHER PUBLICATIONS

Belanger, et al., "Discovery of imidazo[1,2-a]pyrazine-based Aurora kinase inhibitors", Bioorganic & Medicinal Chemistry Letters, 2010, pp. 5170-5174, vol. 20, Elsevier Ltd.
Borbely, et al., "Small-Molecule Inhibitors of NADPH Oxidase 4", J. Med. Chem., 2010, pp. 6758-6762, vol. 53, No. 18, American Chemical Society.
Bullock, et al., "Structural Basis of Inhibitor Specificity of the Human Protooncogene Proviral Insertion Site in Moloney Murine Leukemia Virus (PIM-1) Kinase", J. Med. Chem., 2005, pp. 7604-7614, vol. 48, No. 24, American Chemical Society.
Lubbers, et al., "Design, Synthesis, and Structure-Activity Relationship Studies of ATP Analogues as DNA Gyrase Inhibitors", Bioorganic & Medicinal Chemistry Letters, 2000, pp. 821-826, vol. 10, Elsevier Science Ltd.
Merckx, et al., "Structures of *P. falciparum* Protein Kinase 7 Identify an Activation Motif and Leads for Inhibitors Design", Structure, 2008, pp. 228-238, vol. 16, Elsevier Ltd.

(Continued)

*Primary Examiner* — Niloofar Rahmani
(74) *Attorney, Agent, or Firm* — Chihang Amy Smith; Genomics Institute of the Novartis Research Foundation

(57) ABSTRACT

The present invention provides compounds of formula I:

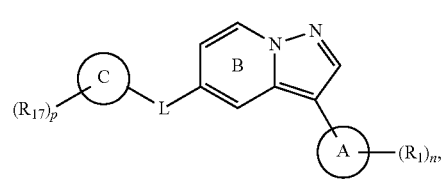

or a pharmaceutically acceptable salt, tautomer, or stereoisomer, thereof, wherein the variables are as defined herein. The present invention further provides pharmaceutical compositions comprising such compounds and methods of using such compounds for treating, preventing, inhibiting, ameliorating, or eradicating the pathology and/or symptomology of a disease caused by a *Plasmodium* parasite, such as malaria.

12 Claims, No Drawings

(56) References Cited

FOREIGN PATENT DOCUMENTS

| WO | WO98/03510 | 1/1998 |
|---|---|---|
| WO | WO01/56555 | 8/2001 |
| WO | WO01/56573 | 8/2001 |
| WO | WO01/83479 | 11/2001 |
| WO | WO02-18382 | 3/2002 |
| WO | WO03/045950 | 6/2003 |
| WO | WO03/091256 | 6/2003 |
| WO | WO2004026871 | 4/2004 |
| WO | WO2004/069837 | 8/2004 |
| WO | WO2004069838 | 8/2004 |
| WO | WO2007/013673 | 2/2007 |
| WO | WO2007/065664 | 6/2007 |
| WO | WO2007/084415 | 7/2007 |
| WO | WO2007/086080 | 8/2007 |
| WO | WO2007/100775 | 9/2007 |
| WO | WO2007/146087 | 12/2007 |
| WO | WO2007/147647 | 12/2007 |
| WO | WO2008/025822 | 3/2008 |
| WO | WO2008/033408 | 3/2008 |
| WO | WO2008/037477 | 4/2008 |
| WO | WO2008/058126 | 5/2008 |
| WO | WO2008078091 | 7/2008 |
| WO | WO2008/130570 | 10/2008 |
| WO | WO2008/156783 | 12/2008 |
| WO | WO2009/008748 | 1/2009 |
| WO | WO2009/012482 | 1/2009 |
| WO | WO2009/017954 | 2/2009 |
| WO | WO2010/017046 | 2/2010 |
| WO | WO2010/017047 | 2/2010 |
| WO | WO2010/030538 | 3/2010 |
| WO | WO2010/034738 | 4/2010 |
| WO | WO2010/059836 | 5/2010 |
| WO | WO2010/064020 | 6/2010 |
| WO | WO2010/074586 | 7/2010 |
| WO | WO2010/090716 | 8/2010 |
| WO | WO2010/108187 | 9/2010 |
| WO | WO2010/117787 | 10/2010 |
| WO | WO2010/118207 | 10/2010 |
| WO | WO2011006143 | 1/2011 |
| WO | WO2011/029027 | 3/2011 |
| WO | WO2011/038097 | 3/2011 |

OTHER PUBLICATIONS

Michalska, "Novel Synthesis of Azaindolizines by Reaction of Isonitrosoflavanone Esters with Pyridine Bases", Tetrahedron Letters, 1971, pp. 2667-2668, vol. 28, Pergamon Press, Great Britain.

Ren, et al., "Discovery of Novel Pim-1 Kinase Inhibitors by a Hierarchical Multistage Virtual Screening Approach Based on SVM Model, Pharmacophore, and Molecular Docking", Journal of Chemical Information and Modeling, 2011, pp. 1364-1375, vol. 51, American Chemical Society.

Shaaban, "Microwave-assistaed synthesis of fused heterocycles incorporating trifluoromethyl moiety", Journal of Fluorine Chemistry, 2008, pp. 1156-1161, vol. 129, Elsevier Ltd.

Williamson, et al., "Structure-guided design of pyrazolo[1,5-a]pyrimidines as inhibitors of human cyclin-dependent kinase 2", Bioorganic & Medicinal Chemistry Letters, 2005, pp. 863-867, vol. 15, Elsevier Ltd.

* cited by examiner

COMPOUNDS AND COMPOSITIONS FOR THE TREATMENT OF PARASITIC DISEASES

CROSS-REFERENCED TO RELATED APPLICATIONS

This application claims the benefit of priority to U.S. Provisional Patent Application No. 61/728,018, filed 19 Nov. 2012; the disclosure of which is incorporated by reference herein in its entirety and for all purposes.

BACKGROUND OF THE INVENTION

1. Field of the Invention

The invention provides a class of compounds, pharmaceutical compositions comprising such compounds and methods of using such compounds to treat or prevent malaria.

2. Background

Malaria is an infectious disease caused by four protozoan parasites: *Plasmodium falciparum; Plasmodium vivax; Plasmodium ovale*; and *Plasmodium malaria*. These four parasites are typically transmitted by the bite of an infected female *Anopheles* mosquito. Malaria is a problem in many parts of the world and over the last few decades the malaria burden has steadily increased. An estimated 1-3 million people die every year from malaria—mostly children under the age of 5. This increase in malaria mortality is due in part to the fact that *Plasmodium falciparum*, the deadliest malaria parasite, has acquired resistance against nearly all available antimalarial drugs, with the exception of the artemisinin derivatives. Further for true causal prophylaxis and interrupt transmission of the disease, prevention of liver stage development is crucial, because development of the proceeding infectious blood stage gametocytes would be block. A single drug effective against hepatichypnozoites, primaquine, is available, but its deployment is curtailed by its potential side effects.

Leishmaniasis is caused by one or more than 20 varieties of parasitic protozoa that belong to the genus *Leishmania*, and is transmitted by the bite of female sand flies. Leishmaniasis is endemic in about 88 countries, including many tropical and sub-tropical areas.

There are four main forms of Leishmaniasis. Visceral leishmaniasis, also called kalaazar, is the most serious form and is caused by the parasite *Leishmania donovani*. Patients who develop visceral leishmaniasis can die within months unless they receive treatment. The two main therapies for visceral leishmaniasis are the antimony derivatives sodium stibogluconate (Pentostam®) and meglumine antimoniate (Glucantim®). Sodium stibogluconate has been used for about 70 years and resistance to this drug is a growing problem. In addition, the treatment is relatively long and painful, and can cause undesirable side effects.

Human African Trypanosomiasis, also known as sleeping sickness, is a vector-borne parasitic disease. The parasites concerned are protozoa belonging to the *Trypanosoma* Genus. They are transmitted to humans by tsetse fly (*Glossina* Genus) bites which have acquired their infection from human beings or from animals harboring the human pathogenic parasites.

Chagas disease (also called American Trypanosomiasis) is another human parasitic disease that is endemic amongst poor populations on the American continent. The disease is caused by the protozoan parasite *Trypanosoma cruzi*, which is transmitted to humans by blood-sucking insects. The human disease occurs in two stages: the acute stage, which occurs shortly after infection and the chronic stage, which can develop over many years. Chronic infections result in various neurological disorders, including dementia, damage to the heart muscle and sometimes dilation of the digestive tract, as well as weight loss. Untreated, the chronic disease is often fatal.

The drugs currently available for treating Chagas disease are Nifurtimox and benzindazole. However, problems with these current therapies include their diverse side effects, the length of treatment, and the requirement for medical supervision during treatment. Furthermore, treatment is really only effective when given during the acute stage of the disease. Resistance to the two frontline drugs has already occurred. The antifungal agent Amphotericin b has been proposed as a second-line drug, but this drug is costly and relatively toxic.

In view of the foregoing, it is desirable to develop novel compounds as antiparasitic agents.

SUMMARY OF THE INVENTION

The invention therefore provides a compound of the formula (I):

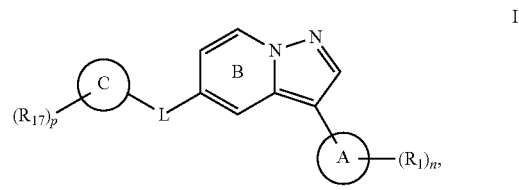

or a pharmaceutical acceptable salt, tautomer or stereoisomer thereof, wherein n is 0, 1, 2 or 3;

p is 0, 1, 2 or 3;

L is selected from the group consisting of *—$(CHR_3)_{1-3}$—, *—$CHR_3N(R_2)$—, *—$CHR_3O$—, *—$CHR_3S$—, *—$CHR_3S(O)$—, *—$CHR_3N(R_2)CHR_3$—, *—$C(O)$—, *—$C(O)N(R_2)$—, *—$C(O)N(R_2)CHR_3$—, *—$N(R_2)$—, *—$N(R_2)CHR_3$—, *—$N(R_2)C(O)$—, *—$N(R_2)C(O)N(R_2)$—, *—$N(R_2)S(O)_2$—, wherein

* represents the point of attachment of L to the pyrazolo[1,5-a]pyridine fused ring depicted in Formula I;

each $R_2$ is independently selected from the group consisting of hydrogen, $C_{1-6}$alkyl, halo$C_{1-6}$alkyl, R—$C_{0-4}$alkylene, and R—$C_{0-4}$alkylene-C(O)—, wherein R is selected from the group consisting of hydroxyl, $C_{1-4}$alkoxy, amino, $C_{1-4}$alkylamino, $C_{3-6}$cycloalkyl, $C_{4-6}$heterocycloalkyl, and $C_{5-6}$heteroaryl, wherein the $C_{3-6}$cycloalkyl, $C_{4-6}$heterocycloalkyl, and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl; and each $R_3$ is independently selected from the group consistin of hydrogen and $C_{1-4}$alkyl;

Ring A is selected from the group consistin of $C_{6-10}$aryl and $C_{3-10}$heteroaryl;

Ring C is selected from the group consisting of $C_{6-10}$aryl, $C_{5-10}$heteroaryl, $C_{5-7}$cycloalkyl, $C_{5-7}$heterocycloalkyl, and a fused bicyclyl comprising a $C_{5-6}$heterocycloalkyl fused to a phenyl;

each $R_1$ is independently selected from the group consisting of halo, cyano, amino, $C_{1-4}$alkyl, $C_{1-4}$alkoxyl, halo-$C_{1-4}$alkyl, —C(O)NR$_7$R$_8$, —NHC(O)R$_{11}$, phenyl, and $C_{5-6}$heteroaryl; wherein
the phenyl and $C_{5-6}$heteroaryl of R$_1$ are each unsubstituted or substituted with 1-2 substituents independently selected from the group consisting of $C_{1-4}$alkyl, amino, halo, and $C_{1-4}$alkylamino;
R$_7$ and R$_8$ are each independently selected from the group consisting of hydrogen, $C_{1-4}$alkyl or halo$C_{1-4}$alkyl;
R$_{11}$ is $C_{1-6}$alkyl unsubstituted or substituted with 1-2 substituents independently selected from the group consisting of amino, $C_{3-6}$cycloalkyl and $C_{4-6}$heterocycloalkyl;
R$_{17}$ is selected from the group consisting of cyano, halo, $C_{1-4}$alkyl, halo-$C_{1-4}$alkyl, oxo, $C_{3-6}$cycloalkyl, and —SO$_2$—$C_{1-4}$alkyl.

In a second aspect, the present invention provides a pharmaceutical composition which contains a compound selected from Formula I, IA, or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which a compound of the invention can prevent, inhibit, ameliorate, or eradicate the pathology and/or symptomology of disease caused by a parasite (such as, for example, *Plasmodium falciparum, Plasmodium vivax, Plasmodium ovale, Plasmodium* malaria, *Trypanosoma cruzi* or a parasite of the *Leishmania* genus such as, for example, *Leishmania donovani*) which method comprises administering to the animal a therapeutically effective amount of a compound selected from Formula I, IA, or a N-oxide derivative, individual isomers and mixture of isomers thereof, or a pharmaceutically acceptable salt thereof.

In a fourth aspect, the present invention provides a compound for treating, preventing, inhibiting, ameliorating, or eradicating the pathology and/or symptomology of a disease caused by a parasite (such as, for example, *Plasmodium falciparum, Plasmodium vivax, Plasmodium ovale, Plasmodium malaria, Trypanosoma cruzi* or a parasite of the *Leishmania* genus such as, for example, *Leishmania donovani*). Particularly, the parasite is a *Plasmodium* which can be at the blood stages or at the hepatic stages, and the disease is malaria.

In a fifth aspect, the present invention provides the use of a compound selected from Formula I or Formula 1a in the manufacture of a medicament for treating a disease caused by a parasite in an animal. The disease may be malaria, leishmaniasis and/or Chagas disease.

In a sixth aspect, the present invention provides a process for preparing compounds selected from Formula I, Formula 1a and the N-oxide derivatives, prodrug derivatives, individual isomers and mixture of isomers thereof, and the pharmaceutically acceptable salts thereof.

Unless specified otherwise, the term "compounds of the present invention" refers to compounds of Fomula (I) and subformulae thereof, salts of the compound, hydrates or solvates of the compounds, salts, as well as all stereoisomers (including diastereoisomers and enantiomers), tautomers and isotopically labeled compounds (including deuterium substitutions). Compounds of the present invention further comprise polymorphs of compounds of formula I (or subformulae thereof) and salts thereof.

DETAILED DESCRIPTION OF THE INVENTION

Definitions

For purposes of interpreting this specification, the following definitions will apply and whenever appropriate, terms used in the singular will also include the plural and vice versa.

"Acyl" as used herein refers to the radical —C(=O)R$_a$, where R$_a$ is hydrogen or a non-hydrogen substituent on the carbonyl carbon, forming different carbonyl-containing groups including, but are not limited to, acids, acid halides, aldehydes, amides, esters, and ketones.

"Alkoxy" as used herein refers the radical —O-alkyl, wherein the alkyl is as defined herein. C$_X$alkoxy and C$_{X-Y}$alkoxy as used herein describe alkoxy groups where X and Y indicate the number of carbon atoms in the alkyl chain. Representative examples of C$_{1-10}$alkoxy include, but are not limited to, methoxy, ethoxy, propoxy, 2-propoxy, butoxy, tert-butoxy, pentyloxy, hexyloxy, heptyloxy, octyloxy and decyloxy. The alkyl portion of the alkoxy may be optionally substituted, and the substituents include those described for the alkyl group below.

"Alkyl" as used herein refers to a fully saturated branched or unbranched hydrocarbon chain having up to 10 carbon atoms. C$_X$ alkyl and C$_{X-Y}$ alkyl as used herein describe alkyl groups where X and Y indicate the number of carbon atoms in the alkyl chain. For example, C$_{1-10}$ alkyl refers to an alkyl radical as defined above containing one to ten carbon atoms. C$_{1-10}$ alkyl includes, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. Alkyl represented along with another radical like arylalkyl, heteroarylalkyl, alkoxyalkyl, alkoxyalkyl, alkylamino, where the alkyl portion shall have the same meaning as described for alkyl and is bonded to the other radical. For example, (C$_{6-10}$)aryl(C$_{1-3}$)alkyl includes, benzyl, phenylethyl, 1-phenylethyl, 3-phenylpropyl, 2-thienylmethyl, 2-pyridinylmethyl and the like.

Unless stated otherwise specifically in the specification, an alkyl group may be unsubstituted or substituted by one or more substituents to the extent that such substitution makes sense chemically. Typical substituents include, but are not limited to halo, hydroxyl, alkoxy, cyano, amino, acyl, aryl, arylalkyl, and cycloalkyl, or an heteroforms of one of these groups, and each of which can be substituted by the substituents that are appropriate for the particular group.

"Alkenyl" as used herein refers to a straight or branched, hydrocarbon chain having up to 10 carbon atoms and at least one carbon-carbon double bond. C$_X$alkenyl and C$_{X-Y}$alkenyl as used herein describe alkenyl groups where X and Y indicate the number of carbon atoms in the alkenyl chain. Examples of C$_{2-7}$alkenyl include vinyl, allyl, isopropenyl, pentenyl, hexenyl, heptenyl, 1-propenyl, 2-butenyl, 2-methyl-2-butenyl, and the like. The alkenyl may be optionally substituted, and the substituents include those described for the alkyl group descried herein.

"Alkynyl" as used herein refers to a straight or branched, hydrocarbon chain having up to 10 carbon atoms and at least one carbon-carbon triple bond. C$_X$alkenyl and C$_{X-Y}$alkenyl as used herein describe alkynyl groups, where X and Y indicate the number of carbon atoms in the alkynyl chain. For example, C$_{2-7}$alkenyl include, but are not limited to, ethynyl, propargyl, 3-methyl-1-pentynyl, 2-heptynyl and the like. An alkynyl may be optionally substituted, and the substituents include those described for the alkyl group described herein.

"Alkylene" as used herein refers to a divalent alkyl group defined herein. Examples of C$_1$-C$_{10}$alkylene includes, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene. An alkylene group may be optionally substituted, and the substituents include those described for the alkyl group described herein.

"Alkenylene" as used herein refers to a divalent alkenyl group defined herein. Examples of $C_{1-3}$alkenylene include, but are not limited to, ethene-1,2-diyl, propene-1,3-diyl, and methylene-1,1-diyl. An alkenylene may be optionally substituted, and the substituents include those described for the alkyl group described herein.

"Alkynylene" as used herein refers to a divalent alkynyl group defined herein. Examples of alkynylene include ethyne-1,2-diylene, propyne-1,3-diylene, and the like. An alkynylene may be optionally substituted, and the substituents include those described for the alkyl group described herein.

"Amino" as used herein refers to the radical —$NH_2$. When an amino is described as "substituted" or "optionally substituted", the term includes NR'R" wherein each R' and R" is independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl or groups or heteroforms of one of these groups, each of which is optionally substituted with the substituents described herein as suitable for the corresponding group.

The term "amino" also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Alkylamino" as used herein refers to the radical —$NR_aR_b$, where at least one of, or both, $R_a$ and $R_b$ are an alkyl group as described herein. An $C_{1-4}$alkylamino group includes —$NHC_{1-4}$alkyl and —$N(C_{1-4}alkyl)_2$; e.g., —$NHCH_3$, —$N(CH_3)_2$, —$NH(CH_2CH_3)$, —$N(CH_2CH_3)_2$, and the like.

"Aromatic" as used herein refers to a moiety wherein the constituent atoms make up an unsaturated ring system, where all atoms in the ring system are $sp^2$ hybridized and the total number of pi electrons is equal to $4n+2$. An aromatic ring may be such that the ring atoms are only carbon atoms or may include carbon and non-carbon atoms (see Heteroaryl).

"Aryl" as used herein refers to a 6-14 membered monocyclic or polycyclic aromatic ring assembly where all the ring atoms are carbon atoms. Typically, the aryl is a 6 membered monocyclic, a 10-12 membered bicyclic or a 14-membered fused tricyclic aromatic ring system. $C_X$aryl and $C_{X-Y}$aryl as used herein describe an aryl group where X and Y indicate the number of carbon atoms in the ring system. $C_{6-14}$aryls include, but are not limited to, phenyl, biphenyl, naphthyl, azulenyl, and anthracenyl.

An aryl may be unsubstituted or substituted by 1-5 (such as one, or two, or three) substituents independently selected from the group consisting of hydroxy, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl, aryl, heteroaryl, cycloalkyl and heterocycloalkyl, wherein each of the aforementioned substitutents may be further substituted by one or more substituents independently selected from halogen, alkyl, hydroxyl or $C_{1-4}$alkoxy groups.

When an "aryl" is represented along with another radical like "arylalkyl", "aryloxyalkyl", "aryloxycarbonyl", "aryloxy-carbonylalkyl", the aryl portion shall have the same meaning as described in the above-mentioned definition of "aryl".

"Aryloxy" as used herein, refers to the radical —O-aryl, wherein aryl is as defined herein.

"Bicyclic" or "bicyclyl" as used here in refers to a ring assembly of two rings where the two rings are fused together, linked by a single bond or linked by two bridging atoms. The rings may be a carbocyclyl, a heterocyclyl, or a mixture thereof.

"Bridging ring" as used herein refers to a polycyclic ring system where two ring atoms that are common to two rings are not directly bound to each other. One or more rings of the ring system may also comprise heteroatoms as ring atoms. Non-exclusive examples of bridging rings include norbornanyl, 7-oxabicyclo[2.2.1]heptanyl, adamantanyl, and the like.

"Carbamoyl" as used herein refers to the radical —C(O)NR_a— where $R_a$ is H, or is an alkyl, alkenyl, alkynyl, acyl, aryl, or arylalkyl group or a heteroform of one of these groups, and each of the alkyl, alkenyl, alkynyl, acyl, aryl, arylalkyl or heteroforms of one of these groups is optionally substituted with the substituents described herein as suitable for the corresponding group.

"Cycloalkyl", as used herein, means a radical comprising a non-aromatic, saturated or partially unsaturated, monocyclic, bicyclic, tricyclic, fused, bridged or spiro polycyclic hydrocarbon ring system of 3-20 carbon atoms. $C_X$cycloalkyl and $C_{X-Y}$cycloalkyl are typically used where X and Y indicate the number of carbon atoms in the ring assembly. For example, $C_{3-6}$cycloalkyl includes cyclopropyl, cyclobutyl, cyclopentyl, cyclohexyl, cyclohexenyl, 2,5-cyclohexadienyl.

Exemplary monocyclic cycloalkyl include, but are not limited to, cyclopropyl, cyclobutyl, cyclopentyl, cyclopentenyl, cyclohexyl and cyclohexenyl and the like. Exemplary bicyclic cycloalkyls include bornyl, norbornanyl, indyl, hexahydroindyl, tetrahydronaphthyl, decahydronaphthyl, bicyclo [2.1.1]hexyl, bicyclo[2.2.1]heptyl, bicyclo[2.2.1]heptenyl, 6,6-dimethylbicyclo[3.1.1]heptyl, 2,6,6-trimethylbicyclo [3.1.1]heptyl, bicyclo[2.2.2]octyl. Exemplary tricyclic cycloalkyl groups include, for example, adamantyl.

A cycloalkyl may be unsubstituted or substituted by one, or two, or three, or more substituents independently selected from the group consisting of hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

"Cycloalkylene", as used herein, refers to a divalent radical comprising a cycloalkyl ring assembly as defined herein.

"Cycloalkoxy", as used herein, refers to —O-cycloalkyl, wherein the cycloalkyl is defined herein. Representative examples of $C_{3-12}$cycloalklyoxy include, but are not limited to, monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyloxy, decahydronaphthyloxy, bicyclo[2.1.1]hexyloxy, bicyclo[2.2.1]heptyloxy, bicyclo[2.2.1]heptenyloxy, 6,6-dimethylbicyclo[3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

"Cyano", as used herein, refers to the radical —CN.

"$EC_{50}$", refers to the molar concentration of an inhibitor or modulator that produces 50% efficacy.

"Fused ring", as used herein, refers to a multi-ring assembly wherein the rings comprising the ring assembly are so linked that the ring atoms that are common to two rings are directly bound to each other. The fused ring assemblies may be saturated, partially saturated, aromatics, carbocyclics, heterocyclics, and the like. Non-exclusive examples of common fused rings include decalin, naphthalene, anthracene, phenanthrene, indole, benzofuran, purine, quinoline, and the like.

"Halo" or "halogen" as used herein refers to fluoro, chloro, bromo, and iodo.

"Haloalkyl", or halo-substituted-alkyl" as used herein, refers to an alkyl as defined herein, which is substituted by one or more halo atoms defined herein. The haloalkyl can be mono-haloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. $C_X$haloalkyl and $C_{X-Y}$haloalkyl are typically used where X and Y indicate the number of carbon atoms in the alkyl chain. Non-limiting examples of $C_{1-4}$haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A $C_{1-4}$ perhaloalkyl group refers to a $C_{1-4}$alkyl group having all hydrogen atoms replaced with halo atoms.

"Heteroaryl", as used herein, refers to a 5-14 membered ring assembly (e.g., a 5-7 membered monocycle, an 8-10 membered bicycle, or a 13-14 membered tricyclic ring system) having 1 to 8 heteroatoms selected from N, O and S as ring atoms and the remaining ring atoms are carbon atoms. The nitrogen atoms of such heteroaryl rings can be optionally quaternerized and the sulfur atoms of such heteroaryl rings can be optionally oxidized. $C_X$heteroaryl and $C_{X-Y}$heteroaryl as used herein describe heteroaryls where X and Y indicate the number of ring atoms in the heteroaryl ring. Typical $C_{5-7}$heteroaryl groups include thienyl, furanyl, imidazolyl, pyrazolyl, pyrrolyl, pyrrolinyl, thiazolyl, 1,3,4-thiadiazolyl, isothiazolyl, oxazolyl, oxadiazole isoxazolyl, triazolyl, tetrazolyl, pyridyl, pyridazinyl, pyrazinyl, pyrazinyl, pyrimidinyl, and the like. Bicyclic or tricyclic $C_{8-14}$heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, quinazolinyle, pteridinyl, indolizine, imidazo[1,2a]pyridine, quinoline, quinolinyl, isoquinoline, phthalazine, quinoxaline, naphthyridine, naphthyridinyl, quinolizine, indolyl, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, purinyl, carbazole, acridine, phenazine, phenothiazene, phenoxazine, 1,2-dihydropyrrolo[3,2,1-hi]indole, indolizine, pyrido[1,2-a]indole and 2(1H)-pyridinone.

A heteroaryl may be unsubstituted or substituted with one or more substituents independently selected from hydroxyl, thiol, cyano, nitro, $C_{1-4}$alkyl, $C_{1-4}$alkenyl, $C_{1-4}$alkynyl, $C_{1-4}$alkoxy, thio$C_{1-4}$alkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups.

When a heteroaryl is represented along with another radical like "heteroaryloxy", "heteroaryloxyalkyl", "heteroaryloxycarbonyl", the heteroaryl portion shall have the same meaning as described in the above-mentioned definition of "heteroaryl".

"Heteroaryloxy", as used herein, refers to an —O-heteroaryl group, wherein the heteroaryl is as defined in this Application.

"Heteroatom", as used herein, refers to an atom that is not a carbon atom. Particular examples of heteroatoms include, but are not limited to nitrogen, oxygen, and sulfur.

"Heterocycloalkyl", as used herein, refers to a 4-20 membered, non-aromatic, saturated or partially unsaturated, monocyclic or polycyclic ring system, comprising 1-8 heteroatoms as ring atoms and that the remaining ring atoms are carbon atoms. The heteroatoms are selected from N, O, and S, preferably O and N. The nitrogen atoms of the heterocycloalkyl can be optionally quaternerized and the sulfur atoms of the heterocycloalkyl can be optionally oxidized. The heterocycloalkyl can include fused or bridged rings as well as spirocyclic rings. $C_X$heterocycloalkyl and $C_{X-Y}$heterocycloalkyl are typically used where X and Y indicate the number of ring atoms in the ring. Typically, the heterocycloalkyl is 4-8-membered monocyclic ring containing 1 to 3 heteroatoms, a 7 to 12-membered bicyclic ring system containing 1-5 heteroatoms, or a 10-15-membered tricyclic ring system containing 1 to 7 heteroatoms. Examples of $C_{4-6}$heterocycloalkyl include azetidinyl, tetrahydrofuran (THF), dihydrofuran, 1,4-dioxane, morpholine, 1,4-dithiane, piperazine, piperidine, 1,3-dioxolane, imidazolidine, imidazoline, pyrazolidinyl, pyrroline, pyrrolidine, tetrahydropyran, dihydropyran, oxathiolane, dithiolane, 1,3-dioxane, 1,3-dithiane, oxathiane, thiomorpholine, and the like A heterocycloalkyl may be unsubstituted or substituted with 1-5 substituents (such as one, or two, or three) each independently selected from hydroxyl, thiol, cyano, nitro, oxo, alkylimino, $C_{1-4}$alkyl, $C_{1-4}$alkenyl, $C_{1-4}$alkynyl, $C_{1-4}$alkoxy, $C_{1-4}$thioalkyl, $C_{1-4}$alkenyloxy, $C_{1-4}$alkynyloxy, halogen, $C_{1-4}$alkylcarbonyl, carboxy, $C_{1-4}$alkoxycarbonyl, amino, $C_{1-4}$alkylamino, di-$C_{1-4}$alkylamino, $C_{1-4}$alkylaminocarbonyl, di-$C_{1-4}$alkylaminocarbonyl, $C_{1-4}$alkylcarbonylamino, $C_{1-4}$alkylcarbonyl($C_{1-4}$alkyl)amino, sulfonyl, sulfamoyl, alkylsulfamoyl, $C_{1-4}$alkylaminosulfonyl where each of the afore-mentioned hydrocarbon groups (e.g., alkyl, alkenyl, alkynyl, alkoxy residues) may be further substituted by one or more residues independently selected at each occurrence from halogen, hydroxyl or $C_{1-4}$alkoxy groups. When a heterocycloalkyl forms part of other groups like "heterocycloalkyl-alkyl", "heterocycloalkoxy", "heterocycloalkyl-aryl", the heteroaryl portion shall have the same meaning as described in the above-mentioned definition of "heteroaryl"

"Heterocycloalkylene", as used herein, refers to a cycloalkylene, as defined in this Application, provided that one or more of the ring member carbon atoms is replaced by a heteroatom.

"Heterocycloalkyl fused to a phenyl" as used herein, refers to a bicyclic fused ring system that one of the ring is heterocycloalkyl as defined above and the other ring is a phenyl. A heterocycloalkyl fused to a phenyl includes but are not limited to benzo[b][1,4]oxazinyl, oxo-benzo[b][1,4]oxazinyl, tetrahydroquinoxalinyl, tetrahydroquinolinyl, indolinyl, benzo[d]imidazolyl, and the like.

"Heterocyclyl", "heterocycle" or "heterocyclo", as used herein, refers to a 3-20 membered, monocyclic or polycyclic ring system containing at least one heteroatom moiety selected from the group consisting of N, O, SO, $SO_2$, (C=O), and S, and preferably N, O, S, optionally contaiing one to four additional heteroatoms in each ring. $C_x$heterocyclyl and $C_{x-y}$heterocyclylare typically used where X and Y indicate the number of ring atoms in the ring system. Unless otherwise specified, a heterocyclyl may be saturated, partially unsaturated, aromatic or partially aromatic.

Hydroxy, as used herein, refers to the radical —OH.

"Hydroxyalkyl" or "hydroxyl-substituted alkyl" as used herein, refers to an alkyl as defined herein, having one or more of the available hydrogen of the alkyl replaced by a hydroxyl group. For example, a hydroxy$C_{1-4}$alkyl includes, but are not limited to, —$CH_2CH_2OH$, —$CH(OH)CH_2CH_2OH$, —$CH(OH)CH_2CH(OH)CH_3$.

"Nitro", as used herein, refers to the radical —$NO_2$.

"Oxo", as used herein, refers to the divalent radical =O

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxym ethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Unsubstituted or substituted" or "optionally substituted" as used herein indicate the substituent bound on the available valance of a named group or radical. "Unsubstituted" as used herein indicates that the named group or radical will have no further non-hydrogen substituents. "Substituted" or "optionally substituted" as used herein indicates that at least one of the available hydrogen atoms of named group or radical has been (or may be) replaced by a non-hydrogen substituent.

"Substituted terminally" as used herein referred to a substituent replacing a hydrogen at a terminal position of the parent molecule. For example $C_{1-4}$alkyl substituted terminally by an amino means —$C_{1-4}$alkylene-amino, which includes —$(CH_2)$—$NH_2$, —$(CH_2)_2$—$NH_2$, —$(CH_2)_3$—$NH_2$, —$(CH_2)CH_2(CH_2$—$NH_2)$, —$(CH_2)_4$—$NH_2$, —$C(CH_2)(CH_2CH_2$—$NH_2)$—$C(CH_3)_2(CH_2$—$NH_2)$, and the like.

Unless otherwise specified, examples of substituents may include, but are not limited to, halo, nitro, cyano, thio, oxy, hydroxy, carbonyloxy, $C_{1-6}$alkoxy, $C_{6-10}$aryloxy, hetero$C_{5-10}$aryloxy, carbonyl, oxycarbonyl, aminocarbonyl, amino, $C_{1-6}$alkylamino, sulfonamido, imino, sulfonyl, sulfinyl, $C_{1-6}$alkyl, $C_{1-6}$haloalkyl, hydroxy$C_{1-6}$alkyl, carbonyl$C_{1-6}$alkyl, thiocarbonyl$C_{1-10}$alkyl, sulfonyl$C_{1-6}$alkyl, sulfinyl$C_{1-6}$alkyl, $C_{1-10}$azaalkyl, imino$C_{1-6}$alkyl, $C_{3-12}$cycloalkyl$C_{1-6}$alkyl, $C_{4-15}$heterocycloalkyl$C_{1-6}$alkyl, $C_{6-10}$aryl$C_{1-6}$alkyl, $C_{5-10}$heteroaryl$C_{1-6}$alkyl, $C_{10-12}$bicycloaryl$C_{1-6}$alkyl, $C_{9-12}$heterobicycloaryl$C_{1-6}$alkyl, $C_{3-12}$cycloalkyl, $C_{4-12}$heterocycloalkyl, $C_{9-12}$bicycloalkyl, $C_{3-12}$heterobicycloalkyl, $C_{4-12}$aryl, hetero$C_{1-10}$aryl, $C_{3-12}$bicycloaryl and $C_{4-12}$heterobicycloaryl.

"Sulfamoyl" as used herein refers to the radical —$S(O)_2NR_aR_b$ where $R_a$ and $R_b$ are independently H, or is an alkyl, alkenyl, alkynyl, acyl, aryl, aryl, cycloalkyl, arylalkyl cycloalkylalkyl group or a heteroform of one of these groups, and each of the alkyl, alkenyl, alkynyl, acyl, aryl, arylalkyl groups or heteroforms of one of these groups, is optionally substituted with the substituents described herein as suitable for the corresponding group.

"Sulfanyl" as used herein, means the radical —S—.

"Sulfinyl", as used herein, means the radical —S(O)—. It is noted that the term "sulfinyl" when referring to a monovalent substituent can alternatively refer to a substituted sulfinyl group, —S(=O)R, where R is hydrogen or a non-hydrogen substituent on the sulfur atom forming different sulfinyl groups including sulfinic acids, sulfinamides, sulfinyl esters, and sulfoxides.

"Sulfonyl", as used herein, means the radical —$S(O)_2$—. It is noted that the term "sulfonyl" when referring to a monovalent substituent can alternatively refer to a substituted sulfonyl group, —$S(=O)_2R$, where R is hydrogen or a non-hydrogen substituent on the sulfur atom forming different sulfonyl groups including sulfonic acids, sulfonamides, sulfonate esters, and sulfones.

"Thiocarbonyl", as used herein, refers to the radical —C(=S)—. It is noted that the term thiocarbonyl when referring to a monovalent substituent can alternatively refer to a substituted thiocarbonyl group, —C(=S)R, where R is hydrogen or a non-hydrogen substituent on the carbon atom forming different thiocarbonyl groups including thioacids, thioamides, thioesters, and thioketones.

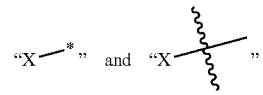

are symbols denoting the point of attachment of X, to other part of the molecule.

Any definition herein may be used in combination with any other definition to describe a composite structural group. By convention, the trailing element of any such definition is that which attaches to the parent moiety. For example, the composite group alkoxyalkyl would represent an alkoxy group attached to the parent molecule through an alkyl group.

It is noted in regard to all of the definitions provided herein that the definitions should be interpreted as being open ended in the sense that further substituents beyond those specified may be included. Hence, a $C_1$alkyl indicates that there is one carbon atom but does not indicate what are the substituents on the carbon atom. Hence, a $C_1$alkyl comprises methyl (i.e., —$CH_3$) as well as —$CR_aR_bR_c$ where $R_a$, $R_b$, and $R_c$ may each independently be hydrogen or any other substituent where the atom attached to the carbon is not a hydrogen atom. Hence, —CF$_3$, —CH$_2$OH and —CH$_2$CN, for example, are all C$_1$alkyls.

DESCRIPTION OF THE PREFERRED EMBODIMENTS

The invention provides a novel class of compounds, pharmaceutical compositions comprising such compounds and methods of using such compounds to treat or prevent diseases or disorders associated with a parasite. In particular, the compounds can be used to treat malaria, leishmaniasis and/or Chagas disease. The compounds of the invention are effective in inhibiting, ameliorating, or eradicating the pathology and/or symptomology of the parasite at both the blood stage and hepatic stage.

In one embodiment, the compounds of the invention are of Formula I:

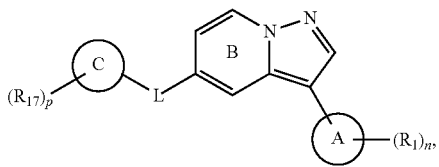

I or a pharmaceutical acceptable salt, enantiomer or tautomer or stereoisomer thereof, wherein n is 0, 1, 2 or 3;
p is 0, 1, 2 or 3;
L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—CHR$_3$N(R$_2$)CHR$_3$—, *—C(O)—, *—C(O)N(R$_2$)—, *—C(O)N(R$_2$)CHR$_3$—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein
* represents the point of attachment of L to the pyrazolo [1,5-a]pyridine fused ring depicted in Formula I;
each R$_2$ is independently selected from the group consisting of hydrogen, C$_{1-6}$alkyl, haloC$_{1-6}$alkyl, R—C$_{0-4}$alkylene, and R—C$_{0-4}$alkylene-C(O)—, wherein R is selected from the group consisting of hydroxyl, C$_{1-4}$alkoxy, amino, C$_{1-4}$alkylamino, C$_{3-6}$cycloalkyl, C$_{4-6}$heterocycloalkyl, and C$_{5-6}$heteroaryl, wherein the C$_{3-6}$cycloalkyl, C$_{4-6}$heterocycloalkyl, and C$_{5-6}$heteroaryl of R are each unsubstituted or substituted with 1-2 substituents independently selected from the group consisting of halo, amino, hydroxyl, C$_{1-4}$alkyl, C$_{1-4}$alkoxy, oxo, and C$_{5-6}$heteroaryl; and.
each R$_3$ is independently selected from the group consisting of hydrogen and C$_{1-4}$alkyl,
Ring A is selected from the group consisting of C$_{6-10}$aryl and C$_{5-10}$heteroaryl;
Ring C is selected from the group consisting of C$_{6-10}$aryl, C$_{5-10}$heteroaryl, C$_{5-7}$cycloalkyl, C$_{5-7}$heterocycloalkyl, and a fused bicyclyl comprising a C$_{5-6}$heterocycloalkyl fused to a phenyl;
each R$_1$ is independently selected from the group consisting of halo, cyano, amino, C$_{1-4}$alkyl, C$_{1-4}$alkoxyl, halo-C$_{1-4}$alkyl, —C(O)NR$_7$R$_8$, —NHC(O)R$_{11}$, phenyl, and C$_{5-6}$heteroaryl; wherein
the phenyl and C$_{5-6}$heteroaryl of R$_1$ are each unsubstituted or substituted with 1-2 substituents independently selected from the group consisting of C$_{1-4}$alkyl, amino, halo, and C$_{1-4}$alkylamino;
R$_7$ and R$_8$ are each independently selected from the group consisting of hydrogen, C$_{1-4}$alkyl and haloC$_{1-4}$alkyl;
R$_{11}$ is C$_{1-6}$alkyl unsubstituted or substituted with 1-2 substituents independently selected from the group consisting of amino, C$_{3-6}$cycloalkyl and C$_{4-6}$heterocycloalkyl;
R$_{17}$ is selected from the group consisting of cyano, halo, C$_{1-4}$alkyl, halo-C$_{1-4}$alkyl, oxo, C$_{3-6}$cycloalkyl, and —SO$_2$—C$_{1-4}$alkyl.

In one embodiment of the compounds of the invention, with reference to Formula I, L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—C(O)—, *—C(O)N(R$_2$)—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein each R$_2$ is independently selected from the group consisting of hydrogen, C$_{1-6}$alkyl, haloC$_{1-6}$alkyl, R—C$_{0-4}$alkylene, and R—C$_{0-4}$alkylene-C(O)—, wherein each R is independently selected from the group consisting of hydroxyl, C$_{1-4}$alkoxy, amino, C$_{1-4}$alkylamino, di-C$_{1-4}$alkylamino, C$_{3-6}$cycloalkyl, C$_{4-6}$heterocycloalkyl, and C$_{5-6}$heteroaryl, wherein said C$_{3-6}$cycloalkyl, C$_{4-6}$heterocycloalkyl and C$_{5-6}$heteroaryl are each unsubstituted or substituted with 1-2 substituents independently selected from the group consisting of C$_{1-4}$alkyl, halo, amino, hydroxyl, C$_{1-4}$alkoxy, oxo, and C$_{5-6}$heteroaryl.

In another variation, L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—C(O)—, *—C(O)N(R$_2$)—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein each R$_2$ is independently selected from the group consisting of hydrogen, C$_{1-6}$alkyl, R—C$_{0-4}$alkylene, wherein R is selected from the group consisting of C$_{1-4}$alkoxy, C$_{1-4}$alkylamino, di-C$_{1-4}$alkylamino, C$_{3-6}$cycloalkyl, C$_{4-6}$heterocycloalkyl and C$_{5-6}$heteroaryl, wherein the C$_{3-6}$cycloalkyl, C$_{4-6}$heterocycloalkyl and C$_{5-6}$heteroaryl of R are each unsubstituted or substituted with 1-2 substituents independently selected from the group consisting of halo, amino, hydroxyl, C$_{1-4}$alkyl, C$_{1-4}$alkoxy, oxo, and C$_{5-6}$heteroaryl.

In another variation, L is selected from the group consisting of *—C(O)N(R$_2$)—, and *—N(R$_2$)C(O)—, wherein each R$_2$ is independently selected from hydrogen, C$_{1-6}$alkyl, and R—C$_{0-4}$alkylene, and wherein R is selected from the group consisting of C$_{3-6}$cycloalkyl, C$_{4-6}$heterocycloalkyl and C$_{5-6}$heteroaryl, each of which is unsubstituted or substituted with 1-2 substituents independently selected from the group consisting of halo, amino, hydroxyl, C$_{1-4}$alkyl, C$_{1-4}$alkoxy, oxo, and C$_{5-6}$heteroaryl In still another variation, L is selected from the group consisting of *—CH(CH$_3$)—, *—CH$_2$CH$_2$—, *—CH$_2$N(CH$_3$)—, *—CH$_2$N(C(O)(CH$_2$)$_{1-2}$NH(CH$_3$))—, *—CH$_2$N(C(O)—(CH$_2$)$_{1-2}$NH$_2$)—, *—CH$_2$N((C(O)—(CH$_2$)$_{1-2}$N(CH$_3$)$_2$)—, *—CH$_2$N(C(O)(CH$_2$)$_{1-2}$OH)—, *—CH(CH$_3$)N(CH$_3$)—, *—CH$_2$O—, *—CH$_2$S—, *—CH$_2$S(O)—, *—C(O)—, *—C(O)N(CH$_3$)—, *—C(O)N(CH$_2$CH$_3$)—, *—C(O)N(CH(CH$_3$)$_2$)—, *—C(O)N(C(CH$_3$)$_3$)—, *—C(O)N(CH$_2$CH(CH$_3$)$_2$)—, *—C(O)N(CH(CH$_3$)CH$_2$CH$_3$)—, *—C(O)N(CH$_2$CH$_2$OCH$_3$)—, *—C(O)N(CH$_2$CH$_2$N(CH$_3$)$_2$)—, *—C(O)N(CH$_3$)CH$_2$—, *—NHCH$_2$—, *—N(CH$_3$)CH$_2$—, *—N(CH$_2$-tetrahydropyran-4-yl)-C(O)—, *—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N((CH$_2$)$_{0-1}$-cyclobutyl)-, *—C(O)N((CH$_2$)$_{0-1}$-cyclopentyl)-, *—C(O)N ((CH₂)₀₋₁-cyclohexyl)-, *—C(O)N(CH₂-tetrahydropyran-4-yl)-, *—C(O)N((CH₂)₂-(1,1-dioxidothiomorpholino-4-yl))-, *—C(O)N(CH₂-1,1-dioxidothiomorpholino-4-yl)-, *—C(O)N((CH₂)₂-tetrahydropyran-4-yl))-, *—C(O)N((CH₂)₁-morpholin-4-yl)-, *—C(O)N(oxetan-3-yl)-, *—C(O)N(CH₂-oxetan-3-yl)-, *—C(O)N(CH(CH₃)—CH₂-1-H-pyrazoly-1-yl)-, *—CH₂N(C(O)—(CH₂)₁₋₂-morpholinyl))-, *—CH₂N(C(O)—(CH₂)₁₋₂-4-methylpiperizin-1-yl)), *—CH₂N(C(O)—(CH₂)₁₋₂-tetrahydropyran-4-yl)-, and *—CH₂N(C(O)(CH₂)₁₋₂-oxetan-3-yl)-.

In still another variation, L is selected from the group consisting of *—CH(CH₃)—, *—CH₂CH₂—, *—CH₂N(CH₃)—, *—CH(CH₃)N(CH₃)—, *—CH₂O—, *—CH₂S—, *—CH₂S(O)—, *—C(O)—, *—C(O)N(CH₃)—, *—C(O)N(CH₃)CH₂—, *—C(O)N(CH₂CH₂OCH₃)—, *—C(O)N(CH₂CH₂N(CH₃)₂)—, *—NHCH₂—, *—N(CH₃)CH₂—, *—N(CH₂-tetrahydropyran-4-yl)-C(O)—, *—N(CH₃)C(O)—, *—N(CH₃)C(O)NH—, *—N(CH₃)S(O)₂—, *—C(O)N((CH₂)₀₋₁-cyclopropyl)-, *—C(O)N(CH₂-tetrahydropyran-4-yl)-, *—C(O)N(oxetan-3-yl)-, and *—C(O)N(CH(CH₃)CH₂-(1-H-pyrazoly-1yl))-.

In a further variation, L is selected from the group consisting of *—C(O)N(CH₃)—, *—C(O)N(CH₂CH₃)—, *—C(O)N(CH(CH₃)₂)—, *—C(O)N(C(CH₃)₃)—, *—C(O)N(CH₂CH(CH₃)₂)—, *—C(O)N(CH(CH₃)CH₂CH₃)—, *—C(O)N((CH₂)₀₋₁-cyclopropyl)-, *—C(O)N((CH₂)₀₋₁-cyclobutyl)-, *—C(O)N((CH₂)₀₋₁-cyclopentyl)-, and *—C(O)N((CH₂)₀₋₁-cyclohexyl)-.

In a particular variation, L is *—C(O)N(CH₃)— or *—N(CH₃)C(O)—. In a particular variation, L is *—C(O)N(CH₃)—. In another particular variation, L is *—N(CH₃)C(O)—. In another particular variation, L is *—N((CH₂)₀₋₂)-tetrahydropyran-4-yl)-C(O)—. In still another particular variation, L is *—C(O)—. In still another particular variation, L is —CH(CH₃)—. In yet still another particular variation, L is *—C(O)N(CH₂-cyclopropyl)-. In yet still another particular variation, L is *—C(O)N(CH₂-cyclopropyl)-.

In still another embodiment of the compounds of the invention, with reference to any one of the above embodiments and variations, Ring A is selected from the group consisting of phenyl, pyridinyl, pyrimidinyl, pyrazinyl, pyridazinyl, pyrrolopyridinyl, indazolyl, each of which is unsubstituted or substituted by (R₁)ₙ.

In one variation, Ring A is selected from the group consisting of

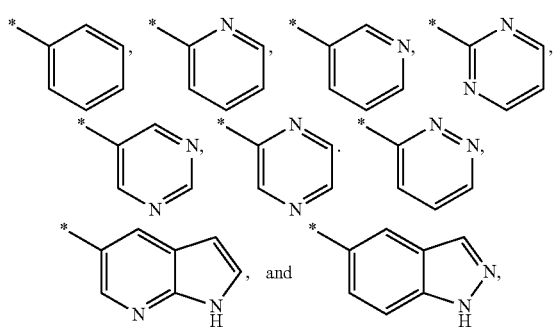

each of which is unsubstituted or substituted by (P₁)ₙ. In another particular variation, Ring A is selected from the group consisting of

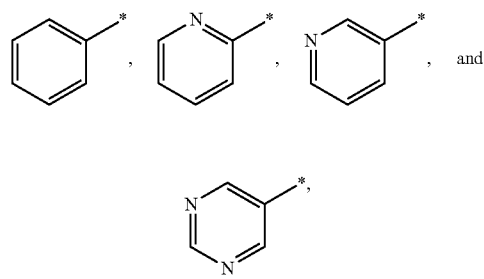

each unsubstituted or substituted by . 1 to 2 R₁ groups.

In a particular variation, Ring A is of the formula

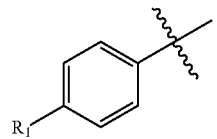

In another particular variation, Ring A is of the formula

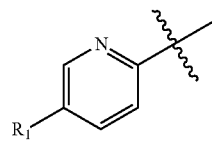

In yet another particular variation, Ring A is of the formula

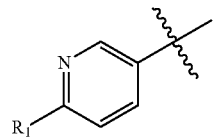

In yet still another particular variation, Ring A is of the formula

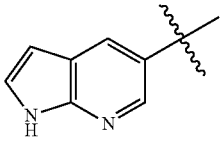

In another embodiment of the compounds of the invention, with reference to any one of the above embodiments and variations, Ring C is selected from the group consisting of

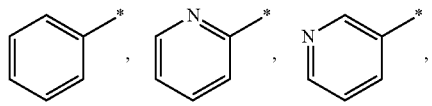

-continued

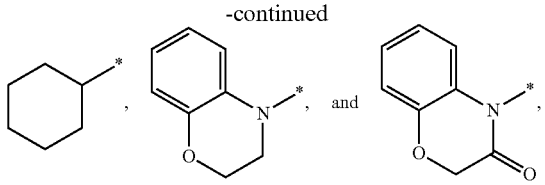

each of which is unsubstituted or substituted by $(R_{17})_p$.

In one variation, Ring C is selected from the group consisting of phenyl and pyridinyl, each unsubstituted or substituted by $(R_{17})_p$.

In another variation, Ring C is of the formula

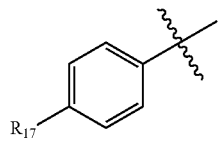

In still another variation, Ring C is of the formula

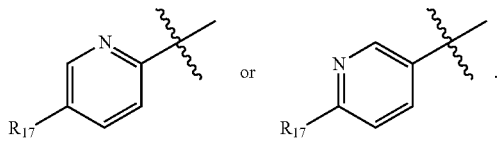

In yet another variation, Ring C is of the formula

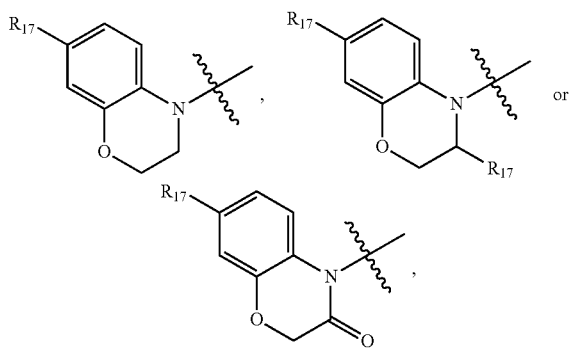

each of which is unsubstituted or substituted by 1 to 3 $(P_{17})$.

In still another embodiment of the compounds of the invention, with reference to any one of the above embodiments and variations, each $R_1$ is independently selected from the group consisting of fluoro, chloro, cyano, methyl, trifluoromethyl, methoxy, —NH$_2$, —C(O)NH$_2$, —C(O)NH(CH$_3$), —C(O)N(CH$_3$)$_2$, —NHC(O)CH$_3$, —NHC(O)CH$_2$NH$_2$, —NHC(O)CH(NH$_2$)(CH$_3$), —NHC(O)CH(NH$_2$)(cyclohexyl), —NHC(O)CH(NH$_2$)CH(CH$_3$)$_2$, —NHC(O)CH(CH$_3$)$_2$,

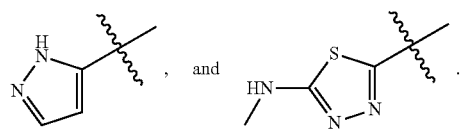

In one variation, each $R_1$ is independently selected from the group consisting of trifluoromethyl, cyano, —NH$_2$—, —C(O)NH$_2$, —C(O)NHCH$_3$, —C(O)N(CH$_3$)$_2$, and —NHC(O)CH(NH$_2$)(CH$_3$). In another variation, $R_1$ is trifluoromethyl. In another variation, is —NH$_2$. In still another variation, $R_1$ is —C(O)NH$_2$. In yet another variation, $R_1$ is —C(O)NHCH$_3$. In yet another variation, $R_1$ is —C(O)N(CH$_3$)$_2$. In still yet another variation $R_1$ is NH$_2$.

In another embodiment of the compound of the invention, with reference to any one of the above embodiments and variations, each $R_{17}$ is independently selected from the group consisting of cyano, halo, $C_{1-4}$alkyl, halo$C_{1-4}$alkyl, —SO$_2$—$C_{1-4}$alkyl, and $C_{3-6}$cycloalkyl.

In one variation, each $R_{17}$ is independently selected from the group consisting of cyano, fluoro, chloro, methyl, trifluoromethyl, 1,1-difluoroethyl, methylsulfonyl, and cyclopropyl.

In another variation, each $R_{17}$ is independently selected from the group consisting of cyano, chloro, fluoro, methylsulfonyl, and trifluoromethyl.

In one particular variation, at least one of $R_{17}$ is cyano. In another particular variation, at least one of $R_{17}$ is trifluoromethyl. In another particular variation, $R_{17}$ is chloro or fluoro. In still another variation, $R_{17}$ is methylsulfonyl. In still another variation, $R_{17}$ is methyl or fluoro. In yet still another varitation, $R_{17}$ is cyano.

In another embodiment of the compound of the invention according to any one of the above embodiments and variations, n is 1 or 2. In another variation, n is 1. In another variation, n is 2.

In another embodiment of the compounds of the present invention, with reference to any one of the above embodiments and variations, p is 1, 2 or 3. In another variation, p is 1. In still another variation, p is 1. In yet still another variation, p is 3.

In a particular embodiment of the compounds of the invention, or a pharmaceutical acceptable salt, tautomer or stereoisomer thereof, the compound is of Formula Ia

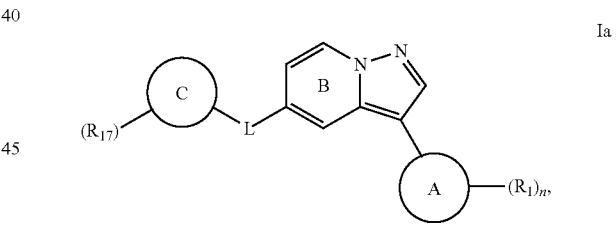

wherein
n is 1 or 2;
Ring A is phenyl, pyridinyl, or pyrimidinyl;
Ring C is phenyl or pyridinyl;
L is *—C(O)NR$_2$— or *—NR$_2$C(O)—, wherein R$_2$ is selected from hydrogen, $C_{1-4}$alkyl, $C_{3-6}$cycloalkyl-($C_{0-4}$)alkylene, $C_{4-6}$heterocycloalkyl-($C_{0-4}$)alkylene, wherein the $C_{4-6}$heterocycloalkyl is selected from the group consisting of piperazinyl, morpholinyl, thiomorpholinyl, tetrahydropyranyl, and oxetanyl, and wherein the $C_{3-6}$cycloalkyl is selected from cyclopropyl, cyclobutyl, cyclopentyl and cyclohexyl;
each R$_1$ is independently *—C(O)NR$_7$R$_8$ or —NH$_2$—, wherein R$_7$ and R$_8$ are each independently hydrogen or $C_{1-4}$alkyl; and
$R_{17}$ is selected from the group consisting of cyano, halo, —NH$_2$—, —C(O)NH$_2$, —C(O)NH(CH$_3$), and —C(O)N(CH$_3$)$_2$.

In one variation of the compounds of the present invention, with reference to the particular embodiment above, Ring A is of the formula

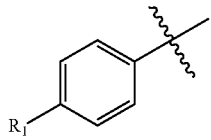

In another variation, Ring A is of the formula

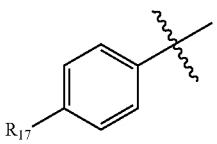

In another variation of the compounds of the present invention, with reference to the particular embodiment and any one of the variations above, Ring C is of the formula

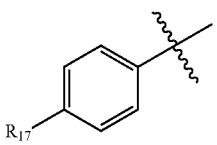

In another variation, Ring C is of the formula

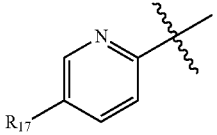

In still another variation of the compounds of the present invention, with reference to the particular embodiment or any one of the variations above, L is *—C(O)N(CH$_3$)— or *—N(CH$_3$)C(O)—. In another variation, L is *—C(O)N(CH$_3$)— In another variation, L is *—N(CH$_3$)C(O)—. In still another variation, L is *—C(O)N(CH$_2$-cyclopropyl)-. In still another variation, L is *—C(O)N(cyclopropyl)-.

In still another variation of the compounds of the present invention, with reference to the particular embodiment or any one of the variations above, R$_1$ is —NH$_2$—. In another variation, R$_1$ is *—C(O)NH$_2$. In another variation, R$_1$ is —C(O)NH$_2$. In still another variation, R$_1$ is —C(O)NCH$_3$.

In still another variation of the compounds of the present invention, with reference to the particular embodiment or any one of the variations above, R$_{17}$ is cyano. In another variation R$_{17}$ is halo.

Particular examples of compounds or a pharmaceutically acceptable salt, tautomer or stereoisomer thereof, according to the present invention include, but are not limited to: N-(4-cyanophenyl)-N-methyl-3-(4-(trifluoromethyl)phenyl)pyrazolo[1,5-a]pyridine-5-carboxamide; 4-fluoro-N-methyl-N-((3-(4-(trifluoromethyl)phenyl)pyrazolo[1,5-a]pyridine-5-yl)methyl)aniline; N-(4-chlorophenyl)-N-methyl-3-(4-(trifluoromethyl)phenyl)pyrazolo[1,5-a]pyridine-5-carboxamide; N-(4-fluorophenyl)-N-methyl-3-(4-(trifluoromethyl)phenyl)pyrazolo[1,5-a]pyridine-5-carboxamide; N-methyl-N-(5-methylpyridin-2-yl)-3-(4-(trifluoromethyl)phenyl)pyrazolo[1,5-a]pyridine-5-carboxamide; 4-chloro-N-methyl-N-((3-(4-(trifluoromethyl)phenyl)pyrazolo[1,5-a]pyridine-5-ylmethyl)aniline; N,5-dimethyl-N-((3-(4-(trifluoromethyl)phenyl)pyrazolo[1,5-a]pyridine-5-ylmethyl)yridine-2-amine; 5-((4-fluorophenoxy)methyl)-3-(4-(trifluoromethyl)phenyl)pyrazolo[1,5-a]pyridine; N-(4-cyanophenyl)-N-(2-methoxyethyl)-3-(4-(trifluoromethyl)phenyl)pyrazolo[1,5-a]pyridine-5-carboxamide; N-(4-cyanophenyl)-N-(2-(dimethylamino)ethyl)-3-(4-(trifluoromethyl)phenyl)pyrazolo[1,5-a]pyridine-5-carboxamide; N-(4-cyanophenyl)-N-((tetrahydro-2H-pyran-4-ylmethyl)-3-(4-(trifluoromethyl)phenyl)pyrazolo[1,5-a]pyridine-5-carboxamide; N-(4-(methylsulfonyl)phenyl)-N-((tetrahydro-2H-pyran-4-ylmethyl)-3-(4-(trifluoromethyl)phenyl)pyrazolo[1,5-a]pyridine-5-carboxamide; N-(5-cyanopyridin-2-yl)-N-methyl-3-(4-(trifluoromethyl)phenyl)pyrazolo[1,5-a]pyridine-5-carboxamide; N-methyl-N-(5-methylpyridin-3-yl)-3-(4-(trifluoromethyl)phenyl)pyrazolo[1,5-a]pyridine-5-carboxamide; 5-(((5-methylpyridin-2-yl)oxy)methyl)-3-(4-(trifluoromethyl)phenyl)pyrazolo[1,5-a]pyridine; 5-(4-fluorophenethyl)-3-(4-(trifluoromethyl)phenyl)pyrazolo[1,5-a]pyridine; N-(4-cyanophenyl)-N-methyl-3-(1-methyl-1H-indazol-5-yl)pyrazolo[1,5-a]pyridine-5-carboxamide; 3-(6-acetamidopyridin-3-yl)-N-(4-cyanophenyl)-N-methylpyrazolo[1,5-a]pyridine-5-carboxamide; 3-(4-carbamoylphenyl)-N-(4-cyanophenyl)-N-methylpyrazolo[1,5-a]pyridine-5-carboxamide; 3-(4-carbamoylphenyl)-N-(4-fluorophenyl)-N-methylpyrazolo[1,5-a]pyridine-5-carboxamide; 5-(((4-fluorophenyl)thio)methyl)-3-(4-(trifluoromethyl)phenyl)pyrazolo[1,5-a]pyridine; 5-(((4-fluorophenyl)sulfinylmethyl-3-(4-(trifluoromethyl)phenyl)pyrazolo[1,5-a]pyridine; 3-(4-(1H-pyrazol-5-yl)phenyl)-N-(4-cyanophenyl)-N-methylpyrazolo[1,5-a]pyridine-5-carboxamide; N-(4-cyanophenyl)-N-methyl-3-(5-(trifluoromethyl)pyridine-2-yl)pyrazolo[1,5-a]pyridine-5-carboxamide; N-(5-cyanopyridin-2-yl)-N-methyl-3-(5-(trifluoromethyl)pyridine-2-yl)pyrazolo[1,5-a]pyridine-5-carboxamide; (S)-3-(4-(2-aminopropanamido)phenyl)-N-(4-cyanophenyl)-N-methylpyrazolo[1,5-a]pyridine-5-carboxamide; 3-(5-carbamoylpyridin-2-yl)-N-(4-cyanophenyl)-N-methylpyrazolo[1,5-a]pyridine-5-carboxamide; 4-cyano-N-methyl-N-(3-(4-(trifluoromethyl)phenyl)pyrazolo[1,5-a]pyridine-5-yl)benzamide; 4-fluoro-N-methyl-N-(3-(4-(trifluoromethyl)phenyl)pyrazolo[1,5-a]pyridine-5-yl)benzamide; 4-cyano-N-methyl-N-(3-(4-(trifluoromethyl)phenyl)pyrazolo[1,5-a]pyridine-5-yl)benzenesulfonamide; 4-fluoro-N-methyl-N-(3-(4-(trifluoromethyl)phenyl)pyrazolo[1,5-a]pyridine-5-yl)benzenesulfonamide; 3-(4-carbamoylphenyl)-N-(5-cyanopyridin-2-yl)-N-methylpyrazolo[1,5-a]pyridine-5-carboxamide; N-methyl-3-(4-(trifluoromethyl)phenyl)-N-(5-(trifluoromethyl)yridine-2-yl)pyrazolo[1,5-a]pyridine-5-carboxamide; N-methyl-N-(5-(methylsulfonyl)pyridine-2-yl)-3-(4-(trifluoromethyl)phenyl)pyrazolo[1,5-a]pyridine-5-carboxamide; N-(4-fluorobenzyl)-3-(4-(trifluoromethyl)phenyl)pyrazolo[1,5-a]pyridine-5-amine; N-(4-fluorobenzyl)-3-(4-(trifluoromethyl)phenyl)pyrazolo[1,5-a]pyridine-5-amine; N-methyl-6-(trifluoromethyl)-N-(3-(4-(trifluoromethyl)phenyl)pyrazolo[1,5-a]pyridine-5-yl)nicotinamide; N-methyl-5-(trifluoromethyl)-N-(3-(4-(trifluoromethyl)phenyl)pyrazolo[1,5-a]pyridine-5-yl)picolinamide; 4-cyano-N-((tetrahydro-2H-pyran-4-ylmethyl)-N-(3-(4-(trifluoromethyl)phenyl)pyrazolo[1,5-a]pyridine-5-yl)benzamide; N-(4-cyanophenyl)-N-methyl-3-(1H-pyrrolo[2,3-b]pyridine-5-yl)pyrazolo[1,5-a]pyridine-5-carboxamide; 3-(6-aminopyridin-3-yl)-N-(4-cyanophenyl)-N-methylpyrazolo[1,5-a]pyridine-5-carboxamide; 3-(4- aminophenyl)-N-(4-cyanophenyl)-N-methylpyrazolo[1,5-a]pyridine-5-carboxamide; 3-(4-(2-aminoacetamido)phenyl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; (S)-3-(4-(2-amino-3-methylbutanamido)phenyl)-N-(4-cyanophenyl)-N-methylpyrazolo[1,5-a]pyridine-5-carboxamide; (S)-3-(4-(2-amino-2-cyclohexylacetamido)phenyl)-N-(4-cyanophenyl)-N-methylpyrazolo[1,5-a]pyridine-5-carboxamide; 3-(4-fluorophenyl)-1-methyl-1-(3-(4-(trifluoromethyl)phenyl)pyrazolo[1,5-a]pyridin-5-yl)urea; 6-(1,1-difluoroethyl)-N-methyl-N-(3-(4-(trifluoromethyl)phenyl)pyrazolo[1,5-a]pyridin-5-yl)nicotinamide; 6-cyclopropyl-N-methyl-N-(3-(4-(trifluoromethyl)phenyl)pyrazolo[1,5-a]pyridin-5-yl)nicotinamide; 4-cyclopropyl-N-methyl-N-(3-(4-(trifluoromethyl)phenyl)pyrazolo[1,5-a]pyridin-5-yl)benzamide; 5-fluoro-N-methyl-N-(3-(4-(trifluoromethyl)phenyl)pyrazolo[1,5-a]pyridin-5-yl)picolinamide; N-methyl-4-(methylsulfonyl)-N-(3-(4-(trifluoromethyl)phenyl)pyrazolo[1,5-a]pyridin-5-yl)benzamide; N-(5-cyanopyridin-2-yl)-N-methyl-3-(1H-pyrrolo[2,3-b]pyridin-5-yl)pyrazolo[1,5-a]pyridine-5-carboxamide; 3-(6-aminopyridin-3-yl)-N-(5-cyanopyridin-2-yl)-N-methylpyrazolo[1,5-a]pyridine-5-carboxamide; 4-chloro-N-methyl-N-(3-(4-(trifluoromethyl)phenyl)pyrazolo[1,5-a]pyridin-5-yl)benzamide; N-(3-(4-carbamoylphenyl)pyrazolo[1,5-a]pyridin-5-yl)-4-fluoro-N-methylbenzamide; 4-fluoro-N-methyl-N-(3-(4-(5-(methylamino)-1,3,4-thiadiazol-2-yl)phenyl)pyrazolo[1,5-a]pyridin-5-yl)benzamide; N-methyl-N-(5-(methylsulfonyl)pyridin-2-yl)-3-(1H-pyrrolo[2,3-b]pyridin-5-yl)pyrazolo[1,5-a]pyridine-5-carboxamide; N-(5-cyanopyridin-2-yl)-N-methyl-3-(5-methylpyridin-2-yl)pyrazolo[1,5-a]pyridine-5-carboxamide; N-(5-cyanopyridin-2-yl)-3-(5-methoxypyridin-2-yl)-N-methylpyrazolo[1,5-a]pyridine-5-carboxamide; 3-(5-carbamoylpyridin-2-yl)-N-(5-cyanopyridin-2-yl)-N-methylpyrazolo[1,5-a]pyridine-5-carboxamide; 3-(4-carbamoylphenyl)-N-methyl-N-(5-(trifluoromethyl)pyridin-2-yl)pyrazolo[1,5-a]pyridine-5-carboxamide; 3-(4-carbamoylphenyl)-N-methyl-N-(5-methylpyridin-2-yl)pyrazolo[1,5-a]pyridine-5-carboxamide; N-(4-fluorophenyl)-N-methyl-3-(4-(methylcarbamoyl)phenyl)pyrazolo[1,5-a]pyridine-5-carboxamide; 4-(5-(1-(methyl(5-methylpyridin-2-yl)amino)ethyl)pyrazolo[1,5-a]pyridin-3-yl)benzamide; 4-(5-(1-(7-fluoro-3-oxo-2H-benzo[b][1,4]oxazin-4(3H)-yl)ethyl)pyrazolo[1,5-a]pyridin-3-yl)benzamide; N-(4-cyanophenyl)-N-methyl-3-(4-(methylcarbamoyl)phenyl)pyrazolo[1,5-a]pyridine-5-carboxamide; N-(4-(5-(1-(methyl(5-methylpyridin-2-yl)amino)ethyl)pyrazolo[1,5-a]pyridin-3-yl)phenyl)acetamide; 3-(4-acetamidophenyl)-N-(5-cyanopyridin-2-yl)-N-methylpyrazolo[1,5-a]pyridine-5-carboxamide; 4-(5-(7-fluoro-3,4-dihydro-2H-benzo[b][1,4]oxazine-4-carbonyl)pyrazolo[1,5-a]pyridin-3-yl)benzamide; 4-(5-(7-fluoro-3-methyl-3,4-dihydro-2H-benzo[b][1,4]oxazine-4-carbonyl)pyrazolo[1,5-a]pyridin-3-yl)benzamide; 4-(5-(7-fluoro-3,4-dihydro-2H-benzo[b][1,4]oxazine-4-carbonyl)pyrazolo[1,5-a]pyridin-3-yl)-N-methylbenzamide; 4-(5-(7-fluoro-3-methyl-3,4-dihydro-2H-benzo[b][1,4]oxazine-4-carbonyl)pyrazolo[1,5-a]pyridin-3-yl)-N-methylbenzamide; N-(5-cyanopyridin-2-yl)-N-methyl-3-(4-(methylcarbamoyl)phenyl)pyrazolo[1,5-a]pyridine-5-carboxamide; N-(5-cyanopyridin-2-yl)-3-(4-(methylcarbamoyl)phenyl)-N-(oxetan-3-yl)pyrazolo[1,5-a]pyridine-5-carboxamide; 3-(6-amino-5-fluoropyridin-3-yl)-N-(4-cyanophenyl)-N-methylpyrazolo[1,5-a]pyridine-5-carboxamide; 3-(4-amino-3,5-dimethylphenyl)-N-(4-cyanophenyl)-N-methylpyrazolo[1,5-a]pyridine-5-carboxamide; 3-(6-amino-5-methylpyridin-3-yl)-N-(4-cyanophenyl)-N-methylpyrazolo[1,5-a]pyridine-5-carboxamide; 3-(4-carbamoylphenyl)-N-(4-cyanocyclohexyl)-N-methylpyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; 3-(6-amino-5-(trifluoromethyl)pyridin-3-yl)-N-(5-cyanopyridin-2-yl)-N-methylpyrazolo[1,5-a]pyridine-5-carboxamide; 3-(6-amino-5-cyanopyridin-3-yl)-N-(5-cyanopyridin-2-yl)-N-methylpyrazolo[1,5-a]pyridine-5-carboxamide; 3-(6-amino-5-chloropyridin-3-yl)-N-(5-cyanopyridin-2-yl)-N-methylpyrazolo[1,5-a]pyridine-5-carboxamide; 3-(6-amino-5-(dimethylcarbamoyl)pyridin-3-yl)-N-(5-cyanopyridin-2-yl)-N-methylpyrazolo[1,5-a]pyridine-5-carboxamide; 3-(6-amino-5-methoxypyridin-3-yl)-N-(5-cyanopyridin-2-yl)-N-methylpyrazolo[1,5-a]pyridine-5-carboxamide; and 3-(4-carbamoylphenyl)-N-(4-chloro-2-formylphenyl)-N-methylpyrazolo[1,5-a]pyridine-5-carboxamide.

Particular examples of the compounds or a pharmaceutically acceptable salt, tautomer or stereoisomer thereof, according to the present invention include, but are not limited to: 3-(4-carbamoylphenyl)-N-(5-cyanopyridin-2-yl)-N-methylpyrazolo[1,5-a]pyridine-5-carboxamide; N-(4-cyanophenyl)-N-methyl-3-(1H-pyrrolo[2,3-b]pyridin-5-yl)pyrazolo[1,5-a]pyridine-5-carboxamide; 3-(6-aminopyridin-3-yl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; N-(5-cyanopyridin-2-yl)-N-methyl-3-(1H-pyrrolo[2,3-b]pyridin-5-yl)pyrazolo[1,5-a]pyridine-5-carboxamide; N-(5-cyanopyridin-2-yl)-N-methyl-3-(4-(methylcarbamoyl)phenyl)pyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; and 3-(6-amino-5-(dimethylcarbamoyl)pyridin-3-yl)-N-(5-cyanopyridin-2-yl)-N-methylpyrazolo[1,5-a]pyridine-5-carboxamide.

It is noted that the compounds of the present invention may be in the form of a pharmaceutically acceptable salt. It is further note that the compounds of the present invention may be a mixture of stereoisomers, or the compound may comprise a single stereoisomer.

Further compounds of the invention are detailed in the Examples, infra.

In another aspect, the present invention is directed to a pharmaceutical composition which includes as an active ingredient a compound according to any one of the above embodiments and variations in combination with a pharmaceutically acceptable carrier, diluent or excipient.

In one embodiment, the pharmaceutical composition further includes a second agent which can be a kinase inhibitor, an anti-malarial drug or an anti-inflammatory agent.

In another embodiment, the pharmaceutical composition includes an antimalarial drug as a second agent. The selections for the antimalarial drug may includes, but are not limited to, artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

In another embodiment, the pharmaceutical composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In yet another embodiment, the pharmaceutical composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the present application is directed to a compound or a pharmaceutical composition according to any one of the above embodiments and variations for use in a therapeutic application.

In another aspect, the present application is directed to a compound or a pharmaceutical composition according to any one of the above embodiments and variations for use as a medicament.

In yet another aspect, the present invention is directed to a method for treating, preventing, inhibiting, ameliorating, or eradicating the pathology and/or symptomology of a disease caused by a *Plasmodium* parasite. The method involves administering to a subject a therapeutically effective amount of a compound or a pharmaceutical composition according to the above embodiments and variations. In addition, the administering may be in combination with a second agent.

In one embodiment of the method of the invention, the method is directed to treatment of malaria; particularly malaria caued by the parasites *Plasmodium falciparum, Plasmodium vivax, Plasmodium ovale*, and *Plasmodium malaria*; more particularly, the parasite *Plasmodium falciparum*. Further, the *Plasmodium* parasite can be at the blood stages or at the hepatic stages.

In the treatment method of the invention, the compounds or pharmaceutical compositions may be administered with prior to, simultaneously with, or after a second agent. The second agent can be a kinase inhibitor, an anti-malarial drug or an anti-inflammatory agent. In one particular variation of the method, the second agent is an anti-malarial drug. The selection of the antimalarial drug, includes, but is not limited to, artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

In another aspect, the invention is directed to a compound, salt, steroisomer, or pharmaceutical composition thereof, according to any one of the above embodiments or variation, for treating, preventing, inhibiting, ameliorating, or eradicating the pathology and/or symptomology of a disease caused by a *Plasmodium* parasite. In one embodiment, the disease is malaria caused by the *Plasmodium* parasite *Plasmodium falciparum, Plasmodium vivax, Plasmodium ovale*, or *Plasmodium malaria*; particularly, the parasite *Plasmodium falciparum*. Further, the *Plasmodium* parasite can be at the blood stages, or the *Plasmodium* parasite can be at the hepatic stages.

In still another aspect, the present invention is directed to the use of the compound, or a salt, a stereoisomer, or a pharmaceutical composition thereof, according to the any one of the above embodiments or variations in the manufacture of a medicament for treating, preventing, inhibiting, ameliorating, or eradicating the pathology and/or symptomology of a disease caused by a *Plasmodium* parasite. In one embodiment, the medicament is for treating malaria causes by the parasite *Plasmodium falciparum, Plasmodium vivax, Plasmodium ovale*, or *Plasmodium malaria*; in particular, the parasite *Plasmodium falciparum*. Further, the *Plasmodium* parasite can be at the blood stages or at the hepatic stages.

The medicament, in addition to the compound of the invention, may further include a second agent. The second agent may be a kinase inhibitor, an anti-malarial drug or an anti-inflammatory agent. In one particular embodiment, the second agent is an anti-malarial drug selected from artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

In another aspect, the invention is related to a kit which comprises a compound of any one of the above embodiments and variations, and optionally a second therapeutic agent. In one particular variation, the kit comprises the compound in a multiple dose form.

Enumerated Embodiments

Various enumerated embodiments of the invention are described herein. It will be recognized that features specified in each embodiment may be combined with other specified features to provide further embodiments of the present invention.

In a first embodiment, the invention provides a compound of the formula (I), or a pharmaceutical acceptable salt, tautomer or stereoisomer thereof,

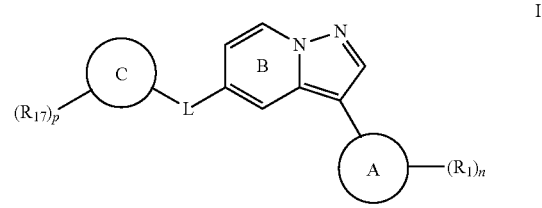

wherein:
n is 0, 1, 2 or 3;
p is 0, 1, 2 or 3;
L is selected from the group consisting of *—$(CHR_3)_{1-3}$—, *—$CHR_3N(R_2)$—, *—$CHR_3O$—, *—$CHR_3S$—, *—$CHR_3S(O)$—, *—$CHR_3N(R_2)CHR_3$—, *—$C(O)$—, *—$C(O)N(R_2)$—, *—$C(O)N(R_2)CHR_3$—, *—$N(R_2)$—, *—$N(R_2)CHR_3$—, *—$N(R_2)C(O)$—, *—$N(R_2)C(O)N(R_2)$—, and *—$N(R_2)S(O)_2$—, wherein
* represents the point of attachment of L to the pyrazolo[1,5-a]pyridine fused ring depicted in Formula I;
each $R_2$ is independently selected from the group consisting of hydrogen, $C_{1-6}$alkyl, halo$C_{1-6}$alkyl, R—$C_{0-4}$alkylene, and R—$C_{0-4}$alkylene-C(O)—, wherein R is selected from the group consisting of hydroxyl, $C_{1-4}$alkoxy, amino, $C_{1-4}$alkylamino, $C_{3-6}$cycloalkyl, $C_{4-6}$heterocycloalkyl, and $C_{5-6}$heteroaryl, wherein the $C_{3-6}$cycloalkyl, $C_{4-6}$heterocycloalkyl, and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl; and
  each $R_3$ is independently selected from the group consisting of hydrogen and $C_{1-4}$alkyl,
Ring A is selected from the group consisting of $C_{6-10}$aryl and $C_{5-10}$heteroaryl;
Ring C is selected from the group consisting of $C_{8-10}$aryl, $C_{5-10}$heteroaryl, $C_{5-7}$cycloalkyl, $C_{5-7}$heterocycloalkyl, and a fused bicyclyl comprising a $C_{5-6}$heterocycloalkyl fused to a phenyl;
each $R_1$ is independently selected from the group consisting of halo, cyano, amino, $C_{1-4}$alkyl, $C_{1-4}$alkoxyl, halo-$C_{1-4}$alkyl, —C(O)N$R_7R_8$, —NHC(O)$R_{11}$, phenyl, and $C_{5-6}$heteroaryl; wherein
  the phenyl and $C_{5-6}$heteroaryl are each unsubstituted or substituted with 1-2 substituents independently selected from the group consisting of $C_{1-4}$alkyl, amino, halo, and $C_{1-4}$alkylamino;
$R_7$ and $R_8$ are each independently selected from hydrogen, $C_{1-4}$alkyl and halo$C_{1-4}$alkyl;
$R_{11}$ is $C_{1-6}$alkyl unsubstituted or substituted with 1-2 substituents independently selected from the group consisting of amino, $C_{3-6}$cycloalkyl and $C_{4-6}$heterocycloalkyl;
$R_{17}$ is selected from the group consisting of cyano, halo, $C_{1-4}$alkyl, halo-$C_{1-4}$alkyl, oxo, $C_{3-6}$cycloalkyl, and —SO$_2$—C$_{1-4}$alkyl.

Embodiment 2

A compound of the formula (I), or a salt, tautomer or stereoisomer thereof, according to embodiment 1, wherein L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—C(O)—, *—C(O)N(R$_2$)—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein
  each $R_2$ is independently selected from the group consisting of hydrogen, $C_{1-6}$alkyl, R—$C_{0-4}$alkylene, wherein R is selected from the group consisting of $C_{1-4}$alkoxy, $C_{1-4}$alkylamino, di-$C_{1-4}$alkylamino, $C_{3-6}$cycloalkyl, $C_{4-6}$heterocycloalkyl and $C_{5-6}$heteroaryl, wherein the $C_{3-6}$cycloalkyl, $C_{4-6}$heterocycloalkyl and $C_{5-6}$heteroaryl of R are each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl.

Embodiment 3

A compound of the formula (I), or a salt, tautomer or stereoisomer thereof, according to embodiment 1, wherein L is selected from the group consisting of *—C(O)N(R$_2$)—, and *—N(R$_2$)C(O)—, wherein each $R_2$ is independently selected from hydrogen, $C_{1-4}$alkyl, and R—$C_{0-4}$alkylene, wherein R is selected from the group consisting of $C_{4-6}$heterocycloalkyl and $C_{5-6}$heteroaryl, each unsubstituted or substituted with 1-2 substituents independently selected from the group consisting of halo, amino, hydroxyl, $C_{1-4}$alkyl, $C_{1-4}$alkoxy, oxo, and $C_{5-6}$heteroaryl.

Embodiment 4

A compound of the formula (I), or a salt, tautomer or stereoisomer thereof, according to embodiment 1, wherein L is selected from the group consisting of *—CH(CH$_3$)—, *—CH$_2$CH$_2$—, *—CH$_2$N(CH$_3$)—, *—CH$_2$N(C(O)(CH$_2$)$_{1-2}$NH(CH$_3$))—, *—CH$_2$N(C(O)—(CH$_2$)$_{1-2}$NH$_2$)—, *—CH$_2$N((C(O)—(CH$_2$)$_{1-2}$N(CH$_3$)$_2$)—, *—CH$_2$N(C(O)(CH$_2$)$_{1-2}$OH)—, *—CH(CH$_3$)N(CH$_3$)—, *—CH$_2$O—, *—CH$_2$S—, *—CH$_2$S(O)—, *—C(O)—, *—C(O)N(CH$_3$)—, *—C(O)N(CH$_2$CH$_3$)—, *—C(O)N(CH(CH$_3$)$_2$)—, *—C(O)N(C(CH$_3$)$_3$)—, *—C(O)N(CH$_2$CH(CH$_3$)$_2$)—, *—C(O)N(CH(CH$_3$)CH$_2$CH$_3$)—, *—C(O)N(CH$_2$CH$_2$OCH$_3$)—, *—C(O)N(CH$_2$CH$_2$N(CH$_3$)$_2$)—, *—C(O)N(CH$_3$)CH$_2$—, *—NHCH$_2$—, *—N(CH$_3$)CH$_2$—, *—N(CH$_2$-tetrahydropyran-4-yl)-C(O)—, *—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N((CH$_2$)$_{0-1}$-cyclobutyl)-, *—C(O)N((CH$_2$)$_{0-1}$-cyclopentyl)-, *—C(O)N((CH$_2$)$_{0-1}$-cyclohexyl)-, *—C(O)N(CH$_2$-tetrahydropyran-4-yl)-, *—C(O)N((CH$_2$)$_2$-(1,1-dioxidothiomorpholino-4-yl)-, *—C(O)N(CH$_2$-1,1-dioxidothiomorpholino-4-yl)-, *—C(O)N((CH$_2$)$_2$-tetrahydropyran-4-yl))-, *—C(O)N((CH$_2$)$_{1-2}$-morpholin-4-yl)-, *—C(O)N(oxetan-3-yl)-, *—C(O)N(CH$_2$-oxetan-3-yl)-, *—C(O)N(CH(CH$_3$)—CH$_2$-1-H-pyrazoly-1-yl)-, *—CH$_2$N(C(O)—(CH$_2$)$_{1-2}$-morpholinyl))-, *—CH$_2$N(C(O)—(CH$_2$)$_{1-2}$-4-methylpiperizin-1-yl)), *—CH$_2$N(C(O)—(CH$_2$)$_{1-2}$-tetrahydropyran-4-yl)-, and *—CH$_2$N(C(O)(CH$_2$)$_{1-2}$-oxetan-3-yl)-.

Embodiment 5

A compound of the formula (I), or a salt, tautomer or stereoisomer thereof, according to embodiment 1, wherein L is selected from the group consisting of *—CH(CH$_3$)—, *—CH$_2$CH$_2$—, *—CH$_2$N(CH$_3$)—, *—CH(CH$_3$)N(CH$_3$)—, *—CH$_2$O—, *—CH$_2$S—, *—CH$_2$S(O)—, *—C(O)—, *—C(O)N(CH$_3$)—, *—C(O)N(CH$_3$)CH$_2$—, *—C(O)N(CH$_2$CH$_2$OCH$_3$)—, *—C(O)N(CH$_2$CH$_2$N(CH$_3$)$_2$)—, *—NHCH$_2$—, *—N(CH$_3$)CH$_2$—, *—N(CH$_2$-tetrahydropyran-4-yl)-C(O)—, *—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N(CH$_2$-tetrahydropyran-4-yl)-, *—C(O)N(oxetan-3-yl)-, and *—C(O)N(CH(CH$_3$)CH$_2$-(1-H-pyrazoly-1-yl))-.

Embodiment 6

A compound of the formula (I), or a salt, tautomer or stereoisomer thereof, according to embodiment 1, wherein L is *—C(O)N(CH$_3$)— or *—N(CH$_3$)C(O)—.

Embodiment 7

A compound of the formula (I), or a salt, tautomer or stereoisomer thereof, according to embodiment 1, wherein L is *—C(O)N(cyclopropyl)-.

Embodiment 8

A compound of the formula (I), or a salt, tautomer or stereoisomer thereof, according to embodiment 1, wherein L is *—C(O)— or —CH(CH$_3$)—.

Embodiment 9

A compound of the formula (I), or a salt, tautomer or stereoisomer thereof, according to embodiments 1 to 8, wherein Ring A is selected from the group consisting of phenyl, pyridinyl, pyrimidinyl, pyrazinyl, pyridazinyl, pyrrolopyridinyl, and indazolyl, each of which is unsubstituted or substituted by $(R_1)_n$.

Embodiment 10

A compound of the formula (I), or a salt, tautomer or stereoisomer thereof, according to any one of embodiments 1 to 8, wherein Ring A is selected from the group consisting of

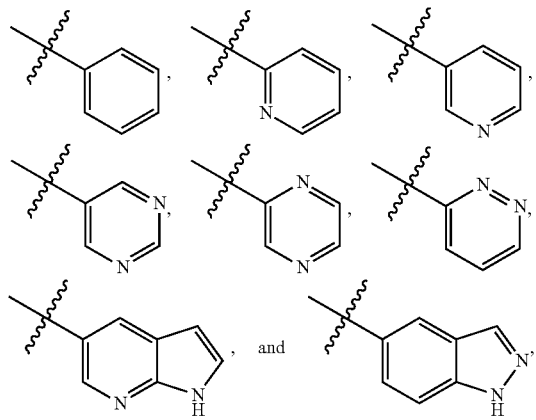

each of which is unsubstituted or substituted by $(R_1)_n$.

Embodiment 11

A compound of the formula (I), or a salt, tautomer or stereoisomer thereof, according to any one of embodiments 1 to 8, wherein Ring A is of the formula

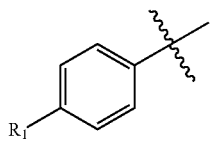

Embodiment 12

A compound of the formula (I), or a salt, tautomer or stereoisomer thereof, according to any one of embodiments 1 to 8, wherein Ring A is of the formula

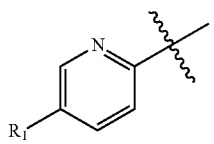

Embodiment 13

A compound of the formula (I), or a salt, tautomer or stereoisomer thereof, according to any one of embodiments 1 to 8, wherein Ring A is of the formula

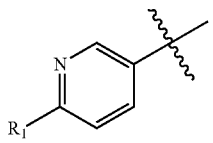

Embodiment 14

A compound of the formula (I), or a salt, tautomer or stereoisomer thereof, according to any one of embodiments 1 to 8, wherein Ring A is of the formula

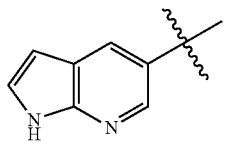

Embodiment 15

A compound of the formula (I), or a salt, tautomer or stereoisomer thereof, according to any one of embodiments 1 to 14, wherein Ring C is selected from the group consisting of

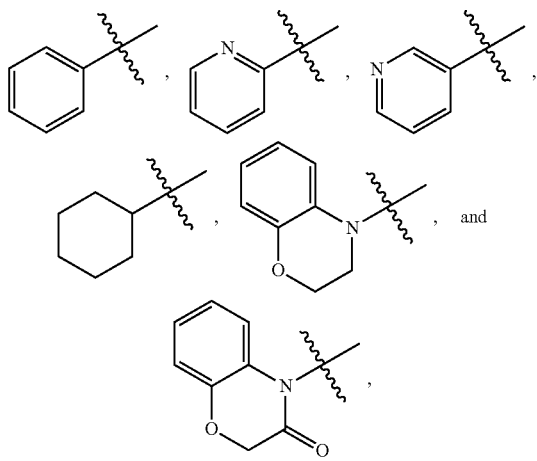

each of which is unsubstituted or substituted by $(R_{17})_p$.

Embodiment 16

A compound of the formula (I), or a salt, tautomer or stereoisomer thereof, according to any one of embodiments 1 to 7 and 9-14, wherein Ring C is selected from the group consisting of phenyl and pyridinyl, each of which is unsubstituted or substituted by $(R_{17})_p$.

Embodiment 17

A compound of the formula (I), or a salt, tautomer or stereoisomer thereof, according to any one of embodiments 1 to 7 and 9-14, wherein Ring C is of the formula

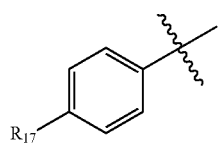

Embodiment 18

A compound of the formula (I), or a salt, tautomer or stereoisomer thereof, according to any one of embodiments 1 to 7 and 9-14, wherein Ring C is of the formula

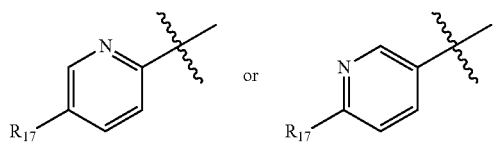

Embodiment 19

A compound of the formula (I), or a salt, tautomer or stereoisomer thereof, according to any one of embodiments 1-2, 4-5 and 8-14, wherein Ring C is of the formula

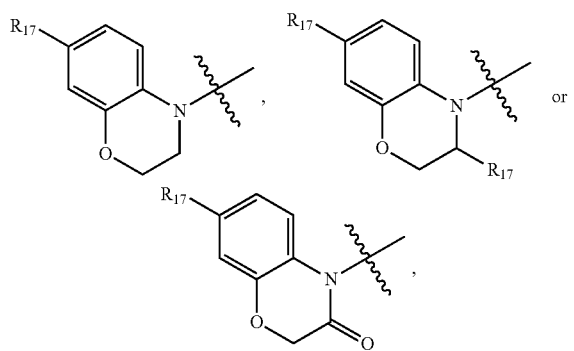

each of which is unsubstituted or substituted by 1 to 3 ($R_{17}$).

Embodiment 20

A compound of the formula (I), or a salt, tautomer or stereoisomer thereof, according to any one of embodiments 1 to 19, wherein each R, is independently selected from the group consisting of fluoro, chloro, cyano, methyl, trifluoromethyl, methoxy, —$NH_2$, —C(O)$NH_2$, —C(O)NH($CH_3$), —C(O)N($CH_3$)$_2$, —NHC(O)$CH_3$, —NHC(O)$CH_2NH_2$, —NHC(O)CH($NH_2$)($CH_3$), —NHC(O)CH($NH_2$)(cyclohexyl), —NHC(O)CH($NH_2$)CH($CH_3$)$_2$, —NHC(O)CH($CH_3$)$_2$,

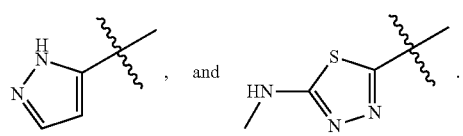

Embodiment 21

A compound of the formula (I), or a salt, tautomer or stereoisomer thereof, according to any one of embodiments 1 to 19, wherein each R, is independently selected from the group consisting of trifluoromethyl, cyano, —$NH_2$—, —C(O)$NH_2$, —C(O)NH$CH_3$, and —C(O)N($CH_3$)$_2$,

Embodiment 22

A compound of the formula (I), or a salt, tautomer or stereoisomer thereof, according to any one of embodiments 1 to 19, wherein R, is trifluoromethyl.

Embodiment 23

A compound of the formula (I), or a salt, tautomer or stereoisomer thereof, according to any one of embodiments 1 to 19, wherein $R_1$ is —$NH_2$.

Embodiment 24

A compound of the formula (I), or a salt, tautomer or stereoisomer thereof, according to any one of embodiments 1 to 19, wherein $R_1$ is —C(O)$NH_2$.

Embodiment 25

A compound of the formula (I), or a salt, tautomer or stereoisomer thereof, according to any one of embodiments 1 to 19, wherein $R_1$ is —C(O)NH$CH_3$.

Embodiment 26

A compound of the formula (I), or a salt, tautomer or stereoisomer thereof, according to any one of embodiments 1 to 19, wherein $R_1$ is —NHC(O)CH($NH_2$)($CH_3$).

Embodiment 27

A compound of the formula (I), or a salt, tautomer or stereoisomer thereof, according to any one of embodiments 1 to 26, wherein each $R_{17}$ is independently selected from the group consisting of cyano, halo, $C_{1-4}$alkyl, —$SO_2$—$C_{1-4}$alkyl, and $C_{3-6}$cycloalkyl.

Embodiment 28

A compound of the formula (I), or a salt, tautomer or stereoisomer thereof, according to any one of embodiments 1 to 26, wherein each $R_{17}$ is independently selected from the group consisting of cyano, fluoro, chloro, methyl, trifluoromethyl, 1,1-difluoroethyl, methylsulfonyl, and cyclopropyl.

Embodiment 29

A compound of the formula (I), or a salt, tautomer or stereoisomer thereof, according to any one of embodiments 1-7, 9-18 and 20-26, $R_{17}$ is cyano.

Embodiment 30

A compound of the formula (I), or a salt, tautomer or stereoisomer thereof, according to any one of embodiments 1-7, 9-18 and 20-26, $R_{17}$ is trifluoromethyl

Embodiment 31

A compound of the formula (I), or a salt, tautomer or stereoisomer thereof, according to any one of embodiments 1-7, 9-18 and 20-26, wherein $R_{17}$ is fluoro or chloro.

Embodiment 32

A compound of the formula (I), or a salt, tautomer or stereoisomer thereof, according to any one of embodiments 1-7, 9-18 and 20-26, wherein $R_{17}$ is methylsulfonyl.

Embodiment 33

A compound of the formula (I), or a salt, tautomer or stereoisomer thereof, according to any one of embodiments 1-2, 4-5, 8-15 and 19, where each $R_{17}$ is methyl.

Embodiment 34

A compound of the formula (I), or a salt, tautomer or stereoisomer thereof, according to embodiment 1, wherein the compound is of Formula Ia

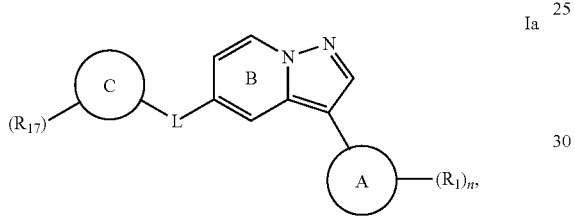

wherein
n is 1 or 2;
Ring A is phenyl, pyridinyl, or pyrimidinyl;
Ring C is phenyl or pyridinyl;
L is *—C(O)NR$_2$— or *—NR$_2$C(O)—, wherein R$_2$ is selected from hydrogen, $C_{1-4}$alkyl, $C_{3-6}$cycloalkyl-($C_{0-4}$)alkylene, $C_{4-6}$heterocycloalkyl-($C_{0-4}$)alkylene, wherein the $C_{4-6}$heterocycloalkyl is selected from the group consisting of piperazinyl, morpholinyl, thiomorpholinyl, tetrahydropyranyl, and oxetanyl, and wherein the $C_{3-6}$cycloalkyl is selected from cyclopropyl, cyclobutyl, cyclopentyl and cyclohexyl;
each $R_1$ is independently *—C(O)N$_7$R$_8$ or —NH$_2$—, wherein R, and R$_8$ are each independently hydrogen or $C_{1-4}$alkyl; and
$R_{17}$ is selected from the group consisting of cyano, halo, —NH$_2$—, —C(O)NH$_2$, —C(O)NH(CH$_3$), and —C(O)N(CH$_3$)$_2$.

Embodiment 35

A compound of the formula (I), or a salt, tautomer or stereoisomer thereof, according to embodiment 34, wherein Ring A is of the formula

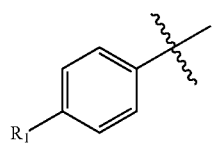

Embodiment 36

A compound of the formula (I), or a salt, tautomer or stereoisomer thereof, according to embodiment 34, wherein Ring A is of the formula

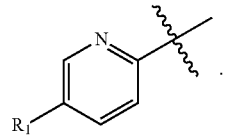

Embodiment 37

A compound of the formula (I), or a salt, tautomer or stereoisomer thereof, according to embodiments 34-36, wherein Ring C is of the formula

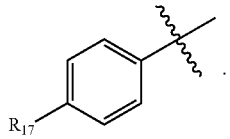

Embodiment 38

A compound of the formula (I), or a salt, tautomer or stereoisomer thereof, according to embodiments 34-36, wherein Ring C is of the formula

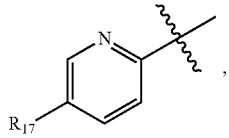

Embodiment 39

A compound of the formula (I), or a salt, tautomer or stereoisomer thereof, according to embodiments 36-38, wherein L is *—C(O)NH(CH$_3$)— or *—NH(CH$_3$)C(O)—.

Embodiment 40

A compound of the formula (I), or a salt, tautomer or stereoisomer thereof, according to embodiments 36-38, wherein L is *—C(O)N(cyclopropyl)-

Embodiment 41

A compound of the formula (I), or a salt, tautomer or stereoisomer thereof, according to embodiments 36-40, wherein $R_1$ is —NH$_2$—.

Embodiment 42

A compound of the formula (I), or a salt, tautomer or stereoisomer thereof, according to embodiments 36-40, wherein $R_1$ is —C(O)NH$_2$ or —C(O)NCH$_3$.

Embodiment 43

A compound of the formula (I), or a salt, tautomer or stereoisomer thereof, according to embodiments 36-42, wherein $R_{17}$ is cyano.

Embodiment 44

A compound of the formula (I), or a salt, tautomer or stereoisomer thereof, according to embodiments 36-42, wherein $R_{17}$ is halo.

Embodiment 45

A compound of the formula (I), or a salt, tautomer or stereoisomer thereof, according to embodiment 1, wherein the compound is selected from the group consisting of: N-(4-cyanophenyl)-N-methyl-3-(4-(trifluoromethyl)phenyl)pyrazolo[1,5-a]pyridine-5-carboxamide; 4-fluoro-N-methyl-N-((3-(4-(trifluoromethyl)phenyl)pyrazolo[1,5-a]pyridine-5-yl)methyl)aniline; N-(4-chlorophenyl)-N-methyl-3-(4-(trifluoromethyl)phenyl)pyrazolo[1,5-a]pyridine-5-carboxamide; N-(4-fluorophenyl)-N-methyl-3-(4-(trifluoromethyl)phenyl)pyrazolo[1,5-a]pyridine-5-carboxamide; N-methyl-N-(5-methylpyridin-2-yl)-3-(4-(trifluoromethyl)phenyl)pyrazolo[1,5-a]pyridine-5-carboxamide; 4-chloro-N-methyl-N-((3-(4-(trifluoromethyl)phenyl)pyrazolo[1,5-a]pyridine-5-yl)methyl)aniline; N,5-dimethyl-N-((3-(4-(trifluoromethyl)phenyl)pyrazolo[1,5-a]pyridine-5-yl)methyl)yridine-2-amine; 5-((4-fluorophenoxy)methyl)-3-(4-(trifluoromethyl)phenyl)pyrazolo[1,5-a]pyridine; N-(4-cyanophenyl)-N-(2-methoxyethyl)-3-(4-(trifluoromethyl)phenyl)pyrazolo[1,5-a]pyridine-5-carboxamide; N-(4-cyanophenyl)-N-(2-(dimethylamino)ethyl)-3-(4-(trifluoromethyl)phenyl)pyrazolo[1,5-a]pyridine-5-carboxamide; N-(4-cyanophenyl)-N-((tetrahydro-2H-pyran-4-yl)methyl)-3-(4-(trifluoromethyl)phenyl)pyrazolo[1,5-a]pyridine-5-carboxamide; N-(4-(methylsulfonyl)phenyl)-N-((tetrahydro-2H-pyran-4-yl)methyl)-3-(4-(trifluoromethyl)phenyl)pyrazolo[1,5-a]pyridine-5-carboxamide; N-(5-cyanopyridin-2-yl)-N-methyl-3-(4-(trifluoromethyl)phenyl)pyrazolo[1,5-a]pyridine-5-carboxamide; N-methyl-N-(5-methylpyridin-3-yl)-3-(4-(trifluoromethyl)phenyl)pyrazolo[1,5-a]pyridine-5-carboxamide; 5-(((5-methylpyridin-2-yl)oxy)methyl)-3-(4-(trifluoromethyl)phenyl)pyrazolo[1,5-a]pyridine; 5-(4-fluorophenethyl)-3-(4-(trifluoromethyl)phenyl)pyrazolo[1,5-a]pyridine; N-(4-cyanophenyl)-N-methyl-3-(1-methyl-1H-indazol-5-yl)pyrazolo[1,5-a]pyridine-5-carboxamide; 3-(6-acetamidopyridin-3-yl)-N-(4-cyanophenyl)-N-methylpyrazolo[1,5-a]pyridine-5-carboxamide; 3-(4-carbamoylphenyl)-N-(4-cyanophenyl)-N-methylpyrazolo[1,5-a]pyridine-5-carboxamide; 3-(4-carbamoylphenyl)-N-(4-fluorophenyl)-N-methylpyrazolo[1,5-a]pyridine-5-carboxamide; 5-(((4-fluorophenyl)thio)methyl)-3-(4-(trifluoromethyl)phenyl)pyrazolo[1,5-a]pyridine; 5-(((4-fluorophenyl)sulfinyl)methyl)-3-(4-(trifluoromethyl)phenyl)pyrazolo[1,5-a]pyridine; 3-(4-(1H-pyrazol-5-yl)phenyl)-N-(4-cyanophenyl)-N-methylpyrazolo[1,5-a]pyridine-5-carboxamide; N-(4-cyanophenyl)-N-methyl-3-(5-(trifluoromethyl)pyridine-2-yl)pyrazolo[1,5-a]pyridine-5-carboxamide; N-(5-cyanopyridin-2-yl)-N-methyl-3-(5-(trifluoromethyl)pyridine-2-yl)pyrazolo[1,5-a]pyridine-5-carboxamide; (S)-3-(4-(2-aminopropanamido)phenyl)-N-(4-cyanophenyl)-N-methylpyrazolo[1,5-a]pyridine-5-carboxamide; 3-(5-carbamoylpyridin-2-yl)-N-(4-cyanophenyl)-N-methylpyrazolo[1,5-a]pyridine-5-carboxamide; 4-cyano-N-methyl-N-(3-(4-(trifluoromethyl)phenyl)pyrazolo[1,5-a]pyridine-5-yl)benzamide; 4-fluoro-N-methyl-N-(3-(4-(trifluoromethyl)phenyl)pyrazolo[1,5-a]pyridine-5-yl)benzamide; 4-cyano-N-methyl-N-(3-(4-(trifluoromethyl)phenyl)pyrazolo[1,5-a]pyridine-5-yl)benzenesulfonamide; 4-fluoro-N-methyl-N-(3-(4-(trifluoromethyl)phenyl)pyrazolo[1,5-a]pyridine-5-yl)benzenesulfonamide; 3-(4-carbamoylphenyl)-N-(5-cyanopyridin-2-yl)-N-methylpyrazolo[1,5-a]pyridine-5-carboxamide; N-methyl-3-(4-(trifluoromethyl)phenyl)-N-(5-(trifluoromethyl)yridine-2-yl)pyrazolo[1,5-a]pyridine-5-carboxamide; N-methyl-N-(5-(methylsulfonyl)pyridine-2-yl)-3-(4-(trifluoromethyl)phenyl)pyrazolo[1,5-a]pyridine-5-carboxamide; N-(4-fluorobenzyl)-3-(4-(trifluoromethyl)phenyl)pyrazolo[1,5-a]pyridine-5-amine; N-(4-fluorobenzyl)-3-(4-(trifluoromethyl)phenyl)pyrazolo[1,5-a]pyridine-5-amine; N-methyl-6-(trifluoromethyl)-N-(3-(4-(trifluoromethyl)phenyl)pyrazolo[1,5-a]pyridine-5-yl)nicotinamide; N-methyl-5-(trifluoromethyl)-N-(3-(4-(trifluoromethyl)phenyl)pyrazolo[1,5-a]pyridine-5-yl)picolinamide; 4-cyano-N-((tetrahydro-2H-pyran-4-ylmethyl)-N-(3-(4-(trifluoromethyl)phenyl)pyrazolo[1,5-a]pyridin-5-yl)benzamide; N-(4-cyanophenyl)-N-methyl-3-(1H-pyrrolo[2,3-b]pyridin-5-yl)pyrazolo[1,5-a]pyridine-5-carboxamide; 3-(6-aminopyridin-3-yl)-N-(4-cyanophenyl)-N-methylpyrazolo[1,5-a]pyridine-5-carboxamide; 3-(4-aminophenyl)-N-(4-cyanophenyl)-N-methylpyrazolo[1,5-a]pyridine-5-carboxamide; 3-(4-(2-aminoacetamido)phenyl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; (S)-3-(4-(2-amino-3-methylbutanamido)phenyl)-N-(4-cyanophenyl)-N-methylpyrazolo[1,5-a]pyridine-5-carboxamide; (S)-3-(4-(2-amino-2-cyclohexylacetamido)phenyl)-N-(4-cyanophenyl)-N-methylpyrazolo[1,5-a]pyridine-5-carboxamide; 3-(4-fluorophenyl)-1-methyl-1-(3-(4-(trifluoromethyl)phenyl)pyrazolo[1,5-a]pyridin-5-yl)urea; 6-(1,1-difluoroethyl)-N-methyl-N-(3-(4-(trifluoromethyl)phenyl)pyrazolo[1,5-a]pyridin-5-yl)nicotinamide; 6-cyclopropyl-N-methyl-N-(3-(4-(trifluoromethyl)phenyl)pyrazolo[1,5-a]pyridin-5-yl)nicotinamide; 4-cyclopropyl-N-methyl-N-(3-(4-(trifluoromethyl)phenyl)pyrazolo[1,5-a]pyridin-5-yl)benzamide; 5-fluoro-N-methyl-N-(3-(4-(trifluoromethyl)phenyl)pyrazolo[1,5-a]pyridin-5-yl)picolinamide; N-methyl-4-(methylsulfonyl)-N-(3-(4-(trifluoromethyl)phenyl)pyrazolo[1,5-a]pyridin-5-yl)benzamide; N-(5-cyanopyridin-2-yl)-N-methyl-3-(1H-pyrrolo[2,3-b]pyridin-5-yl)pyrazolo[1,5-a]pyridine-5-carboxamide; 3-(6-aminopyridin-3-yl)-N-(5-cyanopyridin-2-yl)-N-methylpyrazolo[1,5-a]pyridine-5-carboxamide; 4-chloro-N-methyl-N-(3-(4-(trifluoromethyl)phenyl)pyrazolo[1,5-a]pyridin-5-yl)benzamide; N-(3-(4-carbamoylphenyl)pyrazolo[1,5-a]pyridin-5-yl)-4-fluoro-N-methylbenzamide; 4-fluoro-N-methyl-N-(3-(4-(5-(methylamino)-1,3,4-thiadiazol-2-yl)phenyl)pyrazolo[1,5-a]pyridin-5-yl)benzamide; N-methyl-N-(5-(methylsulfonyl)pyridin-2-yl)-3-(1H-pyrrolo[2,3-b]pyridin-5-yl)pyrazolo[1,5-a]pyridine-5-carboxamide; N-(5-cyanopyridin-2-yl)-N-methyl-3-(5-methylpyridin-2-yl)pyrazolo[1,5-a]pyridine-5-carboxamide; N-(5-cyanopyridin-2-yl)-3-(5-methoxypyridin-2-yl)-N-methylpyrazolo[1,5-a]pyridine-5-carboxamide; 3-(5-carbamoylpyridin-2-yl)-N-(5-cyanopyridin-2-yl)-N-methylpyrazolo[1,5-a]pyridine-5-carboxamide; 3-(4-carbamoylphenyl)-N-methyl-N-(5-(trifluoromethyl)pyridin-2-yl)pyrazolo[1,5-a]pyridine-5-carboxamide; 3-(4-carbamoylphenyl)-N-methyl-N-(5-methylpyridin-2-yl)pyrazolo[1,5-a]pyridine-5-carboxamide; N-(4-fluorophenyl)-N-methyl-3-(4-(methylcarbamoyl)phenyl)pyrazolo[1,5-a]pyridine-5-carboxamide; 4-(5-(1-(methyl(5-methylpyridin-2-yl)amino)ethyl)pyrazolo[1,5-a]pyridin-3-yl)benzamide; 4-(5-(1-(7-fluoro-3-oxo-2H-benzo[b][1,4]oxazin-4(3H)-ylethyl)pyrazolo[1,5-a]pyridin-3-yl)benzamide; N-(4-cyanophenyl)-N-methyl-3-(4-(methylcarbamoyl)phenyl)pyrazolo[1,5-a]pyridine-5-carboxamide; N-(4-(5-(1-(methyl(5-methylpyridin-2-yl)

amino)ethyl)pyrazolo[1,5-a]pyridin-3-yl)phenyl)acetamide; 3-(4-acetamidophenyl)-N-(5-cyanopyridin-2-yl)-N-methylpyrazolo[1,5-a]pyridine-5-carboxamide; 4-(5-(7-fluoro-3,4-dihydro-2H-benzo[b][1,4]oxazine-4-carbonyl)pyrazolo[1,5-a]pyridin-3-yl)benzamide; 4-(5-(7-fluoro-3-methyl-3,4-dihydro-2H-benzo[b][1,4]oxazine-4-carbonyl)pyrazolo[1,5-a]pyridin-3-yl)benzamide; 4-(5-(7-fluoro-3,4-dihydro-2H-benzo[b][1,4]oxazine-4-carbonyl)pyrazolo[1,5-a]pyridin-3-yl)-N-methylbenzamide; 4-(5-(7-fluoro-3-methyl-3,4-dihydro-2H-benzo[b][1,4]oxazine-4-carbonyl)pyrazolo[1,5-a]pyridin-3-yl)-N-methylbenzamide; N-(5-cyanopyridin-2-yl)-N-methyl-3-(4-(methylcarbamoyl)phenyl)pyrazolo[1,5-a]pyridine-5-carboxamide; N-(5-cyanopyridin-2-yl)-3-(4-(methylcarbamoyl)phenyl)-N-(oxetan-3-yl)pyrazolo[1,5-a]pyridine-5-carboxamide; 3-(6-amino-5-fluoropyridin-3-yl)-N-(4-cyanophenyl)-N-methylpyrazolo[1,5-a]pyridine-5-carboxamide; 3-(4-amino-3,5-dimethylphenyl)-N-(4-cyanophenyl)-N-methylpyrazolo[1,5-a]pyridine-5-carboxamide; 3-(6-amino-5-methylpyridin-3-yl)-N-(4-cyanophenyl)-N-methylpyrazolo[1,5-a]pyridine-5-carboxamide; 3-(4-carbamoylphenyl)-N-(4-cyanocyclohexyl)-N-methylpyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; 3-(6-amino-5-(trifluoromethyl)pyridin-3-yl)-N-(5-cyanopyridin-2-yl)-N-methylpyrazolo[1,5-a]pyridine-5-carboxamide; 3-(6-amino-5-cyanopyridin-3-yl)-N-(5-cyanopyridin-2-yl)-N-methylpyrazolo[1,5-a]pyridine-5-carboxamide; 3-(6-amino-5-chloropyridin-3-yl)-N-(5-cyanopyridin-2-yl)-N-methylpyrazolo[1,5-a]pyridine-5-carboxamide; 3-(6-amino-5-(dimethylcarbamoyl)pyridin-3-yl)-N-(5-cyanopyridin-2-yl)-N-methylpyrazolo[1,5-a]pyridine-5-carboxamide; 3-(6-amino-5-methoxypyridin-3-yl)-N-(5-cyanopyridin-2-yl)-N-methylpyrazolo[1,5-a]pyridine-5-carboxamide; and 3-(4-carbamoylphenyl)-N-(4-chloro-2-formylphenyl)-N-methylpyrazolo[1,5-a]pyridine-5-carboxamide.

Embodiment 46

A compound of the formula (I), or a salt, tautomer or stereoisomer thereof, according to embodiment 1, wherein the compound is selected from the group consisting of: 3-(4-carbamoylphenyl)-N-(5-cyanopyridin-2-yl)-N-methylpyrazolo[1,5-a]pyridine-5-carboxamide; N-(4-cyanophenyl)-N-methyl-3-(1H-pyrrolo[2,3-b]pyridin-5-yl)pyrazolo[1,5-a]pyridine-5-carboxamide; 3-(6-aminopyridin-3-yl)-N-(4-cyanophenyl)-N-methylpyrazolo[1,5-a]pyridine-5-carboxamide; (R)-3-(4-(2-aminopropanamido)phenyl)-N-(4-cyanophenyl)-N-methylpyrazolo[1,5-a]pyridine-5-carboxamide; N-(5-cyanopyridin-2-yl)-N-methyl-3-(1H-pyrrolo[2,3-b]pyridin-5-yl)pyrazolo[1,5-a]pyridine-5-carboxamide; N-(5-cyanopyridin-2-yl)-N-methyl-3-(4-(methylcarbamoyl)phenyl)pyrazolo[1,5-a]pyridine-5-carboxamide; 3-(2-aminopyrimidin-5-yl)-N-(4-cyanophenyl)-N-methylpyrazolo[1,5-a]pyridine-5-carboxamide; 3-(6-amino-5-(dimethylcarbamoyl)pyridin-3-yl)-N-(5-cyanopyridin-2-yl)-N-methylpyrazolo[1,5-a]pyridine-5-carboxamide.

Embodiment 47

A pharmaceutical composition comprising at least one compound of any one of embodiments 1 to 46 or a pharmaceutically acceptable salt thereof, and a pharmaceutically acceptable carrier, diluent or excipient.

Embodiment 48

A pharmaceutical composition according to embodiment 47 further comprising a second agent.

Embodiment 49

A pharmaceutical composition according to embodiment 48, wherein the second agent is an antimalarial drug selected from the group consisting of artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

Embodiment 50

A compound according to any one of embodiments 1 to 46 or a pharmaceutical composition according to any one of embodiments 47-49 for use as a medicament.

Embodiment 51

A method for treating, preventing, inhibiting, ameliorating, or eradicating the pathology and/or symptomology of a disease caused by a *Plasmodium* parasite, comprising administering to a subject a therapeutically effective amount of a compound according to any one of claims 1-46 or a composition according to any one of claims 47 to 49, wherein the administering may be in combination with a second agent.

Embodiment 52

A method for treating, preventing, inhibiting, ameliorating, or eradicating the pathology and/or symptomology of a disease caused by a *Plasmodium* parasite, according to embodiment 51, wherein the disease is malaria.

Embodiment 53

A method for treating, preventing, inhibiting, ameliorating, or eradicating the pathology and/or symptomology of a disease caused by a *Plasmodium* parasite according to embodiments 51-52, wherein the *Plasmodium* parasite is at the blood stages.

Embodiment 54

A method for treating, preventing, inhibiting, ameliorating, or eradicating the pathology and/or symptomology of a *Plasmodium* related disease caused by a *Plasmodium* parasite according to embodiments 51-52, wherein the *Plasmodium* parasite is at the hepatic stages.

Embodiment 55

A method for treating, preventing, inhibiting, ameliorating, or eradicating the pathology and/or symptomology of a *Plasmodium* related disease caused by a *Plasmodium* parasite according to embodiments 51-54, wherein the *Plasmodium* parasite is selected from group consisting of *Plasmodium falciparum, Plasmodium vivax, Plasmodium ovale*, and *Plasmodium malaria*.

Embodiment 56

A method for treating, preventing, inhibiting, ameliorating, or eradicating the pathology and/or symptomology of a *Plasmodium* related disease caused by a *Plasmodium* parasite according to embodiments 51-54, wherein the *Plasmodium* parasite is *Plasmodium falciparum*.

Embodiment 57

A method for treating, preventing, inhibiting, ameliorating, or eradicating the pathology and/or symptomology of a *Plasmodium* related disease caused by a *Plasmodium* parasite according to embodiments 51-56, wherein the second agent is selected from a kinase inhibitor, an anti-malarial drug and an anti-inflammatory agent.

Embodiment 58

A method for treating, preventing, inhibiting, ameliorating, or eradicating the pathology and/or symptomology of a disease caused by *Plasmodium* parasite according to embodiment 57, wherein the anti-malarial drug is selected from the group consisting of artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

Embodiment 59

A method for treating, preventing, inhibiting, ameliorating, or eradicating the pathology and/or symptomology of a disease caused by *Plasmodium* parasite according to embodiments 51-58, wherein the compound is administered prior to, simultaneously with, or after the second agent.

Embodiment 60

A compound according to any one of claims 1-46 or a composition according to any one of claims 47 to 49 for treating, preventing, inhibiting, ameliorating, or eradicating the pathology and/or symptomology of a disease caused by a *Plasmodium* parasite.

Embodiment 61

Use of a compound according to any one of embodiments 1-46 or a pharmaceutical composition according to embodiments 47-49 in the manufacture of a medicament for treating, preventing, inhibiting, or ameliorating the pathology and/or symptomology of a disease caused by a *Plasmodium* parasite, wherein the medicament may further include a second agent.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}F$, $^{32}F$, $^{35}S$, $^{36}Cl$, $^{125}I$, respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Plasdmodium or (ii) associated with Plasdmodium activity, or (iii) characterized by activity (normal or abnormal) of Plasdmodium or (2) reduce or inhibit the activity of Plasdmodium; or (3) reduce or inhibit the growth of Plasdmodium. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of Plasdmodium; or at least partially reducing or inhibiting the growth of Plasdmodium.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)—, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Synthesis", John Wiley and Sons, 1991.

Typically, the compounds of formula (I) can be prepared according to synthetic routes 1-6 provided infra., where Ring A, Ring C, $R_1$, $R_2$, $R_{17}$, n and p are as defined in the Summary of the Invention. The following reaction schemes are given to be illustrative, not limiting, descriptions of the synthesis of compounds of the invention. Detailed descriptions of the synthesis of compounds of the invention are given in the Examples, infra.

General Synthetic Route I

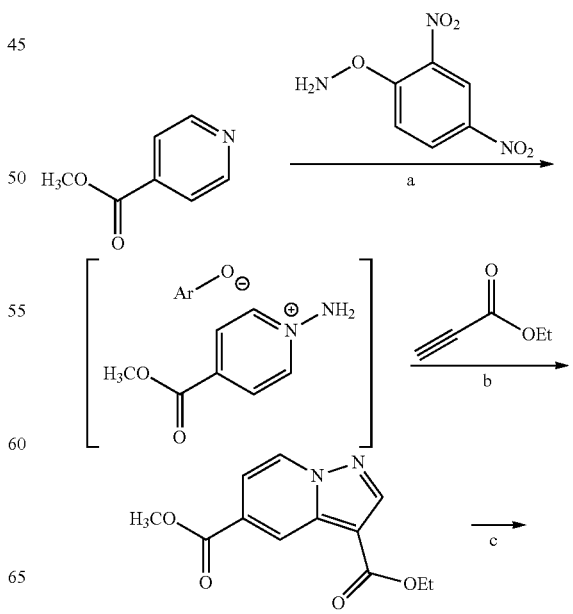

-continued

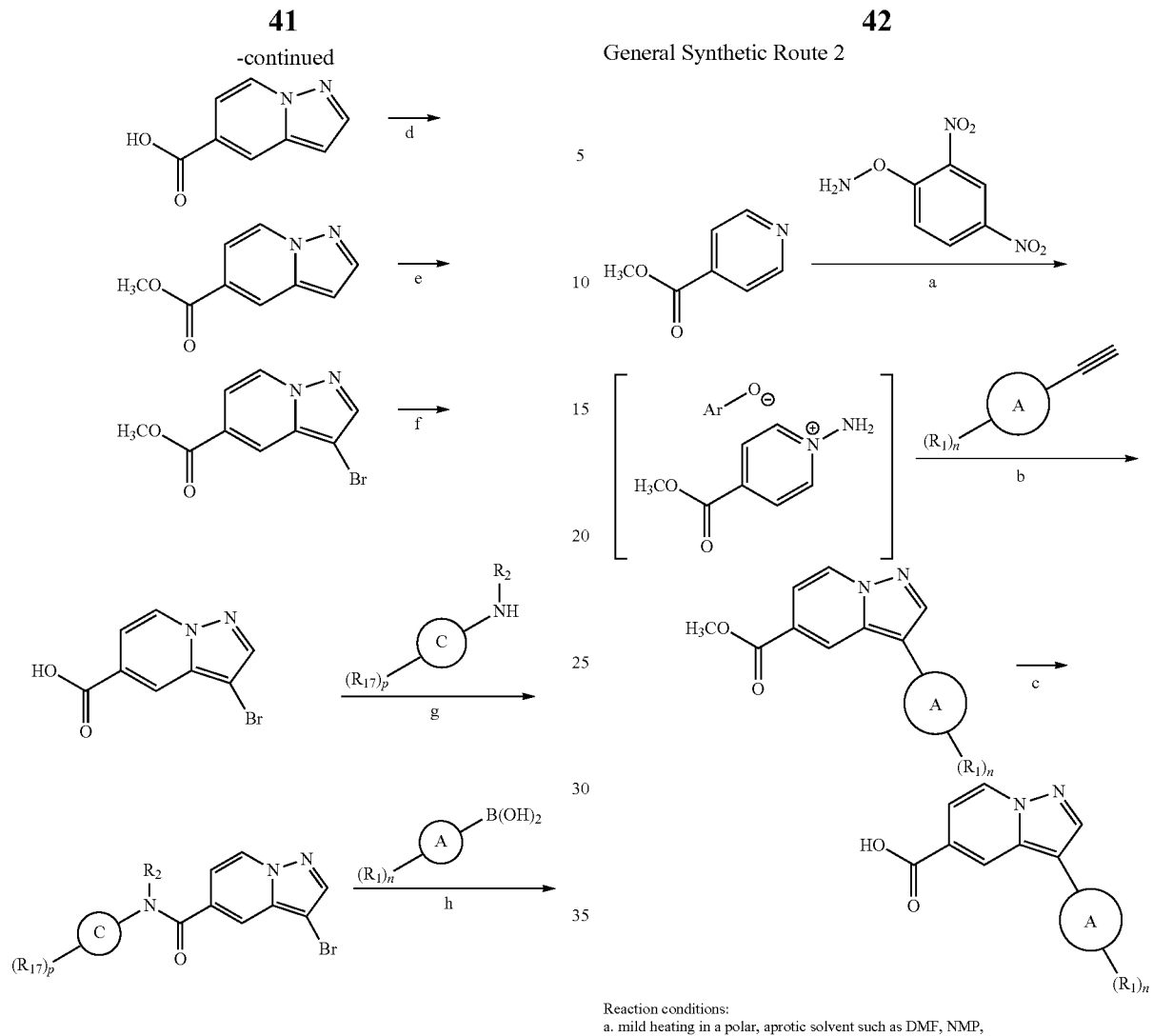

Reaction conditions:
a. mild heating in a polar, aprotic solvent such as DMF, NMP, DMA or DMSO;
b. base such as K₂CO₃ or Na₂CO₃ in a polar organic solvent such as DMF, NMP or DMSO;
c. esters can be hydrolyzed under conventional acidic or basic conditions; decarboxylation occurs when the di-acid is heated at 50-100° C.;
d. esterification can be done in alcohol (MeOH, EtOH) using acid catalysis (AcCl or TMSCl to generate HCl, or catalytic H₂SO₄ or toluene sulfonic acid, for example);
e. N-bromosuccinimide (NBS) or similar brominating agent in CH₂Cl₂, CHCl₃ or CCl₄ at -78° C. to room temperature;
f. conventional base-catalyzed hydrolysis in aqueous alcohol solvent;
g. the carboxylic acid can be activated by various known methods, e.g., forming an acid chloride using oxalyl chloride or thionyl chloride and DMF followed by acylation of an amine of formula ( 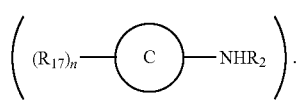 —NHR₂) in a non-reactive solvent using an amine bse such as Et₃N, DIEA (Hunig's base) or DMAP (dimethylaminopyridine). Various amide coupling reagents such as dicyclohexyl carbodiimide can also be used; and
h. Pd-catalyzed Suzuki coupling.

General Synthetic Route 2

Reaction conditions:
a. mild heating in a polar, aprotic solvent such as DMF, NMP, DMA or DMSO;
b. base such as K₂CO₃ or Na₂CO₃ in a polar organic solvent such as DMF, NMP or DMSO;
c. conventional base-catalyzed hydrolysis in aqueous alcohol solvent.

Ring C can then be added using known methods, such as amide formation to link the carboxylic acid with an amine of formula

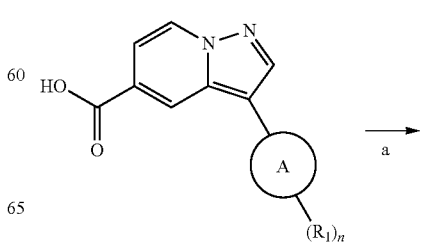

General Synthetic Route 3

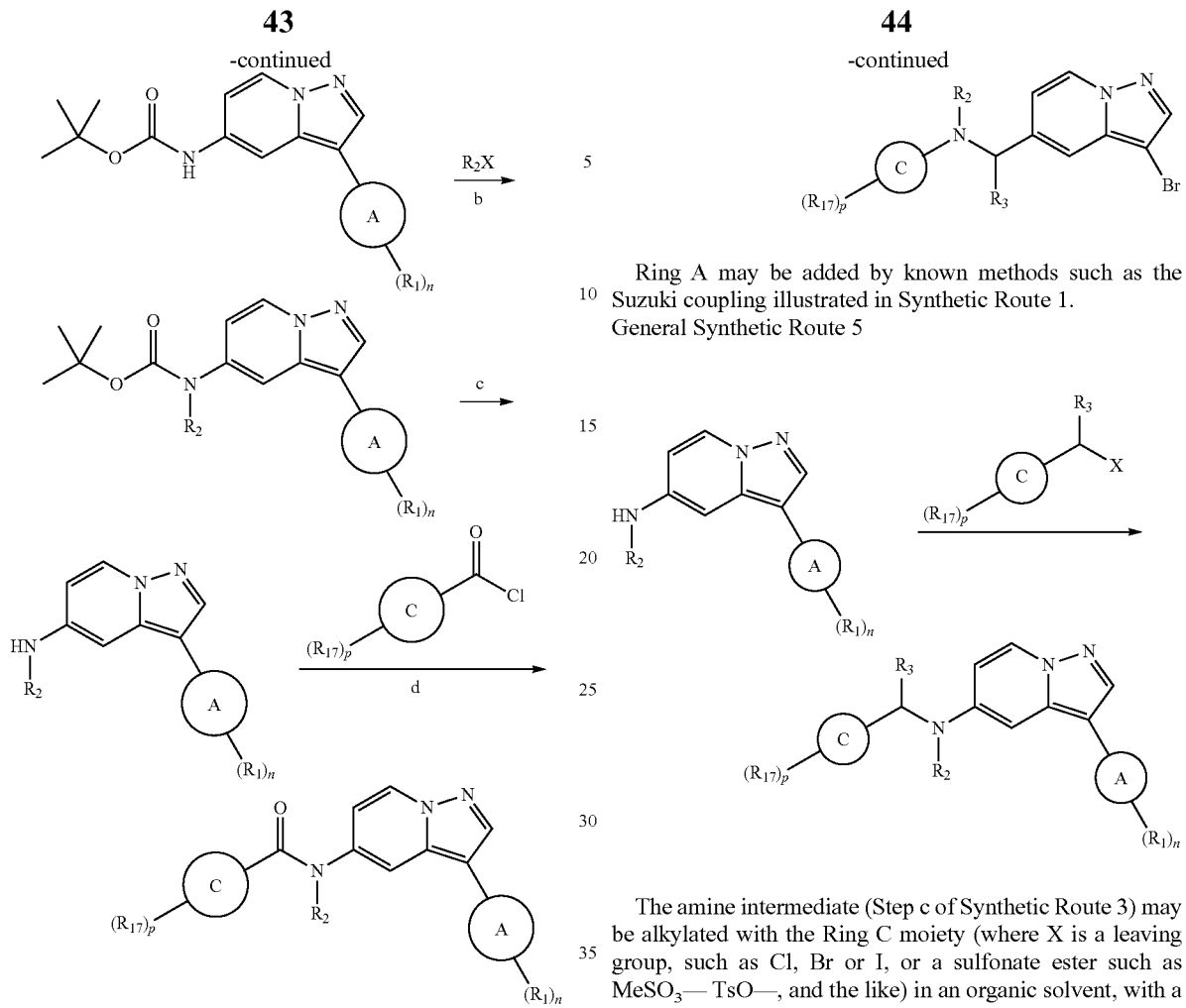

Reaction conditions:
a. Curtius rearrangement of carboxylic acid using diphenyl phosphoryl azide, t-butyl alcohol and an appropriate base.
b. optionally exchanged
hydrogen on the carbamate with an R₂ group by reacting with and R₂X group where X is a leaving group (such as Cl), in basic DMF at room temperature or lightly elevated temperature for a few hours;
c. Acidic cleavage of t-butyl carbamate
d. acylation with acid chlorides in dichloromethane/triethylamine at room temperature.

General Synthetic Route 4

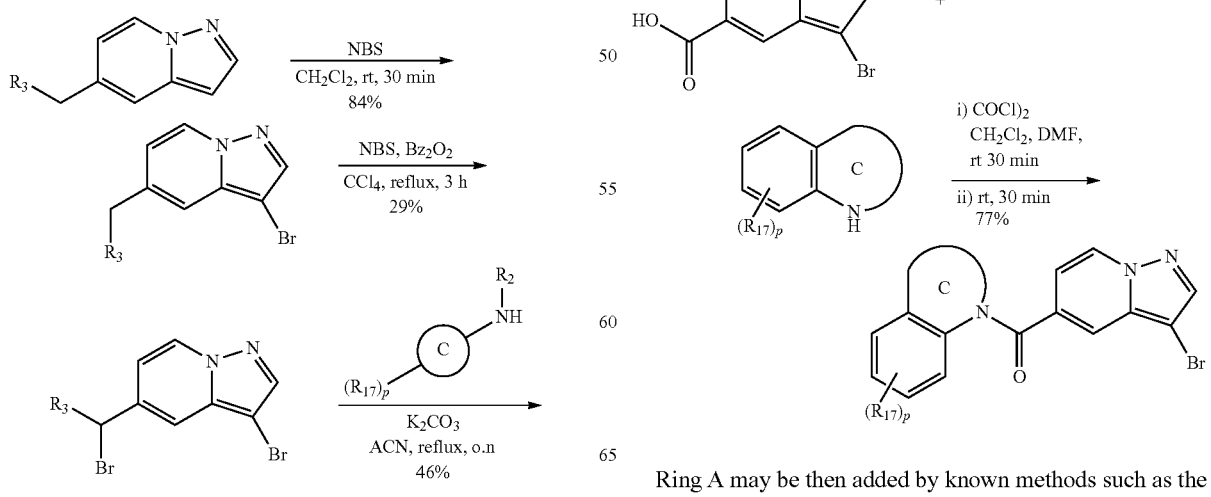

Ring A may be added by known methods such as the Suzuki coupling illustrated in Synthetic Route 1.

General Synthetic Route 5

The amine intermediate (Step c of Synthetic Route 3) may be alkylated with the Ring C moiety (where X is a leaving group, such as Cl, Br or I, or a sulfonate ester such as MeSO₃— TsO—, and the like) in an organic solvent, with a catalytic amount of DMAP and a non-nucleophilic base, at 0° C. to mild heating. Typical organic solvent includes halogenated solvents like DCM or CHCl₃; ether solvents such as THF, dioxane, MTBE, diethyl ether. Typical non-nucleophilic base includes triethylamine, diisopropyl ethylamine, potassium t-butoxide, potassium carbonate, and the like.

General Synthetic Route 6

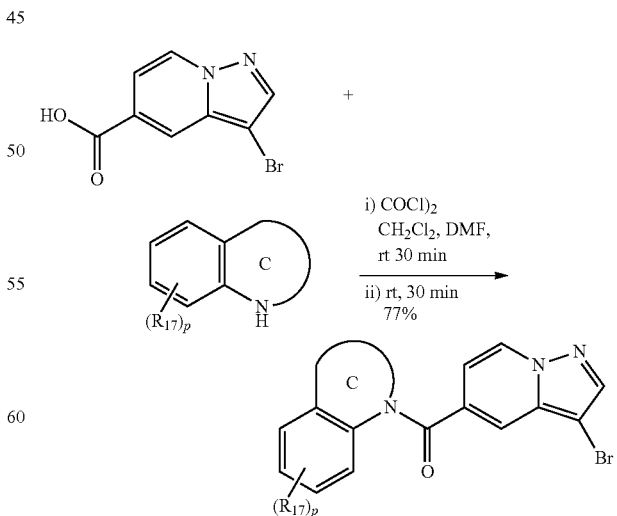

Ring A may be then added by known methods such as the Suzuki coupling illustrated in Synthetic Route I.

General Procedures for Boronic ester synthesis

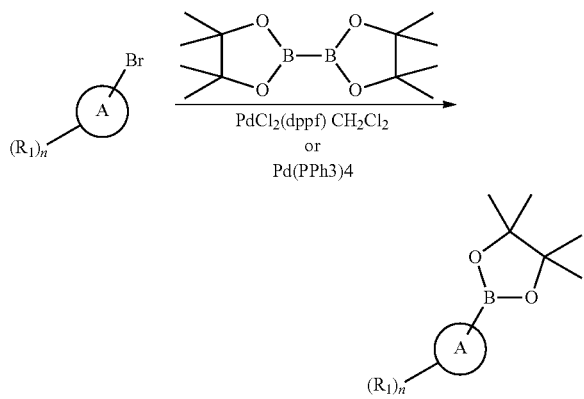

Boronic ester synthesis procedure A: $PdCl_2(dppf).CH_2Cl_2$;

A mixture of bromo compound (1.0 eq.) and bis(pinacolato)diboron (1.1 eq.) and potassium acetate (2.0 eq.) dissolved in 1,4-dioxane (10 vol) was degassed with argon gas for 15 min. Subsequently, $PdCl_2(dppf).CH_2Cl_2$ (0.05 eq.) was added and the reaction mixture was stirred at 85-100° C. for 16 h. The reaction mixture (generally black color) was filtered and concentrated under reduced pressure. The resulting black mixture was used further without any purification.

Boronic Ester Synthesis Procedure B: $Pd(PPh_3)_4$;

A mixture of bromo compound (1.0 eq.) and bis(pinacolato)diboron (1.1 eq.), and potassium acetate (2.0 eq.) dissolved in 1,4-dioxane (10 vol) was degassed with argon gas for 15 min. Subsequently, $Pd_2(dba)_3$ (0.05 eq.) and tricyclohexyl phosphine (0.05 eq.) were added and the reaction mixture was stirred at 90-110° C. for 16 h. The reaction mixture (generally black color) was filtered and concentrated under reduced pressure. The crude product was used further without any purification.

General Procedures for Suzuki Couplings

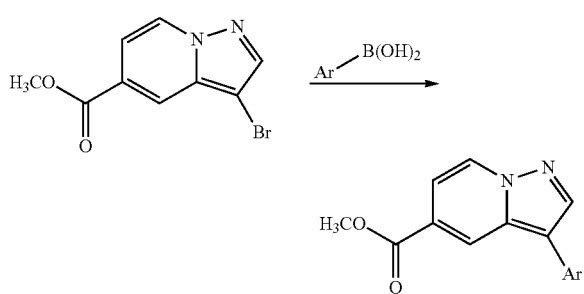

Suzuki Procedure A: SiliaCat® DPP-Pd and $K_2CO_3$:

A mixture of bromo compound (51 mg, 0.2 mmol, 1.0 equiv.), boronic acid (0.22 mmol, 1.1 equiv.), and SiliaCat® DPP-Pd (0.25 mmol/g loading, 34 mg, 0.01 mmol, 0.05 equiv.) was treated with 660 μL dioxane and 220 μL 1 M aq. $K_2CO_3$ and the resulting mixture was allowed to heat overnight at 100 cc in a capped vial. The resulting black mixture was dry-loaded onto silica gel and was purified by silica gel chromatography, eluting with hexanes/EtOAc to give the desired product.

Suzuki Procedure B: $Pd(dppf)Cl_2$ and $K_2CO_3$ in the Microwave:

A mixture of aryl bromide (1.0 equiv.), aryl boronic acid (1.5 equiv.), $K_2CO_3$ (2.5 equiv.), and $Pd(dppf)Cl_2$ (0.05-0.15 equiv.) in THF/water was allowed to heat at 140° C. in a microwave reactor for 40 minutes. Purified by mass-triggered HPLC or silica gel chromatography to provide the desired product.

Suzuki Procedure C: SiliaCat® DPP-Pd/$Pd(dppf)Cl_2$ and $K_2HPO_4$ in the Microwave:

A mixture of aryl bromide (1.0 equiv.), aryl boronic acid (1.5 equiv.), $KH_2PO_4$ (3.5 equiv.), and SiliaCat® DPP-Pd or $Pd(dppf)Cl_2$ (0.05-0.15 equiv.) in THF/water was allowed to heat at 150° C. in a microwave reactor for 40-60 minutes. Purified by mass-triggered HPLC or silica gel chromatography to provide the desired product.

Suzuki Procedure D: $Pd(dppf)Cl_2$, $K_2CO_3$, DME-WATER:

A mixture of aryl bromide (1.0 equiv.), aryl boronic acid (1.5 equiv.), $K_2CO_3$ (3.0 equiv.), and $Pd(dppf)Cl_2$ (0.05-0.15 equiv.) in DME/water was allowed to heat at 110° C. for two hours. Following extraction of the reaction mixture with $CH_2Cl_2$, the combined organic extracts were concentrated and the residue was purified by silica gel chromatography, eluting with hexanes/EtOAc to give the desired product.

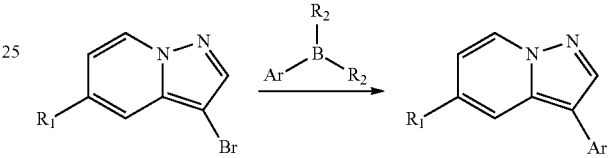

Suzuki Procedure E: $Pd_2(dba)_3$, $P(O-tolyl)_3$, 2M KF Solution in Toluene/Ethanol:

A mixture of aryl bromide (1.0 equiv.), aryl boronic acid (1.2-2.0 equiv.), 2 M aq KF (3 equiv.), and $Pd_2(dba)_3$ (0.1 equiv.), $P(o-tolyl)_3$(0.1 equiv.) in toluene:ethanol (7:3) was degassed and heated to 100° C. for 1-5 h. The crude products were purified by preparative TLC or silica gel chromatography to provide the desired product.

Suzuki Procedure F: $Pd(PPh_3)_4$, 1N $Na_2CO_3$, dioxane:

A mixture of aryl bromide (1.0 equiv.), aryl boronic acid (1.2-2.0 equiv.), 1 N $Na_2CO_3$ (2.0 equiv.), and $Pd(PPh_3)_4$ (0.2 equiv.) in 1,4-dioxane was degassed and heated in a sealed tube to 100° C. (microwave or conventional heating) for 2-6 h. The crude products were purified by preparative TLC or silica gel chromatography to provide the desired product.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

Compounds of the invention are useful in the treatment and/or prevention of infections such as those caused by *Plasmodium falciparum; Plasmodium vivax; Plasmodium ovale*; and *Plasmodium malaria, Trypanosoma cruzi* and parasites of the *Leishmania* genus, such as, for example, *Leishmania donovani*.

*Plasmodia* spp. which causes malaria belong to the phylum, Apicomplexa, which is a large and diverse group of protists that are human or animal parasites. These parasites are unicellular, spore-forming, and possess motile structures such as flagella or pseudopods at certain gamete stages. Most of these parasites possess a unique organelle called apicoplast and an apical complex structure involved in penetrating a host's cell. The pathogenesis associated the diseases caused by these parasites is due to repeated cycles of host-cell invasion, intracellular replication and host-cell lysis. Therefore, understanding parasite proliferation is essential for development of novel drugs and vaccines, for example, to treat malaria.

In vertebrate hosts, the parasite undergoes two main phases of development, the hepathocytic and erythrocytic phases, but it is the erythrocytic phase of its life cycle that causes severe pathology. During the erythrocytic phase, the parasite goes through a complex but well synchronized series of stages, suggesting the existence of tightly regulated signaling pathways.

Calcium serves as an intracellular messenger to control synchronization and development in the erythrocytic life phase. The *Plasmodium* spp. genomes reveal many sequence identities with calcium binding/sensing protein motifs that include Pf39, calmodulin, and calcium dependent protein kinases (CDPKs). *Plasmodium* CDPKs, *Plasmodium* CDPK3 and 4, have been shown to be involved in mosquito infection. CDPK4 has been demonstrated to be essential for the sexual reproduction in the midgut of mosquito by translating the calcium signal into a cellular response and regulating cell cycle progression in the male gametocyte. CDPK3 regulates ookinete gliding motility and penetration of the layer covering the midgut epithelium. *P. falciparum* CDPK1 (PfCDPK1) is expressed during late schizogony of blood stage and in the infectious sporozoite stage and is secreted to the parasitophorous vacuole by an acylation-dependent mechanism. It can be myristoylated and is abundantly found in detergent-resistant membrane fractions isolated from schizogony-phase parasites. Ontology based pattern identification analysis reveals that PfCDPK1 is clustered with genes associated with either parasite egress or erythrocyte invasion. Direct inhibition of PfCDPK1 can arrest the parasite erythrocytic life cycle progression in the late schizogony phase.

Therefore, kinase activity is distributed in all the stages of *P. falciparum* parasite maturation and kinase inhibitors of the present invention can be used for treating *Plasmodium* related diseases.

The in vitro cellular assay, infra, can be used to assess the activity of compounds of the invention against a variety of malarial parasite strains.

In accordance with the foregoing, the present invention further provides a method for preventing or treating malaria in a subject in need of such treatment, which method comprises administering to the subject a therapeutically effective amount of a compound selected from Formula I and Ia or a pharmaceutically acceptable salt, tautomer or stereoisomer, thereof. The required dosage will vary depending on the mode of administration, the particular condition to be treated and the effect desired.

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). Non-limiting examples of compounds which can be used in combination with compounds of the invention are known anti-malarial drugs, for example, artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine, etc.

Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Biological Assays

The activity of a compound according to the present invention for inhibition of parasitemai in infected blood cells and liver cells can be assessed by the following assays. It is understood that the assays illustrate the invention without in any way limiting the scope of the invention.

Assay for P. falciparum Proliferation in Infected Human Blood Cells

Compounds of the invention can be assayed to measure their capacity to inhibit proliferation of P. falciparum parasitemia in infected red blood cells. This parasite proliferation assay measures the increase in parasite DNA content using a DNA intercalating dye, SYBR Green® (INVITROGEN®) which has a high affinity for double stranded DNA.

NF54 or 3D7 P. falciparum strain is grown in complete culturing media until parasitemia reaches 3% to 8% with O+ human erythrocytes. The selection of either strain is of convenience (3D7 is a clone of NF54) and does not make a difference to the assay. 20 μl of screening media is dispensed into 384 well assay plates. 50 nl of compounds of the invention (in DMSO), including antimalarial controls (mefloquine, pyrimethamine and artemisinin), are then transferred into the assay plates, as well as DMSO alone to serve as a negative control for inhibition. Then 30 μl of a suspension of a NF54 or 3D7 P. falciparum infected erythrocytes in screening media is dispensed into the assay plates such that the final hematocrit is 2.5% with a final parasitemia of 0.3%. The plates are placed in a 37° C. incubator for 72 hours in a low oxygen environment containing 93% $N_2$, 4% $CO_2$, and 3% $O_2$ gas mixture. 10 μl of lysis buffer (saponin, triton-X, EDTA) containing a 10× solution of SYBR Green I® in RPMI media is dispensed into the plates. The plates are lidded and kept at room temperature overnight for the lysis of the infected red blood cells. The fluorescence intensity is measured (excitation 425 nm, emission 530 nm) using the Envision™ system (Perkin Elmer). The percentage inhibition of 50%, $EC_K$, is calculated for each compound.

Using the P. falciparum Proliferation Assay above, compounds of the invention exhibit inhibitory efficacy ($EC_{50}$) of typically 10 μM or less, more typically less than 1 μM, most typically less than 200 nM. Compounds of the invention can significantly delay the increase in P. falciparum parasitemia. For example, 3-(4-carbamoylphenyl)-N-(5-cyanopyridin-2-yl)-N-methylpyrazolo[1,5-a]pyridine-5-carboxamide (Example 32), N-(4-cyanophenyl)-N-methyl-3-(1H-pyrrolo[2,3-b]pyridin-5-yl)pyrazolo[1,5-a]pyridine-5-carboxamide (Example 40), 3-(6-aminopyridin-3-yl)-N-(4-cyanophenyl)-N-methylpyrazolo[1,5-a]pyridine-5-carboxamide (Example 41), (R)-3-(4-(2-aminopropanam ido)phenyl)-N-(4-cyanophenyl)-N-methylpyrazolo[1,5-a]pyridine-5-carboxamide (Example 44), N-(5-cyanopyridin-2-yl)-N-methyl-3-(1H-pyrrolo[2,3-b]pyridin-5-yl)pyrazolo[1,5-a]pyridine-5-carboxamide (Example 53), N-(5-cyanopyridin-2-yl)-N-methyl-3-(4-(methylcarbamoyl)phenyl)pyrazolo[1,5-a]pyridine-5-carboxamide (Example 75), and 3-(2-aminopyrimidin-5-yl)-N-(4-cyanophenyl)-N-methylpyrazolo[1,5-a]pyridine-5-carboxamide (Example 83) all have $EC_K$ values of less than 5 nM.

The inhibitory efficacy of the compounds of the invention in delaying the increase in P. falciparum parasitemia in infected human blood cells is provided in Table 1.

TABLE 1

Inhibitory Efficacy of Compounds of the Invention in delaying P. falciparum Proliferation in Infected Human Blood Cells

| Example No. | EC50 (nM) |
| --- | --- |
| 1 | 8 |
| 2 | 342 |
| 3 | 94 |
| 4 | 46 |
| 5 | 88 |
| 6 | 284 |
| 7 | 975 |
| 8 | 532 |
| 9 | 6 |
| 10 | 7 |
| 11 | 6 |
| 12 | 9 |
| 13 | 8 |
| 14 | 134 |
| 15 | 2318 |
| 16 | 477 |
| 17 | 3 |
| 18 | 3 |
| 19 | 1 |
| 20 | 9 |
| 21 | 472 |
| 22 | 25 |
| 23 | 2 |
| 24 | 10 |
| 25 | 7 |
| 26 | 22 |
| 27 | 10 |
| 28 | 7 |
| 29 | 150 |
| 30 | 62 |
| 31 | 143 |
| 32 | 1 |
| 33 | 59 |
| 34 | 22 |
| 35 | 2044 |
| 36 | 390 |
| 37 | 121 |
| 38 | 179 |
| 39 | 831 |
| 40 | 1 |
| 41 | 2 |
| 42 | 18 |
| 43 | 9 |
| 44 | 1 |

TABLE 1-continued

Inhibitory Efficacy of Compounds of the Invention in delaying
*P. falciparum* Proliferation in Infected Human Blood Cells

| Example No. | EC50 (nM) |
| --- | --- |
| 45 | 16 |
| 46 | 18 |
| 47 | >9000 |
| 48 | 288 |
| 49 | 2290 |
| 50 | 3850 |
| 51 | 60 |
| 52 | 13 |
| 53 | 1 |
| 54 | 9 |
| 55 | 32 |
| 56 | 8 |
| 57 | 4 |
| 58 | 30 |
| 59 | 228 |
| 60 | 683 |
| 61 | 20 |
| 62 | ND |
| 63 | 6 |
| 64 | 20 |
| 65 | 504 |
| 66 | 49 |
| 67 | 5 |
| 68 | 6750 |
| 69 | 13 |
| 71 | 3 |
| 72 | 5 |
| 73 | >10,000 |
| 74 | 52 |
| 75 | 4 |
| 76 | 82 |
| 77 | 146 |
| 79 | 7 |
| 80 | 824 |
| 81 | 36 |
| 82 | 1160 |
| 83 | 4 |
| 84 | 6 |
| 85 | 16 |
| 86 | 10 |
| 87 | 41 |
| 88 | 83 |
| 89 | 6 |

Assay for Profiferation of Parasite in Infected Liver Cells

Compounds of the invention can be assayed to measure their capacity to inhibit proliferation of parasites in liver cells. The proliferation is quantified by determine the number of infected cells by immunofluorescence.

Parasites

Due to the difficulty of successfully infecting immortalized human liver cell lines with the human malaria sporozoites (liver-stage parasite), rodent malaria sporozoites from *Plasmodium yoelii* (17XNL) and *P. berghei* (ANKA) are the preferred surrogate. Sporozoites are obtained from *Anopheles stephensi* mosquitoes supplied by the New York University Insectary, which ships the malaria-infected mosquitoes 10-13 days following the ingestion of an infective blood meal.

Cell Line

A transgenic HepG2 cell line expressing the tetraspanin CD81 receptor (HepG2-A16-CD81$^{EGFP}$) is used to increase the infectivity rate of rodent-malaria sporozoites into human cells. HepG2-A16-CD81$^{EGFP}$ cells are stably transformed to express a GFP-CD81 fusion protein. A continuous in vitro culture of this line was maintained at 37° C. in 4% $CO_2$ in complete media (CM) which contains: DMEM (Invitrogen, Carlsbad, USA) supplemented with 10% FCS, 0.29 mg/ml glutamine, 100 units penicillin and 100 µg/ml streptomycin (SigmaAldrich, USA).

*P. yoelii* Sporozoite Invasion Assay

Twenty to twenty-six hours prior to sporozoite infection, 7.5×10$^3$ HepG2-A16-CD81$^{EGFP}$ cells are seeded into 384-well plates (Aurora 384 IQ-EB black plates with clear bottoms; 50 µl of 1.5×10$^5$ cells/ml in CM). These plates are incubated at 37° C. with 4% $CO_2$ overnight. Two hours prior to infection, 50 nl of compound dissolved in DMSO (0.1% final DMSO concentration per well) were transferred with a PinTool (GNF Systems) into the assay plates (10 µM final concentration). A 1:3 serial dilution of atovaquone (10 µM at the highest final concentration) and wells treated only with DMSO were used as positive and negative controls, respectively.

Freshly dissected salivary glands from infected mosquitoes were homogenized in a glass tissue grinder, filtered twice through Nylon cell strainers (40 µm pore size, BD Falcon) and counted using a hemocytometer. The assay plate with HepG2-A16-CD81$^{EGFP}$ cells and compound were then infected with 8×10$^3$ sporozoitesper well and the plates are subjected to a centrifugal force of 650×g to pellet the sporozoites onto the liver cell monolayer. The assay plate is incubated at 37° C. for 2 hours to permit sporozoite invasion, then the media is aspirated from the media plate, and replaced with 50 µl CM (containing a 5× concentration of penicillin/streptomycin; 500 units penicillin and 0.5 mg streptomycin per ml) per well. 50 nl of compound is re-introduced by PinTool and the assay plate incubated for 48 hours at 37° C. before quantification of infected cells by immunofluorescence. The increased antibiotic concentration does not interfere with the parasite or HepG2-A16-CD81$^{EGFP}$ growth.

Atovaquone and uninfected wells were used as controls on each plate. Two replicate plates are tested for each assay.

Immunofluorescence Quantification of Exo-Erythrocytic Forms (EEFs)

After fixing the cells by addition of 12.5 µl of 20% solution of paraformaldehyde (EMS, Hatfield, USA) to each assay well (4% final formaldehyde concentration), membranes were permeabilized with 0.5% Triton-X-100 (Thermo Fisher Scientific) and EEFs were stained using a mouse polyclonal serum raised against the *Plasmodium yoelii* heat shock protein 70 (PyHSP70), a DyLight 649 goat anti-mouse IgG, Fc(gamma) fragment specific secondary antibody (Jackson Immuno Research, Cat#115-495-071) and the Hoechst 33342 nucleic acid dye (Invitrogen, Carlsbad, USA). Stained EEFs were then quantified using the Opera Confocal High Content Screening System (Perkin Elmer, Waltham, USA). Images were collected using a 20× objective lens (20×/0.45 NA, LWD Plan Fluor, Olympus) at a binning of 2, using a 365 nm Xeon arc lamp illumination to detect the Hoechst-labeled nuclei and 635 nm laser line to excite DyLight649-labeled parasites. The image resolution yielded was approximately 0.66 µm/pixel (~0.43 µm 2/pixel). All images were analyzed using a custom Acapella™ (PerkinElmer) script parametrized for this assay. In brief, images from fields inside the well were first discarded as out-of focus when the intensity in the nuclear channel was too low. Then, HepG2-A16-CD81$^{EGFP}$ cells were counted by detecting the nuclei labeled with Hoechst using the nuclei detection libraries available with Acapella™. Parasites were later segmented using the aPyHSP70 immuno-labeling signal, using a custom script library. Once the objects were segmented from the picture, morphological-based (e.g. size, roundness, etc) and intensity-based features were measured for each object detected in the image (i.e. nuclei and parasites). Infection ratio was set as the ratio between parasite number and number of nuclei counted in images considered as "in-focus". $EC_{50}$ values were obtained using parasite area and a custom curve fitting model, and a standard logistic regression model was applied for curve fitting.

Using the *P. yoelii* Sporozoite Invasion Assay, compounds of the invention exhibit inhibitory efficacy ($EC_{50}$) of typically 500 nM or less, more typically less than 200 nM, most typically less than 10 nM. Compounds of the invention show significantly delay of the proliferation of *P. yoelii* in liver cells. For example N-(4-cyanophenyl)-N-methyl-3-(4-(trifluoromethyl)phenyl)pyrazolo[1,5-a]pyridine-5-carboxamide (Example 1), 3-(4-carbamoylphenyl)-N-(4-cyanophenyl)-N-methylpyrazolo[1,5-a]pyridine-5-carboxamide (Example 19), 3-(4-carbamoylphenyl)-N-(5-cyanopyridin-2-yl)-N-methylpyrazolo[1,5-a]pyridine-5-carboxamide (Example 32), 3-(4-carbamoylphenyl)-N-(5-cyanopyridin-2-yl)-N-methylpyrazolo[1,5-a]pyridine-5-carboxamide (Example 67), and N-(5-cyanopyridin-2-yl)-N-methyl-3-(4-(methylcarbamoyl)phenyl)pyrazolo[1,5-a]pyridine-5-carboxamide (Example 75) all have $EC_{50}$ of less than 10 nM.

Inhibitory efficacy of selected compounds in delaying the proliferation of *P. yoelii* Sporozoite in liver cells is listed in Table 2.

TABLE 2

Inhibitory Efficacy of Compounds of the Invention by the *P. yoelii* Sporozoite Invasion Assay

| Example No. | $EC_{50}$ (nM) |
| --- | --- |
| 1 | 7.3 |
| 13 | 17.9 |
| 19 | 4.3 |
| 20 | 13.5 |
| 25 | 229 |
| 27 | 201 |
| 28 | 23.2 |
| 32 | 8.0 |
| 34 | 53.2 |
| 40 | 63.1 |
| 41 | 14.3 |
| 54 | 79 |
| 67 | 4.6 |
| 75 | 2.25 |

EXAMPLES

The present invention is further exemplified, but not to be limited, by the following examples and intermediates that illustrate the preparation of compounds of the invention. It is understood that if there appears to be a discrepancy between the name and structure of a particular compound, the structure is to be considered correct as the compound names were generated from the structures.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

LC-MS Methods

Method 1:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) $H_2O$+0.025% TFA and (B) Acetonitrile+0.025% TFA. Gradient: 0.4 mL/minute, initial 15% B ramp to 95% B over 3.0 minutes, then hold until 4.0 minutes, return to 15% B at 4.1 minutes until end of run, then equilibrated the column for 2.0 minutes; MS Scan: 100 to 1000 amu in 0.5 seconds per channel; Diode Array Detector: 200 nm and 400 nm.

Method 2:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) $H_2O$+0.025% TFA and (B) Acetonitrile+0.025% TFA. Gradient: 0.4 mL/minute, initial 20% B ramp to 90% B over 2.0 minutes, then hold until 4.0 minutes, return to 20% B at 4.1 minutes until end of run, then equilibrated the column for 2.0 minutes; MS Scan: 100 to 1000 amu in 0.5 seconds per channel; Diode Array Detector: 200 nm and 400 nm.

Method 3:

Waters Acquity Binary Gradient Pump; Waters Acquity PDA Detector. Waters Auto sampler; Waters Acquity Evaporative Light Scattering Detector; Waters Quattro micro API Mass Spectrometer with ESI and APCI ion source; UPLC Column: Waters Acquity; BEH; C18 1.7 um 100×2.1 mm; Mobile Phase: (A) $H_2O$+0.025% TFA and (B) Acetonitrile+0.025% TFA. Gradient: 0.3 mL/minute, initial 10% B ramp to 80% B over 4.0 minutes, then hold until 6.0 minutes, return to 10% B at 6.1 minutes until end of run, then equilibrated the column for 2.5 minutes; MS Scan: 100 to 1000 amu in 0.5 seconds per channel; Diode Array Detector: 200 nm and 400 nm; Drift tube temperature: 50° C. and N2 gas flow: 40 Psi for ELSD Detector.

Method 4:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) H2O+0.025% TFA and (B) Acetonitrile+0.025% TFA. Gradient: 0.4 mL/minute, initial 20% B ramp to 80% B over 2.0 minutes, then hold until 4.0 minutes, return to 20% B at 4.1 minutes until end of run, then equilibrated the column for 2.0 minutes; MS Scan: 100 to 1000 amu in 0.5 seconds per channel; Diode Array Detector: 200 nm and 400 nm Method 5:

Waters Acquity Binary Gradient Pump; Waters Acquity PDA Detector. Waters Auto sampler; Waters Quattro micro API Mass Spectrometer with ESI and APCI ion source; UPLC Column: Waters Acquity; BEH; C18 1.7 um 50×2.1 mm; Mobile Phase: (A) H2O+0.025% TFA and (B) Acetonitrile+0.025% TFA. Gradient: 0.4 mL/minute, initial 10% B ramp to 80% B over 3.0 minutes, then hold until 4.0 minutes, return to 20% B at 4.1 minutes until end of run, then equilibrated the column for 2.0 minutes; MS Scan: 100 to 1000 amu in 0.5 seconds per channel; Diode Array Detector: 200 nm and 400 nm Method 6:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters X-Terra; MS; C18; 2.5 um 50×4.6 mm; Mobile Phase: (A) 0.01M Ammonium Bicarbonate in Water and (B) Acetonitrile; Gradient: 1 mL/minute, initial 50% B, ramp to 80% B over 4.0 minutes, and hold until 6.0 minutes, return to 50% B at 6.1 minutes until end of run. The column is re-equilibrated for 3 minutes. MS Scan: 100 to 1200 amu; Diode Array Detector: 200 nm-400 nm.

Method 7:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters X-Bridge; C18; 3.5 um 150× 4.6 mm; Mobile Phase: (A) 0.01M Ammonium Bicarbonate in Water and (B) Acetonitrile; Gradient: 1 mL/minute, initial 20% B, ramp to 80% B over 4.0 minutes, and hold until 8.0 minutes, return to 20% B at 8.1 minutes until end of run. The column is re-equilibrated for 3 minutes. MS Scan: 100 to 1200 amu; Diode Array Detector: 200 nm-400 nm.

Method 8:

Agilent G1379A Degasser; Agilent G1312A Binary Pump; Agilent G1315C Diode Array Detector; Agilent G1367A Auto sampler; Agilent Ion Trap Mass Spectrometer with ESI source; HPLC Column: Waters Symmetry; C18; 3.5 um 75×4.6 mm; Mobile Phase: (A) H$_2$O+0.1% Formic acid and (B) Acetonitrile+0.1%/oFormic acid; Gradient: 1 mL/minute, initial 20% B, ramp to 80% B over 4.0 minutes, and hold until 7.0 minutes, return to 20% B at 7.1 minutes until end of run. The column is re-equilibrated for 3 minutes. MS Scan: 100 to 1200 amu; Diode Array Detector: 200 nm-400 nm.

Intermediate 1-1

Methyl 3-(4-(trifluoromethyl)phenyl)pyrazolo[1,5-a]pyridine-5-carboxylate

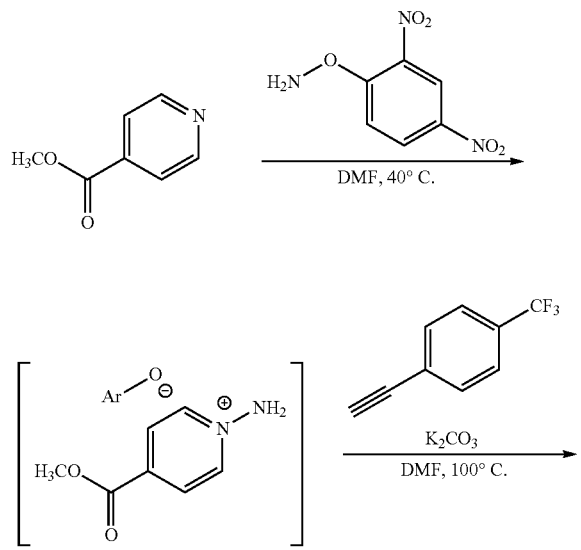

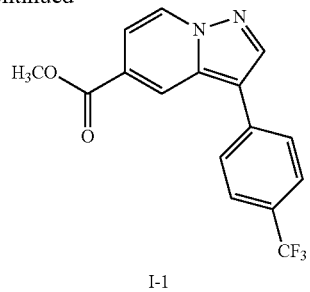

To a solution of methyl isonicotinate (500 μL, 4.23 mmol, 1.0 equiv.) in 2 mL DMF was added O-(2,4-dinitrophenyl)hydroxylamine (1 g, 5.02 mmol, 1.2 equiv.) and the resulting solution was allowed to stir overnight at 40° C., during which time the reaction became heterogeneous. The mixture was allowed to cool to rt before being diluted with 10 mL DMF, then treated with 4-ethynyl-α,α,α-trifluorotoluene (863 μL, 5.29 mmol, 1.25 equiv.) and potassium carbonate (877 mg, 6.35 mmol, 1.5 equiv.). The mixture was allowed to stir overnight at 100° C. The resulting mixture was allowed to cool to rt, and then the solvent was removed under reduced pressure. The residue was diluted with water and the aqueous layer was extracted with EtOAc five times. The combined EtOAc extracts were washed once with water, once with brine, and then dried with MgSO$_4$, filtered, and the solvent removed under reduced pressure. The material was purified by silica gel chromatography, eluting with hexanes/EtOAc (R$_f$=0.26 in 5:1 hexanes/EtOAc) to give 335 mg (25% yield) I-1. $^1$H NMR (400 MHz, CDCl$_3$, δ): 8.52 (m, 2H), 8.23 (s, 1H), 7.72 (s, 4H), 7.40 (dd, J=1.59, 7.50 Hz, 1H), 3.96 (s, 3H).

Intermediate 1-2

3-(4-(trifluoromethyl)phenyl)pyrazolo[1,5-a]pyridine-5-carboxylic acid

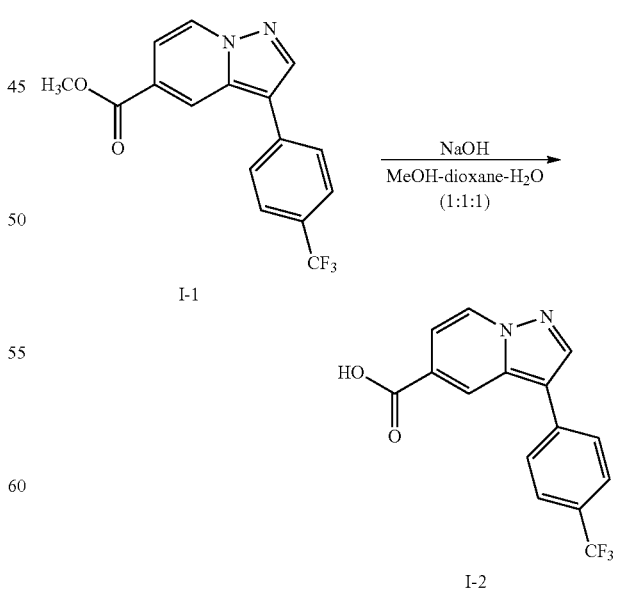

A solution of ester (320 mg, 1 mmol, 1.0 equiv.) in 3 mL 1:1 MeOH-dioxane was treated with 1 N aq. NaOH (1.5 mL, 1.5 mmol, 1.5 equiv.) dropwise over a few minutes, during which time the reaction became heterogeneous. The thick mixture was allowed to stir well at room temperature until complete (approximately three hours). As the reaction progressed, it became homogeneous. The resulting solution was diluted with 6 mL water, then was treated with 1 N aq. HCl (1.5 mL, 1.5 mmol, 1.5 equiv.) dropwise over a few minutes and allowed to stir well several minutes more to break up any clumps. The mixture was filtered and the filter cake was rinsed with water, followed by hexanes. The solid was dried under high vacuum overnight to provide 1-2 (quant.).

Intermediate 1-3

3-ethyl 5-methylpyrazolo[1,5-a]pyridine-3,5-dicarboxylate

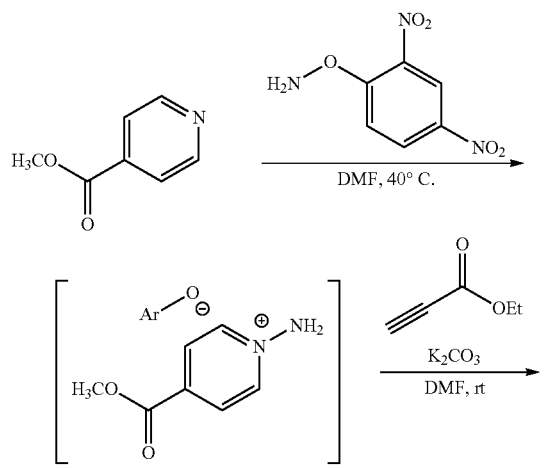

To a solution of methyl isonicotinate (500 μL, 4.23 mmol, 1.0 equiv.) in 2 mL DMF was added O-(2,4-dinitrophenyl) hydroxylamine (1 g, 5.02 mmol, 1.2 equiv.) and the solution was allowed to stir overnight at 40° C., during which time the reaction became heterogeneous. The mixture was allowed to cool to room temperature before being diluted with 10 mL DMF, then treated with ethyl propiolate (536 μL, 5.29 mmol, 1.25 equiv.) and potassium carbonate (877 mg, 6.35 mmol, 1.5 equiv.). The mixture was allowed to stir overnight at rt. After the solvent was removed under reduced pressure, the residue was diluted with water and the aqueous layer was extracted with EtOAc five times. The combined EtOAc extracts were washed once with water and once with brine, then dried with MgSO$_4$, filtered, and the solvent was removed under reduced pressure. The material was purified by silica gel chromatography, eluting with hexanes/EtOAc to give 778 mg (74% yield) of I-3. $^1$H NMR (400 MHz, CDCl$_3$) δ 8.86 (dd, J=0.9, 1.8, 1H), 8.55 (dd, J=0.9, 7.2, 1H), 8.47 (s, 1H), 7.52 (dd, J=1.8, 7.2, 1H), 4.42 (q, J=7.1, 2H), 3.99 (s, 3H), 1.44 (t, J=7.1, 3H).

Intermediate 1-4

Pyrazolo[1,5-a]pyridine-5-carboxylic acid

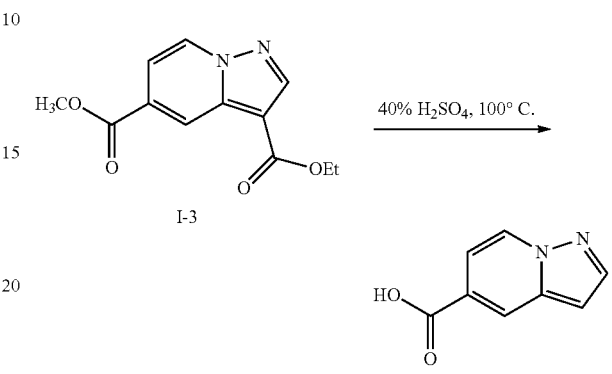

A suspension of diester (8.5 g, 34.2 mmol, 1.0 equiv.) in 150 mL 40% H$_2$SO$_4$ was allowed to heat at 100° C. overnight in a septum-capped vial fitted with a needle outlet to an empty balloon to accommodate the gas evolution. The resulting solution was allowed to cool to rt, then placed in a cold water bath before bringing to approx. pH=2 with NaOH. During this pH adjustment, the acid precipitated and was isolated by filtration. The solid was washed with water, and then dried under high vacuum overnight to provide acid 1-4. $^1$H NMR (400 MHz, DMSO) δ 12.5 (br s, 1H), 8.74 (d, J=7.3, 1H), 8.34 (m, 1H), 8.11 (d, J=2.3, 1H), 7.25 (dd, J=1.9, 7.3, 1H), 6.89 (dd, J=0.8, 2.3, 1H).

Intermediate 1-5

Methyl pyrazolo[1,5-a]pyridine-5-carboxylate

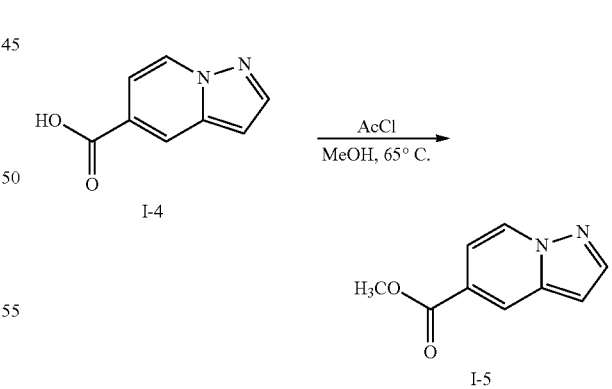

A solution of acid (200 mg, 1.23 mmol, 1.0 equiv.) in 3.7 mL MeOH was allowed to cool to 0° C., then AcCl (370 μL) was added dropwise with efficient stirring. The resulting solution was allowed to warm to rt, then allowed to heat at 65° C. overnight in a sealed vial. The resulting solution was allowed to cool to rt before the solvent was evaporated. The residue was diluted with EtOAc, and then washed with saturated aq. NaHCO$_3$ and brine, dried with MgSO$_4$, filtered, and the solvent was removed under reduced pressure to give 110 mg of the desired ester 1-5, which was taken on without further purification.

and the solvent removed under reduced pressure to give the desired acid 1-7, which was taken on without further purification.

Intermediate 1-6

Methyl 3-bromopyrazolo[1,5-a]pyridine-5-carboxylate

Intermediate 1-8

3-bromo-N-(4-cyanophenyl)-N-methylpyrazolo[1,5-a]pyridine-5-carboxamide

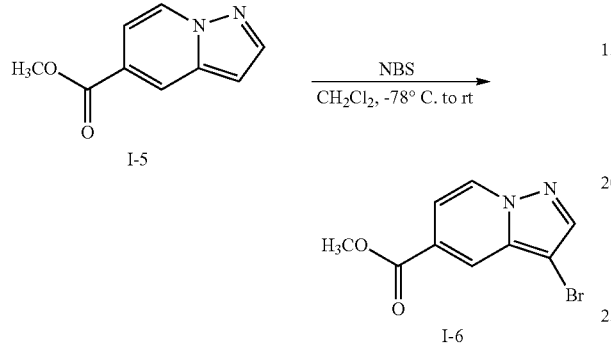

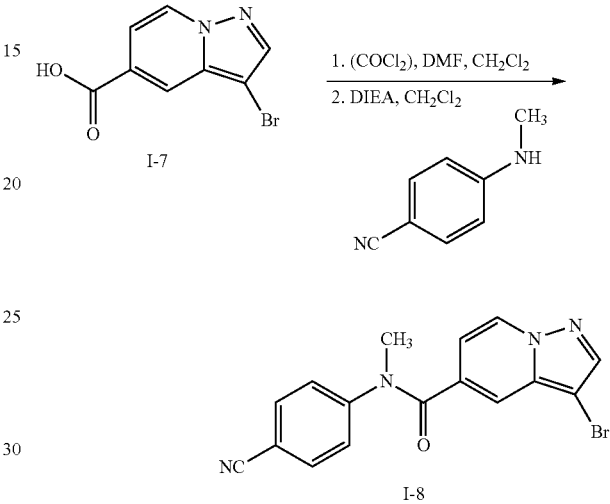

A solution ester (110 mg, 0.62 mmol, 1.0 equiv.) in 6.3 mL CH$_2$Cl$_2$ was allowed to cool to −78° C., then NBS (110 mg, 0.62 mmol, 1.0 equiv.) was added in one portion. The resulting mixture was allowed to warm to rt and then stir at that temperature for one hour. The solvent was removed under reduced pressure and the resulting material was purified by silica gel chromatography, eluting with hexanes/EtOAc to give 1-6. $^1$H NMR (400 MHz, CDCl$_3$, δ): 8.43 (dd, J=0.80, 7.28, 1H), 8.27 (m, 1H), 7.99 (s, 1H), 7.36 (dd, J=1.83, 7.30 Hz, 1H), 3.96 (s, 3H).

Intermediate 1-7

3-bromopyrazolo[1,5-a]pyridine-5-carboxylic acid

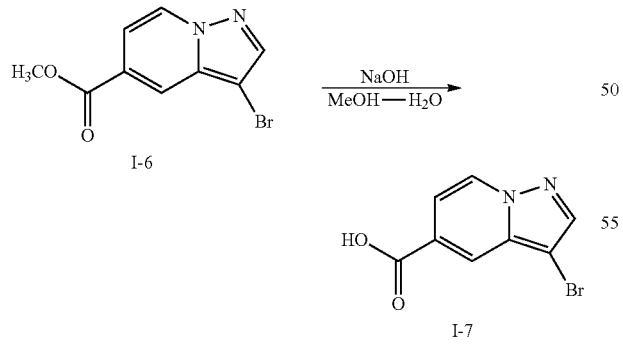

A solution of ester (195 mg, 0.764 mmol, 1.0 equiv.) in 4 mL MeOH was treated with 1 N aq. NaOH (2 mL, 2.0 mmol, 2.6 equiv.) at rt, and then allowed to stir at rt for one hour. Concentrated under reduced pressure, then diluted with water and acidified with 4 N aq. HCl. Extracted 3×10 mL EtOAc, dried the combined organic extracts with Na$_2$SO$_4$, filtered A solution of acid (1.0 equiv.) in CH$_2$Cl$_2$ (~0.05-0.1 M) was treated with oxalyl chloride (2.0-3.0 equiv.) and a catalytic amount of DMF. The resulting solution was allowed to stir at rt for between five minutes and one hour, then was concentrated and dried briefly under high vacuum. The resulting acid chloride was diluted with CH$_2$Cl$_2$ (~0.05-0.1 M), and to this solution was added 4-cyano-N-methylaniline (1.1-3.0 equiv.) and either DIEA or Et$_3$N (3.0 equiv.). The resulting mixture was allowed to stir at room temperature until complete conversion (generally less than three hours). The solvent was removed under reduced pressure, and the residue was purified by silica gel chromatography.

Intermediate 1-9

3-bromo-N-(5-cyanopyridin-2-yl)-N-methylpyrazolo[1,5-a]pyridine-5-carboxamide

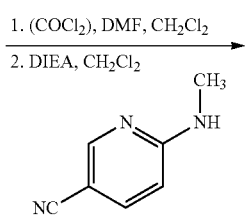

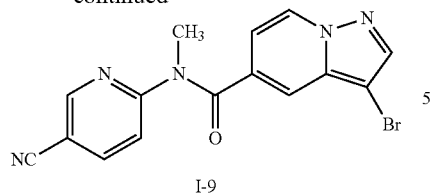

I-9

Intermediate I-9 was prepared according to the procedure described for the synthesis of intermediate I-8 by replacing 4-(methylamino)benzonitrile with 6-(methylamino)nicotinonitrile.

Intermediate I-10

3-bromo-N-methyl-N-(5-(methylsulfonyl)pyridin-2-yl)pyrazolo[1,5-a]pyridine-5-carboxamide

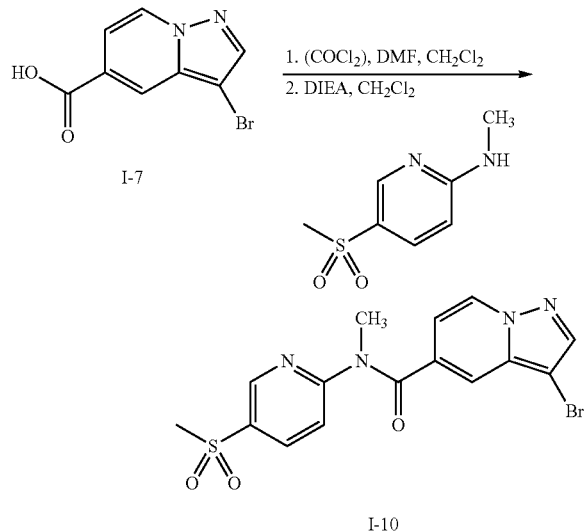

Intermediate I-10 was prepared according to the procedure described for the synthesis of intermediate I-8 by replacing 4-(methylamino)benzonitrile with N-methyl-5-(methylsulfonyl)pyridin-2-amine.

Intermediate I-11

3-bromo-N-methyl-N-(5-(trifluoromethyl)pyridin-2-yl)pyrazolo[1,5-a]pyridine-5-carboxamide

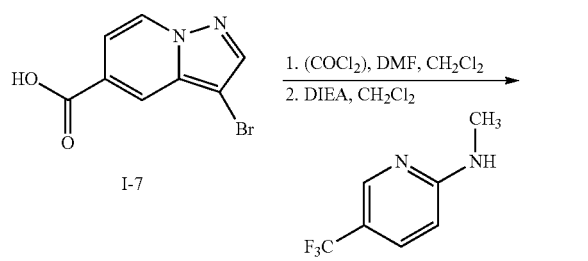

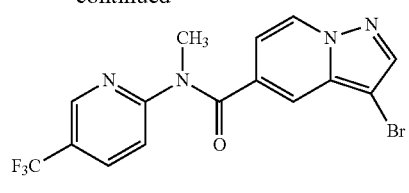

I-11

Intermediate I-11 was prepared according to the procedure described for the synthesis of intermediate I-8 by replacing 4-(methylamino)benzonitrile with N-methyl-5-(trifluoromethyl)pyridin-2-amine.

Intermediate I-12

3-bromo-N-methyl-N-(5-methylpyridin-2-yl)pyrazolo[1,5-a]pyridine-5-carboxamide

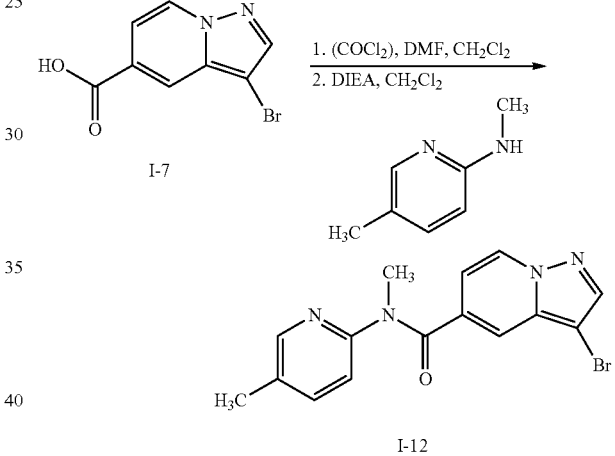

Intermediate I-12 was prepared according to the procedure described for the synthesis of intermediate I-8 by replacing 4-(methylamino)benzonitrile with N,5-dimethylpyridin-2-amine.

Intermediate I-13

3-bromo-N-(4-fluorophenyl)-N-methylpyrazolo[1,5-a]pyridine-5-carboxamide (Example 64)

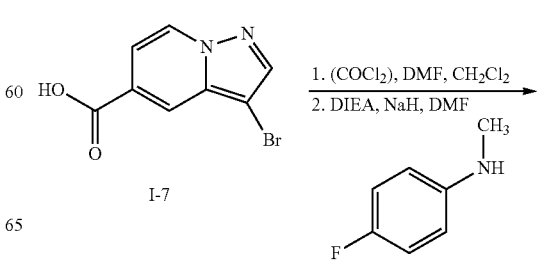

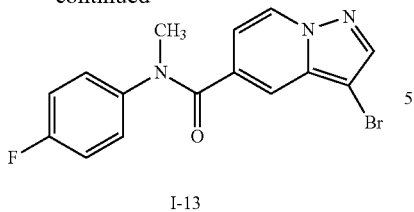

I-13

Intermediate I-13 was prepared according to the procedure described for the synthesis of intermediate I-8 by replacing 4-(methylamino)benzonitrile with 4-fluoro-N-methylaniline. $^1$H NMR (400 MHz, METHANOL-$d_4$) δ 3.49 (s, 3H) 6.80 (d, J=7.53 Hz, 1H) 7.00-7.14 (m, 2H) 7.24-7.37 (m, 2H) 7.50 (s, 1H) 7.97 (s, 1H) 8.38 (d, J=7.28 Hz, 1H); ESI-LC/MS (m/z): [M–H]+349.

Intermediate I-14

3-bromo-N-(4-chloro-2-formylphenyl)-N-methylimidazo[1,2-a]pyrazine-6-carboxamide

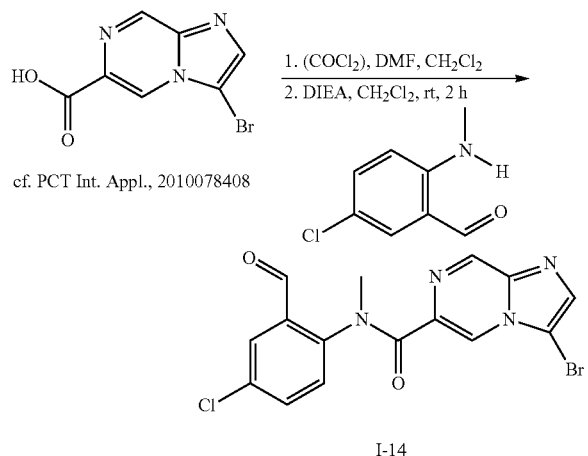

I-14

Intermediate I-14 was prepared according to the procedure described for the synthesis of intermediate I-8 by replacing 4-(methylamino)benzonitrile with 5-chloro-2-(methylamino)benz-aldehyde. $^1$H NMR (400 MHz, CDCL$_3$) δ 10.21 (s, 1H), 8.77 (s, 1H), 8.45-8.48 (m, 1H), 7.77-7.84 (m, 2H), 7.44-7.46 (m, 2H), 7.09-7.11 (m, 1H), 3.52 (s, 3H); ESI-LC/MS (Method 1) (m/z): [M+H]$^+$ 392.89 [M+2H]+394.90 & [M+4H]+396.92.

Intermediate I-15

3-bromo-N-(4-chloro-2-formylphenyl)-N-methylpyrazolo[1,5-a]pyridine-5-carboxamide

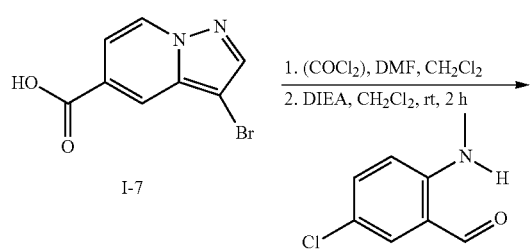

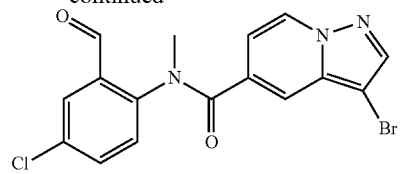

I-15

Intermediate I-15 was prepared according to the procedure described for the synthesis of intermediate I-8 by replacing 4-(methylamino)benzonitrile with 5-chloro-2-(methylamino)benz-aldehyde. $^1$H NMR (400 MHz, CDCL$_3$) δ 10.04 (s, 1H), 8.18-8.28 (m, 1H) 7.90-7.95 (m, 1H) 7.77 (s, 1H) 7.57-7.61 (m, 1H) 7.40 (s, 1H) 6.61 (br. s, 1H) 3.49 (s, 3H); ESI-LC/MS (Method 1) (m/z): [M+H]$^+$ 391.94 & [M+2H]+ 393.89 & [M+4H]+395.91.

Intermediate I-16

3-(4-aminophenyl)-N-(4-cyanophenyl)-N-methylpyrazolo[1,5-a]pyridine-5-carboxamide

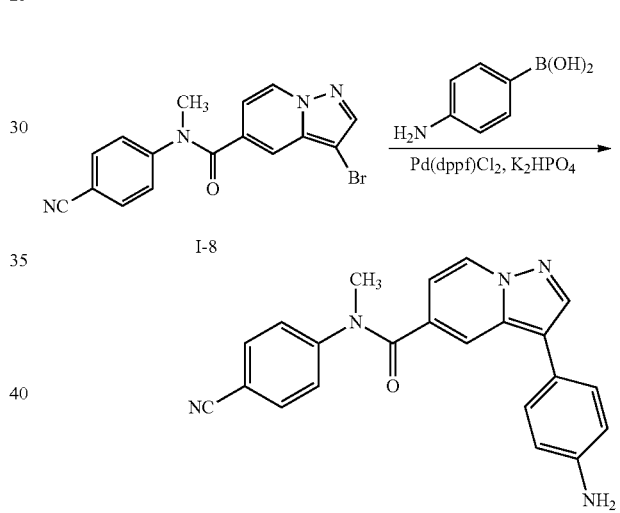

I-16

A mixture of aryl bromide (1.0 equiv.), aryl boronic acid (1.5 equiv.), K$_2$CO$_3$ (2.5 equiv.), and Pd(dppf)Cl$_2$ (0.05-0.15 equiv.) in THF/water was allowed to heat at 140° C. in a microwave reactor for 40 minutes. The resulting mixture was concentrated under reduced pressure and purified by silica gel chromatography to give I-16.

Intermediate I-17

3-bromo-5-ethylpyrazolo[1,5-a]pyridine

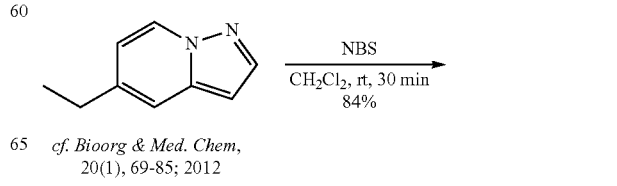

cf. Bioorg & Med. Chem, 20(1), 69-85; 2012

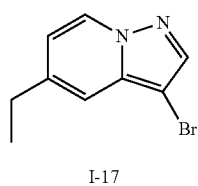

I-17

To a stirred solution of 5-ethylpyrazolo[1,5-a]pyridine (1.1 g, 0.008 mmol) in dichloromethane (10 mL) at 0° C. was added NBS (1.75 g, 0.009 mmol) and reaction mixture was stirred at room temperature for 5 min. Subsequently, water was added and the reaction mixture was extracted with dichloromethane (2×10 mL). The organic layer was washed with water (1×30 mL), sat. NaHCO₃ solution (1×10 mL), brine (1×10 mL), dried over Na₂SO₄ and concentrated to afford 2.1 g (84%) of 3-bromo-5-ethylpyrazolo[1,5-a]pyridine (I-17) as a brownish highly viscous liquid. The crude was progressed to next step without any further purification. ESI-LC/MS (m/z): [M+H]⁺ 225.0, [(M+2)+H]+227.0, RT 2.50 min.

Intermediate I-18

3-bromo-5-(1-bromoethyl)pyrazolo[1,5-a]pyridine

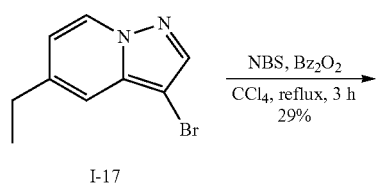

To a stirred solution of 3-bromo-5-ethylpyrazolo[1,5-a]pyridine (I-17, 2.1 g, 0.0094 mmol) in CCl₄ (20 mL) at rt was added NBS (2 g, 0.01 mmol) followed by benzoyl peroxide (1.1 g, 0.004 mmol). The resulting reaction mixture was heated to 77° C. After 2 h, the reaction mixture was allowed to cool to rt and subsequently water (20 mL) was added followed by extraction with dichloromethane (2×20 mL). The combined organic layers were washed with water (1×20 mL), sat NaHCO₃ solution (1×10 mL), brine (1×10 mL), dried over Na₂SO₄ and the solvent was removed under reduced pressure. The resulting crude product was purified by column chromatography over silica gel (petroleum ether/EtOAc, 0-5% EtOAc) to afford 820 mg (29%) of 3-bromo-5-(1-bromoethyl)pyrazolo[1,5-a]pyridine (I-18) as a brown solid. ¹H NMR (400 MHz, CDCl₃) δ 8.45 (d, J=7.91 Hz, 1H), 7.93 (s, 1H), 7.46 (d, J=1.32 Hz, 1H), 6.90-6.92 (dd, J=1.76, 5.71 Hz, 1H), 5.19-5.24 (m, 2H), 2.08 (d, J=7.04 Hz, 3H); ESI-LC/MS (m/z): [M+H]⁺ 302.9, [(M₊2)+H]⁺ 304.9, [(M₊4)+H]⁺ 306.9, RT 2.65 min Intermediate I-19

N-(1-(3-bromopyrazolo[1,5-a]pyridin-5-yl)ethyl)-N,5-dimethylpyridin-2-amine

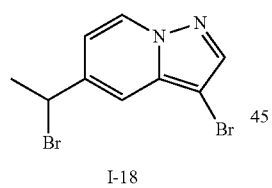

A suspension of 3-bromo-5-(1-bromoethyl)pyrazolo[1,5-a]pyridine (I-18, 400 mg, 1.32 mmol), N,5-dimethylpyridin-2-amine (230 mg, 1.98 mmol) and K₂CO₃ (546 mg, 3.96 mmol) in acetonitrile was heated to 90° C. in a sealed tube for overnight. The reaction mixture was cooled to room temperature and water (10 mL) was added. The aqueous phase was extracted with ethyl acetate (2×10 mL). The combined organic layers were dried over Na₂SO₄ and solvents were removed under reduced pressure. The resulting crude product was purified by column chromatography over silica gel (petroleum ether/EtOAc, 0-4% EtOAc) to afford 210 mg (46%) of N-(1-(3-bromopyrazolo[1,5-a]pyridin-5-yl)ethyl)-N,5-dimethylpyridin-2-amine (I-19) as a yellow solid. ESI-LC/MS (m/z): [M+H]⁺ 345.2, [(M+2)+H]⁺ 347, RT 3.31 min.

Intermediate I-20

(3-bromopyrazolo[1,5-a]pyridin-5-yl)(7-fluoro-2H-benzo[b][1,4]oxazin-4(3H)-yl)methanone

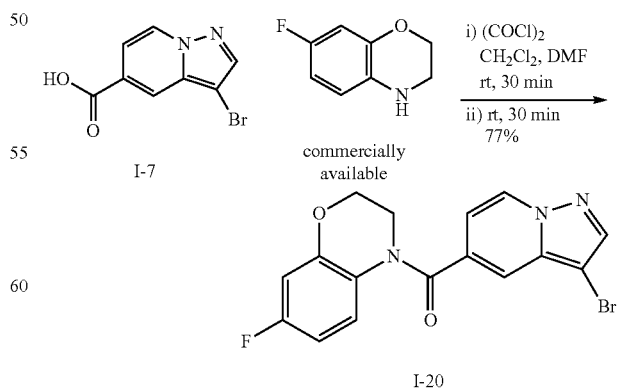

To a solution of 3-bromopyrazolo[1,5-a]pyridine-5-carboxylic acid (I-7, 250 mg, 1.040 mmol) in dichloromethane (10 mL) was added oxalyl chloride (0.25 mL), followed by catalytic amount DMF (0.1 M) at rt and the mixture was stirred for 30 min. The resultant volatiles were removed under reduced pressure to afford a residue of acid chloride. To this residue was added 7-fluoro-3,4-dihydro-2H-benzo[b][1,4]oxazine (191 mg, 1.25 mmol) in dichloromethane (10.0 mL), followed by DIPEA (0.5 mL) and the mixture was stirred at rt for 30 min. The reaction mixture was diluted with dichloromethane (50 mL). The reaction mixture was washed with 1N HCl, sat. NaHCO$_3$ solution, water, brine, dried over Na$_2$SO$_4$, and the solvent was removed under reduced pressure to afford 300 mg (77%) of (3-bromopyrazolo[1,5-a]pyridin-5-yl)(7-fluoro-2H-benzo[b][1,4]oxazin-4(3H)-yl)methanone (I-20) as a brown solid. $^1$H NMR (400 MHz, DMSO-d$_6$) δ 8.87 (d, J=7.68 Hz, 1H), 8.27 (s, 1H), 7.80 (s, 1H), 7.06 (d, J=6.7 Hz, 1H), 6.84 (d, J=10.3 Hz, 1H), 6.65-6.68 (m, 1H), 6.50-6.52 (m, 1H), 4.36 (m, 2H), 3.92 (m, 2H); ESI-LC/MS (m/z): [M+H]$^+$ 376.0, [(M+2)+H]$^+$ 378.0, RT 2.37 min.

Intermediate I-21

2-chloro-N-(4-fluoro-2-hydroxyphenyl)acetamide

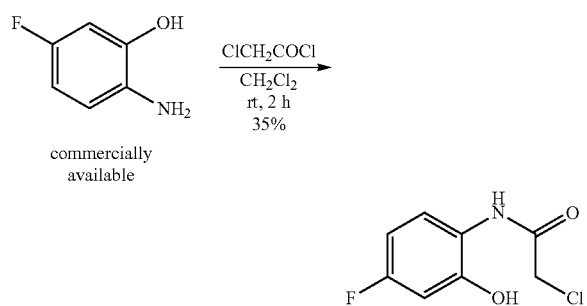

To a solution of 2-amino-5-fluorophenol (1.0 g, 7.87 mmol) in dichloromethane (50 mL) at 0° C. was added 2-Chloroacetyl chloride (978 mg, 8.66 mmol). The reaction mixture was stirred at rt for 2 h, followed by addition of aqueous saturated NaOH solution. The organic layer was washed with brine, dried over Na$_2$SO$_4$ and solvent was removed under reduced pressure to afford 550 mg (35%) of 2-chloro-N-(4-fluoro-2-hydroxyphenyl)acetamide (I-21) as a brown solid. ESI-LC/MS (m/z): (M−H)$^−$ 201.6, RT 2.65 min.

Intermediate I-22

7-fluoro-4-a,5-dihydro-2H-benzo[b][1,4]oxazin-3(4H)-one

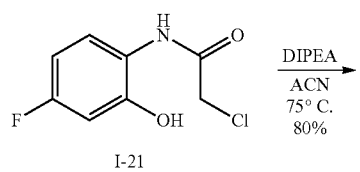

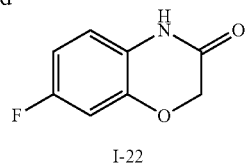

To a solution of 2-chloro-N-(4-fluoro-2-hydroxyphenyl)acetamide (5.5 g, 27 mmol) in acetonitrile (40 mL) was added DIPEA (7 g, 54 mmol) and the reaction solution was stirred at 80° C. for 2 h. The solvent was removed under reduced pressure and the residue was partitioned between dichloromethane (50 mL) and water (50 mL). The organic layer was washed with brine, dried over Na$_2$SO$_4$ and concentrated under reduced pressure to afford 3.5 g (78%) of 7-fluoro-2H-benzo[b][1,4]oxazin-3(4H)-one as a brown solid. $^1$H NMR (400 MHz, CDCl$_3$) δ 8.35 (br. s, 1H) 6.67-6.77 (m, 3H) 4.62 (s, 2H).

Intermediate I-23

7-fluoro-3-methyl-3,4-dihydro-2H-benzo[b][1,4]oxazine

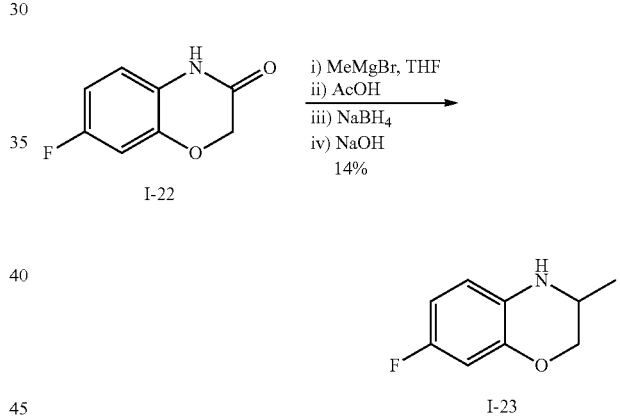

To a stirred solution of 7-fluoro-2H-benzo[b][1,4]oxazin-3(4H)-one (I-22, 1 g, 5.98 mmol) in THF (25 mL) at 0° C. was added 3M CH$_3$MgBr (8 mL, 24 mmol). After additon, the cooling bath was removed and the mixture was heated to 65° C. for 4 h. The reaction mixture was quenched with acetic acid (10 mL) at 0° C. and NaBH$_4$ (568 mg, 15 mmol) was added to the solution. The resulting solution was stirred at rt for overnight. Subsequently, 3N aqueous NaOH solution was cautiously added until pH value of the mixture was adjusted to 10.0. The basic solution was extracted with ethyl acetate (2×30 mL). The combined organic layers were washed with water, brine, dried over Na$_2$SO$_4$ and the solvent was removed under reduced pressure. The resulting crude product was purified by column chromatography over neutral alumina (petroleum ether/EtOAc, 0-15% EtOAc) to afford 135 mg (14%) of 7-fluoro-3-methyl-3,4-dihydro-2H-benzo[b][1,4]oxazine (I-23) as a brown oil. $^1$H NMR (400 MHz, DMSO) δ

6.45-6.55 (m, 3H), 4.16-4.19 (m, 1H), 3.73-3.77 (m, 1H), 3.44-3.51 (m, 2H), 1.17 (d, J=6.34 Hz, 3H).

Intermediate I-24

(3-bromopyrazolo[1,5-a]pyridin-5-yl)(7-fluoro-3-methyl-2H-benzo[b][1,4]oxazin-4(3H)-yl)methanone

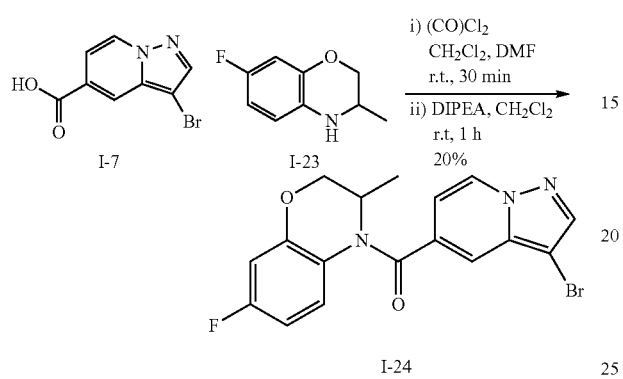

Intermediate I-24 was prepared according to the procedure described for the synthesis of intermediate I-8 by replacing 4-(methylamino)benzonitrile with 7-fluoro-3-methyl-3,4-dihydro-2H-benzo[b][1,4]oxazine (I-23, 350 mg, 2.1 mmol). The resulting crude product was purified by column chromatography over silica gel (chloroform/EtOAc, 0-30% EtOAc) to afford 150 mg (20%) of (3-bromopyrazolo[1,5-a]pyridin-5-yl)(7-fluoro-3-methyl-2H-benzo[b][1,4]oxazin-4(3H)-yl)-methanone (I-24) as an off-white solid. $^1$H NMR (400 MHz, DMSO) δ $^1$H NMR (400 MHz, CDCl$_3$) δ 8.36 (d, J=7.0 Hz, 1H), 7.99 (s, 1H), 7.81 (s, 1H), 6.88 (br. s, 1H), 6.67-6.78 (m, 3H), 6.42-6.46 (m, 1H), 4.82 (br. s, 1H), 4.28-4.35 (m, 2H), 1.33 (d, J=7.0 Hz, 3H).

Intermediate I-25

6-(oxetan-3-ylamino)nicotinonitrile

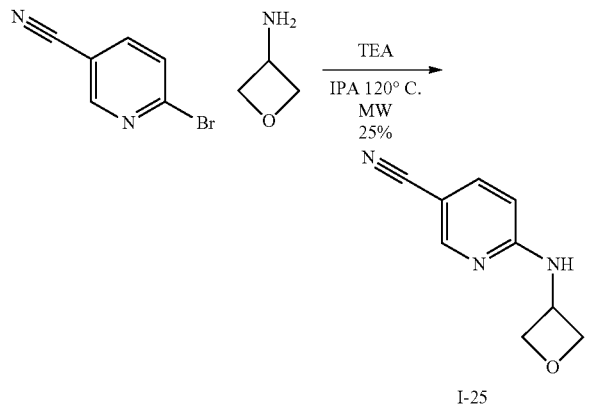

In a microwave vial, oxetan-3-amine (125 mg, 1.736 mmol), triethylamine (526 mg, 5.21 mmol) were added to a solution of 2-bromo-5-cyanopyridine (317 mg, 1.736 mmol) in isopropanol (3 mL). The vial was capped and irradiated in a microwave oven at 120° C. for 5 h. The reaction mixture was partitioned between ethyl acetate (10 mL) and water (10 mL). The organic layer was washed with brine, dried over Na$_2$SO$_4$ and the solvent was removed under reduced pressure. The resulting crude product was purified by column chromatography over silica gel (chloroform/MeOH, 0-5% EtOAc) to afford 75 mg (25%) of 6-(oxetan-3-ylamino)nicotinonitrile (I-25) as an off-white solid. $^1$H NMR (400 MHz, DMSO) δ 8.36 (s, 1H), 7.58-7.61 (dd, J=1.9, 6.9 Hz, 1H), 6.39 (d, J=8.7 Hz, 2H), 5.37 (br. s, 1H), 4.91-5.06 (m, 3H), 4.54-4.57 (m, 2H); ESI-LC/MS (m/z): [M+H]$^+$ 176.2, RT 1.65 min.

Intermediate I-26

3-bromo-N-(5-cyanopyridin-2-yl)-N-(oxetan-3-yl)pyrazolo[1,5-a]pyridine-5-carboxamide

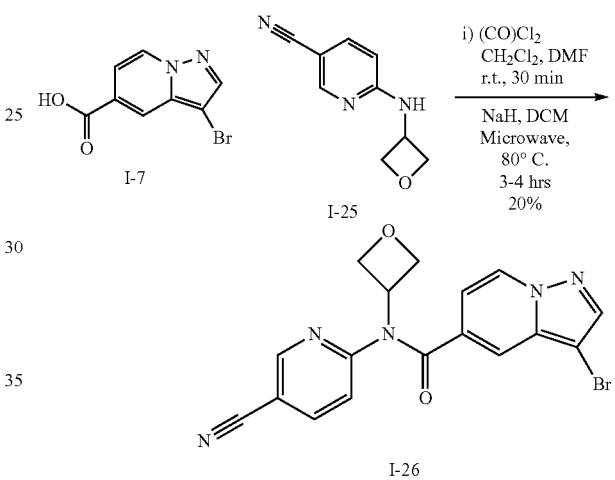

To a solution of 3-bromopyrazolo[1,5-a]pyridine-5-carboxylic acid (I-7, 240 mg, 1 mmol) in dichloromethane (10 mL) was added oxalyl chloride (0.25 mL) and catalytic amounts of anhydrous dimethylformamide at rt. The reaction mixture was stirred for 30 minutes and subsequently the solvent was removed under reduced pressure. To the residual acid chloride was added a solution of 6-(oxetan-3-ylamino)nicotinonitrile (I-25, 175 mg, 1 mmol) in dichloromethane (10 mL). The resulting reaction mixture was quickly transferred to a microwave vial and NaH (60% in mineral oil) (191 mg, 5 mmol) was added. The vial was heatedin a microwave oven at 80° C. for 3 h. The reaction mixture was diluted with dichloromethane (15 mL) and subsequently washed with water, sat. NaHCO$_3$ solution and brine. The organic layer was dried over Na$_2$SO$_4$ and the solvent was removed under reduced pressure. The resulting crude product was purified by column chromatography over silica gel (chloroform/MeOH, 0-10% EtOAc) to afford 75 mg (20%) of 3-bromo-N-(5-cyanopyridin-2-yl)-N-(oxetan-3-yl)pyrazolo[1,5-a]pyridine-5-carboxamide (I-26) as a brown solid. $^1$H NMR (400 MHz, CDCl$_3$) δ 8.45 (d, J=7.0 Hz, 1H), 8.16 (s, 1H), 8.02 (t, J=7.90 Hz, 1H), 7.53 (d, J=0.8 Hz, 1H), 7.33-7.31 (m, 1H), 6.90-6.87 (m, 1H), 6.43 (d, J=10.1 Hz, 1H), 4.67-4.62 (m, 1H), 4.52-4.43 (m, 2H), 4.25-4.19 (m, 1H), 4.03-3.98 (m, 1H); ESI-LC/MS (m/z): [M+H]$^+$ 398.13, [(M+2)+H]$^+$ 400.08, RT 1.25 min.

Intermediate I-27

N-(1-(1H-pyrazol-1-yl)propan-2-yl)-3-bromo-N-(5-cyanopyridin-2-yl)pyrazolo[1,5-a]pyridine-5-carboxamide

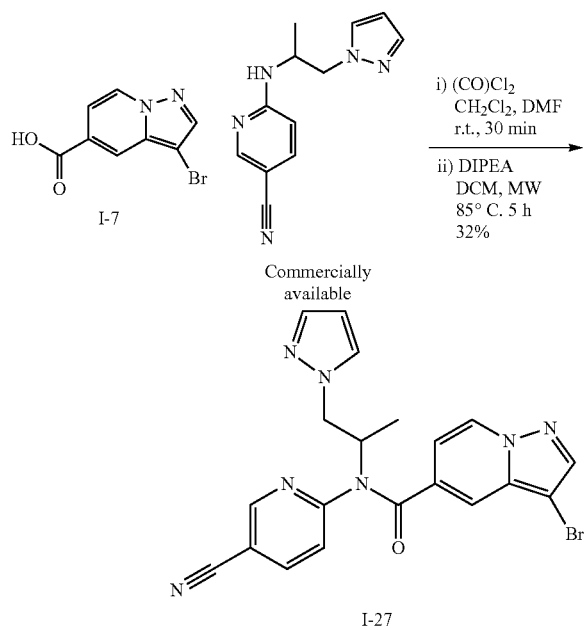

Intermediate I-27 was prepared according to the procedure described for the synthesis of intermediate I-7 by replacing 6-(oxetan-3-ylamino)nicotinonitrile with 6-(1-(1H-pyrazol-1-yl)propan-2-ylamino)nicotinonitrile (283 mg, 1.25 mmol). Microwave irradition at 85° C. for 5 h. The resulting crude product was purified by preparative TLC to afford 180 mg (32%) of N-(1-(1H-pyrazol-1-yl)propan-2-yl)-3-bromo-N-(5-cyanopyridin-2-yl)pyrazolo[1,5-a]pyridine-5-carboxamide (I-27) as a pale brown highly viscous oil. $^1$H NMR (400 MHz, DMSO-d$_6$) δ 8.84 (d, J=2.2 Hz, 1H), 8.60 (d, J=7.1 Hz, 1H), 8.19 (s, 1H), 8.13 (d, J=2.2 Hz, 1H), 7.75 (d, J=1.8 Hz, 1H), 7.38 (d, J=1.3 Hz, 1H), 7.27 (s, 1H), 7.12 (d, J=8.3 Hz, 1H), 6.62 (d, J=1.7 Hz, 1H), 6.19 (t, J=1.7 Hz, 1H), 5.06-5.10 (m, 1H), 4.82-4.87 (m, 1H), 4.43-4.47 (m, 1H), 1.36 (d, J=7.0 Hz, 3H); ESI-LC/MS (m/z): [M+H]$^+$ 450.2, RT 3.73 min.

Intermediate I-28

(5-cyanopyridin-2-yl)(methyl)carbamic chloride

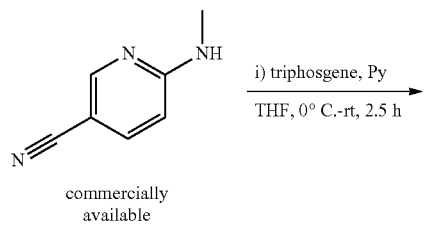

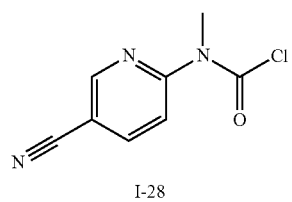

To a solution of bis(trichloromethyl) carbonate (50 mg, 0.17 mmol) in tetrahydrofuran (2.0 mL) was added pyridine (0.04 mL, 0.510 mmol) dropwise under ice-cooling. After stirring under ice-cooling for 30 min, 6-(methylamino)nicotinonitrile (68 mg, 0.510 mmol) was added and the mixture was stirred at room temperature for 2.5 hours. The precipitated solid was filtered off. The filtrate containing (5-cyanopyridin-2-yl)(methyl)carbamic chloride (I-28) was directly used for next step.

Intermediate I-29

3-bromo-N-(5-cyanopyridin-2-yl)-6,7-dihydropyrazolo[1,5-a]pyrazine-5(4H)-carboxamide

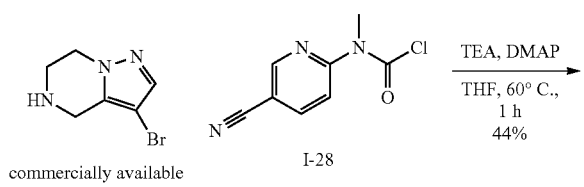

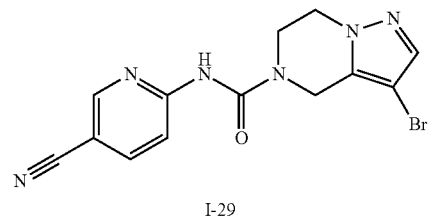

To a solution of (5-cyanopyridin-2-yl)(methyl)carbamic chloride (I-28) in THF (2.0 mL) were added 3-bromo-4,5,6,7-tetrahydropyrazolo[1,5-a]pyrazine (137 mg, 0.680 mmol), triethylamine (0.14 mL, 1.021 mmol) and 4-dimethylaminopyridine (2.0 mg, 0.017 mmol). The mixture was stirred at 60° C. for 1 h. Subsequently, water (25 mL) was added and the mixture was extracted with ethyl acetate. The organic layer was washed with brine, dried over Na$_2$SO$_4$ and the solvent was removed under reduced pressure. The resulting crude product was purified by preparative TLC to afford 60 mg (44%) of 3-bromo-N-(5-cyanopyridin-2-yl)-N-methyl-6,7-dihydropyrazolo-[1,5-a]pyrazine-5(4H)-carboxamide (I-29) as a off white solid. $^1$H NMR (400 MHz, DMSO) δ 8.64 (s, 1H), 8.07 (d, J=8.8 Hz, 1H), 7.60 (s, 1H), 7.18 (d, J=8.4 Hz, 1H), 4.53 (s, 2H), 4.16 (t, J=4.9 Hz, 2H), 3.84 (t, J=4.9 Hz, 2H), 3.26 (s, 3H); ESI-LC/MS (m/z): [M+H]⁺ 360.91, [(M+2)+H]⁺ 362.93, RT 1.63 min.

Intermediate I-30

4-(chloromethyl)-N-methylbenzamide

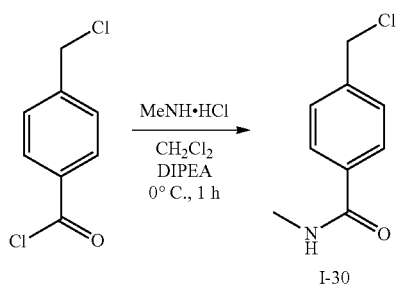

To a solution 4-(chloromethyl)benzoyl chloride (1.0 g, 5.29 mmol) and methylamine.HCl (1.0 g, 5.80 mmol) in dichloromethane (40 mL) was added DIPEA (2.01 g, 15.6 mmol) at 0° C. and stirred for 1 h. The reaction mixture was extracted with water (1×50 mL). The organic layer was extracted with brine (1×50 mL), dried over Na₂SO₄ and the solvent was removed under reduced pressure to afford 1.0 g (quantitative) of 4-(chloromethyl)-N-methylbenzamide (I-30) as an off white solid. $^1$H NMR (400 MHz, DMSO) δ 8.46 (d, J=3.5 Hz, 1H), 7.82 (d, J=8.4 Hz, 2H), 7.51 (d, J=8.3 Hz, 2H), 4.80 (s, 2H), 2.78 (d, J=4.4 Hz, 3H); ESI-LC/MS (m/z): [M+H]⁺ 184.2, RT 2.46 min.

Intermediate I-31

N-methyl-4-((trimethylstannyl)methyl)benzamide

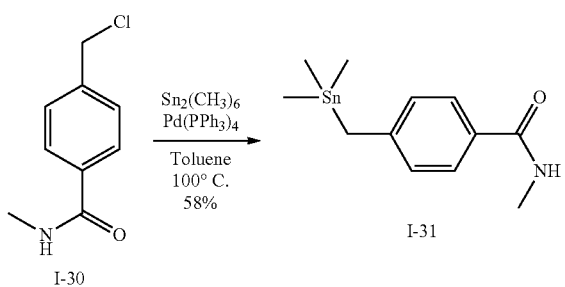

A solution of 4-(chloromethyl)-N-methylbenzamide (I-30, 200 mg, 1.092 mmol) and hexamethylditin (0.26 mL, 1.20 mmol) in toluene (5 mL) was degassed with argon gas for 15 min, followed by addition of Pd(PPh₃)₄ (63.05 mg, 0.054 mmol). The mixture was heated to reflux for 8 h. The reaction mixture was filtered and the solvent was removed under reduced pressure to afford 200 mg (58%) of N-methyl-4-((trimethylstannyl)methyl)benzamide (I-31) as a a brown semi-solid. $^1$H NMR (400 MHz, DMSO-d₆) δ 7.58 (d, J=8.0 Hz, 2H), 7.00 (d, J=7.9 Hz, 2H), 2.99 (d, J=5.8 Hz, 2H), 2.35 (s, 2H), 0.04 (s, 9H); MS (m/z): [M+H]⁺ 314.0.

Intermediate I-32

4-(methylamino)cyclohexanecarbonitrile

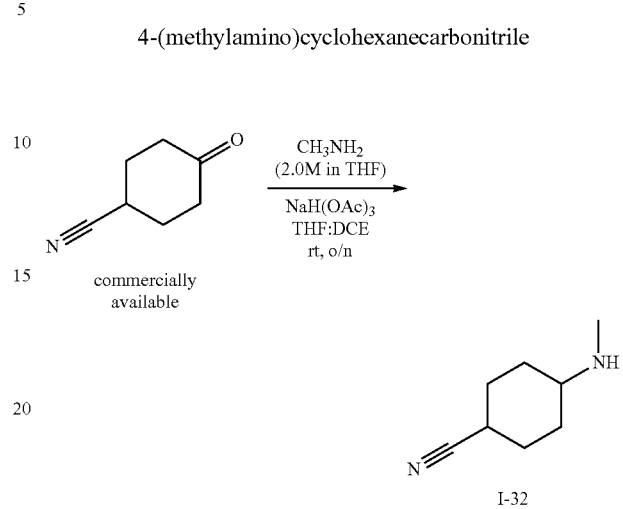

To a solution of 4-cyanocyclohexanone (200 mg, 1.626 mmol) and CH₃NH₂ (2M in THF) (0.8 mL, 1.626 mmol) in THF:CH₂Cl₂ (1:1) (4.0 mL) at 0° C. was added NaBH(OAc)₃ (689 mg, 3.252 mmol) and the resulting mixture was stirred at rt for 48 h. Subsequently, the solvent was removed under reduced pressure and the residue was dissolved in ethyl acetate, washed with water, brine, dried over Na₂SO₄ and concentrated to afford 200 mg (89%) of 4-(methylamino)cyclohexanecarbonitrile as a white solid. $^1$H NMR (400 MHz, DMSO-d₆) 2.91 & 2.61 (two signals, 1H) 2.23-2.24 (m, 3H) 1.02-1.99 (m, 9H); ELSD/MS (Method 3) (m/z): [M+H]⁺ 139.06.

Intermediate I-33

3-bromo-N-(4-cyanocyclohexyl)-N-methylpyrazolo[1,5-a]pyridine-5-carboxamide (Example 84)

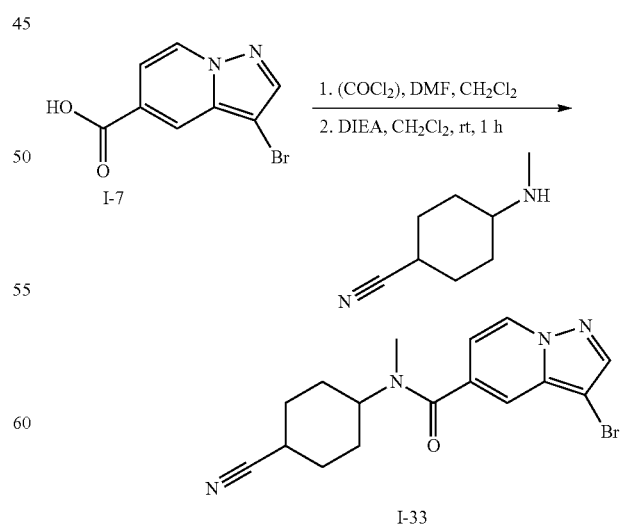

Intermediate I-33 was prepared according to the procedure described for the synthesis of intermediate I-8 by replacing 4-(methylamino)benzonitrile with 4-(methylamino)cyclohexane-carbonitrile. $^1$H NMR (400 MHz, DMSO-d$_6$) 8.77-8.79 (m, 1H) 8.23 (s, 1H) 7.58 (br.s, 1H) 6.95-6.97 (m, 1H) 4.30 & 3.50 (two signals, 1H) 2.76-3.19 (m, 4H) 1.48-1.98 (m, 8H); ESI-LC/MS (Method 1) (m/z): [M+H]$^+$ 361 & [M+2H]$^+$ 363.

Intermediate 1-34

2-amino-5-bromonicotinonitrile

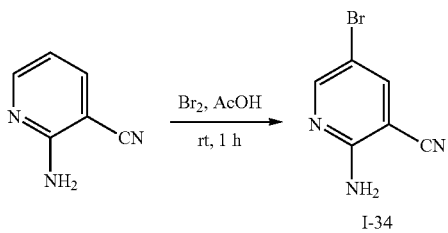

To a solution of 2-aminonicotinonitrile (1.5 g, 12.5 mmol, 1.0 eq.) in AcOH (30 mL) was added Na$_2$CO$_3$ (1.3 g, 12.5 mmol). Bromine (0.7 ml, 13.8 mmol) was added dropwise to the resulting suspension and reaction mixture was stirred at rt for 1 h. The orange precipitate formed was collected by filtration, washed with water and dried to afford 2.0 g (80%) of I-34 as a yellow solid. $^1$H NMR (400 MHz, DMSO) δ 8.27 (s, 1H), 8.15 (s, 1H), 7.12 (brs, 2H).

Intermediate 1-35

2-amino-5-bromonicotinonitrile

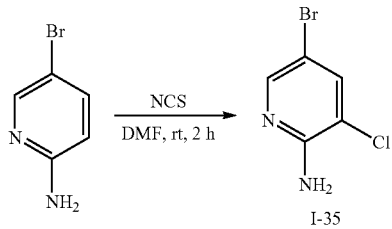

To a solution of 2-amino-5-bromopyridine (3 g, 17.3 mmol, 1.0 eq.) dissolved in DMF (10 ml) was added NCS (2.54 g, 19.07 mmol, 1.1 eq.) and the resulting mixture was stirred at rt for 2 h. Subsequently, 5N NaOH was used to adjust the pH of the reaction mixture to 7-8 followed by extraction with ethyl acetate (2×40 mL). The combined organic layers were washed with water, brine, dried over anhydrous Na$_2$SO$_4$ solution and concentrated under reduced pressure to afford 2.0 g (55%) of 1-35 as a yellow solid. $^1$H NMR (400 MHz, DMSO) δ 7.98 (s, 1H), 7.84 (s, 1H), 6.52 (brs, 2H); ESI-LC/MS (m/z): [M+H]$^+$ 206.96, [(M+2)+H]$^+$ 208.91, RT 1.59 min.

Intermediate 1-36

2-amino-5-bromo-N,N-di methylnicotinamide

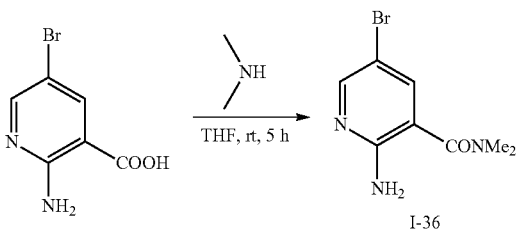

To a stirred solution of 2-amino-5-bromo-3-carboxypyridine (1.0 g, 4.60 mmol, 1.0 eq.), dimethylamine (0.227 g, 5.06 mmol, 1.1 eq.) and TEA (1.2 ml, 9.20 mmol, 2.0 eq.) dissolved in THF (20 mL) was added diethyl cyanophosphate (0.8 ml, 5.06 mmol, 1.1 eq.) drop wise. Stirring at rt was continued for 4 h. The reaction mixture was partitioned between water and ethyl acetate (2×30 mL). The combined organic layers were washed with water, brine, dried over anhydrous Na$_2$SO$_4$ solution and concentrated under reduced pressure. The crude compound was purified by column chromatography over silica gel (100-200 mesh) using a solvent gradient of 4% MeOH in DCM as eluant to afford 500 mg (44%) of 1-36 as a off-white solid. $^1$H NMR (400 MHz, DMSO) δ 8.05 (s, 1H), 7.54 (s, 1H), 6.20 (brs, 2H), 2.90 (brs, 6H); ESI-LC/MS (m/z): [M+H]$^+$ 244.01, [(M+2)+H]$^+$ 246.01, RT 0.84 min.

Intermediate 1-37

3-fluoro-5-(4,4,5,5-tetramethyl-1,3,2-dioxaborolan-2-yl)pyridin-2-amine

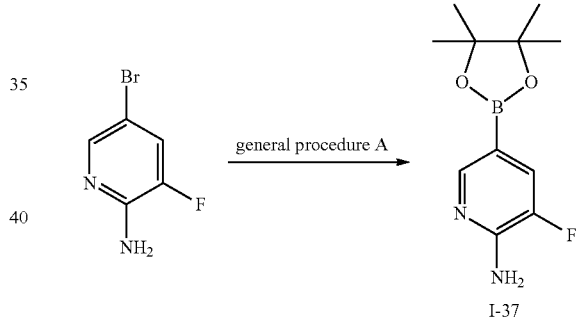

Intermediate I-37 was prepared according to the general boronic ester synthesis procedure A by utilizing 5-bromo-3-fluoropyridin-2-amine (reaction time: 16 h, temperature: 85° C.). ESI-LC/MS (m/z): [M+H]$^+$ 239.1, RT 5.60 min.

Intermediate 1-38

2,6-dimethyl-4-(4,4,5,5-tetramethyl-1,3,2-dioxaborolan-2-yl)aniline

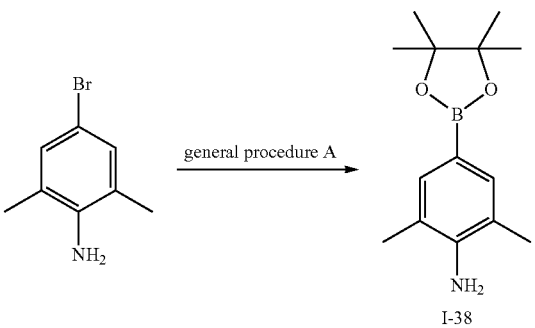

Intermediate I-38 was prepared according to the general boronic ester synthesis procedure A by utilizing 4-bromo-2,6-dimethylaniline (reaction time: 16 h, temperature: 85° C.). ESI-LC/MS (m/z): [M+H]⁺ 248.1, RT 6.67 min.

Intermediate I-39

3-methyl-5-(4,4,5,5-tetramethyl-1,3,2-dioxaborolan-2-yl)pyridin-2-amine

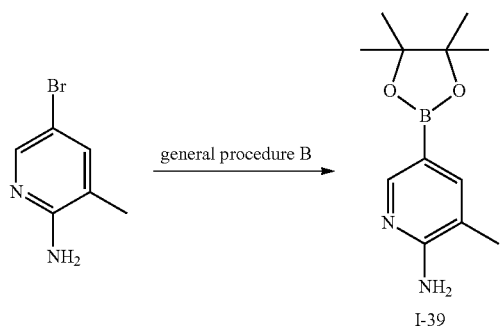

I-39

Intermediate I-39 was prepared according to the general boronic ester synthesis procedure B by utilizing 2-amino-3-methyl-5-bromopyridine (reaction time: 16 h, temperature: 90° C.). ESI-LC/MS (m/z): [M+H]⁺ 235.1, RT 1.26 min.

Intermediate I-40

5-(4,4,5,5-tetramethyl-1,3,2-dioxaborolan-2-yl)pyrimidin-2-amine

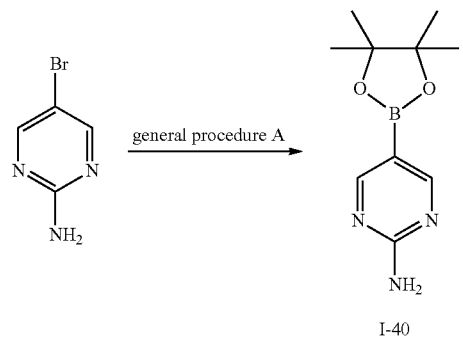

I-40

Intermediate I-40 was prepared according to the general boronic ester synthesis procedure A by utilizing 5-bromopyrimidin-2-amine (reaction time: 5 h, temperature: 100° C.). $^1$H NMR (400 MHz, DMSO) δ 8.59 (s, 2H), 5.43 (brs, 2H), 1.32 (s, 12H);

Intermediate I-41

5-(4,4,5,5-tetramethyl-1,3,2-dioxaborolan-2-yl)-3-(trifluoromethyl)pyridin-2-amine

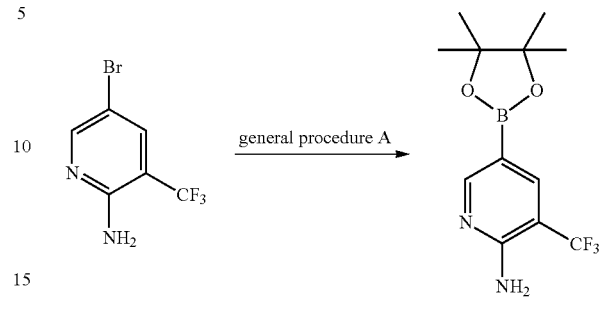

I-41

Intermediate I-41 was prepared according to the general boronic ester synthesis procedure A by utilizing 5-bromo-3-(trifluoromethyl)pyridin-2-amine (reaction time: 5 h, temperature: 100° C.). $^1$H NMR (400 MHz, DMSO) δ 8.37 (s, 1H), 7.80 (s, 1H), 6.89 (s, 2H), 1.27 (s, 12H); ESI-LC/MS (m/z): [M+H]⁺ 289.1, RT 4.83 min.

Intermediate I-42

2-amino-5-(4,4,5,5-tetramethyl-1,3,2-dioxaborolan-2-yl)nicotinonitrile

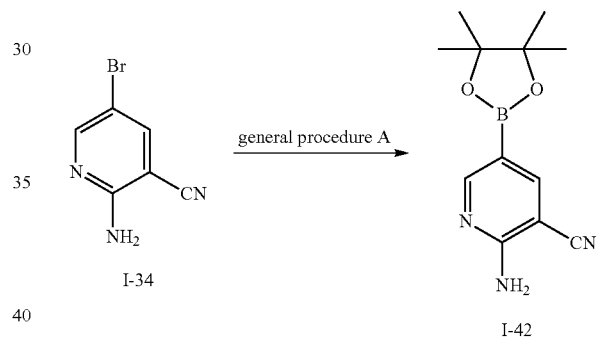

I-42

Intermediate I-42 was prepared according to the general boronic ester synthesis procedure A by utilizing 2-amino-5-bromonicotinonitrile (I-34) (reaction time: 5 h, temperature: 100° C.). $^1$H NMR (400 MHz, DMSO) δ 8.57 (s, 1H), 8.08 (s, 1H), 5.42 (s, 2H), 1.27 (s, 12H); ESI-LC/MS (m/z): [M+H]⁺ 246.1, RT 5.05 min.

Intermediate I-43

3-chloro-5-(4,4,5,5-tetramethyl-1,3,2-dioxaborolan-2-yl)pyridin-2-amine

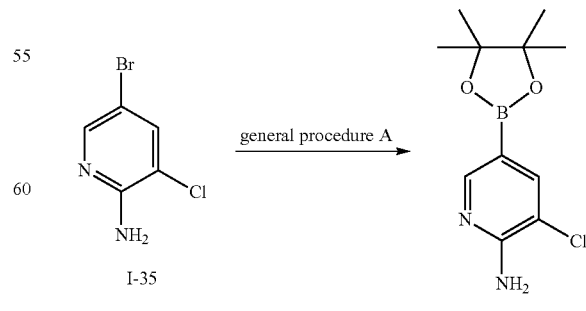

I-43

Intermediate I-43 was prepared according to the general boronic ester synthesis procedure A by utilizing 5-bromo-3-chloropyridin-2-amine (I-35) (reaction time: 16 h, temperature: 100° C.). ¹H NMR (400 MHz, DMSO) δ 8.32 (s, 1H), 7.84 (s, 1H), 5.12 (s, 2H), 1.37 (s, 12H); ESI-LC/MS (m/z): [M+H]⁺ 256.5, RT 1.67 min.

Intermediate I-44

2-amino-N,N-dimethyl-5-(4,4,5,5-tetramethyl-1,3,2-dioxaborolan-2-yl)nicotinamide

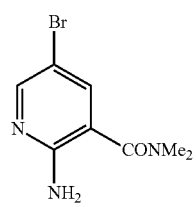

I-36 general procedure A

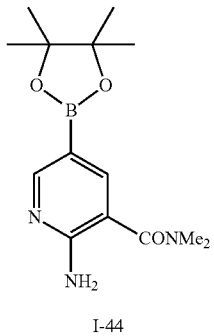

I-44

Intermediate I-44 was prepared according to the general boronic ester synthesis procedure A by utilizing 2-amino-5-bromo-N,N-dimethylnicotinamide (I-36) (reaction time: 16 h, temperature: 100° C.). ESI-LC/MS (m/z): [M-boronicacid]+210.1, RT 0.42 min.

Intermediate I-45

3-methoxy-5-(4,4,5,5-tetramethyl-1,3,2-dioxaborolan-2-yl)pyridin-2-amine

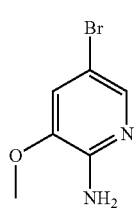

general procedure A

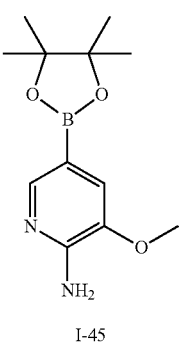

I-45

Intermediate I-45 was prepared according to the general boronic ester synthesis procedure A by utilizing 2-amino-3-methoxy-5-bromopyridine (reaction time: 5 h, temperature: 100° C.). ¹H NMR (400 MHz, DMSO) δ 8.03 (s, 1H), 7.19 (s, 1H), 5.17 (s, 2H), 3.84 (s, 3H), 1.27 (s, 12H).

Intermediate I-46

Methyl 3-(4,4,5,5-tetramethyl-1,3,2-dioxaborolan-2-yl)pyrazolo[1,5-a]pyridine-5-carboxylate

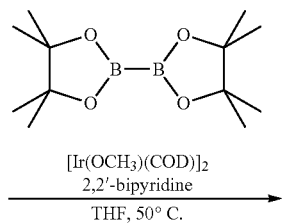

I-5

[Ir(OCH₃)(COD)]₂
2,2'-bipyridine
THF, 50° C.

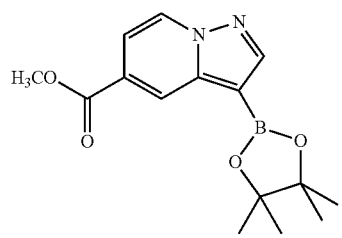

I-46

A solution of pyrazolopyridine (100 mg, 0.568 mmol, 1.0 equiv.) and bis(pinacolato)diboron (158.75 mg, 0.625 mmol, 1.1 equiv.) in 1 mL THF was treated with 2,2'-bipyridine (0.6 mg, 0.00224 mmol, 0.04 equiv.) and (1,5-cyclooctadiene)(methoxy)iridium(I) dimer (0.75 mg, 0.00113 mmol, 0.02 equiv.) at rt. The flask was charged with nitrogen gas, and the resulting mixture was allowed to stir at 50° C. for three hours. The reaction was concentrated and the residue was purified by silica gel chromatography, eluting with CH₂Cl₂/EtOAc to give I-46. ¹H NMR (400 MHz, MeOD) δ 8.68 (dd, J=0.6, 7.2, 1H), 8.60-8.57 (m, 1H), 8.24 (s, 1H), 7.46 (dd, J=1.9, 7.3, 1H), 3.98 (s, 3H), 1.39 (s, 12H).

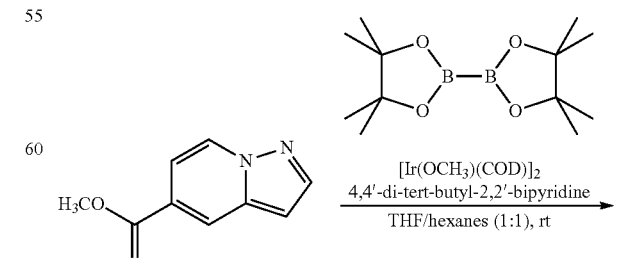

I-5

[Ir(OCH₃)(COD)]₂
4,4'-di-tert-butyl-2,2'-bipyridine
THF/hexanes (1:1), rt

-continued

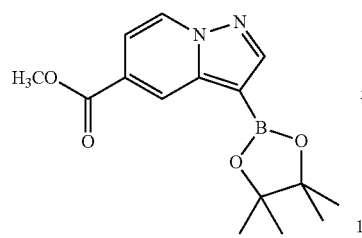

I-46

Alternatively, a solution of pyrazolopyridine (750 mg, 4.26 mmol, 1.0 equiv.) and bis(pinacolato)diboron (1.19 g, 4.69 mmol, 1.1 equiv.) in 10 mL 1:1 THF/hexanes was treated with (1,5-cyclooctadiene)(methoxy)iridium(I) dimer (84 mg, 0.128 mmol, 0.03 equiv.) and 4,4'-di-tert-butyl-2,2'-bipyridine (68 mg, 0.256 mmol, 0.06 equiv.) at rt. The flask was charged with nitrogen gas, and the resulting mixture was allowed to stir at rt overnight. The reaction was concentrated and the residue was purified by silica gel chromatography, eluting with hexanes/EtOAc to give intermediate I-46.

Intermediate I-47

3-(4,4,5,5-tetramethyl-1,3,2-dioxaborolan-2-yl)pyrazolo[1,5-a]pyridine-5-carboxylic acid

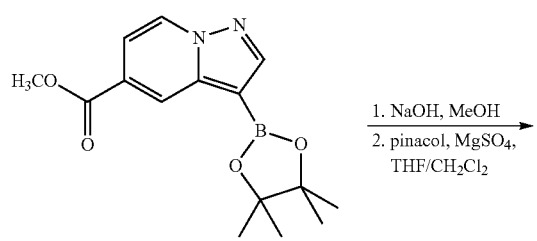

I-46

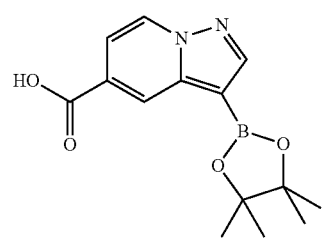

I-47

A solution of ester (400 mg, 1.32 mmol, 1.0 equiv.) in 3 mL MeOH was treated with 1 N aq. NaOH (3 mL, 3.0 mmol, 2.26 equiv.) at rt, and then allowed to stir at rt for 30 minutes. The reaction mixture was then neutralized with 3 mL 1 N aq. HCl, and the resulting white solid was isolated by filtration. The filtrate was extracted with EtOAc and the organic extracts were concentrated. The solid products were combined, and then diluted with 22 mL 10:1 CH$_2$Cl$_2$/THF before pinacol (157 mg, 1.32 mmol, 1.0 equiv.) and 1 g MgSO$_4$ were added. The resulting mixture was allowed to stir at rt for 20 minutes, filtered, and concentrated under reduced pressure. The resulting white solid was triturated with hexanes to give the acid 1-47, which was taken on without further purification.

Intermediate I-48

Methyl 3-(5-(trifluoromethyl)pyridin-2-yl)pyrazolo[1,5-a]pyridine-5-carboxylate

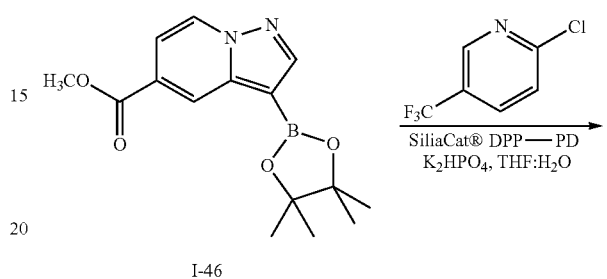

I-46

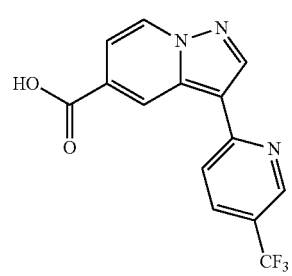

I-48

A mixture of 2-chloro-5-(trifluoromethyl)pyridine (1.5 equiv.), aryl boronic ester (1.0 equiv.), K$_2$HPO$_4$ (3.5 equiv.), and SiliaCat® DPP-Pd or Pd(dppf)C12 (0.05-0.15 equiv.) in THF/water was allowed to heat at 150° C. in a microwave reactor for 40-60 minutes. After cooling to room temperature, the solvent was removed under reduced pressure. The crude residue was purified by mass-triggered HPLC or silica gel chromatography to provide intermediate I-48.

Intermediate I-49

3-(5-(trifluoromethyl)pyridin-2-yl)pyrazolo[1,5-a]pyridine-5-carboxylic acid

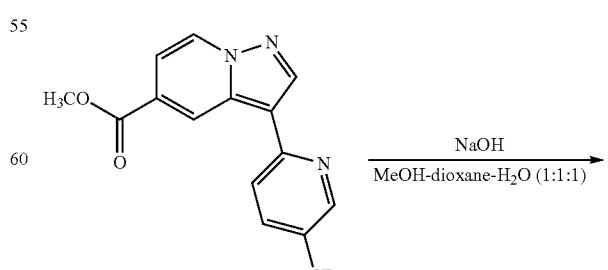

I-48

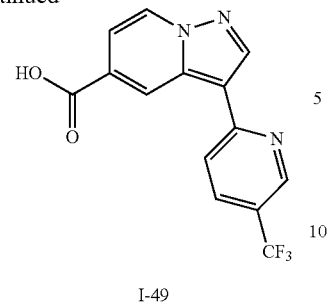

I-49

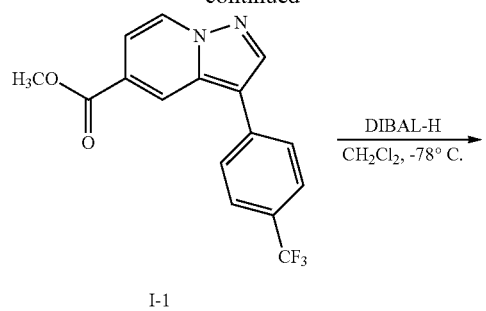

I-1

Intermediate I-49 was prepared according to the procedure described for the synthesis of intermediate I-7.

Intermediate I-50

N-(4-cyanophenyl)-N-methyl-3-(4,4,5,5-tetramethyl-1,3,2-dioxaborolan-2-yl)pyrazolo[1,5-a]pyridine-5-carboxamide

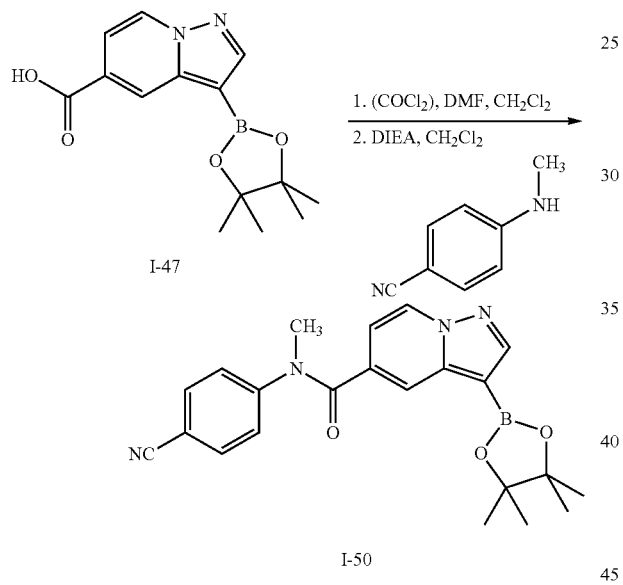

Intermediate I-50 was prepared according to the procedure described for the synthesis of intermediate I-8.

Intermediate I-51 & I-52

(3-(4-(trifluoromethyl)phenyl)pyrazolo[1,5-a]pyridin-5-yl)methanol

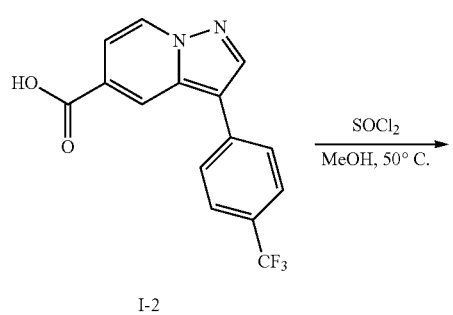

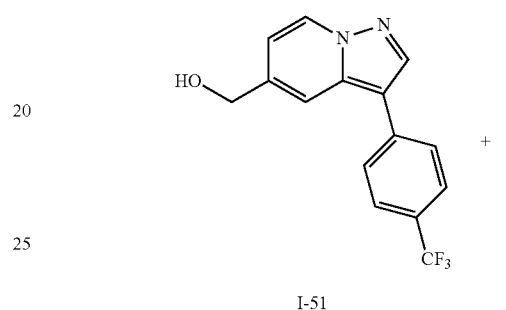

I-51

I-52

A solution of acid (450 mg, 1.47 mmol, 1.0 equiv.) in 8 mL MeOH was treated with $SOCl_2$ (300 μL, 4.14 mmol, 2.8 equiv.) dropwise and the resulting solution was allowed to heat at 50° C. overnight. The solution was diluted with 10 mL $CH_2Cl_2$, then washed with saturated aq. $NaHCO_3$, dried with $Na_2SO_4$, filtered, and concentrated under reduced pressure to give the desired ester (I-1), which was taken on without further purification. $^1$H NMR (400 MHz, $CDCl_3$): 8.52 (m, 2H), 8.23 (s, 1H), 7.72 (s, 4H), 7.40 (dd, J=1.59, 7.50 Hz, 1H), 3.96 (s, 3H).

A solution of the ester (100 mg, 0.31 mmol, 1.0 equiv.) in 3 mL $CH_2Cl_2$ was allowed to cool to −78° C., and then a solution of DIBAL-H (1.0 M in toluene, 1.24 mL, 1.24 mmol, 4.0 equiv.) was added dropwise. The resulting solution was allowed to stir at −78° C. for 90-120 minutes and then was quenched with $Na_2SO_4 \cdot 10H_2O$. The resulting mixture was allowed to stir at rt for 30 minutes, then was filtered and concentrated. The residue was purified by silica gel chromatography, eluting with hexanes/EtOAc to give the desired alcohol (I-51), as well as a small amount of the corresponding aldehyde (I-52).

Intermediate I-53

5-(bromomethyl)-3-(4-(trifluoromethyl)phenyl)pyrazolo[1,5-a]pyridine

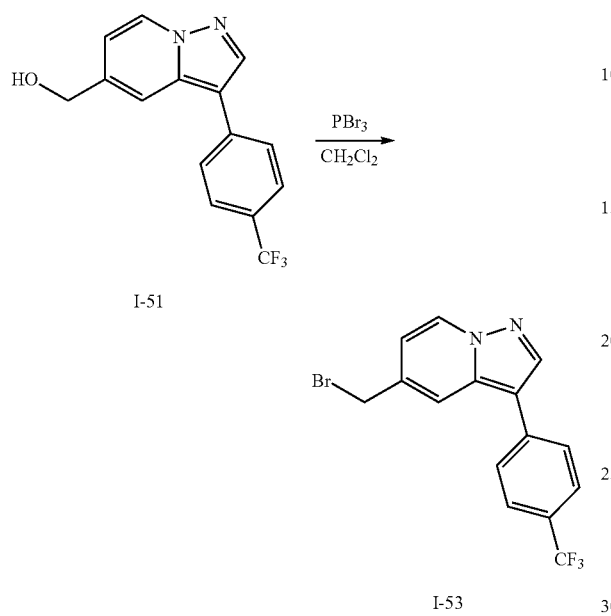

A solution of alcohol (160 mg, 0.546 mmol, 1.0 equiv.) in 3 mL CH$_2$Cl$_2$ was treated with PBr$_3$ (27 µL, 0.273 mmol, 0.5 equiv.) dropwise at rt, then was allowed to stir at rt for two hours. The solution was diluted with 20 mL CH$_2$Cl$_2$, then washed with saturated aq. NaHCO$_3$, dried with Na$_2$SO$_4$, filtered, and concentrated under reduced pressure to give the desired bromide (I-53), which was taken on without further purification.

Intermediate I-54

3-bromo-N-(4-fluorophenyl)-N-methylpyrazolo[1,5-a]pyridine-5-carboxamide

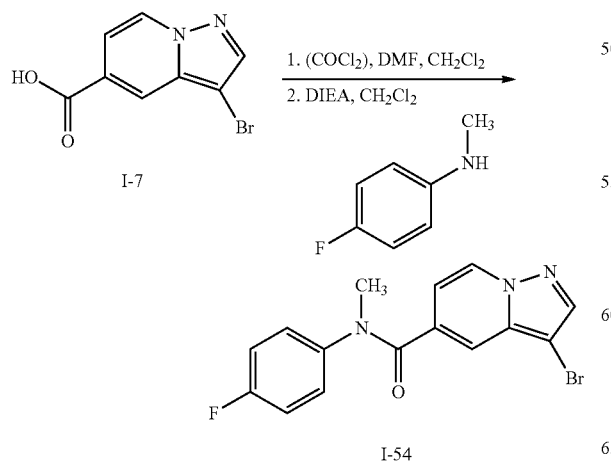

Intermediate I-54 was prepared according to the procedure described for the synthesis of intermediate I-8 by replacing 4-(methylamino)benzonitrile with 4-fluoro-N-methylaniline.

Intermediate I-55

N-(5-cyanopyridin-2-yl)-N-methyl-3-(4,4,5,5-tetramethyl-1,3,2-dioxaborolan-2-yl)pyrazolo[1,5-a]pyridine-5-carboxamide

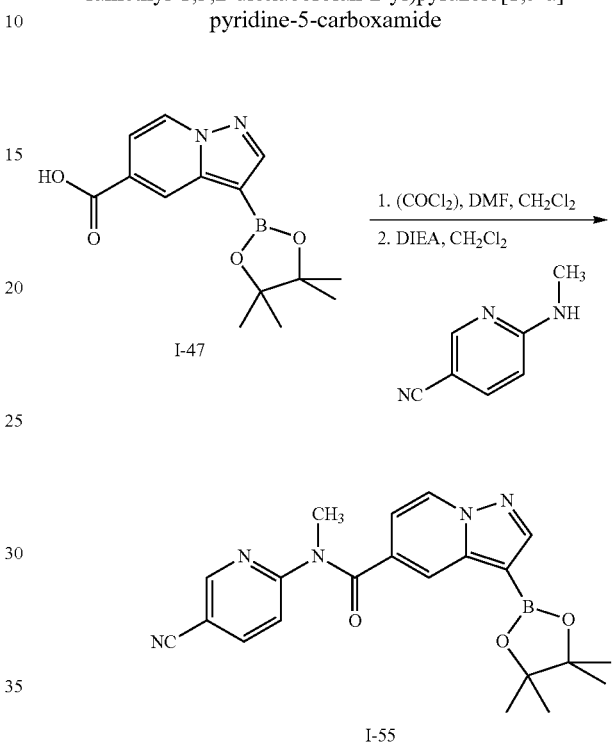

Intermediate I-55 was prepared according to the procedure described for the synthesis of intermediate I-8 by replacing 4-(methylamino)benzonitrile with 6-(methylamino)nicotinonitrile.

Intermediate I-56 tert-butyl (3-(4-(trifluoromethyl)phenyl)pyrazolo[1,5-a]pyridin-5-yl)carbamate

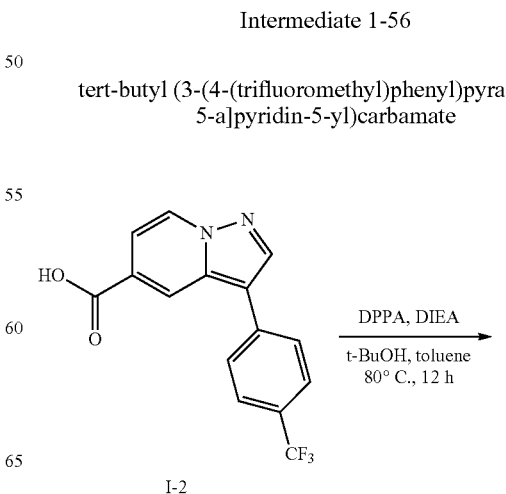

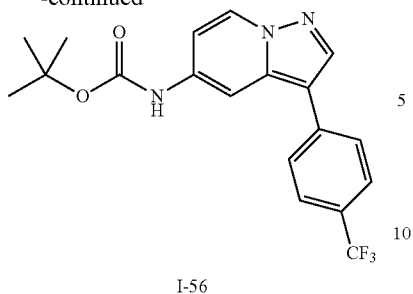

I-56

A mixture of pyrazolopyridine (153 mg, 0.50 mmol), DPPA (0.129 mL, 0.60 mmol), t-BuOH (0.5 mL) and toluene (2.0 mL) was heated to 80° C. overnight. After cooling to room temperature, water was added to the reaction mixture and extracted with dichloromethane. The combined organic layers were washed with brine and dried over anhydrous Na$_2$SO$_4$. The solvent was removed and the product was purified by silica gel chromatography, eluting with ethyl acetate and hexanes. $^1$H NMR (400 MHz, DMSO) δ 9.88 (s, 1H), 8.67 (d, J=7.6, 1H), 8.40 (d, J=7.8, 1H), 8.30-8.07 (m, 1H), 7.91-7.64 (m, 4H), 7.00 (dd, J=2.1, 7.5, 1H), 1.59-1.41 (m, 9H).

Intermediate 1-57 tert-butyl methyl(3-(4-(trifluoromethyl)phenyl)pyrazolo[1,5-a]pyridin-5-yl)carbamate

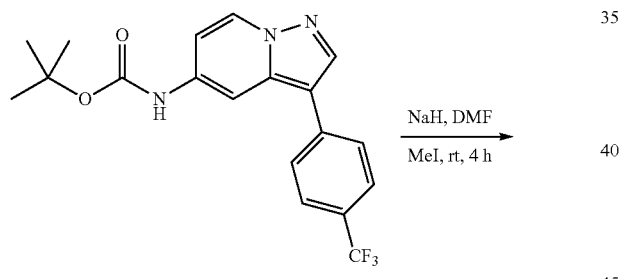

NaH (7 mg, 0.15 mmol) was added to a solution of pyrazolopyridine in DMF (2.0 mL). The reaction stirred at room temperature for 15 minutes. Methyl iodide was added (0.018 mL, 0.12 mmol) and the reaction stirred for 4 hours at room temperature. The reaction was quenched with water and extracted with ethyl acetate. The combined organic layers were washed with brine and dried over anhydrous Na$_2$SO$_4$. The solvent was removed and the material was purified by silica gel chromatography, eluting with ethyl acetate and hexanes. $^1$H NMR (400 MHz, MeOD) δ 8.44 (d, J=7.5, 1H), 8.20 (s, 1H), 7.77-7.59 (m, 5H), 6.94 (d, J=5.3, 1H), 3.26 (s, 3H), 1.41 (s, 9H).

Intermediate 1-58

N-methyl-3-(4-(trifluoromethyl)phenyl)pyrazolo[1,5-a]pyridin-5-amine

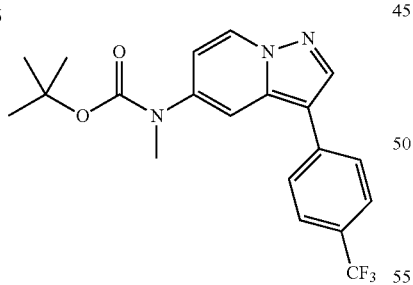

To a solution of pyrazolopyridine (30 mg, 0.80 mmol) in dioxane (1.0 mL) was added 4N HCl in dioxane and the reaction stirred at room temperature for 2 hours. The resultant HCl salt was filtered and dried to give the desired product. No further purification was necessary.

Intermediate 1-59 tert-butyl 4-fluorobenzyl(3-(4-(trifluoromethyl)phenyl)pyrazolo[1,5-a]pyridin-5-yl)carbamate

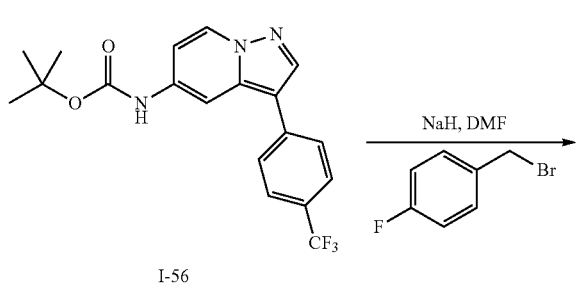

-continued

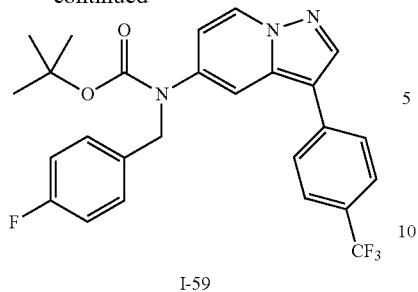

I-59

Intermediate I-59 was prepared according to the procedure described for the synthesis of intermediate I-57 by replacing methyl iodide with 4-fluorobenzyl bromide.

Intermediate I-60 tert-butyl ((tetrahydro-2H-pyran-4-yl)methyl)(3-(4-(trifluoromethyl)phenyl)pyrazolo[1,5-a]pyridin-5-yl)carbamate

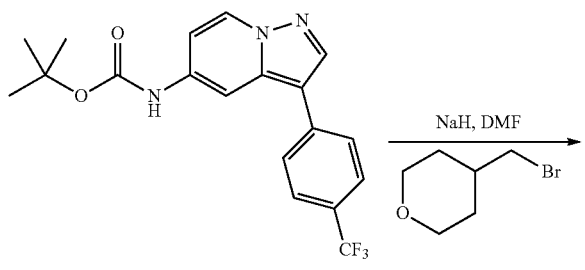

Intermediate I-60 was prepared according to the procedure described for the synthesis of intermediate I-25 by replacing methyl iodide with 4-(bromomethyl)tetrahydro-2H-pyran.

Intermediate I-61

N-((tetrahydro-2H-pyran-4-yl)methyl)-3-(4-(trifluoromethyl)phenyl)pyrazolo[1,5-a]pyridin-5-amine

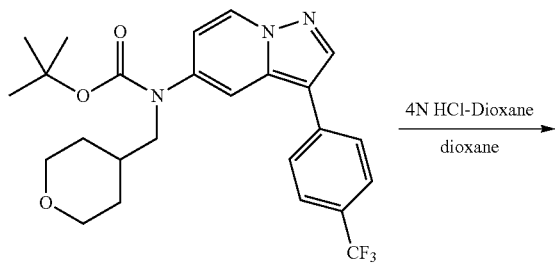

-continued

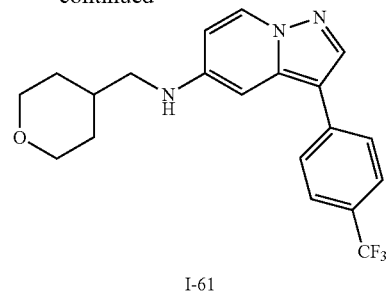

I-61

Intermediate I-29 was prepared according to the procedure described for the synthesis of intermediate I-57.

Intermediate I-62 tert-butyl (3-bromopyrazolo[1,5-a]pyridin-5-yl)carbamate

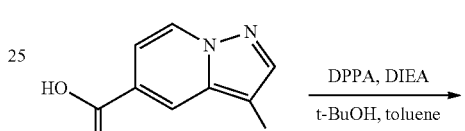

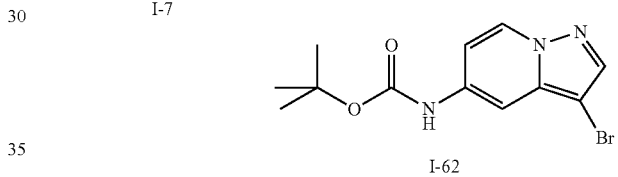

To a mixture of pyrazolopyridine (240 mg, 1.00 mmol), diisopropylethylamine (0.160 mL, 1.00 mmol), t-BuOH (1.00 mL) and toluene (4.00 mL) was added dry 4 angstrom molecular sieves. The reaction stirred at room temperature for 30 minutes. DPPA (0.260 mL, 1.20 mmol) was added and the reaction was heated to 80° C. overnight. After cooling to room temperature, the material was purified by silica gel chromatography, eluting with ethyl acetate and hexanes.

Intermediate I-63 tert-butyl (3-bromopyrazolo[1,5-a]pyridin-5-yl)(methyl)carbamate

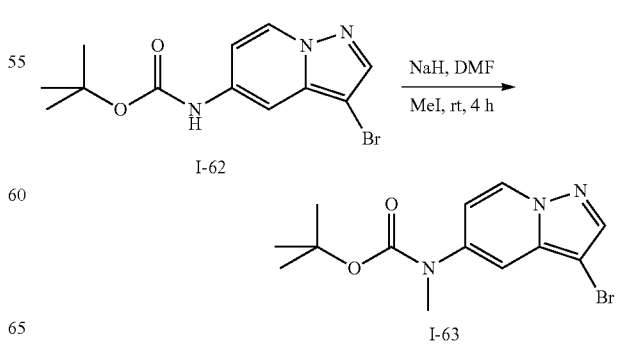

Intermediate I-63 was prepared according to the procedure described for the synthesis of intermediate I-57.

Intermediate 1-63

3-bromo-N-methylpyrazolo[1,5-a]pyridin-5-amine

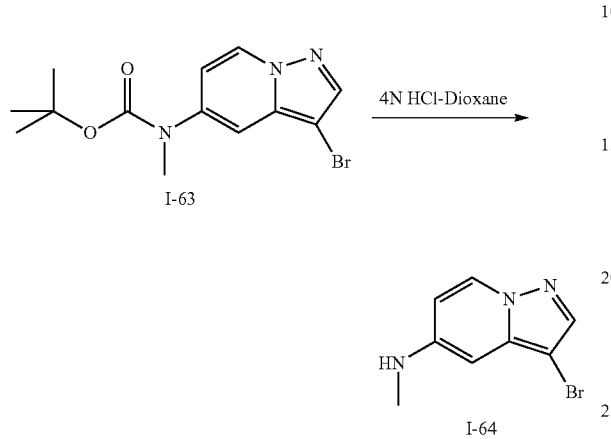

Intermediate I-64 was prepared according to the procedure described for the synthesis of intermediate I-58.

Intermediate 1-65

N-(3-bromopyrazolo[1,5-a]pyridin-5-yl)-4-fluoro-N-methylbenzamide

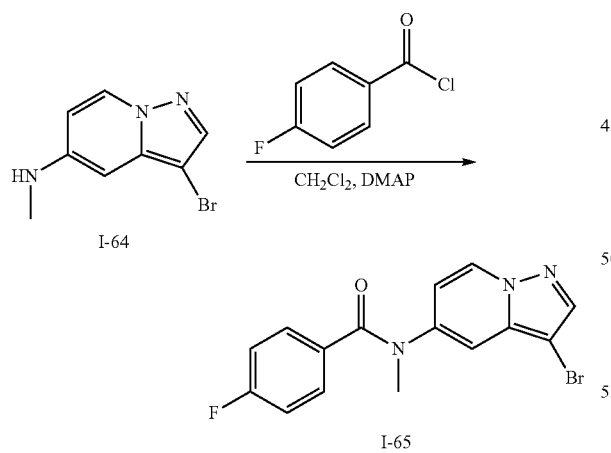

To a solution of pyrazolopyridine (22.6 mg, 0.10 mmol) in dichloromethane (2.0 mL) was added triethylamine (0.042 mL, 0.30 mmol) and a catalytic amount of DMAP. The reaction was cooled to 0° C. and 4-fluorobenzoyl chloride was added. The reaction warmed to room temperature and stirred for 2 hours. The reaction was diluted with water and extracted with dichloromethane. The organic extracts were washed with brine and dried over anhydrous $Na_2SO_4$. The solvent was removed and the material was purified by silica gel chromatography, eluting with ethyl acetate and hexanes.

Intermediate 1-66

3-bromo-N-methyl-N-(5-(methylsulfonyl)pyridin-2-yl)pyrazolo[1,5-a]pyridine-5-carboxamide

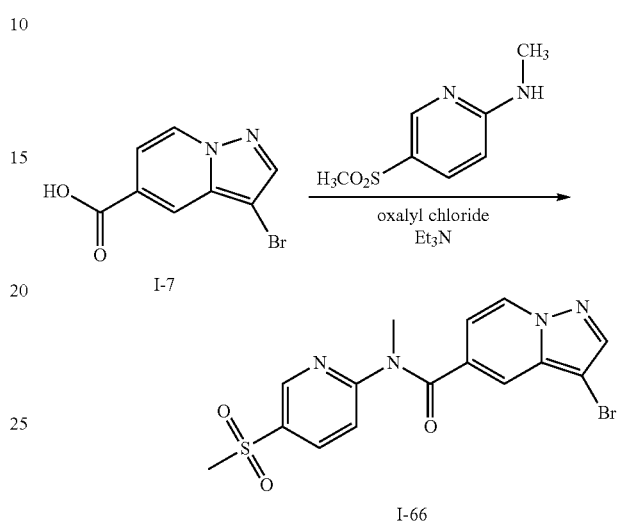

Intermediate I-66 was prepared according to the procedure described for the synthesis of intermediate I-8 by replacing 4-(methylamino)benzonitrile with N-methyl-5-(methylsulfonyl)pyridin-2-amine.

Intermediate 1-67

4-(1-(3-Bromopyrazolo[1,5-a]pyridin-5-yl)ethyl)-7-fluoro-2H-benzo[b][1,4]oxazin-3(4H)-one

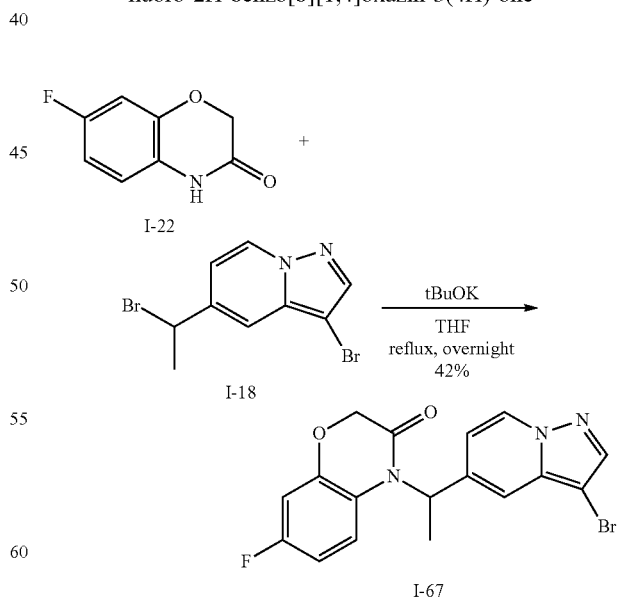

Potassium tert-butoxide (75 mg, 0.666 mmol) was added to a stirred solution of 7-fluoro-2H-benzo[b][1,4]oxazin-3 (4H)-one (I-22, 100 mg, 0.606 mmol) in dry THF at rt. After 5 min, a solution of 3-bromo-5-(1-bromoethyl) pyrazolo[1, 5-a]pyridine (I-18, 202 mg, 0.666 mmol) in dry THF was added drop wise to reaction mixture at rt. The resulting reaction mixture was heated to reflux for overnight and subsequently cooled to room temperature. The reaction mixture was diluted with water (10 mL) and extracted with ethyl acetate (2×10 mL). The combined organic layers were dried over Na$_2$SO$_4$ and concentrated under reduced pressure. The crude compound was purified by column chromatography over silica gel (chloroform/EtOAc, 0-4% EtOAc) to afford 110 mg (42%) of 4-(1-(3-bromopyrazolo[1,5-a]pyridin-5-yl) ethyl)-7-fluoro-2H-benzo[b][1,4]oxazin-3(4H)-onel-67 as a yellow solid. ESI-LC/MS (Method 1) (m/z): [M+H]$^+$ 389.9, [(M+2)+H]$^+$ 391.9.

Example 1

N-(4-cyanophenyl)-N-methyl-3-(4-(trifluoromethyl) phenyl)pyrazolo[1,5-a]pyridine-5-carboxamide

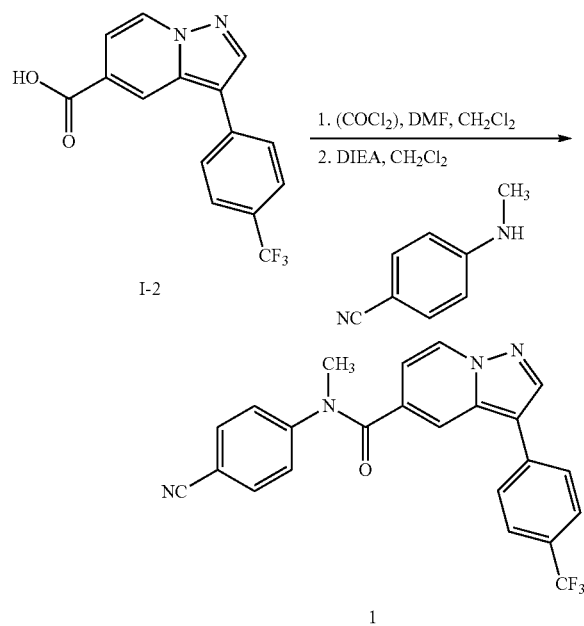

A solution of acid (1.0 equiv.) in CH$_2$Cl$_2$ (~0.05-0.1 M) was treated with oxalyl chloride (2.0-3.0 equiv.) and a catalytic amount of DMF. The resulting solution was allowed to stir at rt for between five minutes and one hour, then was concentrated and dried briefly under high vacuum. The resulting acid chloride was diluted with CH$_2$Cl$_2$ (~0.05-0.1 M), and to this solution was added 4-(methylamino)benzonitrile (1.1-3.0 equiv.) and either DIEA or Et$_3$N (3.0 equiv.). The resulting mixture was allowed to stir at rt until complete conversion (generally less than three hours). The solvent was removed under reduced pressure, and the residue was purified by silica gel chromatography, eluting with hexanes/ethyl acetate to provide 1. $^1$H NMR (400 MHz, CDCl$_3$) δ 8.30 (dd, J=0.7, 7.3, 1H), 8.16 (s, 1H), 7.82 (m, 1H), 7.66 (d, J=8.2, 2H), 7.60 (d, J=8.6, 2H), 7.47 (d, J=8.1, 2H), 7.23 (obscured by CDCl$_3$ peak, 2H), 6.64 (dd, J=1.8, 7.3, 1H), 3.54 (s, 3H). ESI-MS (m/z): [M+H]$^+$ 421.1, RT 1.8703 min. ESI-LC/MS m/z 421.1 (M+H)+; r.t.=1.871.

Example 2

4-fluoro-N-methyl-N-((3-(4-(trifluoromethyl)phenyl) pyrazolo[1,5-a]pyridine-5-yl)methyl)aniline

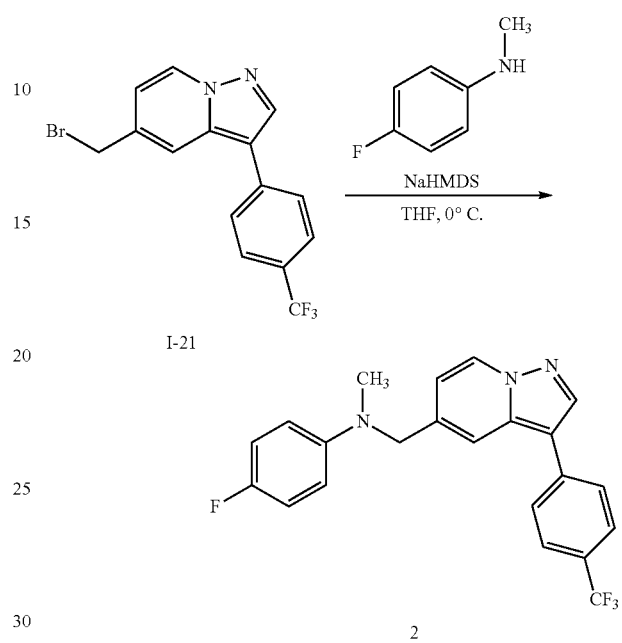

A solution of N-methyl aniline (18.8 mg, 0.15 mmol, 1.5 equiv.) in 0.5 mL THF was allowed to cool to 0° C., then a solution of NaHMDS (1.0 M in THF, 150 μL, 0.15 mmol, 1.5 equiv.) was added dropwise. After allowing the resulting solution to stir at 0° C. for 10 minutes, a solution of bromide (35.4 mg, 0.10 mmol, 1.0 equiv.) in 0.5 mL THF was added dropwise. The reaction mixture was allowed to stir at 0° C. for another 10-20 minutes, and then the reaction was quenched with water and concentrated under reduced pressure. The residue was diluted with MeOH-DMSO and the resulting solution was purified by mass-triggered HPLC to provide 2 as the TFA salt. $^1$H NMR (400 MHz, CDCl$_3$) δ 8.44 (d, J=7.2, 1H), 8.14 (s, 1H), 7.65 (d, J=8.3, 2H), 7.59 (m, 3H), 6.94 (m, 2H), 6.72 (m, 3H), 4.48 (s, 2H), 2.99 (s, 3H). ESI-MS (m/z): [M+H]+400.2, RT 2.409 min.

Example 3

N-(4-chlorophenyl)-N-methyl-3-(4-(trifluoromethyl) phenyl)pyrazolo[1,5-a]pyridine-5-carboxamide

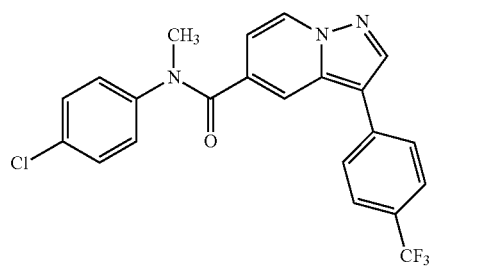

Example 3 was prepared according to the procedure described for the synthesis of Example 1 by replacing 4-(methylamino)benzonitrile with 4-chloro-N-methylaniline. ESI-LC/MS m/z 430.1 (M+H)+; r.t.=2.275.

Example 4

N-(4-fluorophenyl)-N-methyl-3-(4-(trifluoromethyl)phenyl)pyrazolo[1,5-a]pyridine-5-carboxamide

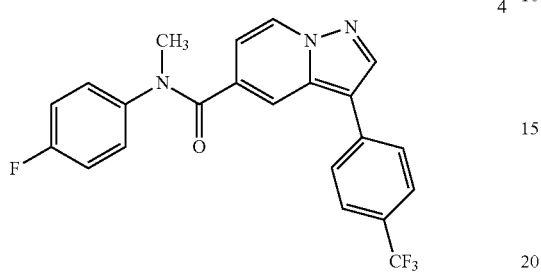

4

Example 4 was prepared according to the procedure described for the synthesis of Example 1 by replacing 4-(methylamino)benzonitrile with 4-fluoro-N-methylaniline. ESI-LC/MS m/z 414.1 (M+H)+; r.t.=2.165.

Example 5

N-methyl-N-(5-methylpyridin-2-yl)-3-(4-(trifluoromethyl)phenyl)pyrazolo[1,5-a]pyridine-5-carboxamide

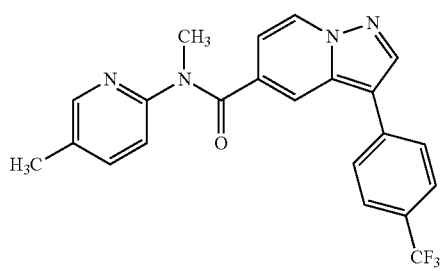

5

Example 5 was prepared according to the procedure described for the synthesis of Example 1 by replacing 4-(methylamino)benzonitrile with N,5-dimethylpyridin-2-amine. ESI-LC/MS m/z 411.2 (M+H)+; r.t.=2.005.

Example 6

4-chloro-N-methyl-N-((3-(4-(trifluoromethyl)phenyl)pyrazolo[1,5-a]pyridine-5-yl)methyl)aniline

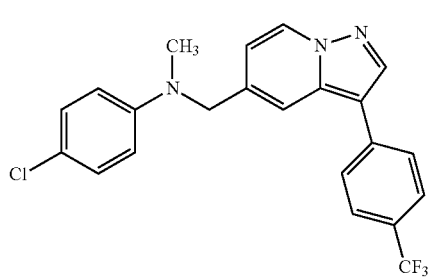

6

Example 6 was prepared according to the procedure described for the synthesis of Example 2 by replacing 4-fluoro-N-methylaniline with 4-chloro-N-methylaniline. $^1$H NMR (400 MHz, CDCl$_3$) δ 8.48 (d, J=7.2, 1H), 8.15 (s, 1H), 7.66 (d, J=8.3, 2H), 7.62-7.55 (m, 3H), 7.18 (d, J=9.1, 2H), 6.74-6.65 (m, 3H), 4.53 (s, 2H), 3.03 (s, 3H). $^1$H NMR (400 MHz, CDCl$_3$) δ 8.48 (d, J=7.2, 1H), 8.15 (s, 1H), 7.66 (d, J=8.3, 2H), 7.61-7.55 (m, 3H), 7.18 (d, J=9.1, 2H), 6.75-6.65 (m, 3H), 4.53 (s, 2H), 3.03 (s, 3H). ESI-MS (m/z): [M+H]$^+$ 416.1, RT 2.5357 min.

Example 7

N,5-dimethyl-N-((3-(4-(trifluoromethyl)phenyl)pyrazolo[1,5-a]101yridine-5-yl)methyl)pyridine-2-amine

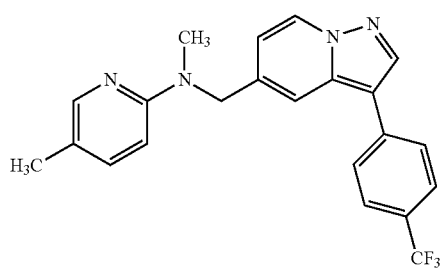

7

Example 7 was prepared according to the procedure described for the synthesis of Example 2 by replacing 4-fluoro-N-methylaniline with N,5-dimethylpyridin-2-amine (2.0 equiv) and using 2.0 equiv of NaHMDS. $^1$H NMR (400 MHz, CDCl$_3$) δ 8.50 (d, J=7.2, 1H), 8.18 (s, 1H), 8.03 (s, 1H), 7.73-7.65 (m, 3H), 7.62 (d, J=8.2, 3H), 6.82 (d, J=9.2, 1H), 6.66 (dd, J=1.8, 7.2, 1H), 4.88 (s, 2H), 3.37 (s, 3H), 2.27 (s, 3H). $^1$H NMR (400 MHz, CDCl$_3$) δ 8.50 (d, J=7.2, 1H), 8.18 (s, 1H), 8.03 (s, 1H), 7.72-7.66 (m, 3H), 7.62 (d, J=8.2, 3H), 6.82 (d, J=9.2, 1H), 6.66 (dd, J=1.8, 7.2, 1H), 4.88 (s, 2H), 3.37 (s, 3H), 2.27 (s, 3H). ESI-MS (m/z): [M+H]$^+$ 397.2, RT 1.5837 min.

Example 8

5-((4-fluorophenoxy)methyl)-3-(4-(trifluoromethyl)phenyl)pyrazolo[1,5-a]pyridine

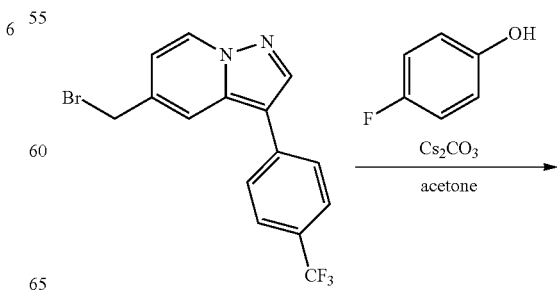

I-53

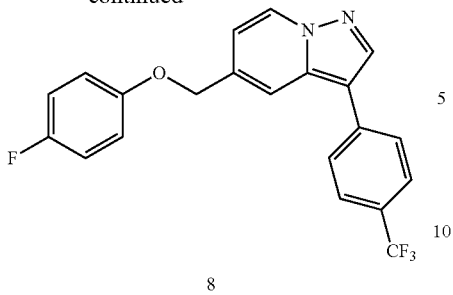

8

A mixture of pyrazolopyridine alkyl bromide (I-53) (17.7 mg, 0.05 mmol, 1.0 equiv.), 4-fluorophenol (11.2 mg, 0.1 mmol, 2.0 equiv.), and $Cs_2CO_3$ (48 mg, 0.15 mmol, 3.0 equiv.) in acetone was allowed to stir at rt for one hour. The mixture was filtered and purified by mass-triggered HPLC to provide 8. $^1$H NMR (400 MHz, $CDCl_3$) δ 8.51 (d, J=7.2, 1H), 8.17 (s, 1H), 7.83 (s, 1H), 7.68 (d, J=1.6, 4H), 7.05-6.82 (m, 5H), 5.07 (s, 2H). ESI-MS (m/z): [M+H]$^+$ 387.1, RT 2.5104 min.

Example 9

N-(4-cyanophenyl)-N-(2-methoxyethyl)-3-(4-(trifluoromethyl)phenyl)pyrazolo[1,5-a]pyridine-5-carboxamide

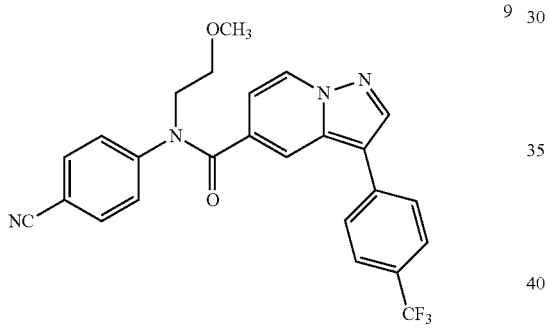

9

Example 9 was prepared according to the procedure described for the synthesis of Example 1 by replacing 4-(methylamino)benzonitrile with 4-((2-methoxyethyl)amino)benzonitrile. ESI-LC/MS m/z 465.2 (M+H)+; r.t.=2.098.

Example 10

N-(4-cyanophenyl)-N-(2-(dimethylamino)ethyl)-3-(4-(trifluoromethyl)phenyl)pyrazolo[1,5-a]pyridine-5-carboxamide

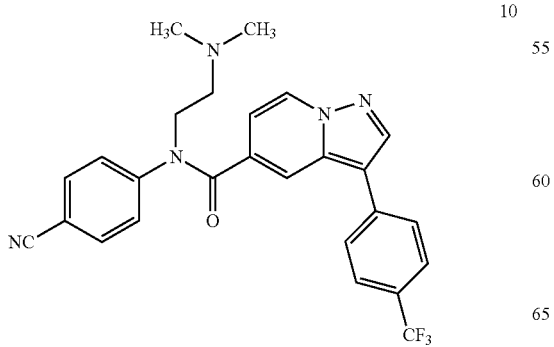

10

Example 10 was prepared according to the procedure described for the synthesis of Example 1 by replacing 4-(methylamino)benzonitrile with 4-((2-(dimethylamino)ethyl)amino)benzonitrile. ESI-LC/MS m/z 478.2 (M+H)$^+$; r.t.=1.550.

Example 11

N-(4-cyanophenyl)-N-((tetrahydro-2H-pyran-4-yl)methyl)-3-(4-(trifluoromethyl)phenyl)pyrazolo[1,5-a]pyridine-5-carboxamide

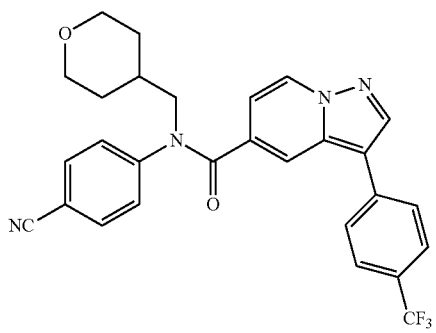

11

Example 11 was prepared according to the procedure described for the synthesis of Example 1 by replacing 4-(methylamino)benzonitrile with 4-(((tetrahydro-2H-pyran-4-yl)methyl)amino)benzonitrile. ESI-LC/MS m/z 505.2 (M+H)+; r.t.=1.997.

Example 12

N-(4-(methylsulfonyl)phenyl)-N-((tetrahydro-2H-pyran-4-yl)methyl)-3-(4-(trifluoromethyl)phenyl)pyrazolo[1,5-a]pyridine-5-carboxamide

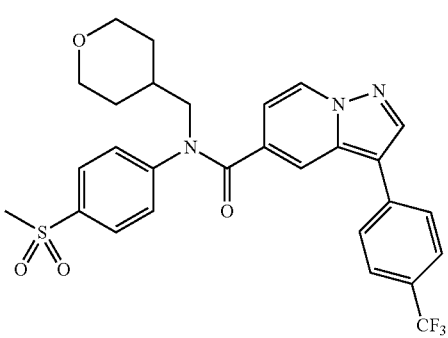

12

Example 12 was prepared according to the procedure described for the synthesis of Example 1 by replacing 4-(methylamino)benzonitrile with 4-(methylsulfonyl)-N-((tetrahydro-2H-pyran-4-yl)methyl)aniline. ESI-LC/MS m/z 558.2 (M+H)+; r.t.=1.828.

Example 13

N-(5-cyanopyridin-2-yl)-N-methyl-3-(4-(trifluoromethyl)phenyl)pyrazolo[1,5-a]pyridine-5-carboxamide

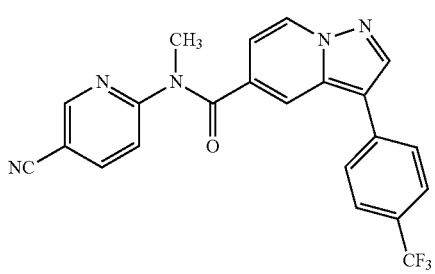

13

Example 13 was prepared according to the procedure described for the synthesis of Example 1 by replacing 4-(methylamino)benzonitrile with 6-(methylamino)nicotinonitrile. Purification by silica gel chromatography, eluting with hexane/ethyl acetate provided the desired product (13). $^1$H NMR (400 MHz, CDCl$_3$) δ 8.67 (dd, J=0.8, 2.3, 1H), 8.41 (dd, J=0.7, 7.2, 1H), 8.21 (s, 1H), 7.98 (m, 1H), 7.80 (dd, J=2.3, 8.6, 1H), 7.69 (d, J=8.2, 2H), 7.59 (d, J=8.1, 2H), 7.35 (dd, J=0.8, 8.7, 1H), 6.73 (dd, J=1.9, 7.2, 1H), 3.62 (s, 3H). ESI-MS (m/z): [M+H]$^+$ 422.1, RT 1.9712 min. Anal. Calcd for C$_{22}$H$_{14}$F$_3$N$_5$O$_+$0.2H$_2$O: C, 62.18; H, 3.42; N, 16.48. Found: C, 62.26, 62.26; H, 3.39, 3.38; N, 16.40, 16.38.

Example 14

N-methyl-N-(5-methylpyridin-3-yl)-3-(4-(trifluoromethyl)phenyl)pyrazolo[1,5-a]pyridine-5-carboxamide

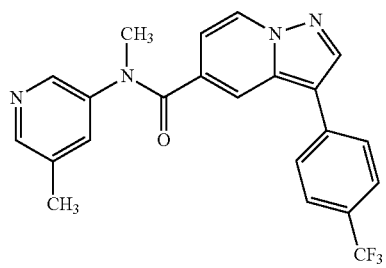

14

Example 14 was prepared according to the procedure described for the synthesis of Example 1 by replacing 4-(methylamino)benzonitrile with N,5-dimethylpyridin-3-amine. The reaction was purified by mass-triggered HPLC to provide the desired product, 14. ESI-MS (m/z): [M+H]$^+$ 411.2, RT 1.5164 min.

Example 15

5-(((5-methylpyridin-2-yl)oxy)methyl)-3-(4-(trifluoromethyl)phenyl)pyrazolo[1,5-a]pyridine

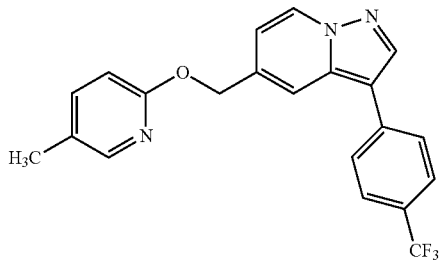

15

Example 15 was prepared according to the procedure described for the synthesis of Example 8 by replacing 4-fluorophenol with 1.5 equiv. of 5-methylpyridin-2-ol and using 2.0 equiv. Cs$_2$CO$_3$ in acetonitrile (to replace acetone). The reaction was purified by mass-triggered HPLC to provide the desired product. $^1$H NMR (400 MHz, MeOD) δ 8.57 (d, J=7.2, 1H), 8.32 (s, 1H), 7.91 (s, 1H), 7.84 (d, J=8.2, 2H), 7.74 (d, J=8.3, 2H), 7.61 (s, 1H), 7.47 (dd, J=2.5, 9.2, 1H), 6.94 (dd, J=1.8, 7.2, 1H), 6.57 (d, J=9.2, 1H), 5.26 (s, 2H), 2.12 (s, 3H). ESI-MS (m/z): [M+H]$^+$ 384.1, RT 1.8029 min.

Example 16

5-(4-fluorophenethyl)-3-(4-(trifluoromethyl)phenyl)pyrazolo[1,5-a]pyridine

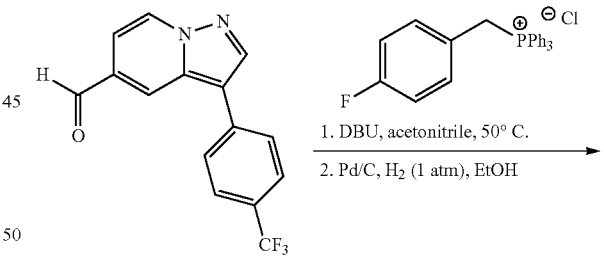

I-52

1. DBU, acetonitrile, 50° C.
2. Pd/C, H$_2$ (1 atm), EtOH

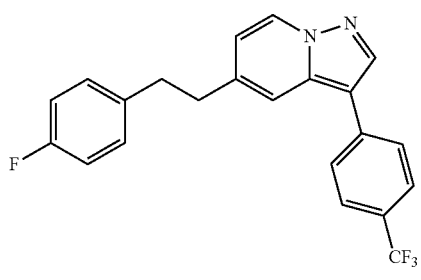

16

A mixture of pyrazolopyridine aldehyde (I-52) (48 mg, 0.165 mmol, 1.0 equiv.) and Wittig salt (74 mg, 0.18 mmol, 1.1 equiv.) in acetonitrile was treated with DBU (28 mg, 0.18 mmol, 1.1 equiv.). The resulting mixture was allowed to stir at 50° C. for two hours, and then the reaction mixture was concentrated. The residue was purified by silica gel chromatography, eluting with hexanes/EtOAc to give the desired olefin. A solution of olefin (22 mg, 0.0575 mmol, 1.0 equiv.) in 5 mL EtOH was purged with nitrogen gas, then 10% Pd/C (5 mg) was added. The resulting mixture was purged with hydrogen gas and allowed to stir at room temperature overnight under an atmosphere of hydrogen gas. The mixture was then filtered through Celite® and purified by mass-triggered HPLC to provide the desired product. $^1$H NMR (400 MHz, CDCl$_3$) δ 8.40 (d, J=7.6, 1H), 8.12 (s, 1H), 7.66 (d, J=8.3, 2H), 7.59 (d, J=8.2, 2H), 7.42 (s, 1H), 7.10 (dd, J=5.4, 8.6, 2H), 6.96 (t, J=8.7, 2H), 6.63 (dd, J=1.8, 7.1, 1H), 2.95 (s, 4H). ESI-MS (m/z): [M+H]$^+$ 385.2, RT 2.5863 min.

Example 17

N-(4-cyanophenyl)-N-methyl-3-(1-methyl-1H-indazol-5-yl)pyrazolo[1,5-a]pyridine-5-carboxamide

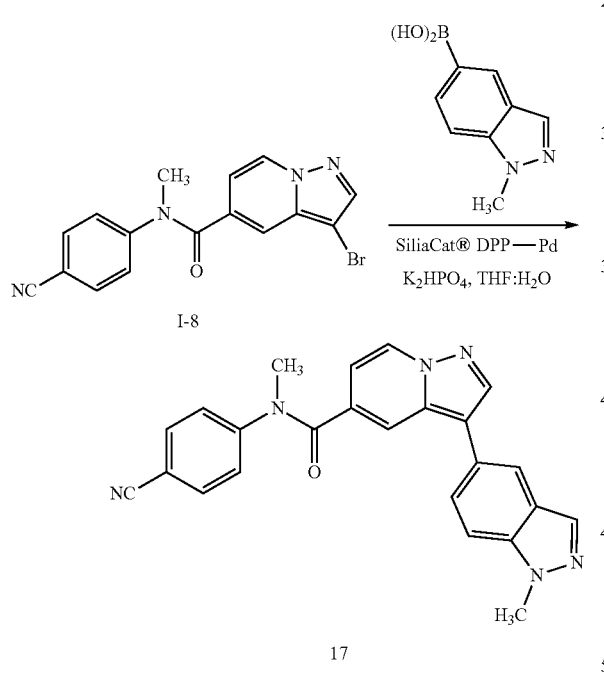

A mixture of aryl bromide (I-8) (1.0 equiv.), (1-methyl-1H-indazol-5-yl)boronic acid (1.5 equiv.), KH$_2$PO$_4$ (3.5 equiv.), and SiliaCat® DPP-Pd or Pd(dppf)Cl$_2$ (0.05-0.15 equiv.) in THF/water was allowed to heat at 150° C. in a microwave reactor for 40-60 minutes. The solvent was removed under reduced pressure and the crude material was purified by silica gel chromatography eluting with ethyl acetate and hexanes. $^1$H NMR (400 MHz, CDCl$_3$) δ 8.28 (dd, J=0.8, 7.4, 1H), 8.12 (s, 1H), 8.01 (d, J=0.8, 1H), 7.80 (m, 1H), 7.65 (s, 1H), 7.60 (d, J=8.6, 2H), 7.44 (d, J=8.6, 1H), 7.36 (dd, J=1.5, 8.6, 1H), 7.22 (obscured by CDCl$_3$ peak, 2H), 6.62 (dd, J=1.9, 7.3, 1H), 4.11 (s, 3H), 3.53 (s, 3H). ESI-MS (m/z): [M+H]+407.1, RT 1.6596 min. Anal. Calcd for C$_{24}$H$_{18}$N$_6$O+0.1H$_2$O: C, 70.61; H, 4.49; N, 20.59. Found: C, 70.59, 70.57; H, 4.43, 4.43; N, 20.57, 20.57.

Example 18

3-(6-acetamidopyridin-3-yl)-N-(4-cyanophenyl)-N-methylpyrazolo[1,5-a]pyridine-5-carboxamide

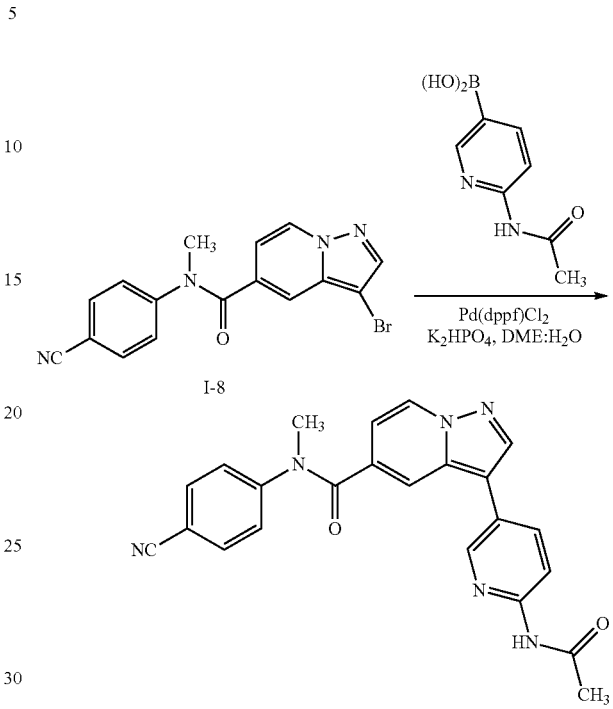

A mixture of aryl bromide (I-8) (1.0 equiv.), (6-acetamidopyridin-3-yl)boronic acid (1.5 equiv.), K$_2$CO$_3$ (3.0 equiv.), and Pd(dppf)Cl$_2$ (0.05-0.15 equiv.) in DME/water was allowed to heat at 110° C. for two hours. Following extraction of the reaction mixture with CH$_2$Cl$_2$, the combined organic extracts were concentrated and the residue was purified by silica gel chromatography, eluting with hexanes/EtOAc to give the desired product. $^1$H NMR (400 MHz, MeOD) δ 8.48 (dd, J=0.8, 7.0, 1H), 8.35 (d, J=2.4, 1H), 8.26 (s, 1H), 8.18 (d, J=8.4, 1H), 7.81 (dd, J=2.4, 8.6, 1H), 7.78 (s, 1H), 7.71 (d, J=8.6, 2H), 7.48 (d, J=8.6, 2H), 6.87 (dd, J=1.8, 7.3, 1H), 3.55 (s, 3H), 2.21 (s, 3H). ESI-MS (m/z): [M+H]$^+$ 411.2, RT 1.2806 min.

Example 19

3-(4-carbamoylphenyl)-N-(4-cyanophenyl)-N-methylpyrazolo[1,5-a]pyridine-5-carboxamide

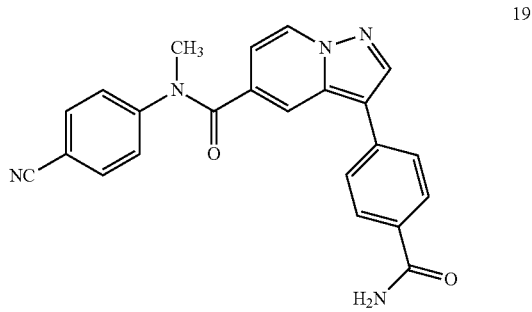 [SMILES: CN(C(=O)c1ccn2ncc(-c3ccc(C(N)=O)cc3)c2c1)c1ccc(C#N)cc1]

Example 19 was prepared according to the procedure described for the synthesis of Example 17 by replacing (1-methyl-1H-indazol-5-yl)boronic acid with (4-carbamoylphenyl)boronic acid. The reaction was purified by silica gel chromatography, eluting with hexanes/EtOAc to give 19 as the desired product. $^1$H NMR (400 MHz, MeOD) δ 8.49 (dd, J=0.8, 7.2, 1H), 8.31 (s, 1H), 7.97 (d, J=8.4, 2H), 7.84 (s, 1H), 7.74 (d, J=8.6, 2H), 7.53-7.46 (2d, J=8.6, 4H), 6.91 (dd, J=1.6, 7.2, 1H), 3.56 (s, 3H). ESI-MS (m/z): [M+H]$^+$ 397.2, RT 1.3648 min. Anal. Calcd for $C_{23}H_{17}N_5O_2$+0.5$H_2O$: C, 68.31; H, 4.49; N, 17.32. Found: C, 68.61, 68.54; H, 4.46, 4.40; N, 17.07, 16.99.

Example 20

3-(4-carbamoylphenyl)-N-(4-fluorophenyl)-N-methylpyrazolo[1,5-a]pyridine-5-carboxamide

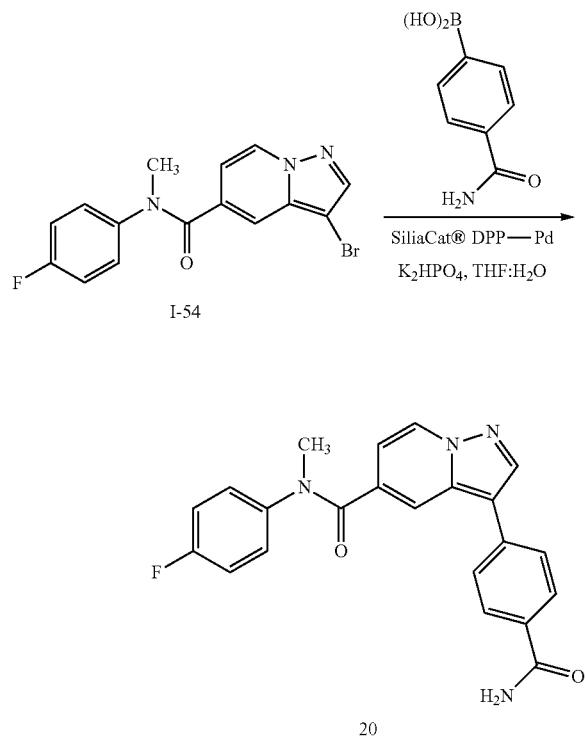

A mixture of aryl bromide (I-54) (1.0 equiv.), (4-carbamoylphenyl)boronic acid (1.5 equiv.), $KH_2PO_4$ (3.5 equiv.), and SiliaCat® DPP-Pd or Pd(dppf)Cl2 (0.05-0.15 equiv.) in THF/water was allowed to heat at 150° C. in a microwave reactor for 40-60 minutes. The solvent was removed under reduced pressure and the crude material was purified by silica gel chromatography, eluting with hexanes/EtOAc to give 20 as the desired product. $^1$H NMR (400 MHz, CDCl$_3$) δ 8.28 (dd, J=0.8, 7.2, 1H), 8.14 (s, 1H), 7.84 (dt, J=2.0, 8.4, 2H), 7.74 (s, 1H), 7.42 (d, J=8.4, 2H), 7.14-7.08 (m, 2H), 7.06-6.99 (m, 2H), 6.75 (dd, J=1.8, 7.4, 1H), 6.07 (br s, 1H), 5.56 (br s, 1H), 3.49 (s, 3H). ESI-MS (m/z): [M+H]$^+$ 389.1, RT 1.4322 min. Anal. Calcd for $C_{22}H_{17}FN_4O_2$+0.4$H_2O$: C, 66.79; H, 4.54; N, 14.16. Found: C, 66.97, 66.74; H, 4.49, 4.43; N, 14.20, 14.16.

Example 21

5-(((4-fluorophenyl)thio)methyl)-3-(4-(trifluoromethyl)phenyl)pyrazolo[1,5-a]pyridine

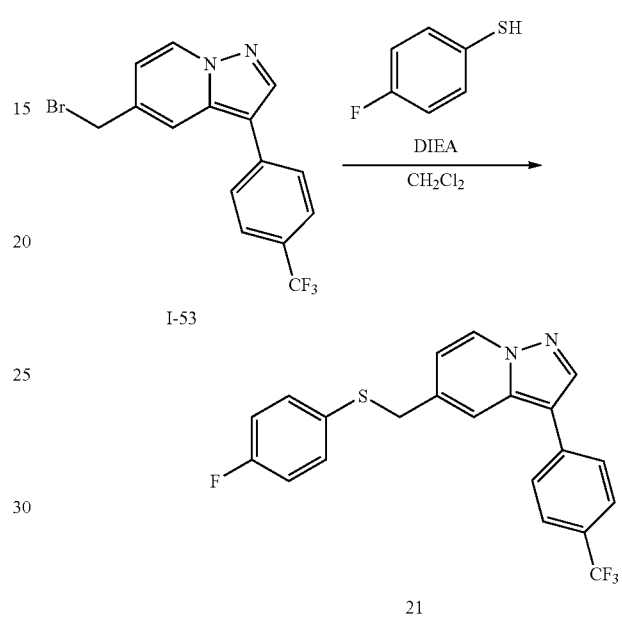

A solution of pyrazolopyridine alkyl bromide (I-53) (45 mg, 0.127 mmol, 1.0 equiv.) and 4-fluorobenzenethiol (24 mg, 0.19 mmol, 1.5 equiv.) in $CH_2Cl_2$ was treated with DIEA (33 mg, 0.254 mmol, 2.0 equiv.) and the resulting solution was allowed to stir at rt for 20 minutes. The reaction was concentrated and the residue was purified by silica gel chromatography, eluting with hexanes/EtOAc to give 21 as the desired product. $^1$H NMR (400 MHz, CDCl$_3$) δ 8.41 (d, J=7.2, 1H), 8.11 (s, 1H), 7.64 (d, J=8.1, 2H), 7.50 (d, J=8.1, 2H), 7.36-7.27 (m, 3H), 6.96 (t, J=8.7, 2H), 6.78 (dd, J=1.9, 7.2, 1H), 4.00 (s, 2H). ESI-MS (m/z): [M+H]$^+$ 403.1, RT 2.5275 min.

Example 22

5-(((4-fluorophenyl)sulfinyl)methyl)-3-(4-(trifluoromethyl)phenyl)pyrazolo[1,5-a]pyridine

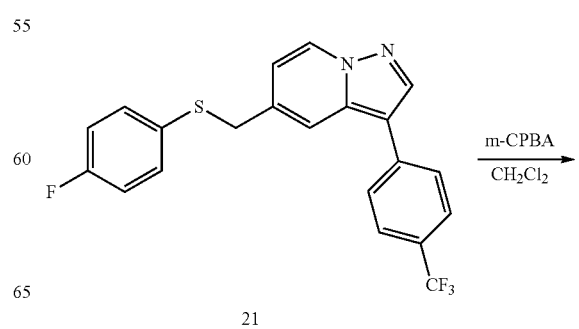

-continued

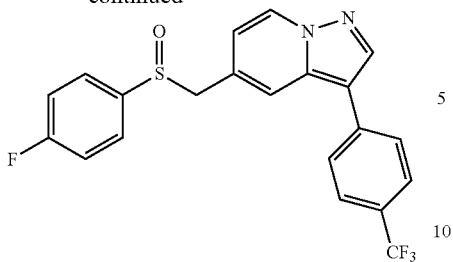

22

A solution of sulfide (21) (30 mg, 0.75 mmol, 1.0 equiv.) in 1 mL of CH$_2$Cl$_2$ was treated with m-CPBA (77% purity, 16.6 mg, 0.75 mmol, 1.0 equiv.) and the resulting mixture was allowed to sitr at rt for 20 minutes. The reaction was concentrated and the residue was purified by silica gel chromatography, eluting with hexanes/EtOAc to give 22 as the desired product. $^1$H NMR (400 MHz, CDCl$_3$) δ 8.38 (d, J=7.2, 1H), 8.15 (s, 1H), 7.66 (d, J=8.2, 2H), 7.53 (d, J=8.0, 2H), 7.49-7.43 (m, 2H), 7.32 (d, J=0.7, 1H), 7.20-7.13 (m, 2H), 6.46 (dd, J=1.8, 7.1, 1H), 4.12 (d, J=12.9, 1H), 3.95 (d, J=12.9, 1H). ESI-MS (m/z): [M+H]$^+$ 419.1, RT 2.0051 min.

Example 23

3-(4-(1H-pyrazol-5-yl)phenyl)-N-(4-cyanophenyl)-N-methylpyrazolo[1,5-a]pyridine-5-carboxamide

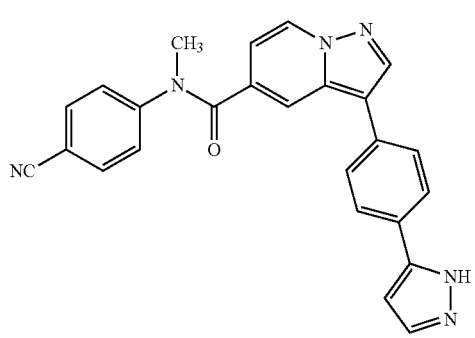

23

Example 23 was prepared according to the procedure described for the synthesis of Example 17 by replacing (1-methyl-1H-indazol-5-yl)boronic acid with ((4-(1H-pyrazol-5-yl)phenyl)boronic acid. The reaction was purified by mass-triggered HPLC to provide 23 as the desired product. $^1$H NMR (400 MHz, CDCl$_3$) δ 8.30 (dd, J=0.9, 7.3, 1H), 8.15 (s, 1H), 7.83-7.78 (m, 3H), 7.65 (d, J=2.3, 1H), 7.64-7.59 (m, 2H), 7.41-7.34 (m, 2H), 7.25-7.21 (m, 2H), 6.70-6.65 (m, 2H), 3.54 (s, 3H). ESI-MS (m/z): [M+H]$^+$ 419.2, RT 1.5585 min.

Example 24

N-(4-cyanophenyl)-N-methyl-3-(5-(trifluoromethyl)109yridine-2-yl)pyrazolo[1,5-a]pyridine-5-carboxamide

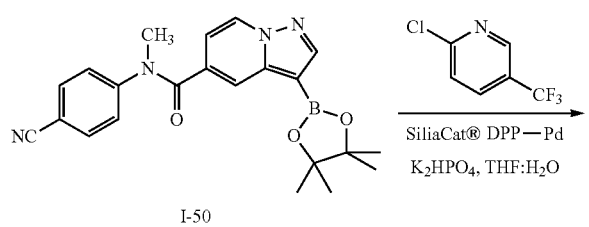

-continued

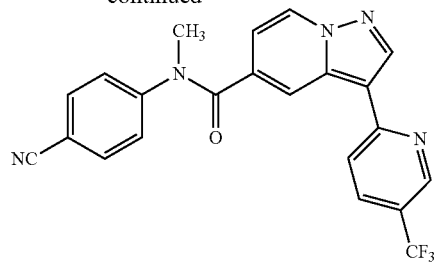

24

A mixture of 2-chloro-5-(trifluoromethyl)pyridine (1.0 equiv.), 1-50 (1.5 equiv.), KH$_2$PO$_4$ (3.5 equiv.), and SiliaCat® DPP-Pd or Pd(dppf)Cl2 (0.05-0.15 equiv.) in THF/water was allowed to heat at 150° C. in a microwave reactor for 40-60 minutes. The solvent was removed under reduced pressure and the crude material was purified by silica gel chromatography eluting with ethyl acetate and hexanes. $^1$H NMR (400 MHz, CDCl$_3$) δ 8.77 (s, 1H), 8.63 (dd, J=0.8, 2.0, 1H), 8.40 (s, 1H), 8.33 (dd, J=0.8, 7.2, 1H), 7.88 (dd, J=2.4, 8.4, 1H), 7.66 (d, J=8.4, 1H), 7.56 (dt, J=2.1, 8.7, 2H), 7.25 (app dt, obscured by CDCl$_3$ peak, 2H), 6.79 (dd, J=1.9, 7.2, 1H), 3.56 (s, 3H). ESI-MS (m/z): [M+H]$^+$ 422.1, RT 1.8535 min.

Example 25

N-(5-cyanopyridin-2-yl)-N-methyl-3-(5-(trifluoromethyl)109yridine-2-yl)pyrazolo[1,5-a]pyridine-5-carboxamide

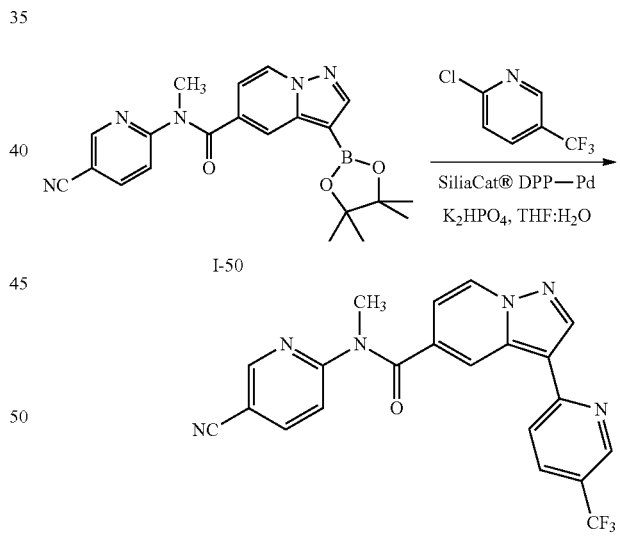

25

A mixture of 2-chloro-5-(trifluoromethyl)pyridine (1.0 equiv.), 1-50 (1.5 equiv.), KH$_2$PO$_4$ (3.5 equiv.), and SiliaCat® DPP-Pd or Pd(dppf)Cl2 (0.05-0.15 equiv.) in THF/water was allowed to heat at 150° C. in a microwave reactor for 40-60 minutes. The solvent was removed under reduced pressure and the crude material was purified by silica gel chromatography with ethyl acetate and hexanes. $^1$H NMR (400 MHz, MeOD) δ 8.88-8.84 (m, 1H), 8.73 (dd, J=0.8, 2.4, 1H), 8.69 (s, 1H), 8.65 (dd, J=1.2, 2.4, 1H), 8.61 (dd, J=0.8, 7.2, 1H), 8.09-8.02 (m, 2H), 7.99 (d, J=8.5, 1H), 7.53 (dd, J=0.8, 8.5, 1H), 7.02 (dd, J=2.0, 7.2, 1H), 3.65 (s, 3H). ESI-MS (m/z): [M+H]+ 423.0, RT 1.8535 min.

Example 26

(S)-3-(4-(2-aminopropanamido)phenyl)-N-(4-cyanophenyl)-N-methylpyrazolo[1,5-a]pyridine-5-carboxamide

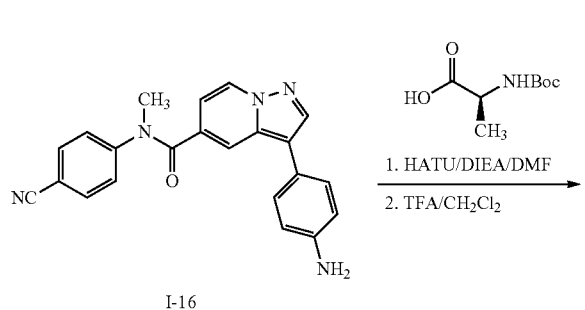

I-16

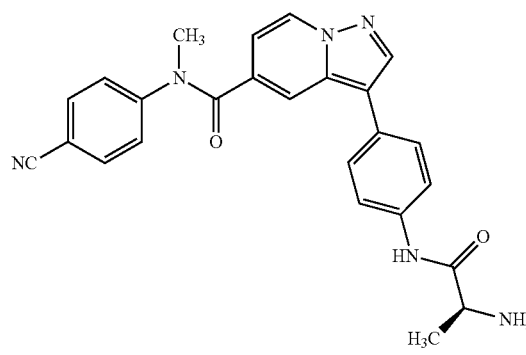

26

A solution of the aniline (30 mg, 0.082 mmol, 1.0 equiv.) in CH₂Cl₂ was treated with N-Boc-L-Ala-OH (18.5 mg, 0.098 mmol, 1.2 equiv.), followed by HATU (34.3 mg, 0.0902 mmol, 1.1 equiv.) and DIEA (21 mg, 0.16 mmol, 2.0 equiv.). The resulting mixture was allowed to stir at rt for two hours, and then was purified by silica gel chromatography, eluting with CH₂Cl₂/EtOAc to give the desired N-Boc coupled product. The N-Boc alanine amide (35 mg) was dissolved in 1 mL CH₂Cl₂ and 1 mL TFA was added. The resulting solution was allowed to stir at rt for 30 minutes, and the solvents were removed under reduced pressure. The residue was taken up in 2 mL EtOAc and 3 mL hexanes was added to precipitate the product TFA salt, which was isolated by filtration and dried under high vacuum. A solution of the TFA salt (16 mg) in 20% MeOH/CH₂Cl₂ was run through a 100 mg cartridge of Varian Stratospheres™ PL-HCO₃ MP resin. The solvents were removed under reduced pressure, and the residue was dissolved in 10% MeOH/CH₂Cl₂ and run through a 200 mg cartridge of Varian Stratospheres™ PL-HCO₃ MP resin. The solvents were removed under reduced pressure to provide 26 as the free base. ¹H NMR (400 MHz, MeOD) δ 8.45 (dd, J=0.8, 7.2, 1H), 8.18 (s, 1H), 7.75-7.71 (m, 3H), 7.68 (d, J=8.6, 2H), 7.47 (d, J=8.6, 2H), 7.32 (d, J=8.6, 2H), 6.87 (dd, J=1.8, 7.3, 1H), 3.61 (q, J=6.9, 1H), 3.55 (s, 3H), 1.40 (d, J=6.9, 3H). ESI-MS (m/z): [M+H]+ 439.1, RT 1.1711 min.

Example 27

3-(5-carbamoylpyridin-2-yl)-N-(4-cyanophenyl)-N-methylpyrazolo[1,5-a]pyridine-5-carboxamide

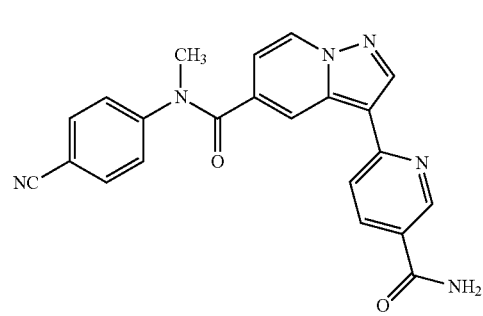

27

Example 27 was prepared according to the procedure described for the synthesis of Example 25 by replacing 2-chloro-5-(trifluoromethyl)pyridine with 6-chloronicotinamide. Purification by silica gel chromatography, eluting with hexanes/EtOAc, then 5% MeOH/CH₂Cl₂ gave the desired product. ¹H NMR (400 MHz, DMSO) δ 9.04 (dd, J=0.8, 2.3, 1H), 8.81 (s, 1H), 8.68 (dd, J=0.8, 7.2, 1H), 8.56 (s, 1H), 8.22 (dd, J=2.3, 8.4, 1H), 8.14 (s, 1H), 7.94 (d, J=8.3, 1H), 7.81 (d, J=8.7, 2H), 7.58 (s, 1H), 7.54 (d, J=8.6, 2H), 6.85 (dd, J=1.9, 7.2, 1H), 3.47 (s, 3H). ESI-MS (m/z): [M+H]+ 397.1, RT 1.2047 min.

Example 28

4-cyano-N-methyl-N-(3-(4-(trifluoromethyl)phenyl)pyrazolo[1,5-a]pyridine-5-yl)benzamide

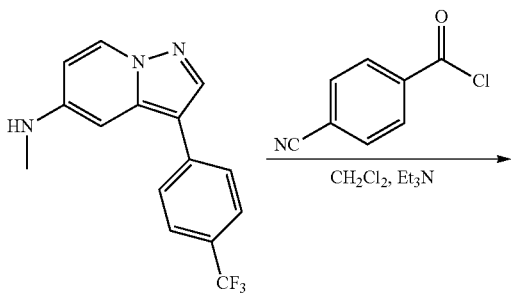

I-58

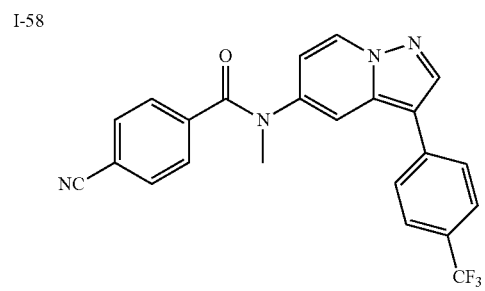

28

To a solution of pyrazolopyridine (15 mg, 0.05 mmol) in CH₂Cl₂ containing triethylamine (0.020 mL, 3.00 mmol) at 0° C. was added 4-cyanobenzoyl chloride (14 mg, 1.50 mmol). The reaction was allowed to warm to room temperature and stir for 1 hour. The reaction was diluted with water and extracted with dichloromethane. The organic extracts were washed with brine and dried over anhydrous Na₂SO₄. The solvent was removed and the residue was purified by mass-trigger HPLC. ¹H NMR (400 MHz, MeOD) δ 8.54 (d, J=7.4, 1H), 8.29 (s, 1H), 7.66 (ddd, J=8.1, 12.9, 29.8, 9H), 6.92 (dd, J=2.2, 7.4, 1H), 3.56 (s, 3H); MS m/z 421.0 (M+H)⁺.

Example 29

4-fluoro-N-methyl-N-(3-(4-(trifluoromethyl)phenyl) pyrazolo[1,5-a]pyridine-5-yl)benzamide

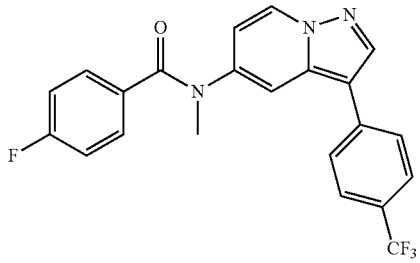

29

Example 29 was prepared according to the procedure described for the synthesis of Example 28 by replacing 4-cyanobenzoyl chloride with 4-fluorobenzoyl chloride. ¹H NMR (400 MHz, MeOD) δ 8.43 (d, J=7.4, 1H), 8.18 (s, 1H), 8.06-7.84 (m, 1H), 7.60 (d, J=8.3, 2H), 7.50 (d, J=8.5, 3H), 7.40 (dd, J=5.3, 8.8, 2H), 7.08 (t, J=8.8, 1H), 6.96 (t, J=8.8, 2H), 6.78 (d, J=7.4, 1H), 3.45 (s, 3H); MS m/z 414.1 (M+H)⁺.

Example 30

4-cyano-N-methyl-N-(3-(4-(trifluoromethyl)phenyl) pyrazolo[1,5-a]pyridine-5-yl)benzenesulfonamide

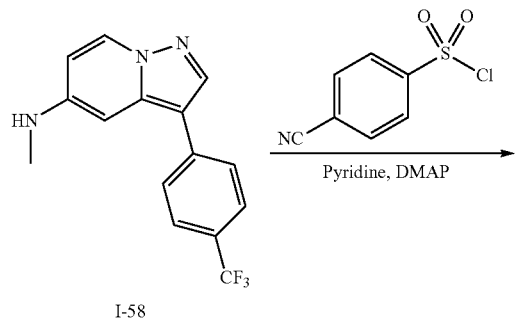

I-58

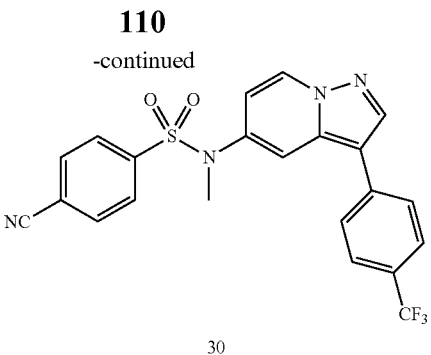

30

To a solution of pyrazolopyridine (15 mg, 0.05 mmol) and a catalytic amount of DMAP in pyridine (1.0 mL) at 0° C. was added 4-cyanobenzene-1-sulfonyl chloride (18 mg, 0.08 mmol). The reaction was allowed to warm to room temperature and stir overnight. The reaction was diluted with water and extracted with dichloromethane. The organic extracts were washed with saturated CuSO₄ solution and brine, dried over anhydrous Na₂SO₄. The solvent was removed and the crude material was purified by mass-triggered HPLC. ¹H NMR (400 MHz, MeOD) δ 8.57 (d, J=7.6, 1H), 8.34 (s, 1H), 7.95 (d, J=8.3, 2H), 7.83 (d, J=8.4, 2H), 7.73 (s, 4H), 7.61 (s, 1H), 6.85 (d, J=7.5, 1H), 3.32 (s, 3H, obscured by MeOD peak); MS m/z 457.0 (M+H)⁺.

Example 31

4-fluoro-N-methyl-N-(3-(4-(trifluoromethyl)phenyl) pyrazolo[1,5-a]pyridine-5-yl)benzenesulfonamide

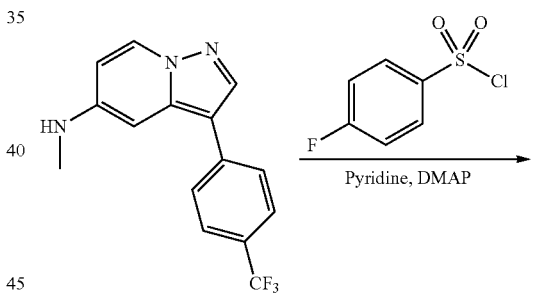

I-58

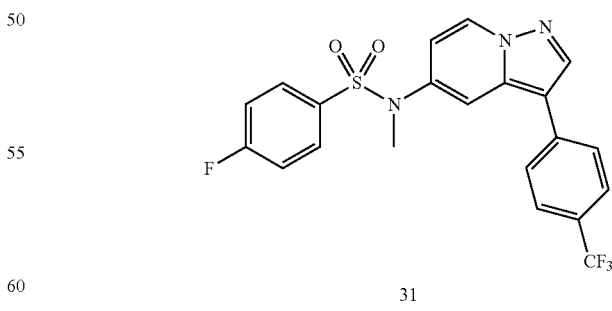

31

Example 31 was prepared according to the procedure described for the synthesis of Example 30 by replacing 4-cyanobenzene-1-sulfonyl chloride with 4-fluorobenzene-1-sulfonyl chloride. ESI-LC/MS m/z 450.0 (M+H)+; r.t.=1.954.

Example 32

3-(4-carbamoylphenyl)-N-(5-cyanopyridin-2-yl)-N-methylpyrazolo[1,5-a]pyridine-5-carboxamide

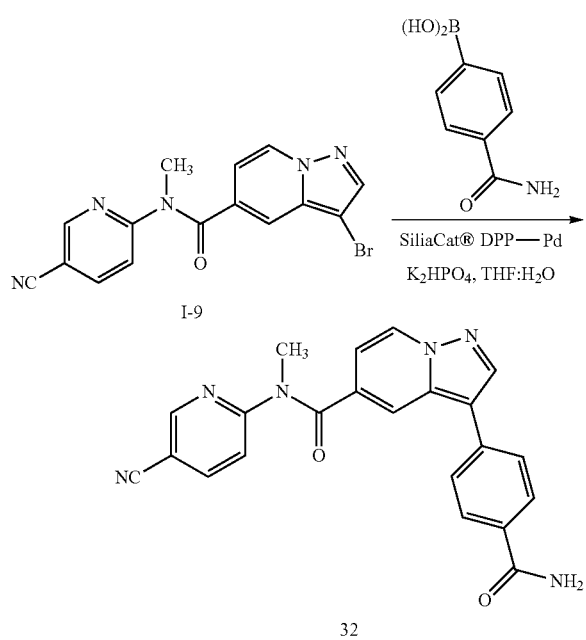

Example 32 was prepared from intermediate I-9 according to the procedure described for the synthesis of Example 17 by replacing (1-methyl-1H-indazol-5-yl)boronic acid with (4-carbamoylphenyl)boronic acid. The reaction was purified by silica gel chromatography, eluting with dichloromethane/ethyl acetate then 5% methanol/dichloromethane to give 32 as the desired product. $^1$H NMR (400 MHz, DMSO) δ 8.87 (dd, J=0.6, 2.2, 1H), 8.72 (dd, J=0.7, 7.2, 1H), 8.53 (s, 1H), 8.26 (dd, J=2.3, 8.6, 1H), 8.03 (s, 1H), 8.00-7.91 (m, 3H), 7.67-7.57 (m, 3H), 7.40 (s, 1H), 6.85 (dd, J=1.8, 7.2, 1H), 3.53 (s, 3H). ESI-MS (m/z): [M+H]$^+$ 398.1, RT 1.2637 min.

Example 33

N-methyl-3-(4-(trifluoromethyl)phenyl)-N-(5-(trifluoromethyl)pyridine-2-yl)pyrazolo[1,5-a]pyridine-5-carboxamide

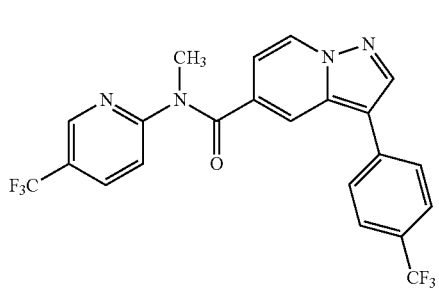

Example 33 was prepared according to the procedure described for the synthesis of Example 1 by replacing 4-(methylamino)benzonitrile with N-methyl-5-(trifluoromethyl) pyridine-2-amine. The reaction was purified by mass-triggered HPLC to provide 33 as the desired product. ESI-MS (m/z): [M+H]$^+$ 465.1, RT 2.0724 min.

Example 34

N-methyl-N-(5-(methylsulfonyl)114yridine-2-yl)-3-(4-(trifluoromethyl)phenyl)pyrazolo[1,5-a]pyridine-5-carboxamide

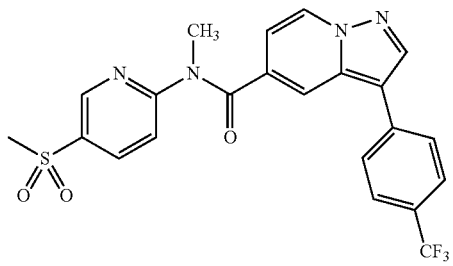

Example 33 was prepared according to the procedure described for the synthesis of Example 1 by replacing 4-(methylamino)benzonitrile with N-methyl-5-(methylsulfonyl) pyridine-2-amine. The reaction was purified by silica gel chromatography, eluting with hexanes/EtOAc, followed by purification by mass-triggered HPLC to provide 34 as the desired product. $^1$H NMR (400 MHz, MeOD) δ 8.89 (d, J=2.4, 1H), 8.56 (d, J=7.2, 1H), 8.35 (s, 1H), 8.23 (dd, J=2.5, 8.6, 1H), 7.91 (s, 1H), 7.75 (d, J=8.3, 2H), 7.66 (d, J=8.2, 2H), 7.56 (d, J=8.6, 1H), 6.94 (dd, J=1.8, 7.3, 1H), 3.65 (s, 3H), 3.12 (s, 3H). ESI-MS (m/z): [M+H]$^+$ 475.1, RT 1.7860 min.

Example 35

N-(4-fluorobenzyl)-3-(4-(trifluoromethyl)phenyl)pyrazolo[1,5-a]pyridine-5-amine

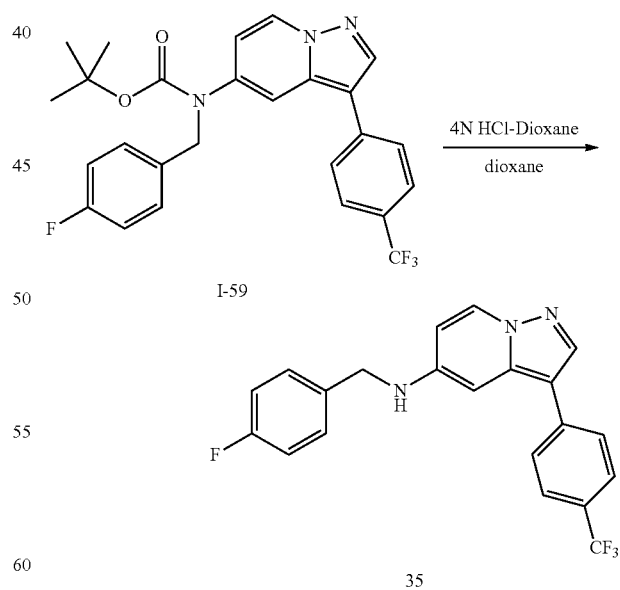

To a stirred solution of pyrazolopyridine (25 mg, 0.05 mmol) in dioxane (1.0 mL) was added 4N HCl in dioxane (1.0 mL). The reaction was monitored by LCMS and when the reaction was complete, the resultant HCl salt was filtered and dried to give 35. ESI-LC/MS m/z 386.1 (M+H)+; r.t.=2.167.

Example 36

N-(4-fluorobenzyl)-N-methyl-3-(4-(trifluoromethyl)phenyl)pyrazolo[1,5-a]pyridine-5-amine

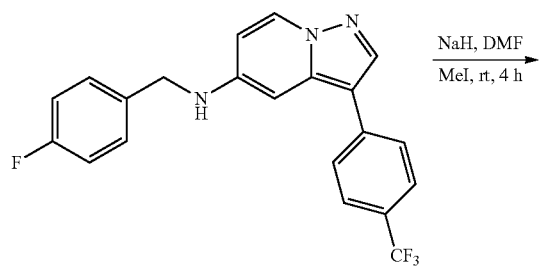

NaH (5 mg, 0.08 mmol) was added to a solution of pyrazolopyridine (19 mg, 0.05 mmol) and DMF (1.0 mL). MeI (0.020 mL, 0.06 mmol) was added and the reaction was stirred for 4 h at room temperature. The reaction was quenched by addition of H₂O. The solution was extracted with ethyl acetate. The combined extracts were washed with brine, dried over anhydrous Na₂SO₄ and concentrated. The crude material was purified by silica gel chromatography, eluting with ethyl acetate and hexanes. ¹H NMR (400 MHz, MeOD) δ 8.21 (d, J=8.7, 1H), 8.02 (s, 1H), 7.57 (q, J=8.7, 4H), 7.19 (dd, J=5.4, 8.5, 2H), 6.98 (t, J=8.8, 2H), 6.78-6.63 (m, 2H), 4.60 (s, 2H), 3.09 (s, 3H); MS m/z 400.2 (M+H)⁺.

Example 37

N-methyl-6-(trifluoromethyl)-N-(3-(4-(trifluoromethyl)phenyl)pyrazolo[1,5-a]pyridine-5-yl)nicotinamide

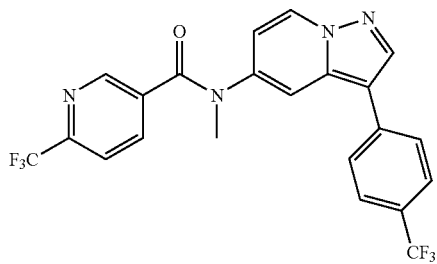

Example 37 was prepared according to the procedure described for the synthesis of Example 28 by replacing 4-cyanobenzoyl chloride with 6-(trifluoromethyl)nicotinoyl chloride. ¹H NMR (400 MHz, MeOD) δ 8.69 (s, 1H), 8.48 (d, J=7.5, 1H), 8.20 (s, 1H), 7.97 (d, J=8.1, 1H), 7.63 (dd, J=8.2, 24.5, 5H), 7.48 (d, J=8.1, 2H), 6.86 (dd, J=2.2, 7.4, 1H), 3.48 (s, 3H). ESI-LC/MS m/z 465.1 (M+H)⁺; r.t.=1.696.

Example 38

N-methyl-5-(trifluoromethyl)-N-(3-(4-(trifluoromethyl)phenyl)pyrazolo[1,5-a]pyridine-5-yl)picolinamide

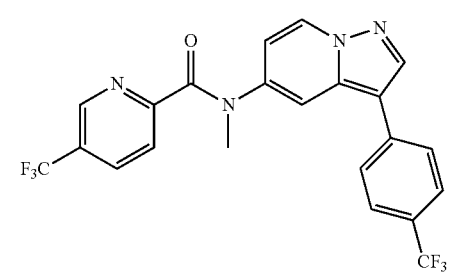

Example 38 was prepared according to the procedure described for the synthesis of Example 28 by replacing 4-cyanobenzoyl chloride with 5-(trifluoromethyl)picolinoyl chloride. ¹H NMR (400 MHz, CDCl₃) δ 8.56 (s, 1H), 8.35 (d, J=7.4, 1H), 8.08 (s, 1H), 7.94 (d, J=6.9, 1H), 7.81 (d, J=8.2, 1H), 7.59 (d, J=8.2, 2H), 7.40 (d, J=7.8, 2H), 7.32 (s, 1H), 6.63 (s, 1H), 3.51 (s, 3H). ESI-LC/MS m/z 465.1 (M+H)+; r.t.=1.740.

Example 39

4-cyano-N-((tetrahydro-2H-pyran-4-yl)methyl)-N-(3-(4-(trifluoromethyl)phenyl)pyrazolo[1,5-a]pyridin-5-yl)benzamide

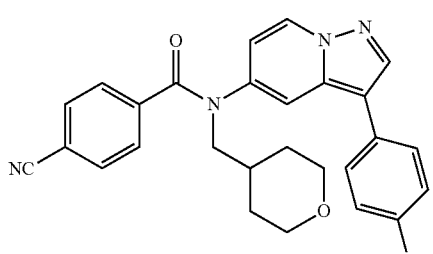

Example 39 was prepared according to the procedure described for the synthesis of Example 28. ¹H NMR (400 MHz, CDCl₃) δ 8.35 (d, J=7.4, 1H), 8.09 (s, 1H), 7.61 (d, J=8.1, 2H), 7.52 (d, J=8.4, 2H), 7.43 (d, J=8.5, 2H), 7.29 (d, J=8.1, 2H), 7.17 (s, 1H), 6.50 (dd, J=2.3, 7.4, 1H), 3.97-3.81

(m, 4H), 3.25 (dd, J=9.8, 11.7, 2H), 1.96 (d, J=13.1, 1H), 1.55 (d, J=18.6, 2H), 1.45-1.29 (m, 2H). ESI-LC/MS m/z 505.1 (M+H)⁺; r.t.=1.689.

Example 40

N-(4-cyanophenyl)-N-methyl-3-(1H-pyrrolo[2,3-b]pyridin-5-yl)pyrazolo[1,5-a]pyridine-5-carboxamide

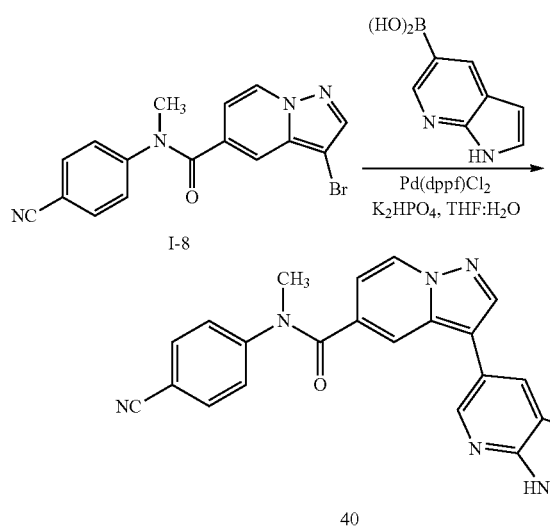

A mixture of aryl bromide (I-8) (1.0 equiv.), (1H-pyrrolo[2,3-b]pyridin-5-yl)boronic acid (1.5 equiv.), K₂HPO₄ (2.5 equiv.), and Pd(dppf)C12 (0.05-0.15 equiv.) in THF/water was allowed to heat at 80° C. overnight. The solvent was removed and the crude residue was purified by silica gel chromatography, eluting with hexanes/EtOAc, then 5% MeOH/CH₂Cl₂ gave the desired product. ¹H NMR (400 MHz, DMSO) δ 11.76 (s, 1H), 8.64 (dd, J=0.7, 7.2, 1H), 8.39 (s, 1H), 8.33 (d, J=2.1, 1H), 7.88 (d, J=2.0, 1H), 7.84 (d, J=8.6, 2H), 7.79 (s, 1H), 7.59-7.50 (m, 3H), 6.79 (dd, J=1.8, 7.2, 1H), 6.53 (dd, J=1.8, 3.4, 1H), 3.46 (s, 3H). ESI-MS (m/z): [M+H]⁺ 393.1, RT 1.1533 min.

Example 41

3-(6-aminopyridin-3-yl)-N-(4-cyanophenyl)-N-methylpyrazolo[1,5-a]pyridine-5-carboxamide

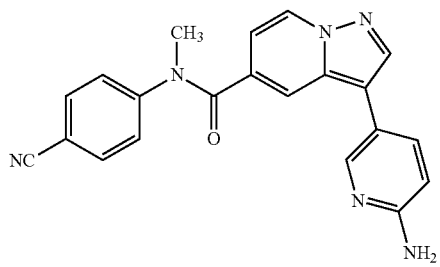

Example 41 was prepared according to the procedure described for the synthesis of Example 40 by replacing (1H-pyrrolo[2,3-b]pyridin-5-yl)boronic acid with (6-aminopyridin-3-yl)boronic acid. The reaction was purified by silica gel chromatography, eluting with hexanes/EtOAc, then 5% MeOH/CH₂Cl₂, followed by purification by mass-triggered HPLC and a NaHCO₃/EtOAc workup gave the desired product. ¹H NMR (400 MHz, MeOD) δ 8.43 (dd, J=0.7, 7.3, 1H), 8.12 (s, 1H), 7.93 (d, J=1.6, 1H), 7.72 (d, J=8.6, 2H), 7.68 (s, 1H), 7.50 (dd, J=2.4, 8.6, 1H), 7.46 (d, J=8.6, 2H), 6.83 (dd, J=1.8, 7.3, 1H), 6.69 (d, J=8.6, 1H), 3.54 (s, 3H). ESI-MS (m/z): [M+H]⁺ 369.1, RT 0.8592 min.

Example 42

3-(4-aminophenyl)-N-(4-cyanophenyl)-N-methylpyrazolo[1,5-a]pyridine-5-carboxamide

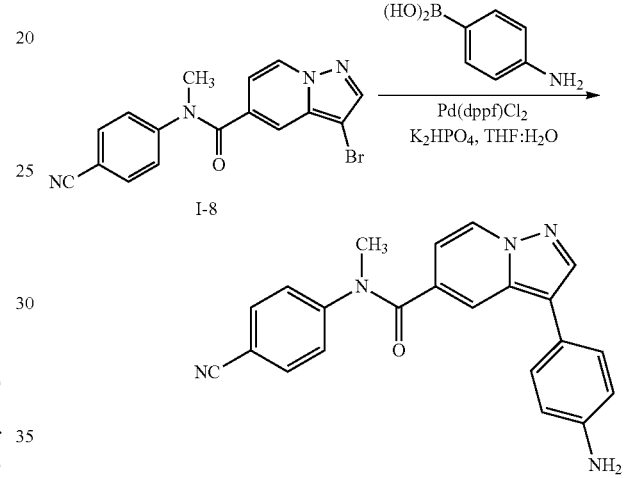

A mixture of aryl bromide (I-8) (1.0 equiv.), (4-aminophenyl)boronic acid (1.5 equiv.), K₂HPO₄ (2.5 equiv.), and Pd(dppf)C12 (0.05-0.15 equiv.) in THF/water was allowed to heat at 110° C. overnight. The solvent was removed and the crude residue was by silica gel chromatography, eluting with hexanes/EtOAc gave the desired product. ESI-MS (m/z): [M+H]⁺ 368.1, RT 1.0446 min.

Example 43

3-(4-(2-aminoacetamido)phenyl)-N-(4-cyanophenyl)-N-methylpyrazolo[1,5-a]pyridine-5-carboxamide

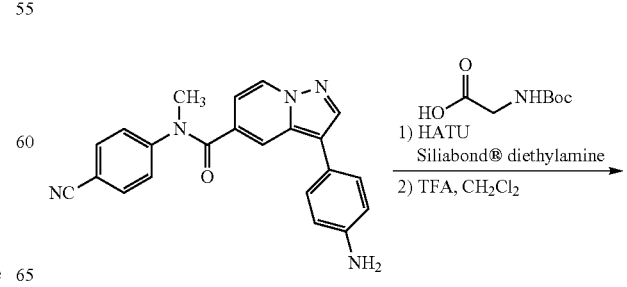

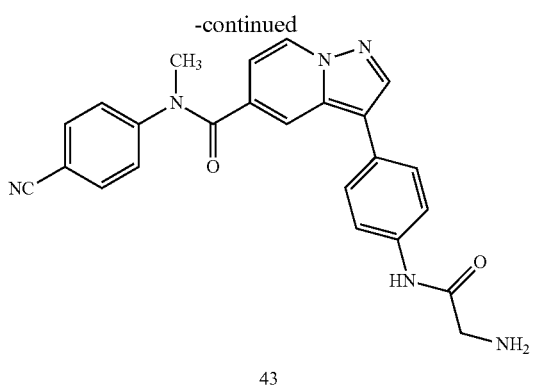

43

A solution of Example 42 (1.0 equiv.) in CH₂Cl₂ (~0.1 M) was treated with 2-((tert-butoxycarbonyl)amino)acetic acid (1.2 equiv.), followed by HATU (1.1 equiv(2.5 equiv.). The resulting mixture was allowed to stir at rt for two hours, and then was filtered and treated with one volume of TFA. The resulting solution was allowed to stir at rt for 30 minutes, and the solvents were removed under reduced pressure. The residue was purified by mass-triggered HPLC to provide the desired product. ESI-MS (m/z): [M+H]⁺ 425.1, RT 1.1033 min.

Example 44

(R)-3-(4-(2-aminopropanamido)phenyl)-N-(4-cyanophenyl)-N-methylpyrazolo[1,5-a]pyridine-5-carboxamide

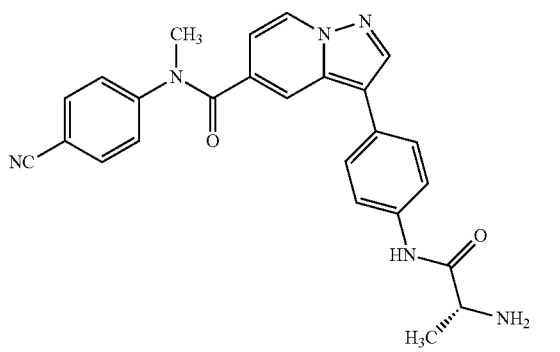

44

Example 44 was prepared according to the procedure described for the synthesis of Example 43 by replacing 2-((tert-butoxycarbonyl)amino)acetic acid with (R)-2-((tert-butoxycarbonyl)amino)propanoic acid. ESI-MS (m/z): [M+H]⁺ 439.2, RT 1.0950 min.

Example 45

(S)-3-(4-(2-amino-3-methylbutanamido)phenyl)-N-(4-cyanophenyl)-N-methylpyrazolo[1,5-a]pyridine-5-carboxamide

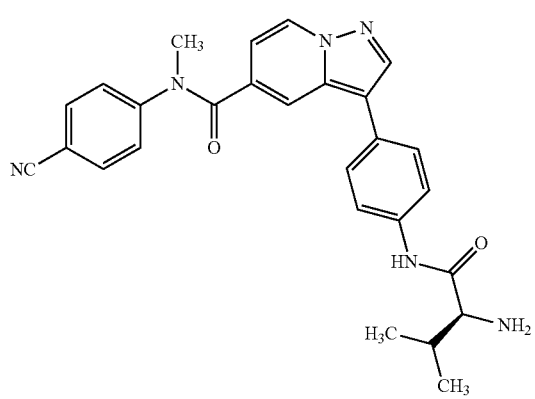

45

Example 45 was prepared according to the procedure described for the synthesis of Example 43 by replacing 2-((tert-butoxycarbonyl)amino)acetic acid with (S)-2-((tert-butoxycarbonyl)amino)-3-methylbutanoic acid. ESI-LC/MS m/z 467.2 (M+H)⁺; RT=1.230.

Example 46

(S)-3-(4-(2-amino-2-cyclohexylacetamido)phenyl)-N-(4-cyanophenyl)-N-methylpyrazolo[1,5-a]pyridine-5-carboxamide

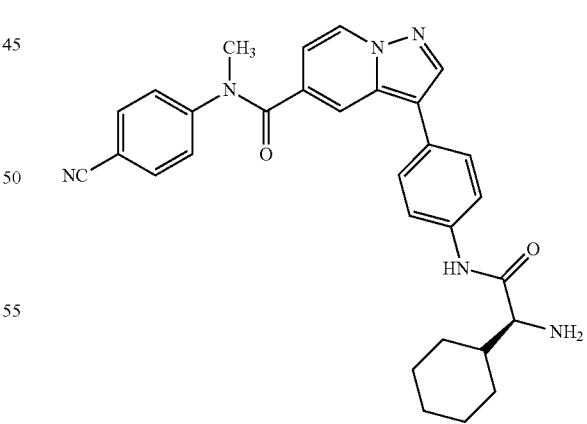

46

Example 46 was prepared according to the procedure described for the synthesis of Example 43 by replacing 2-((tert-butoxycarbonyl)amino)acetic acid with (S)-2-((tert-butoxycarbonyl)amino)-2-cyclohexylacetic acid. ESI-MS (m/z): [M+H]⁺ 507.2, RT 1.4154 min.

Example 47

3-(4-fluorophenyl)-1-methyl-1-(3-(4-(trifluoromethyl)phenyl)pyrazolo[1,5-a]pyridin-5-yl)urea

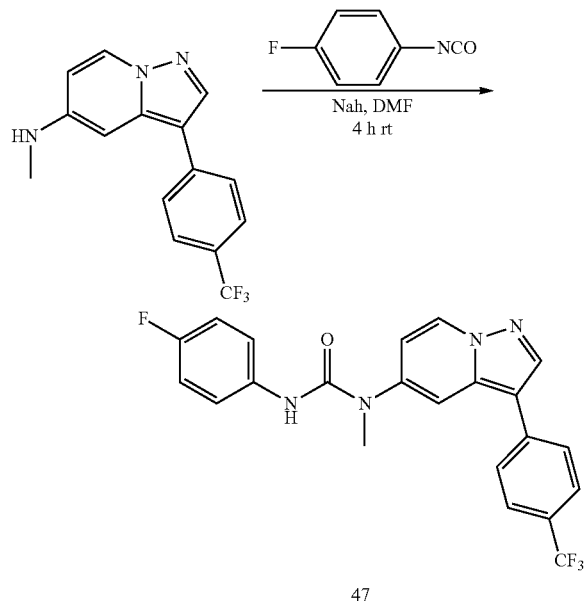

47

NaH (8 mg, 0.15 mmol) was added to a solution of pyrazolopyridine (30 mg, 0.10 mmol) and DMF (2.0 mL). The reaction was stirred at room temperature for 15 minutes. The isocyanate was added and the reaction stirred at room temperature for an additional 4 hours. The reaction ws quenched with water and extracted with ethyl acetate. The combined organic extracts were washed with brine and dried over anhydrous Na$_2$SO$_4$. The solvent was removed and the material was purified by silica gel chromatography eluting with ethyl acetate and hexanes. $^1$H NMR (400 MHz, CDCl$_3$) δ 8.49 (d, J=7.3, 1H), 8.16 (s, 1H), 7.61 (dd, J=8.5, 25.1, 5H), 7.19 (s, 3H), 6.89 (t, J=7.5, 2H), 6.76 (d, J=7.3, 1H), 6.31 (s, 1H), 3.33 (s, 3H).

Example 48

6-(1,1-difluoroethyl)-N-methyl-N-(3-(4-(trifluoromethyl)phenyl)pyrazolo[1,5-a]pyridin-5-yl)nicotinamide

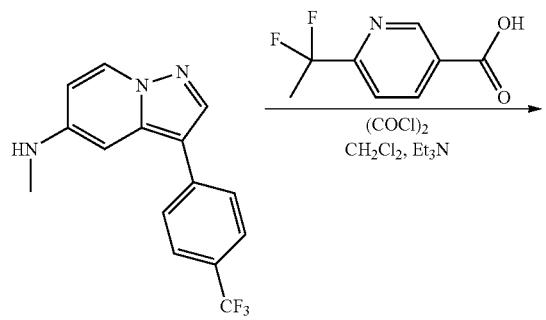

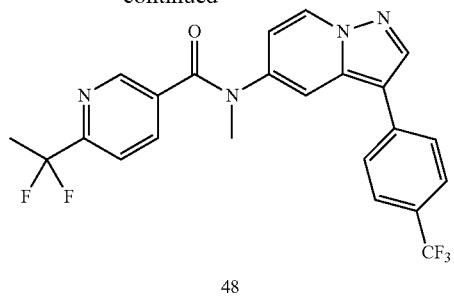

48

To a solution of 6-(1,1-difluoroethyl)nicotinic acid (28 mg, 0.15 mmol) in dichloromethane (1.00 mL) was added triethyl amine (0.042 mL, 0.30 mmml) and a catalytic amount of DMF. The reaction was cooled to 0° C. Oxallyl chloride was added dropwise and the reaction mixture was stirred for 30 minutes. The solvent was removed and the solid was dried under vacuum for 15 minutes. To the crude acid chloride was added dichloromethane (1.00 mL) and triethylamine (0.042 mL, 0.30 mmol) followed by the amine (29 mg, 0.10 mmol) at 0° C. The reaction was allowed to warm to room temperature and stir for two hours. The reaction was quenched with water, extracted with dichloromethane, washed with brine, dried over Na$_2$SO$_4$ and concentrated. The reaction was purified by silica gel chromatography, eluting with ethyl acetate and hexanes. $^1$H NMR (400 MHz, CDCl$_3$) δ 8.67 (s, 1H), 8.46 (d, J=7.4, 1H), 8.17 (s, 1H), 7.92 (d, J=8.1, 1H), 7.69 (d, J=8.1, 2H), 7.63 (d, J=8.1, 1H), 7.41 (d, J=7.9, 2H), 7.35 (s, 1H), 6.64 (d, J=7.3, 1H), 3.60 (s, 3H). ESI-LC/MS m/z 461.1 (M+H)+; r.t.=1.993.

Example 49

6-cyclopropyl-N-methyl-N-(3-(4-(trifluoromethyl)phenyl)pyrazolo[1,5-a]pyridin-5-yl)nicotinamide

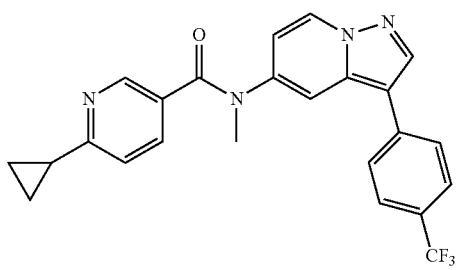

49

Example 49 was prepared according to the procedure described for the synthesis of Example 48 by replacing 6-(1,1-difluoroethyl)nicotinic acid with 6-cyclopropylnicotinic acid. ESI-LC/MS m/z 437.1 (M+H)$^+$; RT=1.640.

Example 50

4-cyclopropyl-N-methyl-N-(3-(4-(trifluoromethyl)phenyl)pyrazolo[1,5-a]pyridin-5-yl)benzamide

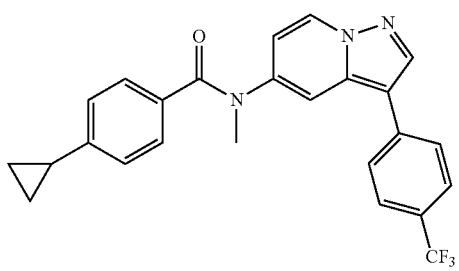

50

Example 50 was prepared according to the procedure described for the synthesis of Example 48 by replacing 6-(1,1-difluoroethyl)nicotinic acid with 4-cyclopropylbenzoic acid. ESI-LC/MS m/z 436.0 (M+H)+; RT=2.408.

Example 51

5-fluoro-N-methyl-N-(3-(4-(trifluoromethyl)phenyl)pyrazolo[1,5-a]pyridin-5-yl)picolinamide

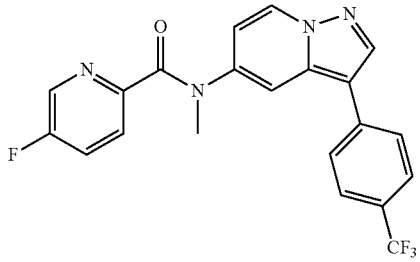

51

Example 51 was prepared according to the procedure described for the synthesis of Example 48 by replacing 6-(1,1-difluoroethyl)nicotinic acid with 5-fluoropicolinic acid. $^1$H NMR (400 MHz, CDCl$_3$) δ 7.71 (d, J=7.4, 1H), 7.48 (s, 1H), 7.46 (s, 1H), 7.00 (s, 1H), 6.95-6.78 (m, 6H), 6.08 (d, J=7.4, 1H), 2.80 (d, J=38.0, 3H). ESI-LC/MS m/z 415.0 (M+H)+; r.t.=2.158.

Example 52

N-methyl-4-(methylsulfonyl)-N-(3-(4-(trifluoromethyl)phenyl)pyrazolo[1,5-a]pyridin-5-yl)benzamide

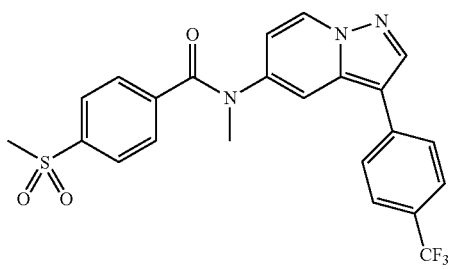 [SMILES: CN(C(=O)c1ccn2ncc(-c3ccc(C(F)(F)F)cc3)c2c1)c1ccc(S(C)(=O)=O)cn1]

52

Example 52 was prepared according to the procedure described for the synthesis of Example 48 by replacing 6-(1,1-difluoroethyl)nicotinic acid with 4-(methylsulfonyl)benzoic acid. ESI-LC/MS m/z 474.1 (M+H)+; RT=2.071

Example 53

N-(5-cyanopyridin-2-yl)-N-methyl-3-(1H-pyrrolo[2,3-b]pyridin-5-yl)pyrazolo[1,5-a]pyridine-5-carboxamide

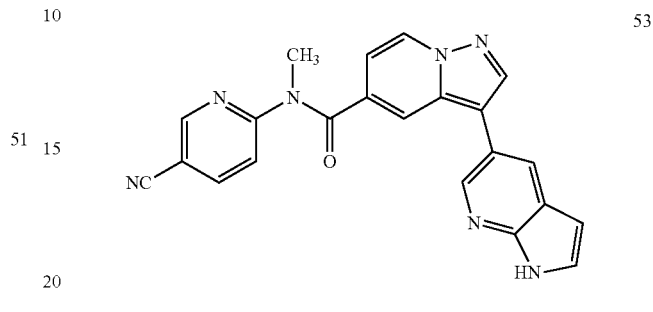

53

Example 53 was prepared from intermediate I-9 according to the procedure described for the synthesis of Example 32 by replacing (4-carbamoylphenyl)boronic acid with (1H-pyrrolo[2,3-b]pyridin-5-yl)boronic acid. Purification by silica gel chromatography, eluting with hexanes/EtOAc, and then 5% EtOH/EtOAc gave the desired product. $^1$H NMR (400 MHz, DMSO) δ 11.76 (s, 1H), 8.88 (dd, J=0.6, 2.3, 1H), 8.70 (dd, J=0.8, 7.2, 1H), 8.44 (s, 1H), 8.38 (d, J=2.1, 1H), 8.26 (dd, J=2.3, 8.6, 1H), 7.99 (d, J=2.0, 1H), 7.91 (s, 1H), 7.60 (dd, J=0.5, 8.6, 1H), 7.57-7.50 (m, 1H), 6.82 (dd, J=1.8, 7.2, 1H), 6.51 (dd, J=1.8, 3.4, 1H), 3.53 (s, 3H). ESI-MS (m/z): [M+H]+ 394.0, RT 1.4237 min.

Example 54

3-(6-aminopyridin-3-yl)-N-(5-cyanopyridin-2-yl)-N-methylpyrazolo[1,5-a]pyridine-5-carboxamide

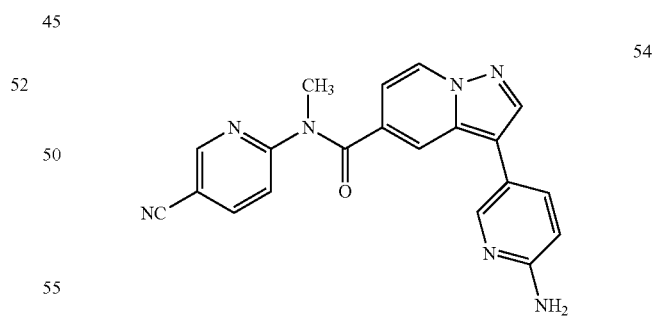

54

Example 54 was prepared from intermediate I-9 according to the procedure described for the synthesis of Example 32 by replacing (4-carbamoylphenyl)boronic acid with (6-aminopyridin-3-yl)boronic acid. Purification by silica gel chromatography, eluting with hexanes/EtOAc, and then 10% EtOH/EtOAc gave the desired product. $^1$H NMR (400 MHz, DMSO) δ 8.84 (d, J=2.3, 1H), 8.63 (dd, J=0.7, 7.3, 1H), 8.29 (s, 1H), 8.23 (dd, J=2.3, 8.6, 1H), 8.09 (d, J=2.2, 1H), 7.86-7.80 (m, 1H), 7.58 (d, J=8.6, 1H), 7.54 (dd, J=2.5, 8.5, 1H), 6.75 (dd, J=1.8, 7.2, 1H), 6.54 (d, J=8.6, 1H), 6.05 (s, 2H), 3.52 (s, 3H). ESI-MS (m/z): [M+H]$^+$ 370.0, RT 1.2469 min.

Example 55

4-chloro-N-methyl-N-(3-(4-(trifluoromethyl)phenyl)pyrazolo[1,5-a]pyridin-5-yl)benzamide

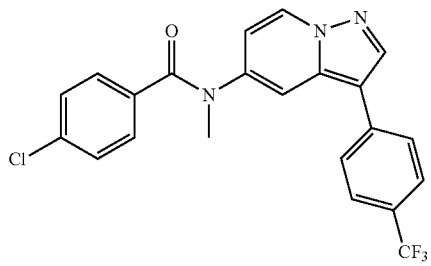

Example 25 was prepared according to the procedure described for the synthesis of Example 28 by replacing 4-cyanobenzoyl chloride with 4-fluorobenzoyl chloride. $^1$H NMR (400 MHz, CDCl$_3$) δ 8.33 (d, J=7.5, 1H), 8.07 (s, 1H), 7.58 (d, J=8.2, 2H), 7.42-7.26 (m, 4H), 7.26-7.12 (m, 3H), 6.53 (dd, J=2.3, 7.4, 1H), 3.47 (s, 3H). ESI-LC/MS m/z 430.0 (M+H)+; r.t.=2.376.

Example 56

N-(3-(4-carbamoylphenyl)pyrazolo[1,5-a]pyridin-5-yl)-4-fluoro-N-methylbenzamide

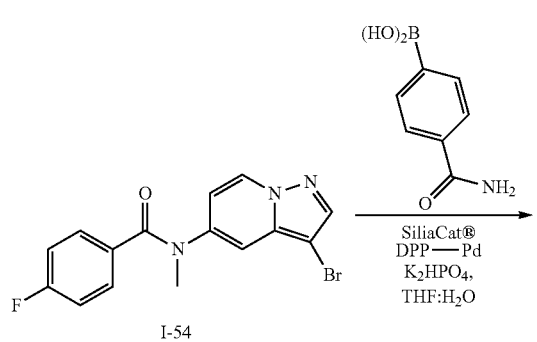

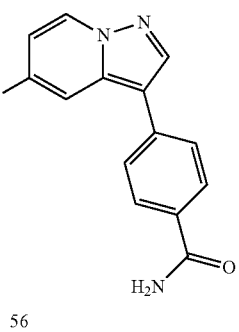

Example 56 was prepared from intermediate I-54 according to the procedure described for the synthesis of Example 17 by replacing (1-methyl-1H-indazol-5-yl)boronic acid with (4-carbamoylphenyl)boronic acid. ESI-LC/MS m/z 389.1 (M+H)+; r.t.=1.603.

Example 57

4-fluoro-N-methyl-N-(3-(4-(5-(methylamino)-1,3,4-thiadiazol-2-yl)phenyl)pyrazolo[1,5-a]pyridin-5-yl)benzamide

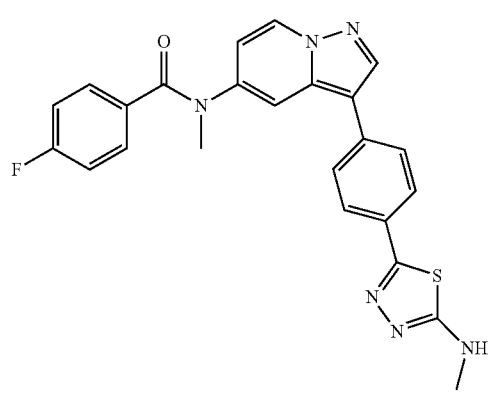

Example 57 was prepared from intermediate I-54 according to the procedure described for the synthesis of Example 17 by replacing (1-methyl-1H-indazol-5-yl)boronic acid with (4-(5-(methylamino)-1,3,4-thiadiazol-2-yl)phenyl)boronic acid. $^1$H NMR (400 MHz, MeOD) δ 8.53 (d, J=7.4, 1H), 8.29 (s, 1H), 7.85 (d, J=8.4, 2H), 7.66-7.45 (m, 5H), 7.07 (t, J=8.8, 2H), 6.90 (dd, J=2.3, 7.5, 1H), 3.56 (s, 3H), 3.12 (s, 3H). ESI-LC/MS m/z 459.0 (M+H)$^+$; r.t.=1.708.

Example 58

N-methyl-N-(5-(methylsulfonyl)pyridin-2-yl)-3-(1H-pyrrolo[2,3-b]pyridin-5-yl)pyrazolo[1,5-a]pyridine-5-carboxamide

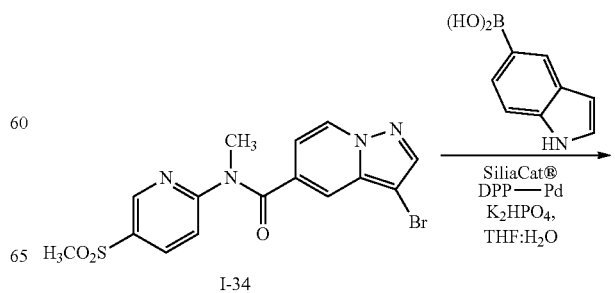

-continued

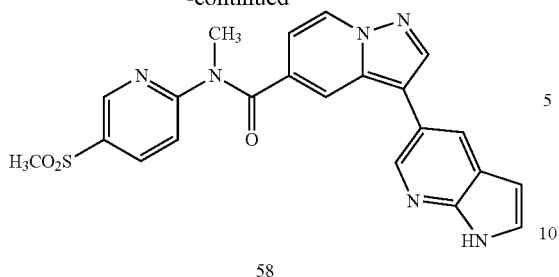

58

Example 58 was prepared from intermediate I-66 according to the procedure described for the synthesis of Example 17 by replacing (1-methyl-1H-indazol-5-yl)boronic acid with (1H-pyrrolo[2,3-b]pyridin-5-yl)boronic acid. ESI-MS (m/z): [M+H]⁺ 447.0, RT 1.3983 min. ESI-LC/MS m/z 447.0 (M+H)⁺; r.t.=1.398.

Example 59

N-(5-cyanopyridin-2-yl)-N-methyl-3-(5-methylpyridin-2-yl)pyrazolo[1,5-a]pyridine-5-carboxamide

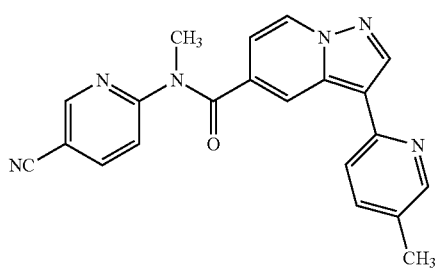

59

Example 29 was prepared according to the procedure described for the synthesis of Example 25 by replacing 2-chloro-5-(trifluoromethyl)pyridine with 2-chloro-5-methylpyridine. The reaction was purified by mass-triggered HPLC to provide the desired product. ESI-MS (m/z): [M+H]⁺ 369.1, RT 1.3394 min.

Example 60

N-(5-cyanopyridin-2-yl)-3-(5-methoxypyridin-2-yl)-N-methylpyrazolo[1,5-a]pyridine-5-carboxamide

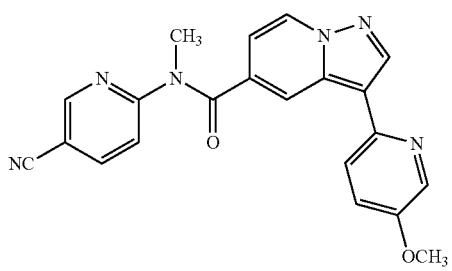

60

Example 60 was prepared according to the procedure described for the synthesis of Example 25 by replacing 2-chloro-5-(trifluoromethyl)pyridine with 2-chloro-5-methoxypyridine. The reaction was purified by mass-triggered HPLC to provide the desired product. ESI-MS (m/z): [M+H]⁺ 385.1, RT 1.5073 min.

Example 61

3-(5-carbamoylpyridin-2-yl)-N-(5-cyanopyridin-2-yl)-N-methylpyrazolo[1,5-a]pyridine-5-carboxamide

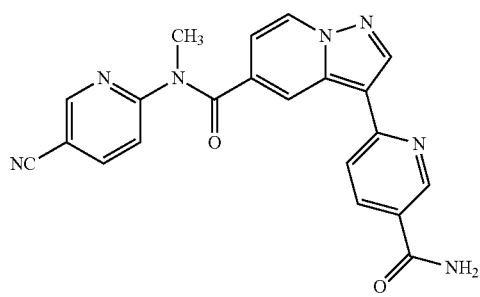

61

Example 61 was prepared according to the procedure described for the synthesis of Example 25 by replacing 2-chloro-5-(trifluoromethyl)pyridine with 6-chloronicotinamide. The reaction was purified by mass-triggered HPLC to provide the desired product. ESI-MS (m/z): [M+H]⁺ 398.1, RT 1.4232 min.

Example 62

3-(4-carbamoyl phenyl)-N-methyl-N-(5-(trifluoromethyl)pyridin-2-yl)pyrazolo[1,5-a]pyridine-5-carboxamide

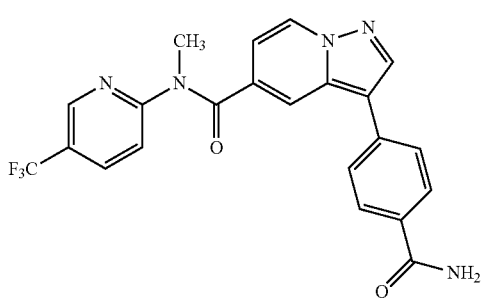

62

Example 62 was prepared according to the procedure described for the synthesis of Example 32. The reaction was purified by mass-triggered HPLC to provide the desired product. ESI-MS (m/z): [M+H]+ 440.0, RT 1.7179 min.

Example 63

3-(4-carbamoylphenyl)-N-methyl-N-(5-methylpyridin-2-yl)pyrazolo[1,5-a]pyridine-5-carboxamide

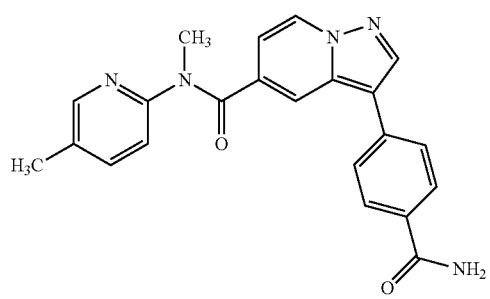

Example 63 was prepared according to the procedure described for the synthesis of Example 32. The reaction was purified by mass-triggered HPLC to provide the desired product. ESI-MS (m/z): [M+H]+ 386.1, RT 1.4742 min.

Example 64

N-(4-fluorophenyl)-N-methyl-3-(4-(methylcarbamoyl)phenyl)pyrazolo[1,5-a]pyridine-5-carboxamide

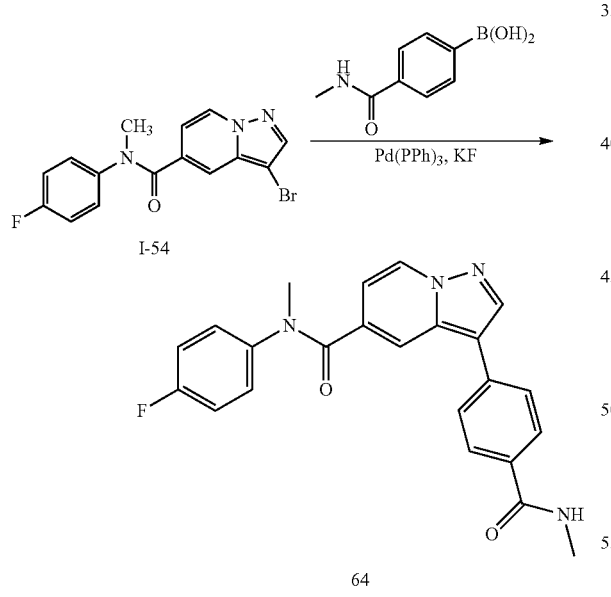

A mixture of aryl bromide (I-54, 1.0 equiv.), (4-(methylcarbamoyl)phenyl)boronic acid (2.0 equiv.), KF (2.0 equiv.), and Pd(PPh)$_3$ (0.05 equiv.) in 1,4-dioxane/DME/water was allowed to heat at 100° C. in a microwave reactor for 5 minutes. Following extraction of the reaction mixture with ethyl acetate, the solvent was removed under reduced pressure and the residue was purified by silica gel chromatography, eluting with ethyl acetate and hexanes to give 64 as the desired product. $^1$H NMR (400 MHz, Methanol-d$_4$) δδ ppm 8.46 (d, J=8.00 Hz, 1H) 8.26 (s, 1H), 7.89 (d, J=8.00 Hz, 2H) 7.76 (s, 1H), 7.49 (d, J=8.00 Hz, 2H) 7.32-7.35 (m, 2H) 7.12 (t, J=8.00 Hz, 2H) 6.91 (d, J=8.00 Hz, 1H) 3.50 (s, 3H) 2.96 (s, 3H); ESI-MS (m/z): [M+H]+ 403.

Example 65

4-(5-(1-(methyl(5-methylpyridin-2-yl)amino)ethyl)pyrazolo[1,5-a]pyridin-3-yl)benzamide

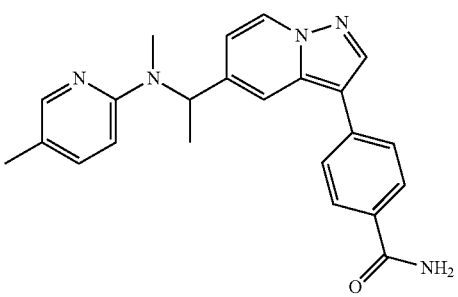

Example 65 was prepared from intermediate I-19 according to general Suzuki procedure E. A mixture of aryl bromide (I-19, 1.0 equiv.), (4-carbamoylphenyl)boronic acid (1.5 equiv.), 2 M aq KF (3 equiv.), and Pd$_2$(dba)$_3$ (0.1 equiv.), P(o-tolyl)$_3$(0.1 equiv.) in toluene:ethanol (7:3) was degassed and heated to 90° C. for 4 h. The crude product was purified by silica gel chromatography, eluting with ethyl acetate and hexanes to give 65 as the desired product. $^1$H NMR (400 MHz, DMSO-d$_6$): δ 8.65 (d, J=7.50 Hz, 1H), 8.43 (s, 1H), 7.97 (d, J=8.3 Hz, 4H), 7.75 (d, J=7.9 Hz, 3H), 7.42-7.40 (m, 1H), 7.38 (d, J=5.0 Hz, 1H), 6.75 (d, J=7.10 Hz, 1H), 6.60 (d, J=8.8 Hz, 1H), 6.14-6.11 (m, 1H), 2.70 (s, 3H), 2.15 (s, 3H), 1.57 (d, J=7.9 Hz, 3H); ESI-MS (m/z): [M+H]+ 386.1.

Example 66

4-(5-(1-(7-fluoro-3-oxo-2H-benzo[b][1,4]oxazin-4(3H)-yl)ethyl)pyrazolo[1,5-a]pyridin-3-yl)benzamide

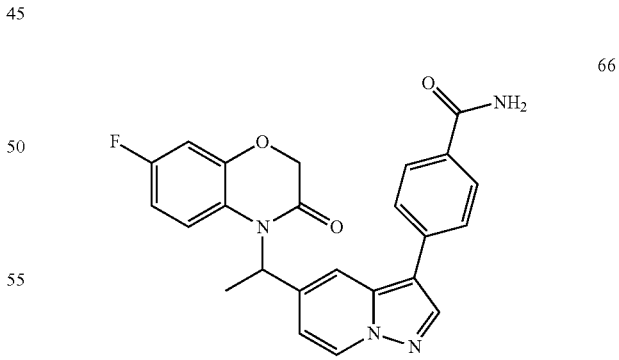

Example 66 was prepared from intermediate I-67 according to general Suzuki procedure E. A mixture of aryl bromide (I-67, 1.0 equiv.), (4-carbamoylphenyl)boronic acid (1.5 equiv.), 2 M aq KF (3 equiv.), and Pd$_2$(dba)$_3$ (0.1 equiv.), P(o-tolyl)$_3$(0.1 equiv.) in toluene:ethanol (7:3) was degassed and heated to 90° C. for 7 h. The crude compound was purified by silica gel chromatography, eluting with 2% MeOH/DCM to give 4-(5-(1-(7-fluoro-3-oxo-2H-benzo[b][1,4]oxazin-4

(3H)-Aethyl)pyrazolo[1,5-a]pyridin-3-yl)benzamide 66 as the desired product (37%). $^1$H NMR (400 MHz, DMSO-d$_6$). δ 8.69 (d, J=7.50 Hz, 1H), 8.47 (s, 1H), 8.01 (s, 1H), 7.98 (d, J=8.4 Hz, 1H), 7.90 (s, 1H), 7.80 (d, J=8.4 Hz, 2H), 7.37 (br. s, 1H), 7.02 (dd, J=3.1, 9.4 Hz, 1H), 6.96-6.92 (m, 1H), 6.82 (dd, J=1.8, 7.3 Hz, 1H), 6.73 (dt, J=3.0, 8.6, Hz, 1H), 6.16-6.21 (m, 1H), 4.80 (m, 2H), 1.85 (d, J=7.0 Hz, 3H); ESI-LC/MS (Method 1) (m/z): [M+H]$^+$ 431.

Example 67

N-(4-cyanophenyl)-N-methyl-3-(4-(methylcarbamoyl)phenyl)pyrazolo[1,5-a]pyridine-5-carboxamide

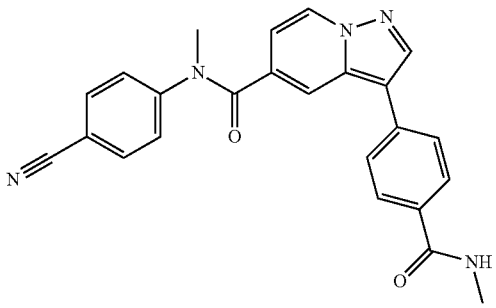

67

Example 67 was prepared from intermediate I-8 according to general Suzuki procedure F. A mixture of aryl bromide (I-8) (1.0 equiv.), (4-(methylcarbamoyl)phenyl)boronic acid (1.2 equiv.), Na$_2$CO$_3$ (2.0 equiv.), and Pd(PPh$_3$)$_4$ (0.1 equiv.) in dioxane was allowed to heat at 100° C. in microwave reactor for 40 minutes. The reaction was filtered over celite and the filtrate was concentrated under reduced pressure. The residue was purified by silica gel chromatography, eluting with hexanes/EtOAc to give 67 as the desired product. $^1$H NMR (400 MHz, DMSO-d$_6$) δ ppm 8.66 (d, J=7.28 Hz, 1H) 8.48 (s, 2H) 7.91 (d, J=8.03 Hz, 2H) 7.81-7.88 (m, 3H) 7.54 (t, J=7.78 Hz, 4H) 6.83 (d, J=7.53 Hz, 1H) 3.46 (s, 3H) 2.82 (d, J=4.02 Hz, 3H). ESI-MS (m/z): [M+H]$^+$ 410.

Example 68

N-(4-(5-(1-(methyl(5-methylpyridin-2-yl)amino)ethyl)pyrazolo[1,5-a]pyridin-3-yl)phenyl)acetamide

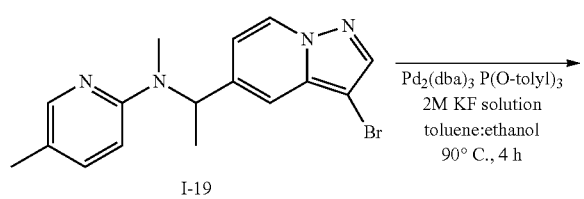

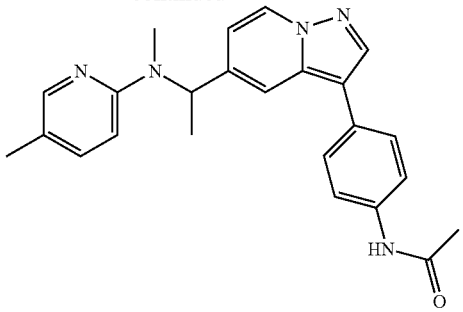

68

Example 68 was prepared from intermediate I-19 according to the procedure described for the synthesis of Example 65 (general Suzuki procedure E) by replacing (4-carbamoylphenyl)boronic acid with (4-acetamidophenyl)boronic acid. The crude product was purified by silica gel chromatography, eluting with ethyl acetate and hexanes to give 68 as the desired product. $^1$H NMR (400 MHz, DMSO-d$_6$) δ 10.01 (s, 1H), 8.60 (d, J=7.5 Hz, 1H), 8.27 (s, 1H), 7.97 (s, 1H), 7.66-7.68 (m, 3H), 7.58 (d, J=8.6 Hz, 2H), 7.40 (d, J=7.0 Hz, 1H), 6.68 (d, J=7.5 Hz, 1H), 6.63 (d, J=8.6 Hz, 1H), 6.11 (d, J=6.5 Hz, 1H), 2.7 (s, 3H), 2.1 (s, 3H), 2.0 (s, 3H), 1.55 (d, J=7.0 Hz, 3H); ESI-LC/MS (Method 2) (m/z): [M+H]$^+$ 400.

Example 69

3-(4-acetamidophenyl)-N-(5-cyanopyridin-2-yl)-N-methylpyrazolo[1,5-a]pyridine-5-carboxamide

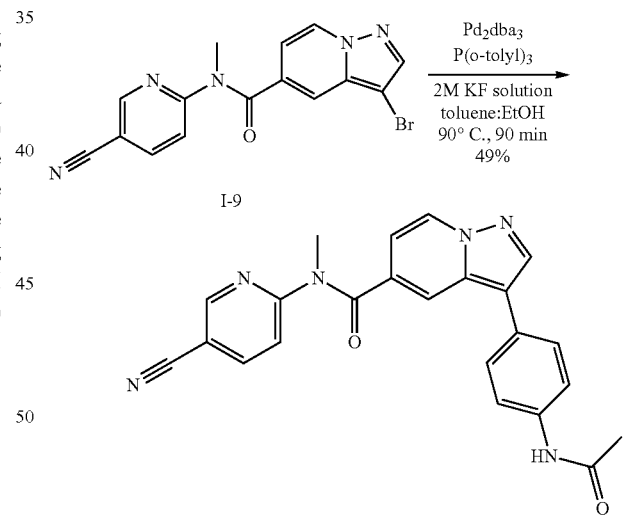

Example 69 was prepared from intermediate I-9 according to the procedure described for the synthesis of Example 65 (general Suzuki procedure E) by replacing (4-carbamoylphenyl)boronic acid with (4-acetamidophenyl)boronic acid. The crude product was purified by column chromatography over silica gel (MeOH/CH$_2$Cl$_2$, 0-2% MeOH) to give 68 as the desired product. $^1$H NMR (400 MHz, DMSO-d$_6$): δ 10.0 (s, 1H), 8.85 (m, 1H), 8.66 (d, J=7.3 Hz, 1H), 8.38 (s, 1H), 8.24 (dd, J=2.1, 8.5 Hz, 1H), 7.93 (s, 1H), 7.66 (d, J=8.6 Hz), 7.61 (d, J=8.6 Hz, 3H), 7.47 (d, J=8.6 Hz, 2H), 6.78 (dd, J=1.6, 7.3 Hz, 1H), 3.5 (s, 3H), 2.06 (s, 3H); ESI-MS (method 2) (m/z): [M+H]$^+$ 411.21.

Example 71

4-(5-(7-fluoro-3,4-dihydro-2H-benzo[b][1,4]ox-azine-4-carbonyl)pyrazolo[1,5-a]pyridin-3-yl)benzamide

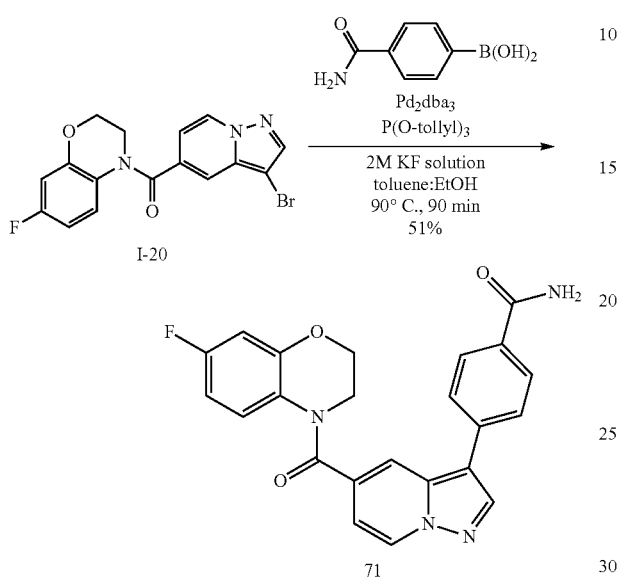

Example 71 was prepared from intermediate I-20 according to the procedure described for the synthesis of Example 65 (general Suzuki procedure E). The crude product was purified by column chromatography over silica gel (MeOH/Chloroform, 0-5% MeOH). to give 71 as the desired product. $^1$H NMR (400 MHz, DMSO-d$_6$ at 80° C.): δ 9.75 (s, 1H), 8.76 (d, J=7.0 Hz, 1H), 8.40 (s, 1H), 8.11 (s, 1H), 7.57-7.68 (m, 4H), 7.28-7.32 (m, 1H), 6.97-6.99 (m, 1H), 6.84-6.87 (m, 1H), 6.68-6.72 (m, 1H), 4.6 (bs, 1H), 4.22-4.4 (m, 2H), 2.06 (s, 3H), 1.195 (d, J=6.6 Hz, 3H); ESI-MS (method 2) (m/z): [M+H]$^+$ 445.

Example 72

4-(5-(7-fluoro-3-methyl-3,4-dihydro-2H-benzo[b][1,4]oxazine-4-carbonyl)pyrazolo[1,5-a]pyridin-3-yl)benzamide

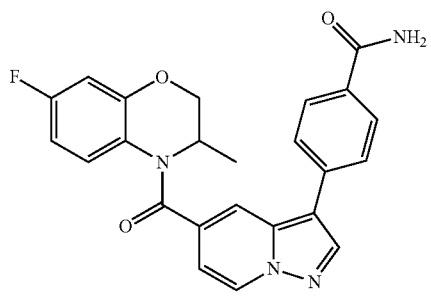

Example 72 was prepared from intermediate I-24 according to the procedure described for the synthesis of Example 65 (general Suzuki procedure E). The crude product was purified by silica gel chromatography (MeOH/Chloroform, 0-5% MeOH) to give 72 as the desired product. $^1$H NMR (400 MHz, DMSO-d$_6$ at 80° C.): δ 8.73 (d, J=7.0 Hz, 1H), 8.47 (s, 1H), 8.10 (s, 1H), 7.94 (d, J=8.4 Hz, 2H), 7.69 (d, J=8.3 Hz, 2H), 7.35-7.31 (m, 3H), 6.99-7.02 (m, 1H), 6.78-6.82 (m, 1H), 6.59-6.65 (m, 1H), 4.63 (d, J=6.2 Hz, 1H), 4.36-4.39 (m, 1H), 4.21-4.24 (m, 1H), 1.22 (d, J=7.0 Hz, 3H); ESI-MS (method 2) (m/z): [M+H]$^+$ 431.

Example 73

4-(5-(7-fluoro-3,4-dihydro-2H-benzo[b][1,4]oxazine-4-carbonyl)pyrazolo[1,5-a]pyridin-3-yl)-N-methylbenzamide

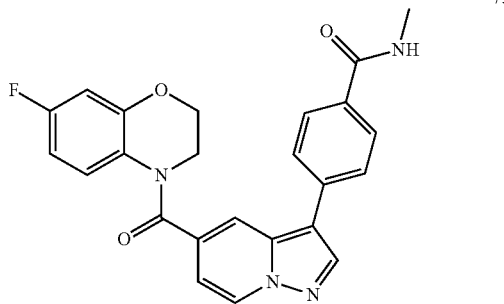

Example 73 was prepared from intermediate I-20 according to the procedure described for the synthesis of Example 65 (general Suzuki procedure E) by replacing (4-carbamoylphenyl)boronic acid with (4-(methylcarbamoyl)phenyl)boronic acid. The residue was purified column chromatography over silica gel (MeOH/Chloroform, 0-2% MeOH) to give 73 as the desired product. $^1$H NMR (400 MHz, CDCl$_3$): δ 9.99 (s, 1H), 8.77 (d, J=7.03 Hz, 1H), 8.40 (d, J=1.31 Hz, 1H), 8.10 (s, 1H), 7.57-7.67 (m, 5H), 6.99-7.01 (m, 1H), 6.83-6.85 (m, 1H), 6.69 (m, 1H), 4.36 (m, 2H), 3.94 (m, 2H), 2.05 (s, 3H); ESI-MS (method 1) (m/z): [M+H]$^+$ 431.15.

Example 74

4-(5-(7-fluoro-3-methyl-3,4-dihydro-2H-benzo[b][1,4]oxazine-4-carbonyl)pyrazolo[1,5-a]pyridin-3-yl)-N-methylbenzamide

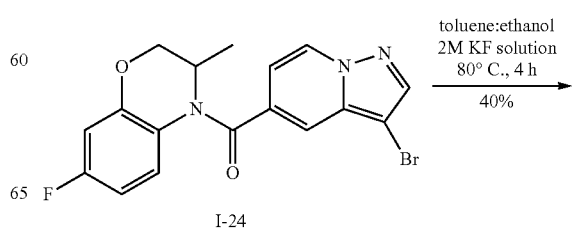

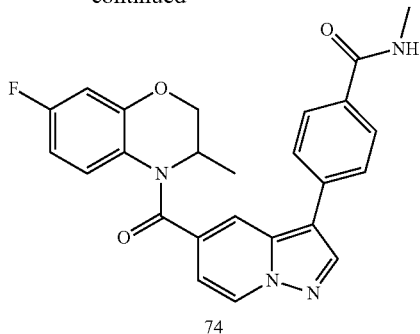

74

Example 74 was prepared from intermediate I-24 according to the procedure described for the synthesis of Example 65 (general Suzuki procedure E) by replacing (4-carbamoylphenyl)boronic acid with (4-(methylcarbamoyl)phenyl)boronic acid. The crude product was purified by column chromatography over silica gel (MeOH/Chloroform, 0-5% MeOH) to give 74 as the desired product. $^1$H NMR (400 MHz, DMSO-d$_6$ at 80° C.): δ 9.75 (s, 1H), 8.76 (d, J=7.0 Hz, 1H), 8.40 (s, 1H), 8.11 (s, 1H), 7.57-7.68 (m, 4H), 7.28-7.32 (m, 1H), 6.97-6.99 (m, 1H), 6.84-6.87 (m, 1H), 6.68-6.72 (m, 1H), 4.6 (bs, 1H), 4.22-4.4 (m, 2H), 2.06 (s, 3H), 1.195 (d, J=6.6 Hz, 3H); ESI-MS (m/z): [M+H]$^+$ 445.

Example 75

N-(5-cyanopyridin-2-yl)-N-methyl-3-(4-(methylcarbamoyl)phenyl)pyrazolo[1,5-a]pyridine-5-carboxamide

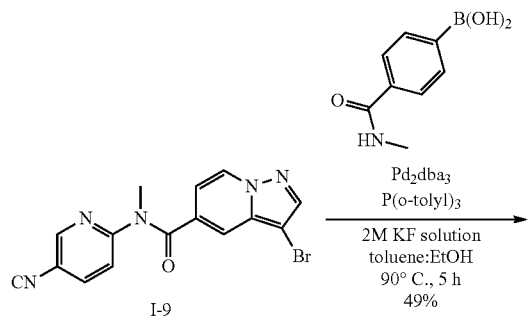

75

Example 75 was prepared from intermediate I-9 according to the procedure described for the synthesis of Example 65 (general Suzuki procedure E) by replacing (4-carbamoylphenyl)boronic acid with (4-(methylcarbamoyl)phenyl)boronic acid. The crude product was purified by column chromatography over silica gel (MeOH/Chloroform, 0-2% MeOH) to give 74 as the desired product. $^1$H NMR (400 MHz, DMSO-d$_6$): δ 8.86 (d, J=1.6 Hz, 1H), 8.71 (dd, J=0.7, 7.3 Hz, 1H), [8.53 (s), 8.49 (d, J=4.6 Hz) 2H], 8.26 (dd, J=2.3, 8.7 Hz, 1H), [7.99 (d, J=0.7 Hz), 7.92 (d, J=8.5 Hz) 3H], 7.65 (m, 3H), 6.84 (dd, J=1.9, 7.3 Hz, 1H), 3.53 (s, 3H), 2.81 (d, J=4.6 Hz, 3H)ESI-MS (Method 2) (m/z): [M+H]$^+$ 411.2.

The difference with Method 2 used here is Gradient: 0.4 mL/minute, initial 20% B ramp to 80% B over 2.0 minutes, (instead of ramp to 90% over 2.0 minutes in Method 2), then hold until 4.0 minutes, return to 20% B at 4.1 minutes until end of run.

Example 76

N-(5-cyanopyridin-2-yl)-3-(4-(methylcarbamoyl)phenyl)-N-(oxetan-3-yl)pyrazolo[1,5-a]pyridine-5-carboxamide

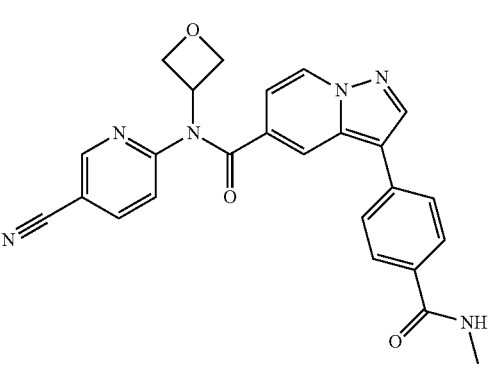

76

Example 76 was prepared from intermediate I-26 according to the procedure described for the synthesis of Example 64 by replacing (4-carbamoylphenyl)boronic acid with (4-(methylcarbamoyl)phenyl)boronic acid. The residue was purified by silica gel chromatography, eluting with ethyl acetate and hexanes to give 76 as the desired product. $^1$H NMR (400 MHz, METHANOL-d$_4$) 8.66 (d, J=7.28 Hz, 1H) 8.52 (s, 1H) 8.38 (s, 1H) 7.93-8.00 (m, 3H) 7.75 (d, J=8.78 Hz, 2H) 7.40 (dd, J=7.28, 1.76 Hz, 1H) 7.00 (dd, J=9.91, 1.88 Hz, 1H) 6.38 (d, J=10.29 Hz, 1H) 4.52-4.62 (m, 1H) 4.46 (d, J=1.00 Hz, 2H) 4.32 (t, J=11.42 Hz, 1H) 4.14 (dd, J=11.92, 7.15 Hz, 1H) 2.96 (s, 3H); ESI-MS (m/z): [M+H]$^+$ 443.

Example 77

N-(1-(1H-pyrazol-1-yl)propan-2-yl)-3-(4-carbamoylphenyl)-N-(5-cyanopyridin-2-yl)pyrazolo[1,5-a]pyridine-5-carboxamide

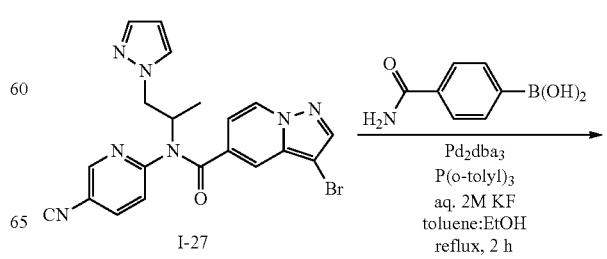

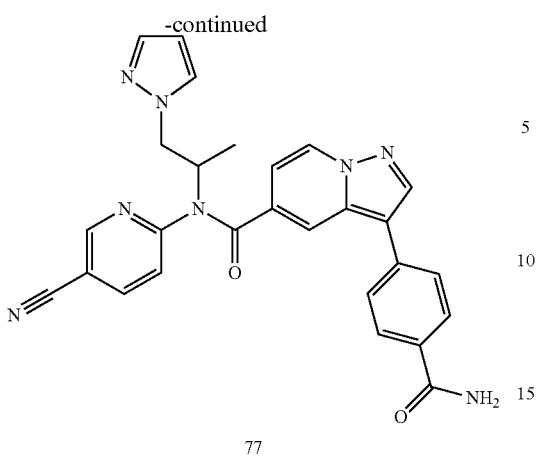

77

Example 77 was prepared from intermediate I-27 according to the procedure described for the synthesis of Example 65 (general Suzuki procedure E). The residue was purified by preparative TLC (silica gel GF 254) using 3% methanol in chloroform as eluant to give 77 as the desired product. ¹H NMR (400 MHz, DMSO) δ 8.90 (s, 1H), 8.63 (d, J=7.5 Hz, 1H), 8.47 (s, 1H), 8.15 (d, J=8.3 Hz, 1H), 8.03 (s, 1H), 7.99 (d, J=8.3 Hz, 2H), 7.75 (s, 1H), 7.61 (s, 1H), 7.51 (d, J=7.9 Hz, 2H), 7.39 (s, 1H), 7.34 (s, 1H), 7.17 (d, J=8.3 Hz, 1H), 6.68 (d, J=7.0 Hz, 1H), 6.14 (s, 1H), 5.75 (m, 1H), 4.85-4.86 (m, 1H), 4.47-4.48 (m, 1H), 1.35 (d, J=7.0 Hz, 3H); ESI-LC/MS (Method 2) (m/z): [M+H]⁺ 491.3, RT 1.32 min. The difference with Method-2 used here is Gradient: 0.4 mL/minute, initial 20% B ramp to 80% B over 2.0 minutes, (instead of ramp to 90% over 2.0 minutes in Method 2) then hold until 4.0 minutes, return to 20% B at 4.1 minutes until end of run.

Example 79

3-(6-amino-5-fluoropyridin-3-yl)-N-(4-cyanophenyl)-N-methylpyrazolo[1,5-a]pyridine-5-carboxamide

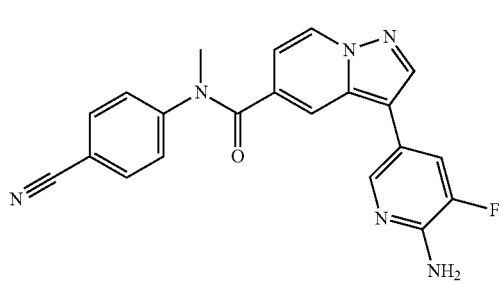

79

A mixture of 3-bromo-N-(4-cyanophenyl)-N-methylpyrazolo[1,5-a]pyridine-5-carboxamide (I-8; 400 mg, 1.10 mmol 1.0 eq), 3-fluoro-5-(4,4,5,5-tetramethyl-1,3,2-dioxaborolan-2-yl)pyridin-2-amine (I-37, 550 mg, 2.20 mmol 2.0 eq) and 1N Na₂CO₃ solution (4.0 mL) in 1,4-dioxane (10 mL) was degassed with argon gas for 10 min. Subsequently, tetrakis(triphenyl phosphine)-palladium(0) (250 mg, 0.22 mmol 0.2 eq) was added and the reaction mixture was stirred in a sealed tube at 100° C. for 2.5 h (cf. general Suzuki Procedure F). The solvent was removed under reduced pressure. Purification by silica gel chromatography, eluting with 5% MeOH/CH₂Cl₂ provided 79 as the desired product (37%). ¹H NMR (400 MHz, DMSO) δ 8.58 (d, J=7.0 Hz, 1H), 8.31 (s, 1H), 7.91 (s, 1H), 7.78 (d, J=8.8 Hz, 3H), 7.53 (d, J=8.30 Hz, 2H), 7.46 (d, J=12.3 Hz, 1H), 6.74 (d, J=7.0 Hz, 1H), 6.30 (s, 2H), 3.45 (s, 3H); ESI-LC/MS (m/z): [M+H]⁺ 387.10, RT 1.71 min.

Example 80

3-(4-amino-3,5-dimethylphenyl)-N-(4-cyanophenyl)-N-methylpyrazolo[1,5-a]pyridine-5-carboxamide

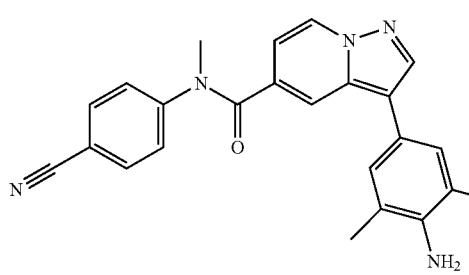

80

Example 80 was prepared from intermediate I-8 according to the procedure described for the synthesis of Example 79 by replacing 3-fluoro-5-(4,4,5,5-tetramethyl-1,3,2-dioxaborolan-2-yl)pyridin-2-amine (I-37) with 2,6-dimethyl-4-(4,4,5,5-tetramethyl-1,3,2-dioxaborolan-2-yl)aniline (I-38). Purification by silica gel chromatography, eluting with 5% MeOH/CH₂Cl₂ provided 80 as the desired product (34%) ¹H NMR (400 MHz, DMSO) δ 8.54 (d, J=7.10 Hz, 1H), 8.15 (s, 1H) I-37, 7.81 (d, J=8.40 Hz, 2H), 7.65 (s, 1H), 7.52 (d, J=8.3 Hz, 2H), 6.87 (s, 2H), 6.72 (d, J=7.40 Hz, 1H), 4.65 (s, 2H), 3.45 (s, 3H), 2.14 (s, 6H); ESI-LC/MS (m/z): [M+H]⁺ 396.16, RT 1.51 min.

Example 81

3-(6-amino-5-methylpyridin-3-yl)-N-(4-cyanophenyl)-N-methylpyrazolo[1,5-a]pyridine-5-carboxamide

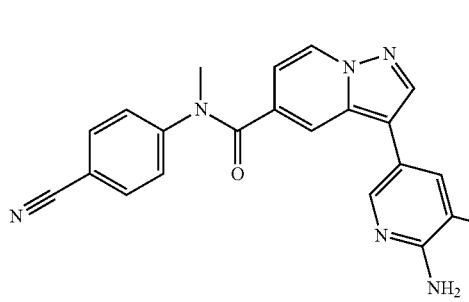

81

Example 81 was prepared from intermediate I-8 according to the procedure described for the synthesis of Example 79 by replacing 3-fluoro-5-(4,4,5,5-tetramethyl-1,3,2-dioxaborolan-2-yl)pyridin-2-amine (I-37) with 3-methyl-5-(4,4,5,5-tetramethyl-1,3,2-dioxaborolan-2-yl)pyridin-2-amine (I-39). Purification by silica gel chromatography, eluting with 5% MeOH/CH₂Cl₂ provided 81 as the desired product (44%). ¹H NMR (400 MHz, DMSO) δ 8.56 (d, J=7.50 Hz, 1H), 8.23 (s, 1H), 7.91 (s, 1H), 7.79 (d, J=8.30 Hz, 1H), 7.71 (s, 1H), 7.52

(d, J=8.30 Hz, 1H), 7.31 (s, 1H), 6.72 (d, J=7.50 Hz, 1H), 5.80 (s, 2H), 3.44 (s, 3H), 2.11 (s, 3H); ESI-LC/MS (m/z): [M+H]+ 383.07, RT 1.66 min.

Example 82

3-(4-carbamoylphenyl)-N-(4-cyanocyclohexyl)-N-methylpyrazolo[1,5-a]pyridine-5-carboxamide

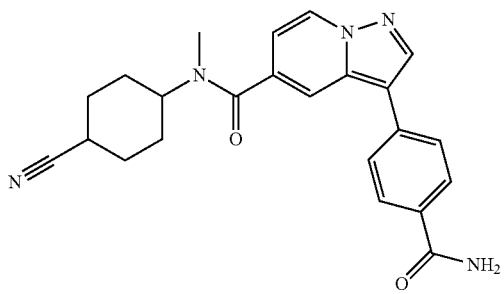

Example 82 was prepared from intermediate I-33 according to the procedure described for the synthesis of Example 65 (general Suzuki procedure E). The residue was purified by silica gel chromatography, eluting with 3% MeOH/CHCl$_3$ to give 82 as the desired product (30%). $^1$H NMR (400 MHz, DMSO) δ 8.68 (d, J=6.6 Hz, 1H), 8.38 (s, 1H), 7.97-8.01 (m, 3H), 7.76-7.78 (m, 2H), 6.97 (m, 1H), 4.42 & 3.62 (two broad signals, 1H), 3.30 (m, 3H), 1.50-2.59 (m, 8H); ESI-LC/MS (m/z): [M+H]+ 402.14, RT 1.02 min.

Example 83

3-(2-aminopyrimidin-5-yl)-N-(4-cyanophenyl)-N-methylpyrazolo[1,5-a]pyridine-5-carboxamide

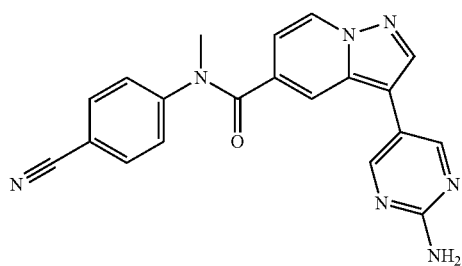

Example 83 was prepared from intermediate I-8 according to the procedure described for the synthesis of Example 79 by replacing 3-fluoro-5-(4,4,5,5-tetramethyl-1,3,2-dioxaborolan-2-yl)pyridin-2-amine (I-37) with 5-(4,4,5,5-tetramethyl-1,3,2-dioxaborolan-2-yl)pyrimidin-2-amine (I-40). Purification by silica gel chromatography, eluting with 5% MeOH/CH$_2$Cl$_2$ provided 83 as the desired product (27%). $^1$H NMR (400 MHz, DMSO) δ 8.59 (d, J=7.50 Hz, 1H), 8.37 (s, 1H), 8.31 (s, 1H), 7.77 (s, 3H), 7.52 (d, J=7.90 Hz, 2H), 6.73 (s, 3H), 3.30 (s, 3H); ESI-LC/MS (m/z): [M+H]+ 370.10, RT 0.93 min.

Example 84

3-(6-amino-5-(trifluoromethyl)pyridin-3-yl)-N-(5-cyanopyridin-2-yl)-N-methylpyrazolo[1,5-a]pyridine-5-carboxamide

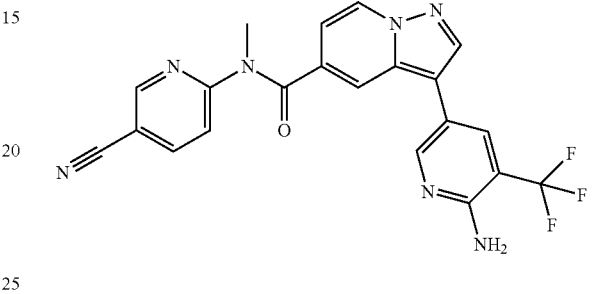

Example 84 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 5-(4,4,5,5-tetramethyl-1,3,2-dioxaborolan-2-yl)-3-(trifluoro-methyl)pyridin-2-amine (I-41). Purification by silica gel chromatography, eluting with 1% MeOH/CHCl$_3$ gave the desired product (41%). $^1$H NMR (400 MHz, DMSO) δ 8.82 (d, J=1.2 Hz, 1H), 8.64 (d, J=7.1 Hz, 1H), 8.39-8.41 (m, 2H), 8.21 (dd, J=2.2, 6.1 Hz, 1H), 7.80-7.86 (m, 2H), 7.58 (d, J=8.7 Hz, 1H), 6.78-6.81 (m, 1H), 6.52-6.56 (m, 2H), 3.52 (s, 1H); ESI-LC/MS (m/z): [M+H]+ 438.08, RT 1.37 min.

Example 85

3-(6-amino-5-cyanopyridin-3-yl)-N-(5-cyanopyridin-2-yl)-N-methylpyrazolo[1,5-a]pyridine-5-carboxamide

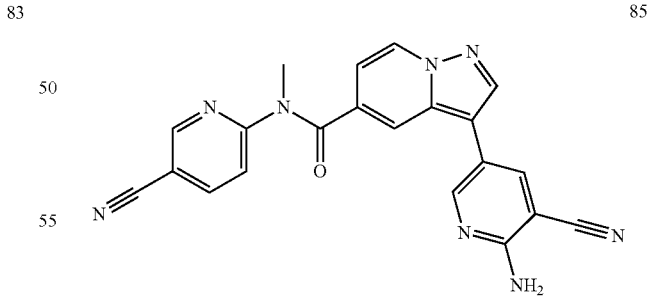

Example 85 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 2-amino-5-(4,4,5,5-tetramethyl-1,3,2-dioxaborolan-2-yl)nicotino-nitrile (I-42). Purification by silica gel chromatography, eluting with 5% MeOH/CH$_2$Cl$_2$ provided 85 the desired product(23%). $^1$H NMR (400 MHz, DMSO) δ 8.83 (d, J=1.70 Hz, 1H), 8.66 (d, J=7.10 Hz, 1H), 8.45 (d, J=2.60 Hz, 1H), 8.40 (s, 1H), 8.21 (dd, J=2.2, 6.6 Hz, 1H), 8.06 (d, J=2.10 Hz, 1H), 7.98 (s, 1H), 7.60 (d, J=8.70 Hz, 1H), 7.00 (s, 2H), 6.78 (d, J=8.8 Hz, 1H), 3.52 (s, 3H); ESI-LC/MS (m/z): [M+H]+395.09, RT 1.45 min.

Example 86

3-(6-amino-5-chloropyridin-3-yl)-N-(5-cyanopyridin-2-yl)-N-methylpyrazolo[1,5-a]pyridine-5-carboxamide

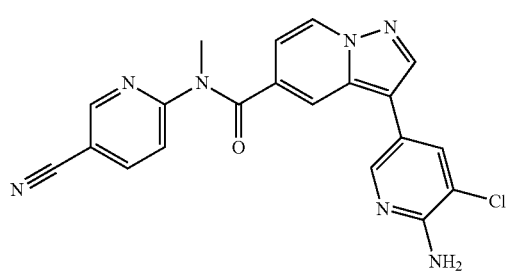

86

Example 86 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 3-chloro-5-(4,4,5,5-tetramethyl-1,3,2-dioxaborolan-2-yl)pyridin-2-amine (I-43). Purification by preparative TLC provided 86 the desired product (41%). $^1$H NMR (400 MHz, DMSO) δ 8.85 (s, 1H), 8.65 (d, J=7.50 Hz, 1H), 8.36 (s, 1H), 8.22 (d, J=8.8 Hz, 1H), 8.11 (s, 1H), 7.79 (s, 1H), 7.65 (s, 1H), 7.58 (d, J=8.8 Hz, 1H), 6.79 (d, J=7.0 Hz, 1H), 6.40 (s, 2H), 3.52 (s, 3H); ESI-LC/MS (m/z): [M+H]$^+$ 404.09, RT 1.27 min.

Example 87

3-(6-amino-5-(dimethylcarbamoyl)pyridin-3-yl)-N-(5-cyanopyridin-2-yl)-N-methylpyrazolo[1,5-a]pyridine-5-carboxamide

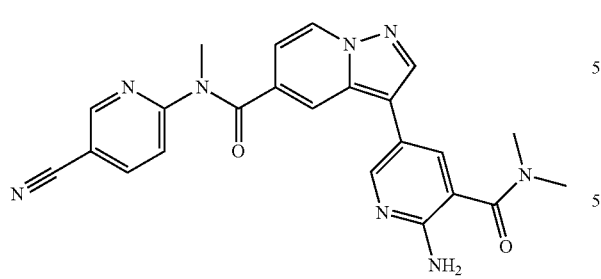

87

Example 87 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 2-amino-N,N-dimethyl-5-(4,4,5,5-tetramethyl-1,3,2-dioxaborolan-2-yl)nicotinamide (I-44). Purification by preparative TLC provided 87 as the desired product (10%). $^1$H NMR (400 MHz, DMSO) δ 8.81 (d, J=2.2 Hz, 1H), 8.64 (d, J=7.0 Hz, 1H), 8.35 (s, 1H), 8.20 (d, J=2.2 Hz, 2H), 8.17 (d, J=2.20 Hz, 1H), 7.80 (s, 1H), 7.55 (d, J=8.8 Hz, 1H), 7.48 (d, J=2.2 Hz, 1H), 6.76 (dd, J=1.7, 7.0 Hz, 1H), 3.52 (s, 3H), 2.97 (s, 6H); ESI-LC/MS (m/z): [M+H]$^+$ 441.11, RT 1.54 min.

Example 88

3-(6-amino-5-methoxypyridin-3-yl)-N-(5-cyanopyridin-2-yl)-N-methylpyrazolo[1,5-a]pyridine-5-carboxamide

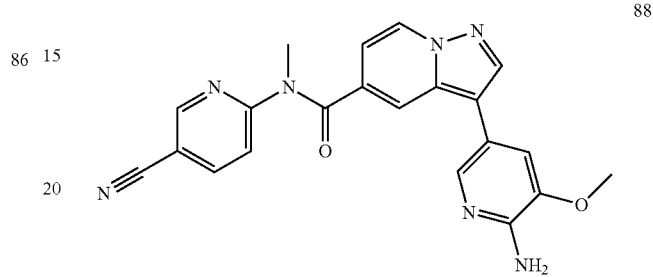

88

Example 88 was prepared from intermediate I-9 according to the procedure described for the synthesis of Example 79 by replacing 3-fluoro-5-(4,4,5,5-tetramethyl-1,3,2-dioxaborolan-2-yl)pyridin-2-amine (I-37) with 3-methoxy-5-(4,4,5,5-tetramethyl-1,3,2-dioxaborolan-2-yl)-pyridin-2-amine (I-45). Purification by silica gel chromatography, eluting with 5% MeOH/CH$_2$Cl$_2$ provided 88 as the desired product (36%). $^1$H NMR (400 MHz, DMSO) δ 8.78 (s, 1H), 8.62 (d, J=7.40 Hz, 1H), 8.33 (s, 1H), 8.28-8.20 (dd, J=2.2, 6.60 Hz, 1H), 7.86 (s, 1H), 7.66 (s, 1H), 7.58 (d, J=8.8 Hz, 1H), 7.16 (s, 1H), 6.77 (d, J=5.70 Hz, 1H), 5.79 (s, 2H), 3.84 (s, 3H), 3.52 (s, 3H); ESI-LC/MS (m/z): [M+H]$^+$ 400.06, RT 1.11 min.

Example 89

3-(4-carbamoylphenyl)-N-(4-chloro-2-formylphenyl)-N-methylpyrazolo[1,5-a]pyridine-5-carboxamide

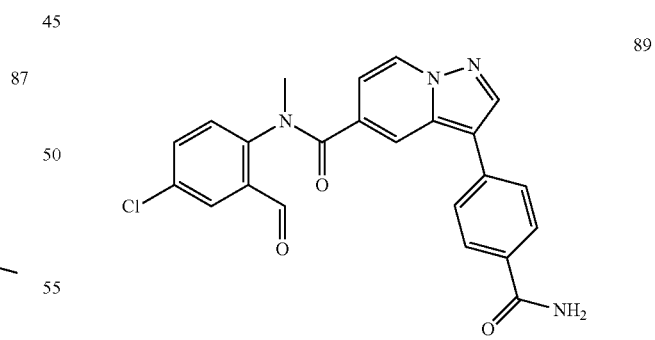

89

Example 89 was prepared from intermediate I-15 according to the procedure described for the synthesis of Example 65 (general Suzuki procedure E). The crude product was purified by preparative TLC to give 89 as the desired product. $^1$H NMR (400 MHz, DMSO) δ 10.02 (s, 1H), 8.62 (d, J=7.0 Hz, 1H), 8.44 (s, 1H), 8.02-7.86 (m, 3H), 7.86 (s, 2H), 7.74 (d, J=5.2 Hz, 1H), 7.63 (s, 1H), 7.43-7.35 (m, 3H), 6.81 (d, J=7.0 Hz, 1H), 3.80 (s, 3H); ESI-LC/MS (m/z): [M+H]$^+$ 433.2, RT 4.75 min.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:

1. A compound of Formula I,

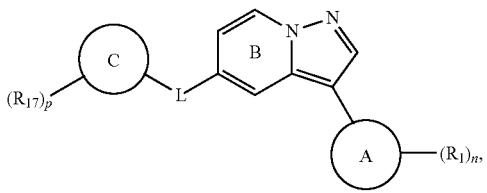

or a pharmaceutical acceptable salt, tautomer or stereoisomer thereof, wherein
n is 0, 1, 2 or 3;
p is 0, 1, 2 or 3;
L is selected from the group consisting of *—(CHR$_3$)$_{1-3}$—, *—CHR$_3$N(R$_2$)—, *—CHR$_3$O—, *—CHR$_3$S—, *—CHR$_3$S(O)—, *—CHR$_3$N(R$_2$)CHR$_3$—, *—C(O)—, *—C(O)N(R$_2$)—, *—C(O)N(R$_2$)CHR$_3$—, *—N(R$_2$)—, *—N(R$_2$)CHR$_3$—, *—N(R$_2$)C(O)—, *—N(R$_2$)C(O)N(R$_2$)—, *—N(R$_2$)S(O)$_2$—, wherein
  * represents the point of attachment of L to the pyrazolo[1,5-a]pyridine fused ring depicted in Formula I;
  each R$_2$ is independently selected from the group consisting of hydrogen, C$_{1-6}$alkyl, haloC$_{1-6}$alkyl, R—C$_{0-4}$alkylene, and R—C$_{0-4}$alkylene-C(O)—, wherein R is selected from the group consisting of hydroxyl, C$_{1-4}$alkoxy, amino, C$_{1-4}$alkylamino, C$_{3-6}$cycloalkyl, C$_{4-6}$heterocycloalkyl, and C$_{5-6}$heteroaryl, wherein the C$_{3-6}$cycloalkyl, C$_{4-6}$heterocycloalkyl, and C$_{5-6}$heteroaryl of R are each unsubstituted or substituted with 1-2 substituents independently selected from the group consisting of halo, amino, hydroxyl, C$_{1-4}$alkyl, C$_{1-4}$alkoxy, oxo, and C$_{5-6}$heteroaryl; and
  each R$_3$ is independently selected from the group consisting of hydrogen and C$_{1-4}$alkyl;
Ring A is selected from the group consisting of C$_{6-10}$aryl and C$_{3-10}$heteroaryl;
Ring C is selected from the group consisting of C$_{6-10}$aryl, C$_{5-10}$heteroaryl, C$_{5-7}$cycloalkyl, C$_{5-7}$heterocycloalkyl, and fused bicyclyl comprising a C$_{5-6}$heterocycloalkyl fused to a phenyl;
each R$_1$ is independently selected from the group consisting of halo, cyano, amino, C$_{1-4}$alkyl, C$_{1-4}$alkoxyl, halo-C$_{1-4}$alkyl, —C(O)NR$_7$R$_8$, —NHC(O)R$_{11}$, phenyl, and C$_{5-6}$heteroaryl; wherein
  the phenyl and C$_{5-6}$heteroaryl of R$_1$ are each unsubstituted or substituted with 1-2 substituents independently selected from the group consisting of C$_{1-4}$alkyl, amino, halo, and C$_{1-4}$alkylamino;
R$_7$ and R$_8$ are each independently selected from hydrogen, C$_{1-4}$alkyl and haloC$_{1-4}$alkyl;
R$_{11}$ is C$_{1-6}$alkyl, unsubstituted or substituted with 1-2 substituents independently selected from the group consisting of amino, C$_{3-6}$cycloalkyl and C$_{4-6}$heterocycloalkyl;
R$_{17}$ is selected from the group consisting of cyano, halo, C$_{1-4}$alkyl, halo-C$_{1-4}$alkyl, oxo, C$_{3-6}$cycloalkyl, and —SO$_2$—C$_{1-4}$alkyl.

2. The compound of claim 1, wherein L is selected from the group consisting of *—C(O)N(R$_2$)—, and *—N(R$_2$)C(O)—, wherein each R$_2$ is independently selected from hydrogen, C$_{1-4}$alkyl, and R—C$_{0-4}$alkylene, and wherein R is selected from the group consisting of C$_{4-6}$heterocycloalkyl and C$_{5-6}$heteroaryl, each of which is unsubstituted or substituted with 1-2 substituents independently selected from the group consisting of halo, amino, hydroxyl, C$_{1-4}$alkyl, C$_{1-4}$alkoxy, oxo, and C$_{5-6}$heteroaryl.

3. The compound of claim 1, wherein L is selected from the group consisting of *—CH(CH$_3$)—, *—CH$_2$CH$_2$—, *—CH$_2$N(CH$_3$)—, *—CH$_2$N(C(O)(CH$_2$)$_{1-2}$NH(CH$_3$))—, *—CH$_2$N(C(O)—(CH$_2$)$_{1-2}$NH$_2$)—, *—CH$_2$N((C(O)—(CH$_2$)$_{1-2}$N(CH$_3$)$_2$)—, *—CH$_2$N(C(O)(CH$_2$)$_{1-2}$OH)—, *—CH(CH$_3$)N(CH$_3$)—, *—CH$_2$O—, *—CH$_2$S—, *—CH$_2$S(O)—, *—C(O)—, *—C(O)N(CH$_3$)—, *—C(O)N(CH$_2$CH$_3$)—, *—C(O)N(CH(CH$_3$)$_2$)—, *—C(O)N(C(CH$_3$)$_3$)—, *—C(O)N(CH$_2$CH(CH$_3$)$_2$)—, *—C(O)N(CH(CH$_3$)CH$_2$CH$_3$)—, *—C(O)N(CH$_2$CH$_2$OCH$_3$)—, *—C(O)N(CH$_2$CH$_2$N(CH$_3$)$_2$)—, *—C(O)N(CH$_3$)CH$_2$—, *—NHCH$_2$—, *—N(CH$_3$)CH$_2$—, *—N(CH$_2$-tetrahydropyran-4-yl)-C(O)—, *—N(CH$_3$)C(O)—, *—N(CH$_3$)C(O)NH—, *—N(CH$_3$)S(O)$_2$—, *—C(O)N((CH$_2$)$_{0-1}$-cyclopropyl)-, *—C(O)N((CH$_2$)$_{0-1}$-cyclobutyl)-, *—C(O)N((CH$_2$)$_{0-1}$-cyclopentyl)-, *—C(O)N((CH$_2$)$_{0-1}$-cyclohexyl)-, *—C(O)N(CH$_2$-tetrahydropyran-4-yl)-, *—C(O)N((CH$_2$)$_2$-(1,1-dioxidothiomorpholino-4-yl))-, *—C(O)N(CH$_2$-1,1-dioxidothiomorpholino-4-yl)-, *—C(O)N((CH$_2$)$_2$-tetrahydropyran-4-yl))-, *—C(O)N((CH$_2$)$_{1-2}$-morpholin-4-yl)-, *—C(O)N(oxetan-3-yl)-, *—C(O)N(CH$_2$-oxetan-3-yl)-, *—C(O)N(CH(CH$_3$)—CH$_2$-1-H-pyrazoly-1-yl)-, *—CH$_2$N(C(O)—(CH$_2$)$_{1-2}$-morpholinyl))-, *—CH$_2$N(C(O)—(CH$_2$)$_{1-2}$-4-methylpiperizin-1-yl))-, *—CH$_2$N(C(O)—(CH$_2$)$_{1-2}$-tetrahydropyran-4-yl)-, and *—CH$_2$N(C(O)(CH$_2$)$_{1-2}$-oxetan-3-yl)-.

4. The compound according to claim 1, wherein Ring A is selected from the group consisting of phenyl, pyridinyl, pyrimidinyl, pyrazinyl, pyridazinyl, pyrrolopyridinyl, and indazolyl, each of which is unsubstituted or substituted by (R$_1$)$_n$.

5. The compound according to claim 1, wherein Ring C is selected from the group consisting of

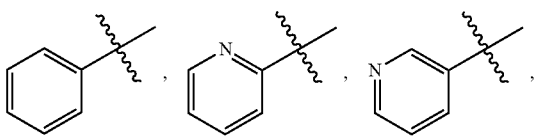

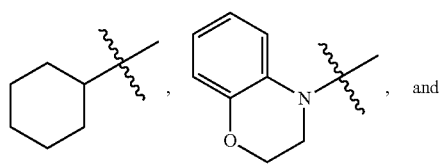

and

-continued

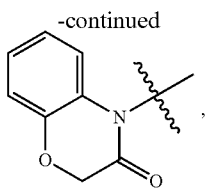

each of which is unsubstituted or substituted by $(R_{17})_p$.

6. The compound according to claim 1, wherein Ring C is selected from the group consisting of phenyl and pyridinyl, each of which is unsubstituted or substituted by $(R_{17})_p$.

7. The compound according to claim 1, wherein each $R_1$ is independently selected from the group consisting of trifluoromethyl, cyano, —$NH_2$—, —$C(O)NH_2$, —$C(O)NHCH_3$, —$C(O)N(CH_3)_2$, and —$NHC(O)CH(NH_2)(CH_3)$.

8. The compound according to claim 1, wherein each $R_{17}$ is independently selected from the group consisting of cyano, halo, $C_{1-4}$alkyl, halo$C_{1-4}$alkyl, —$SO_2$—$C_{1-4}$alkyl, and $C_{3-6}$cycloalkyl.

9. The compound of claim 1, wherein the compound is of Formula Ia:

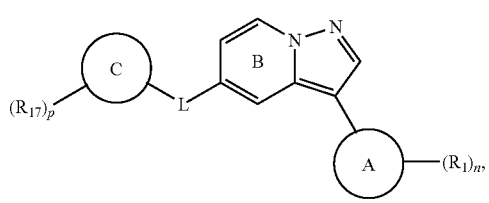

or a pharmaceutical acceptable salt, tautomer or stereoisomer thereof, wherein
n is 1 or 2;
p is 1 or 2;
Ring A is phenyl, pyridinyl, or pyrimidinyl;
Ring C is phenyl or pyridinyl;
L is *—$C(O)NR_2$— or *—$NR_2C(O)$—, wherein $R_2$ is selected from hydrogen, $C_{1-4}$alkyl, $C_{3-6}$cycloalkyl-$(C_{0-4})$alkylene, $C_{4-6}$heterocycloalkyl-$(C_{0-4})$alkylene, wherein the $C_{4-6}$heterocycloalkyl is selected from the group consisting of piperazinyl, morpholinyl, thiomorpholinyl, tetrahydropyranyl, and oxetanyl, and wherein the $C_{3-6}$cycloalkyl is selected from cyclopropyl, cyclobutyl, cyclopentyl and cyclohexyl;
each $R_1$ is independently *—$C(O)NR_7R_8$ or —$NH_2$—, wherein $R_7$ and $R_8$ are each independently hydrogen or $C_{1-4}$alkyl; and
$R_{17}$ is selected from the group consisting of cyano, halo, —$NH_2$—, —$C(O)NH_2$, —$C(O)NH(CH_3)$, and —$C(O)N(CH_3)_2$.

10. The compound of claim 1, wherein the compound, or a pharmaceutical acceptable salt, tautomer or stereoisomer thereof, is selected from the group consisting of:
N-(4-cyanophenyl)-N-methyl-3-(4-(trifluoromethyl)phenyl)pyrazolo[1,5-a]pyridine-5-carboxamide;
4-fluoro-N-methyl-N-((3-(4-(trifluoromethyl)phenyl)pyrazolo[1,5-a]pyridine-5-yl)methyl)aniline;
N-(4-chlorophenyl)-N-methyl-3-(4-(trifluoromethyl)phenyl)pyrazolo[1,5-a]pyridine-5-carboxamide;
N-(4-fluorophenyl)-N-methyl-3-(4-(trifluoromethyl)phenyl)pyrazolo[1,5-a]pyridine-5-carboxamide;
N-methyl-N-(5-methylpyridin-2-yl)-3-(4-(trifluoromethyl)phenyl)pyrazolo[1,5-a]pyridine-5-carboxamide;
4-chloro-N-methyl-N-((3-(4-(trifluoromethyl)phenyl)pyrazolo[1,5-a]pyridine-5-yl)methyl)aniline;
N,5-dimethyl-N-((3-(4-(trifluoromethyl)phenyl)pyrazolo[1,5-a]pyridine-5-yl)methyl)yridine-2-amine;
5-((4-fluorophenoxy)methyl)-3-(4-(trifluoromethyl)phenyl)pyrazolo[1,5-a]pyridine;
N-(4-cyanophenyl)-N-(2-methoxyethyl)-3-(4-(trifluoromethyl)phenyl)pyrazolo[1,5-a]pyridine-5-carboxamide;
N-(4-cyanophenyl)-N-(2-(dimethylamino)ethyl)-3-(4-(trifluoromethyl)phenyl)pyrazolo[1,5-a]pyridine-5-carboxamide;
N-(4-cyanophenyl)-N-((tetrahydro-2H-pyran-4-ylmethyl)-3-(4-(trifluoromethyl)phenyl)pyrazolo[1,5-a]pyridine-5-carboxamide;
N-(4-(methylsulfonyl)phenyl)-N-((tetrahydro-2H-pyran-4-ylmethyl)-3-(4-(trifluoromethyl)phenyl)pyrazolo[1,5-a]pyridine-5-carboxamide;
N-(5-cyanopyridin-2-yl)-N-methyl-3-(4-(trifluoromethyl)phenyl)pyrazolo[1,5-a]pyridine-5-carboxamide;
N-methyl-N-(5-methylpyridin-3-yl)-3-(4-(trifluoromethyl)phenyl)pyrazolo[1,5-a]pyridine-5-carboxamide;
5-(((5-methylpyridin-2-yl)oxy)methyl)-3-(4-(trifluoromethyl)phenyl)pyrazolo[1,5-a]pyridine;
5-(4-fluorophenethyl)-3-(4-(trifluoromethyl)phenyl)pyrazolo[1,5-a]pyridine;
N-(4-cyanophenyl)-N-methyl-3-(1-methyl-1H-indazol-5-yl)pyrazolo[1,5-a]pyridine-5-carboxamide;
3-(6-acetamidopyridin-3-yl)-N-(4-cyanophenyl)-N-methylpyrazolo[1,5-a]pyridine-5-carboxamide;
3-(4-carbamoylphenyl)-N-(4-cyanophenyl)-N-methylpyrazolo[1,5-a]pyridine-5-carboxamide;
3-(4-carbamoylphenyl)-N-(4-fluorophenyl)-N-methylpyrazolo[1,5-a]pyridine-5-carboxamide;
5-(((4-fluorophenyl)thio)methyl)-3-(4-(trifluoromethyl)phenyl)pyrazolo[1,5-a]pyridine;
5-(((4-fluorophenyl)sulfinylmethyl)-3-(4-(trifluoromethyl)phenyl)pyrazolo[1,5-a]pyridine;
3-(4-(1H-pyrazol-5-yl)phenyl)-N-(4-cyanophenyl)-N-methylpyrazolo[1,5-a]pyridine-5-carboxamide;
N-(4-cyanophenyl)-N-methyl-3-(5-(trifluoromethyl)pyridine-2-yl)pyrazolo[1,5-a]pyridine-5-carboxamide;
N-(5-cyanopyridin-2-yl)-N-methyl-3-(5-(trifluoromethyl)pyridine-2-yl)pyrazolo[1,5-a]pyridine-5-carboxamide;
(S)-3-(4-(2-aminopropanamido)phenyl)-N-(4-cyanophenyl)-N-methylpyrazolo[1,5-a]pyridine-5-carboxamide;
3-(5-carbamoylpyridin-2-yl)-N-(4-cyanophenyl)-N-methylpyrazolo[1,5-a]pyridine-5-carboxamide;
4-cyano-N-methyl-N-(3-(4-(trifluoromethyl)phenyl)pyrazolo[1,5-a]pyridine-5-yl)benzamide;
4-fluoro-N-methyl-N-(3-(4-(trifluoromethyl)phenyl)pyrazolo[1,5-a]pyridine-5-yl)benzamide;
4-cyano-N-methyl-N-(3-(4-(trifluoromethyl)phenyl)pyrazolo[1,5-a]pyridine-5-yl)benzenesulfonamide;
4-fluoro-N-methyl-N-(3-(4-(trifluoromethyl)phenyl)pyrazolo[1,5-a]pyridine-5-yl)benzenesulfonamide;
3-(4-carbamoylphenyl)-N-(5-cyanopyridin-2-yl)-N-methylpyrazolo[1,5-a]pyridine-5-carboxamide; N-methyl-3-(4-(trifluoromethyl)phenyl)-N-(5-(trifluoromethyl)yridine-2-yl)pyrazolo[1,5-a]pyridine-5-carboxamide;
N-methyl-N-(5-(methylsulfonyl)pyridine-2-yl)-3-(4-(trifluoromethyl)phenyl)pyrazolo[1,5-a]pyridine-5-carboxamide;
N-(4-fluorobenzyl)-3-(4-(trifluoromethyl)phenyl)pyrazolo[1,5-a]pyridine-5-amine N-(4-fluorobenzyl)-3-(4-(trifluoromethyl)phenyl)pyrazolo[1,5-a]pyridine-5-amine;
N-methyl-6-(trifluoromethyl)-N-(3-(4-(trifluoromethyl)phenyl)pyrazolo[1,5-a]yridine-5-yl)nicotinamide;
N-methyl-5-(trifluoromethyl)-N-(3-(4-(trifluoromethyl)phenyl)pyrazolo[1,5-a]yridine-5-yl)picolinamide;
4-cyano-N-((tetrahydro-2H-pyran-4-ylmethyl)-N-(3-(4-(trifluoromethyl)phenyl)pyrazolo[1,5-a]pyridin-5-yl)benzamide;
N-(4-cyanophenyl)-N-methyl-3-(1H-pyrrolo[2,3-b]pyridin-5-yl)pyrazolo[1,5-a]pyridine-5-carboxamide;
3-(6-aminopyridin-3-yl)-N-(4-cyanophenyl)-N-methylpyrazolo[1,5-a]pyridine-5-carboxamide;
3-(4-aminophenyl)-N-(4-cyanophenyl)-N-methylpyrazolo[1,5-a]pyridine-5-carboxamide;
3-(4-(2-aminoacetamido)phenyl)-N-(4-cyanophenyl)-N-methylpyrazolo[1,5-a]pyridine-5-carboxamide;
(R)-3-(4-(2-aminopropanamido)phenyl)-N-(4-cyanophenyl)-N-methylpyrazolo[1,5-a]pyridine-5-carboxamide;
(S)-3-(4-(2-amino-3-methylbutanamido)phenyl)-N-(4-cyanophenyl)-N-methylpyrazolo[1,5-a]pyridine-5-carboxamide;
(S)-3-(4-(2-amino-2-cyclohexylacetamido)phenyl)-N-(4-cyanophenyl)-N-methylpyrazolo[1,5-a]pyridine-5-carboxamide;
3-(4-fluorophenyl)-1-methyl-1-(3-(4-(trifluoromethyl)phenyl)pyrazolo[1,5-a]pyridin-5-yl)urea;
6-(1,1-difluoroethyl)-N-methyl-N-(3-(4-(trifluoromethyl)phenyl)pyrazolo[1,5-a]pyridin-5-yl)nicotinamide;
6-cyclopropyl-N-methyl-N-(3-(4-(trifluoromethyl)phenyl)pyrazolo[1,5-a]pyridin-5-yl)nicotinamide;
4-cyclopropyl-N-methyl-N-(3-(4-(trifluoromethyl)phenyl)pyrazolo[1,5-a]pyridin-5-yl)benzamide;
5-fluoro-N-methyl-N-(3-(4-(trifluoromethyl)phenyl)pyrazolo[1,5-a]pyridin-5-yl)picolinamide;
N-methyl-4-(methylsulfonyl)-N-(3-(4-(trifluoromethyl)phenyl)pyrazolo[1,5-a]pyridin-5-yl)benzamide;
N-(5-cyanopyridin-2-yl)-N-methyl-3-(1H-pyrrolo[2,3-b]pyridin-5-yl)pyrazolo[1,5-a]pyridine-5-carboxamide;
3-(6-aminopyridin-3-yl)-N-(5-cyanopyridin-2-yl)-N-methylpyrazolo[1,5-a]pyridine-5-carboxamide;
4-chloro-N-methyl-N-(3-(4-(trifluoromethyl)phenyl)pyrazolo[1,5-a]pyridin-5-yl)benzamide;
N-(3-(4-carbamoylphenyl)pyrazolo[1,5-a]pyridin-5-yl)-4-fluoro-N-methylbenzamide
4-fluoro-N-methyl-N-(3-(4-(5-(methylamino)-1,3,4-thiadiazol-2-yl)phenyl)pyrazolo[1,5-a]pyridin-5-yl)benzamide;
N-methyl-N-(5-(methylsulfonyl)pyridin-2-yl)-3-(1H-pyrrolo[2,3-b]pyridin-5-yl)pyrazolo[1,5-a]pyridine-5-carboxamide;
N-(5-cyanopyridin-2-yl)-N-methyl-3-(5-methylpyridin-2-yl)pyrazolo[1,5-a]pyridine-5-carboxamide;
N-(5-cyanopyridin-2-yl)-3-(5-methoxypyridin-2-yl)-N-methylpyrazolo[1,5-a]pyridine-5-carboxamide;
3-(5-carbamoylpyridin-2-yl)-N-(5-cyanopyridin-2-yl)-N-methylpyrazolo[1,5-a]pyridine-5-carboxamide;
3-(4-carbamoylphenyl)-N-methyl-N-(5-(trifluoromethyl)pyridin-2-yl)pyrazolo[1,5-a]pyridine-5-carboxamide;
3-(4-carbamoylphenyl)-N-methyl-N-(5-methylpyridin-2-yl)pyrazolo[1,5-a]pyridine-5-carboxamide;
N-(4-fluorophenyl)-N-methyl-3-(4-(methylcarbamoyl)phenyl)pyrazolo[1,5-a]pyridine-5-carboxamide;
4-(5-(1-(methyl(5-methylpyridin-2-yl)amino)ethyl)pyrazolo[1,5-a]pyridin-3-yl)benzamide;
4-(5-(1-(7-fluoro-3-oxo-2H-benzo[b][1,4]oxazin-4(3H)-yl)ethyl)pyrazolo[1,5-a]pyridin-3-yl)benzamide;
N-(4-cyanophenyl)-N-methyl-3-(4-(methylcarbamoyl)phenyl)pyrazolo[1,5-a]pyridine-5-carboxamide;
N-(4-(5-(1-(methyl(5-methylpyridin-2-yl)amino)ethyl)pyrazolo[1,5-a]pyridin-3-yl)phenyl)acetamide;
3-(4-acetamidophenyl)-N-(5-cyanopyridin-2-yl)-N-methylpyrazolo[1,5-a]pyridine-5-carboxamide;
4-(5-(7-fluoro-3,4-dihydro-2H-benzo[b][1,4]oxazine-4-carbonyl)pyrazolo[1,5-a]pyridin-3-yl)benzamide;
4-(5-(7-fluoro-3-methyl-3,4-dihydro-2H-benzo[b][1,4]oxazine-4-carbonyl)pyrazolo[1,5-a]pyridin-3-yl)benzamide;
4-(5-(7-fluoro-3,4-dihydro-2H-benzo[b][1,4]oxazine-4-carbonyl)pyrazolo[1,5-a]pyridin-3-yl)-N-methylbenzamide;
4-(5-(7-fluoro-3-methyl-3,4-dihydro-2H-benzo[b][1,4]oxazine-4-carbonyl)pyrazolo[1,5-a]pyridin-3-yl)-N-methylbenzamide;
N-(5-cyanopyridin-2-yl)-N-methyl-3-(4-(methylcarbamoyl)phenyl)pyrazolo[1,5-a]pyridine-5-carboxamide;
N-(5-cyanopyridin-2-yl)-3-(4-(methylcarbamoyl)phenyl)-N-(oxetan-3-yl)pyrazolo[1,5-a]pyridine-5-carboxamide;
N-(1-(1H-pyrazol-1-yl)propan-2-yl)-3-(4-carbamoylphenyl)-N-(5-cyanopyridin-2-yl)pyrazolo[1,5-a]pyridine-5-carboxamide;
3-(6-amino-5-fluoropyridin-3-yl)-N-(4-cyanophenyl)-N-methylpyrazolo[1,5-a]pyridine-5-carboxamide;
3-(4-amino-3,5-dimethylphenyl)-N-(4-cyanophenyl)-N-methylpyrazolo[1,5-a]pyridine-5-carboxamide;
3-(6-amino-5-methylpyridin-3-yl)-N-(4-cyanophenyl)-N-methylpyrazolo[1,5-a]pyridine-5-carboxamide;
3-(4-carbamoylphenyl)-N-(4-cyanocyclohexyl)-N-methylpyrazolo[1,5-a]pyridine-5-carboxamide;
3-(2-aminopyrimidin-5-yl)-N-(4-cyanophenyl)-N-methylpyrazolo[1,5-a]pyridine-5-carboxamide;
3-(6-amino-5-(trifluoromethyl)pyridin-3-yl)-N-(5-cyanopyridin-2-yl)-N-methylpyrazolo[1,5-a]pyridine-5-carboxamide;
3-(6-amino-5-cyanopyridin-3-yl)-N-(5-cyanopyridin-2-yl)-N-methylpyrazolo[1,5-a]pyridine-5-carboxamide;
3-(6-amino-5-chloropyridin-3-yl)-N-(5-cyanopyridin-2-yl)-N-methylpyrazolo[1,5-a]pyridine-5-carboxamide;
3-(6-amino-5-(dimethylcarbamoyl)pyridin-3-yl)-N-(5-cyanopyridin-2-yl)-N-methylpyrazolo[1,5-a]pyridine-5-carboxamide;
3-(6-amino-5-methoxypyridin-3-yl)-N-(5-cyanopyridin-2-yl)-N-methylpyrazolo[1,5-a]pyridine-5-carboxamide; and
3-(4-carbamoylphenyl)-N-(4-chloro-2-formylphenyl)-N-methylpyrazolo[1,5-a]pyridine-5-carboxamide.

11. A pharmaceutical composition comprising at least one compound according to claim 1, or a pharmaceutically acceptable salt thereof, and a pharmaceutically acceptable carrier, diluent or excipient.

12. The pharmaceutical composition according to claim 11, further comprising a second agent, wherein the second agent is an antimalarial drug selected from artemisinin, artemether, artesunate, arteflene, dihydroartemisinin, chlorproguanil, trimethoprim, chloroquine, quinine, mefloquine, amodiaquine, atovaquone, proguanil, lumefantrine, piperaquine, pyronaridine, halofantrine, pyrimethamine-sulfadoxine, quinacrine, pyrimethamine-dapsone, quinidine, amopyroquine, sulphonamides, primaquine, ferroquine, tafenoquine, arterolane, and pyronaridine.

* * * * *